US012583852B2

(12) United States Patent
Hong et al.

(10) Patent No.: US 12,583,852 B2
(45) Date of Patent: Mar. 24, 2026

(54) HETEROCYCLE DERIVATIVE

(71) Applicant: JW PHARMACEUTICAL CORPORATION, Seoul (KR)

(72) Inventors: Woo Sang Hong, Gyeonggi-do (KR); Joo Young Cha, Gyeonggi-do (KR); Sun Ea Choi, Seoul (KR); Isak Im, Seoul (KR); Chi-Ho Yun, Gyeonggi-do (KR); Jae Ho Jang, Seoul (KR); Chae Lim Jung, Gyeonggi-do (KR); Sei Ho Chin, Gyeonggi-do (KR); Jiknyeo Kim, Gyeonggi-do (KR); Joongsoo Kim, Gyeonggi-do (KR); Sang Hak Lee, Gyeonggi-do (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 1112 days.

(21) Appl. No.: 17/052,192

(22) PCT Filed: May 2, 2019

(86) PCT No.: PCT/KR2019/005261

§ 371 (c)(1),
(2) Date: Nov. 1, 2020

(87) PCT Pub. No.: WO2019/212256

PCT Pub. Date: Nov. 7, 2019

(65) Prior Publication Data

US 2022/0259199 A1 Aug. 18, 2022

(30) Foreign Application Priority Data

May 2, 2018 (KR) ........................ 10-2018-0050910

(51) Int. Cl.

| | |
|---|---|
| ***C07D 471/04*** | (2006.01) |
| ***A61P 17/14*** | (2006.01) |
| ***C07D 487/04*** | (2006.01) |
| ***C07D 519/00*** | (2006.01) |
| ***C07F 9/6561*** | (2006.01) |

(52) U.S. Cl.

CPC ............ *C07D 471/04* (2013.01); *A61P 17/14* (2018.01); *C07D 487/04* (2013.01); *C07D 519/00* (2013.01); *C07F 9/6561* (2013.01)

(58) Field of Classification Search

CPC ... C07F 9/6561; C07D 471/04; C07D 487/04; C07D 519/00; A61P 17/14

See application file for complete search history.

(56) References Cited

U.S. PATENT DOCUMENTS

| | | | | |
|---|---|---|---|---|
| 3,872,133 | A | 3/1975 | Fleckenstein et al. | |
| 3,957,782 | A | 5/1976 | Hoehn | |
| 4,822,799 | A | 4/1989 | Kathawala | |
| 2004/0052822 | A1 | 3/2004 | Kohara et al. | |
| 2005/0277655 | A1 | 12/2005 | Ding et al. | |
| 2007/0054915 | A1 * | 3/2007 | Arora | A61P 25/28 514/249 |
| 2010/0298557 | A1 | 11/2010 | Yaki et al. | |
| 2012/0232062 | A1 * | 9/2012 | Yang | C07D 471/04 435/375 |
| 2013/0085144 | A1 * | 4/2013 | Kaloun | A61P 29/00 514/249 |
| 2014/0107151 | A1 | 4/2014 | Goldstein et al. | |

FOREIGN PATENT DOCUMENTS

| | | | |
|---|---|---|---|
| CN | 1972943 | A | 5/2007 |
| CN | 101228160 | A | 7/2008 |
| CN | 101243090 | A | 8/2008 |
| CN | 104684554 | B | 5/2017 |
| CN | 107174585 | A | 9/2017 |
| CN | 104854101 | B | 5/2018 |
| CN | 114008026 | A | 2/2022 |
| EP | 0339358 | A1 | 11/1989 |
| EP | 3725777 | A1 | 10/2020 |
| GB | 1391244 | A | 4/1975 |
| GB | 1552730 | A | 9/1979 |
| JP | 4949991 | A | 5/1974 |
| JP | 03287513 | A | 12/1991 |
| KR | 1020100121222 | A1 | 11/2010 |
| KR | 1020150085962 | A1 | 7/2015 |
| PL | 239236 | A1 | 9/1983 |
| PL | 239236 | B1 | 11/2021 |
| RU | 2340611 | C2 | 12/2008 |
| RU | 2600976 | C2 | 10/2016 |

(Continued)

OTHER PUBLICATIONS

Allah-Abdu, H.H.M., et al., "Synthesis and preliminary biological screening of 6-aminopyrazolo[3,4-b]pyridine derivatives", Der Pharma Chemica, 2016, pp. 9-16, vol. 8, No. 16, Publisher: www.derpharmachemica.com.
CAS Registry No. 1177710-94-9, Aug. 30, 2009.
CAS Registry No. 1177961-26-0, Aug. 30, 2009.
CAS Registry No. 2128705-62-2, Sep. 19, 2017.
Hahn, W.E., et al., "Disperse dyes derived from 3-arylazo-5-cyano-4-methyl-1H-pyrazolo[3,4- b]pyridine", Chemia Stosowana, 1986, pp. 421-429, vol. 30, No. 3.
Kandeel, M.M., et al., "Design, synthesis and cytoxic activity of some novel compounds containing pyrazolo[3,4-d] pyrimidines nucleus", J. Chem. Sci., 2013, pp. 1029-1043, vol. 125, No. 5.
Kopecky, D.J., et al., "Identification and optimization of N3, N6-diaryl-1H-pyrazolo[3,4-d]pyrimidine-3,6-diamines as a novel class of ACK1 inhibitorss", Bioorganic & Medicinal Chemistry Letters, 2008, pp. 6352-6356, vol. 18, Publisher: Elsevier.

(Continued)

*Primary Examiner* — Kara R. McMillian

(74) *Attorney, Agent, or Firm* — HULTQUIST, PLLC; Steven J. Hultquist

(57) ABSTRACT

The present invention relates to a novel heterocycle derivative, a salt thereof, or an isomer thereof. More specifically, the present invention relates to a novel heterocycle derivative effective for the therapy for hair loss such as androgenic alopecia and alopecia areata and having an excellent preventive effect of hair loss, a salt or isomer thereof, and a composition comprising same as an effective ingredient for prevention of hair loss.

6 Claims, 1 Drawing Sheet

(56) References Cited

FOREIGN PATENT DOCUMENTS

| | | | |
|---|---|---|---|
| WO | 02062795 | A2 | 8/2002 |
| WO | 03068773 | A1 | 8/2003 |
| WO | 2004018473 | A2 | 3/2004 |
| WO | 2005028480 | A2 | 3/2005 |
| WO | 2005028480 | A3 | 3/2005 |
| WO | 2006063820 | A1 | 6/2006 |
| WO | 2006091737 | A1 | 8/2006 |
| WO | 2007023110 | A2 | 3/2007 |
| WO | 2007024680 | A1 | 3/2007 |
| WO | 2008112695 | A2 | 9/2008 |
| WO | 2009023978 | A1 | 2/2009 |
| WO | 2011019780 | A1 | 2/2011 |
| WO | 2011146313 | A1 | 11/2011 |
| WO | 2012030924 | A1 | 3/2012 |
| WO | 2012158810 | A1 | 11/2012 |
| WO | 2013067302 | A1 | 5/2013 |
| WO | 2014016433 | A1 | 1/2014 |
| WO | 2014071832 | A1 | 5/2014 |
| WO | 2015157125 | A1 | 10/2015 |
| WO | 2018208132 | A1 | 11/2018 |

OTHER PUBLICATIONS

Metwally, S.A., et al., "Synthesis and Some Reactions of 3-Methyl-4-aryl-1-phenl-1H-pyrazolo[3,4-d]pyrimidine-6-thiols", Croatica Chemica Acta, 1986, pp. 483-489, vol. 59, No. 2.

Michellys, P-Y, et al., "Design and Synthesis of Novel Selective Anaplastic Lymphoma Kinase Inhibitors", Biorganic & Medicinal Chemistry Letters, 2015, pp. 1090-1096, vol. 26, No. 3.

Molina, P., et al., "Heterocyclization Reactions of Conjugated Heterocumulenes. Synthesis of Pyridine Derivatives by a Tandem Aza Wittig/Electrocyclization Strategy", Chem. Ber., 1989, pp. 307-313, vol. 122.

Molina, P., et al., "Fused Dihydropyrimidines by a Tandem Aza-Wittig-Heterocmulene-Mediated Annulation Reaction Synthesis of 4,5-Dihydropyrazolo[3,4-d] pyrimidine Derivatives", Synthesis, 1990, pp. 469-473, vol. 6.

Yang, L-L, et al., "Discovery of N6-phynyl-1H-pyrazolo[3,4-d]pyrimidine-3,6-diamine derivatives as novel CK1 inhibitors using common-feature pharmacophore model based virtual screening and hit-to-lead optimization", European Journal of Medicinal Chemistry, 2012, pp. 30-38, vol. 56.

Younes, M.I., et al., "Reactions Of 6-Amino-5-Cyano-3-Methyl-1,4-Diphenl-1H4H-Pyranoo[2,3-c] Pyrazole and Its Methanimidate", Journal of Chinese Chemical Society, 1990, pp. 617-623, vol. 37.

Hahn, W.E., et al., "Disperse dyes derived from 3-arylazo-5-cyano-4-methyl-1H-pyrazolo[3,4- b]pyridine", Chemia Stosowana, 1986, pp. 421-429, vol. 30, No. 3, English Translation.

Identification of Compound of Chemical Abstracts Registry No. 1520513-58-9 Examination Report No. 3 in Counterpart Australian Application 2019264078, STN Entry Date: Jan. 15, 2014, Compound: 6-butyl-3-ethyl-1,4,6,7-tetrahydro-1-methyl-5H-pyrazolo[3,4-b]pyrazin-5-one.

Identification of Compound of Chemical Abstracts Registry No. 1521744-88-6 Examination Report No. 3 in Counterpart Australian Application 2019264078, STN Entry Date: Jan. 16, 2014, Compound: 1-ethyl-1,4,6,7-tetrahydro-3-methyl-6-(phenylmethyl)-5H-pyrazolo[3,4-b]pyrazin-5-one.

Identification of Compound of Chemical Abstracts Registry No. 1525517-55-8 Examination Report No. 3 in Counterpart Australian Application 2019264078, STN Entry Date: Jan. 20, 2014, Compound: 1,4,6,7-tetrahydro-6-(2-methoxyethyl)-1,3-dimethyl-5H-pyrazolo[3,4-b]pyrazin-5-one.

Identification of Compound of Chemical Abstracts Registry No. 2094291-81-1 Examination Report No. 3 in Counterpart Australian Application 2019264078, STN Entry Date: May 2, 2017, Compound: 4-chloro-N-[3-(2-methoxyethoxy)propyl]-1,3,5-trimethyl-1H-pyrazolo[3,4-b]pyridin-6-amine.

Examination Report No. 3 for standard patent application AU2019264078, Jun. 14, 2022, Australian Government, IP Australia.

Safieh, K.A. A., et al., "Synthesis of Some 1,3-Dimethyl-6-substituted-1H-pyrazolo[3,4-b]pyrazin-5(4H)-ones", ZNaturforsch, 2011, pp. 1136-1140, vol. 66b, Publisher: Verlag de Zeitschrift fur Naturforschung.

Notice of Allowance Issued in Counterpart Russian Patent Application No. 2020139247 on Feb. 7, 2023.

Office Action issued on Aug. 26, 2022 for counterpart Australian Patent Application No. 2022204211, Aug. 26, 2022.

CAS Registry No. 2242350-12-3; STN Entry Date: Aug. 31, 2018; 1-[(4-Chloro-1,3,5-trimethyl-1H-pyrazolo[3,4-b]pyridin-6-yl)amino]-2,3-dihydro-1H-inden-2-ol, Aug. 3, 2028.

Office Action issued in counterpart Canadian Patent Application No. 3098988 on Feb. 8, 2023.

CAS Registry No. 1404307-02-31; N6-(4-Chlorophenyl)-1H-pyrazolo[3,4-d]pyrimidine-3-6-diamine, Nov. 30, 2012.

Office Action issued in counterpart Chinese Patent Application No. 2019800421177 on Jan. 19, 2023.

Search Report Issued in counterpart Chinese Patent Application No. 2019800421177 on Jan. 12, 2023.

Botchkarev, V., et al., "Noggin is required for induction of the hair follicle growth phase in postnatal skin", "The FASEP Journal", Oct. 2001, pp. 2205-2214, vol. 15.

Botchkarev, V., et al., "Molecular Control of Epithelial-Mesenchymal Interactions During Hair Follicle Cycling", "J Investig. Dermatol. Symp. Proc.", Jun. 2003, pp. 46-55, vol. 8, No. 1, Publisher: The Society for Investigative Dermatology, Inc.

Kwack, M.H., et al., "Dihydrotestosterone-Inducible Dickkopf 1 from Balding Dermal Papilla Cells Causes Apoptosis in Follicular Keratinocytes", "Journal of Investigative Dermatology", 2008, pp. 262-269, vol. 128, Publisher: The Society for Investigative Dermatology.

Lei, M., et al., "Getting to the Core of the Dermal Papilla", "Journal of Investigative Dermagology", 2017, pp. 2250-2253, vol. 137, Publisher: www.jidonline.org.

"CAS Registry No. 1945244-74-5", Jul. 5, 2016, Publisher: SR Chemical Library.

"CAS Registry No. 1954976-06-7", Jul. 19, 2016, Publisher: SR Chemical Library.

"CAS Registry No. 1957673-73-2", Jul. 22, 2016, Publisher: SR Chemical Library.

"CAS Registry No. 2056937-19-8", Jan. 20, 2017, Publisher: SR Chemical Library.

"CAS Registry No. 2128370-14-7", Sep. 19, 2017, Publisher: SR Chemical Library.

"CAS Registry No. 2128476-63-9", Sep. 19, 2017, Publisher: SR Chemical Library.

Notice of Allowance issued on Mar. 27, 2024 for Korean Patent Application 10-2020-7029158.

English Translation of Notice of Allowance issued on Mar. 27, 2024 for Korean Patent Application 10-2020-7029158.

Office Action issued for Apr. 29, 2024 Egyptian Patent Application 2020111714.

English Translation of Apr. 29, 2024 Office Action issued for Egyptian Patent Application 2020111714.

* cited by examiner

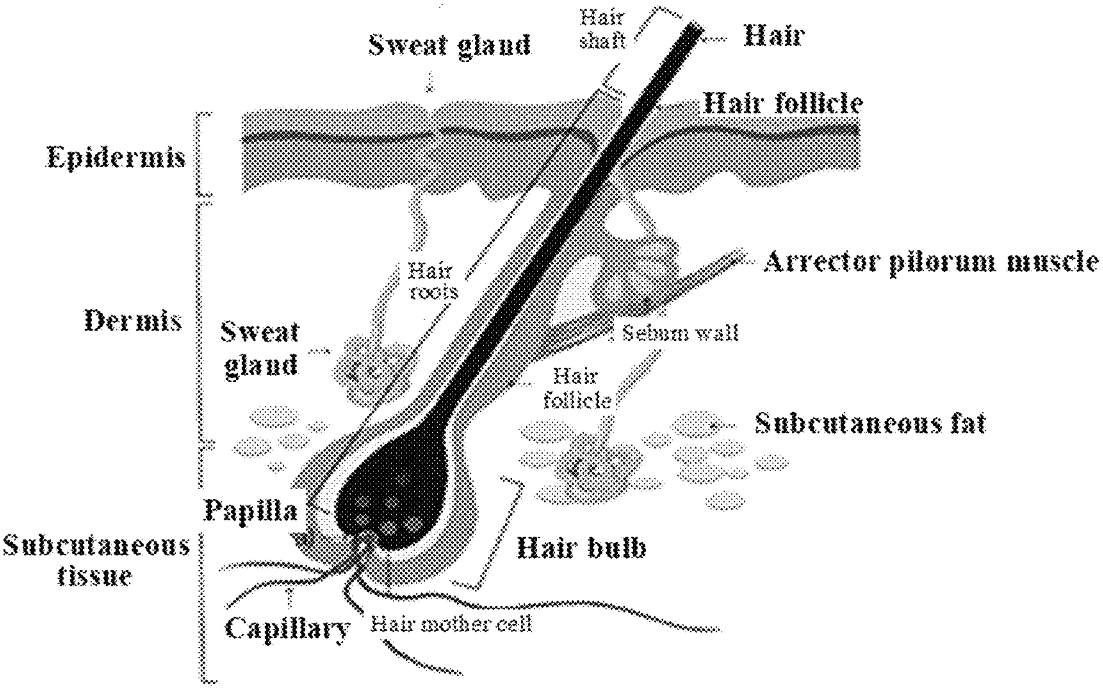
Hair shaft
Hair
Sweat gland
Hair follicle
Epidermis
Hair roots
Arrector pilorum muscle
Dermis
Sweat gland
Sebum wall
Hair follicle
Subcutaneous fat
Papilla
Subcutaneous tissue
Hair bulb
Capillary
Hair mother cell

HETEROCYCLE DERIVATIVE

CROSS-REFERENCE TO RELATED APPLICATIONS

This application is a U.S. national phase under the provisions of 35 U.S.C. § 371 of International Patent Application No. PCT/KR19/05261 filed May 2, 2019, which in turn claims priority under 35 U.S.C. § 119 of Korean Patent Application No. 10-2018-0050910 filed May 2, 2018. The disclosures of such international patent application and Korean priority patent application are hereby incorporated herein by reference in their respective entireties, for all purposes.

TECHNICAL FIELD

The present invention relates to a novel heterocycle derivative, a salt or isomer thereof, a composition for preventing or treating hair loss containing the same as an active ingredient, and a method for preventing or treating hair loss using the same, and more particularly, to a novel heterocycle derivative having excellent therapeutic and preventive effects on hair loss such as androgenic alopecia and alopecia areata, a salt or isomer thereof, a composition for preventing or treating hair loss containing the same as an active ingredient, and a method for preventing or treating hair loss using the same.

BACKGROUND ART

Hair follicles are skin organs for producing hair in the body, and surround the hair roots in the dermis under the epidermis and provide nutrients. Humans have an average of about 100,000 very small hair follicles which grow into about 100,000 hairs. Such a hair follicle has been considered to be produced as a single mini-organ only during embryonic growth, but studies on a number of modulators that regenerate lost hairs have been reported (Non-Patent Document 1).

Hairs in normal human are naturally lost at an average rate of 50 to 100 hairs every day. Each hair is created within the hair bulb in the hair follicle. As cells are divided within the hair follicles, older cells are pushed out and grow to form hairs. In general, hair undergoes repeated growth and loss through three essential stages in the growth cycle, namely anagen, catagen and telogen. About 88% of the hair is in the anagen, only about 1% is in the catagen, and the rest is in the telogen (Non-Patent Document 1).

Alopecia refers to a condition in which abnormal hair loss increases because the proportion of hair in anagen, among these three stages, is decreased, and the proportion of hair in catagen or telogen is increased. Also, both the size and density of hair follicles are greatly decreased. When hair loss progresses in this way, first, the hair on the crown or forehead becomes thinner and weaker and the number of hairs that fall out increases.

Hair loss is classified into androgenetic alopecia (AGA), which is characterized by scalp hair loss in men and women with age, alopecia areata (AA), which is usually microscopic inflammatory and recoverable, and is referred to as "local alopecia", and alopecia associated with chemotherapy or radiation therapy. About 70 to 80% of hair loss at present is due to genetic factors, but the remaining 20 to 30% is caused by various factors irrelevant to genetic factors, such as stress, changes in modern eating habits, drinking, smoking, cleaning chemical ingredients, pollution, fine dust and UV radiation. In addition, hair loss is caused by a variety of factors such as hair cycle abnormality and hair root weakening resulting from the action of male hormones, functional deterioration or inhibition of proliferation of dermal papilla cells and germinal matrix cells associated with hair cycle control, abnormal changes in the hair cycle due to decreased flow of blood to the scalp, aging, skin diseases, anticancer drugs, mental stress, physical stimulation, nutritional deficiencies, and pathological factors (diseases and drugs).

Among them, a typical cause of hair loss in androgenetic alopecia is testosterone, a male hormone, which is converted into dihydrotestosterone (DHT) by 5 alpha-reductase, acting on the hair follicles to weaken dermal papilla cells and germinal matrix cells, and shrink hair follicles and thereby lead to catagen. The major hair-related proteins, expression of which is improved by DHT, are TGF-b and DKK-1, which are known to interfere with hair growth, among which TGF-b is a telogen-inducing protein and DKK-1 inhibits the division of epithelial cells such as germinal matrix cells, to suppress hair growth and thereby lead to hair loss. In addition, many novel target proteins related to hair growth and new hair generation in dermal papilla cells have been identified through active research results (Patent Document 1, Non-Patent Document 4, and Non-Patent Document 5).

The effects of products commercially available as hair-growth-promoting or anti-hair-loss agents on the hair include the effect of inducing anagen, the effect of prolonging anagen, the effect of inhibiting 5$\alpha$-reductase (finasteride), the effect of promoting blood circulation (minoxidil), a bactericidal effect, an anti-dandruff effect, a moisturizing effect and an antioxidant effect, but these conventional formulations have insufficient effects of preventing hair loss and promoting hair growth. Hair growth and circulation are achieved by mutual signals between dermal papilla cells and germinal matrix cells. The signals of the dermal papilla cells enable the continuous division of germinal matrix cells, and the germinal matrix cells stimulate the dermal papilla cells to thereby thicken the hair. In particular, dermal papilla cells are present at the bottom of the hair follicles, supply oxygen and nutrients to the cells constituting hair follicles and hair roots, and play a key role in regulating hair growth and cycles of hair follicles.

Therefore, when the proliferation of dermal papilla cells is promoted, hair becomes healthy, hair growth can be promoted, and hair loss can be prevented. Hair growth proceeds as the epithelial cells surrounding the dermal papilla divide to form a hair shaft, so dermal papilla cells play a crucial role in regulating the division of epithelial cells. In addition, in male pattern hair loss, the site where the male hormone acts on the hair follicles is also the dermal papilla, so dermal papilla cells play a very important role in hair growth (FIG. 1).

Previous studies reported that hair follicles are activated by dermal papilla cells, and in particular, proliferation and differentiation of dermal papilla cells are primarily involved in the progression of the hair growth cycle and hair formation (Non-Patent Document 2). In addition, during anagen, in which hair grows, dermal papilla cells actively proliferate and differentiate, whereas, during catagen, telogen, and exogen in which hair growth stops and hair loss occurs, dermal papilla cells are killed (Non-Patent Document 3). Therefore, the proliferation and death of dermal papilla cells are closely related to hair growth and hair loss. Thus, prolonging catagen by inducing proliferation of dermal papilla cells or shortening telogen and exogen by inhibiting apoptosis is a potential approach to alleviating and treating hair loss.

Accordingly, the present inventors synthesized a novel heterocycle derivative and found that the heterocycle derivative induces proliferation of dermal papilla cells, thereby preventing hair loss and promoting hair growth and being remarkably effective in hair loss disorders such as androgenetic alopecia and alopecia areata. Based on this finding, the present invention was completed.

PRIOR ART DOCUMENTS

Patent Documents (Patent Document 1) Korean Patent Laid-open No. 10-2010-0121222 (2010. 11. 17).

(Patent Document 2) Korean Patent Laid-open No. 10-2015-0085962 (2015. 07. 27).

Non-Patent Documents (Non-patent Document 1) Martel J. L., Badri T., Anatomy, Head, Hair, Follicle. Book, StatPearls Publishing LLC, Jan. 10, 2018

(Non-patent Document 2) Botchkarev V. A., Kishimoto J., Molecular control of epithelial-mesenchymal interactions during hair follicle cycling. J Investig. Dermatol. Symp. Proc. 8, 46-55, 2003

(Non-patent Document 3) Botchkarev V. A., Batchkareva N. V., Nakamura M, Noggin is required for induction of the hair follicle growth phase in postnatal skin. FASEB J 15, 2205-2214, 2001

(Non-patent Document 4) Mingxing Lei, Li yang, Cheng-Ming Chuong, Getting to the Core of the Dermal Papilla. J. Invest. Dermatol. 137, 2250-2253, 2017

(Non-patent Document 5) Kwack M. H., Sung Y. K., Chung E. J., Im S. U., Ahn J. S., Kim M. K., Kim J. C. Dihydrotestosterone-inducible dickkopf 1 from balding dermal papilla cells causes apoptosis in follicular keratinocytes. J. Invest. Dermatol., 128, 262-269, 2008

DISCLOSURE

Therefore, the present invention has been made in view of the above problems, and it is one object of the present invention to provide a novel heterocycle derivative compound for promoting proliferation of dermal papilla cells that play a pivotal role in hair growth, and a salt or isomer thereof.

It is another object of the present invention to provide a composition for preventing or treating hair loss containing the novel cycle derivative compound, or a salt or isomer thereof as an active ingredient, and a cosmetic or therapeutic agent for alopecia containing the composition.

It is another object of the present invention to provide a method for preventing or treating hair loss, including administering the novel cyclic derivative compound, or a salt or isomer thereof to a subject in need of prevention or treatment.

In accordance with one aspect of the present invention, the above and other objects can be accomplished by the provision of a compound represented by the following Formula 1, or a salt or isomer thereof:

[Formula 1]

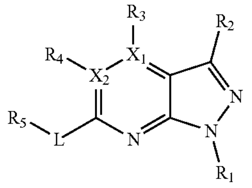

wherein $R_1$, $R_2$, $R_3$ and $R_4$ are each independently a hydrogen atom, alkyl, cycloalkyl, halogen, hydroxy, carboxyl, amino, cyano, alkylalkoxy phosphate, $—NR_6R_7$, $—CH_2NR_8R_9$, $—CONR_{10}R_{11}$, $—SO_2R_{12}$, $—CH_2SO_2R_{13}$, $—N{=}NR_{42}$ (wherein $R_6$ to $R_{13}$ and $R_{42}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl, heteroarylcarbonyl or hydroxy), allyl, aryl, aryl substituted with halogen or haloalkyl, alkylcarbonyl, cycloalkylcarbonyl, arylcarbonyl, alkylarylcarbonyl, alkoxycarbonyl, haloalkyl, cycloalkoxy, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl or the alkoxy is $C_1$-$C_6$, the cycloalkyl is $C_3$-$C_{10}$, the allyl is $C_2$-$C_{20}$, the aryl is $C_6$-$C_{20}$, and the heteroaryl and the heterocycloalkyl are monovalent radicals containing a heteroatom selected from fluorine, oxygen, sulfur and nitrogen;

$R_5$ is aryl, alkyl, alkylheteroaryl, alkylalkoxy or $—NR_{14}R_{15}$, (wherein $R_{14}$ and $R_{15}$ are independently a hydrogen atom, alkyl, cycloalkyl, aryl, alkoxy, alkylalkoxy, alkylcarbonyl, cycloalkylcarbonyl, arylcarbonyl alkoxycarbonyl, alkylalkoxycarbonyl or heteroarylcarbonyl), or a polycyclic functional group fused with 2 to 4 functional groups selected from the group consisting of aryl, heteroaryl, cycloalkyl and heterocycloalkyl, wherein the heteroaryl and the heterocycloalkyl contain 1 to 4 heteroatoms selected from N, O and S, and the aryl, the heteroaryl, the cycloalkyl and the heterocycloalkyl are unsubstituted, or are substituted with alkyl, haloalkyl, alkylester, $—NR_{16}R_{17}$ (wherein $R_{16}$ and $R_{17}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), cycloalkyl, heterocycloalkyl, halogen, aryl, alkoxy, alkylcarbonyl, cycloalkylcarbonyl, arylcarbonyl, alkoxycarbonyl, alkylalkoxycarbonyl or heteroarylcarbonyl, wherein the alkyl or the alkoxy is $C_1$-$C_6$, the cycloalkyl is $C_3$-$C_{10}$, the aryl is $C_6$-$C_2$a, and the heteroaryl and the heterocycloalkyl are monovalent radicals containing a heteroatom selected from fluorine, oxygen, sulfur and nitrogen;

$X_1$ and $X_2$ are each independently nitrogen (N) or carbon (C), with the proviso that at least one carbon (C) is included;

$\overline{---}$ is a single bond or a double bond; and

L is a single bond, $—CH_2—$, $—NH—$, $—CH_2NH—$, $—O—$, $—S—$, or $—NR_{18}$ (wherein $R_{18}$ is independently a hydrogen atom, alkyl, cycloalkyl, aryl, alkoxy, alkylalkoxy, alkyl carbonyl, cycloalkylcarbonyl, arylcarbonyl, alkoxycarbonyl, alkylalkoxycarbonyl or heteroarylcarbonyl), straight- or branched-chain alkylene, cycloalkylene, haloalkylene, arylene, heteroalkylene, heteroarylene, arylenealkylene, alkylenearylene, alkyleneheteroarylene, heteroarylenealkylene, alkylene ester or alkylene amide, wherein the alkylene is $C_1$-$C_6$, the cycloalkylene is $C_3$-$C_{10}$, the arylene is $C_6$-$C_{20}$, and the heteroalkylene or heteroarylene is a divalent radical containing a heteroatom selected from fluorine, oxygen, sulfur and nitrogen.

In accordance with another aspect of the present invention, provided are a composition for preventing or treating hair loss containing the novel cycle derivative compound, or a salt or isomer thereof as an active ingredient, and a cosmetic or therapeutic agent for alopecia containing the composition.

In accordance with another aspect of the present invention, provided is a method for preventing or treating hair loss, including administering the composition for preventing or treating hair loss containing the novel cyclic derivative compound or a salt or isomer thereof to a subject in need of prevention or treatment.

In accordance with another aspect of the present invention, provided is the use of the composition for preventing or treating hair loss containing the novel cyclic derivative compound or a salt or isomer thereof for the prevention or treatment of hair loss.

DESCRIPTION OF DRAWINGS

FIG. 1 is a schematic diagram illustrating the structure of hair.

BEST MODE

Unless defined otherwise, all technical and scientific terms used herein have the same meanings as appreciated by those skilled in the field to which the present invention pertains. In general, the nomenclature used herein is well-known in the art and is ordinarily used.

Accordingly, the present inventors synthesized a novel heterocycle derivative and found that the heterocycle derivative induces proliferation of dermal papilla cells, thereby preventing hair loss and promoting hair growth and being remarkably effective in hair loss such as androgenetic alopecia and alopecia areata.

In one aspect, the present invention is directed to a compound represented by Formula 1.

In another aspect, the present invention is directed to a compound represented by Formula 1, or a salt or isomer thereof.

Hereinafter, the present invention will be described in more detail.

[Formula 1]

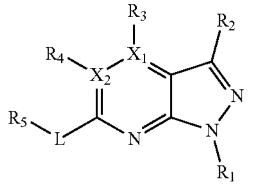

wherein $R_1$, $R_2$, $R_3$ and $R_4$ are each independently a hydrogen atom, alkyl, cycloalkyl, halogen, hydroxy, carboxyl, amino, cyano, alkylalkoxy phosphate, —$NR_6R_7$, —$CH_2NR_8R_9$, —$CONR_{10}R_{11}$, —$SO_2R_{12}$, —$CH_2SO_2R_{13}$, —N═$NR_{42}$ (in which $R_6$ to $R_{13}$ and $R_{42}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkyl alkoxycarbonyl, heteroarylcarbonyl or hydroxy), allyl, aryl, aryl substituted with halogen or haloalkyl, alkylcarbonyl, cycloalkylcarbonyl, arylcarbonyl, alkylarylcarbonyl, alkoxycarbonyl, haloalkyl, cycloalkoxy, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl or the alkoxy is $C_1$-$C_6$, the cycloalkyl is $C_3$-$C_{10}$, the allyl is $C_2$-$C_{20}$, the aryl is $C_6$-$C_{20}$, and the heteroaryl and heterocycloalkyl are monovalent radicals containing a heteroatom selected from fluorine, oxygen, sulfur and nitrogen;

$R_5$ is aryl, alkyl, alkylheteroaryl, alkylalkoxy or —$NR_{14}R_{15}$, (wherein $R_{14}$ and $R_{15}$ are independently a hydrogen atom, alkyl, cycloalkyl, aryl, alkoxy, alkylalkoxy, alkylcarbonyl, cycloalkylcarbonyl, arylcarbonyl alkoxycarbonyl, alkylalkoxycarbonyl or heteroarylcarbonyl), or a polycyclic functional group fused with 2 to 4 functional groups selected from the group consisting of aryl, heteroaryl, cycloalkyl and heterocycloalkyl, wherein the heteroaryl and heterocycloalkyl contain 1 to 4 heteroatoms selected from N, O, and S, and the aryl, the heteroaryl, the cycloalkyl and the heterocycloalkyl are unsubstituted, or are substituted with alkyl, haloalkyl, alkylester, —$NR_{16}R_{17}$ (wherein $R_{16}$ and $R_{17}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), cycloalkyl, heterocycloalkyl, halogen, aryl, alkoxy, alkylcarbonyl, cycloalkylcarbonyl, arylcarbonyl, alkoxycarbonyl, alkylalkoxycarbonyl or heteroarylcarbonyl, wherein the alkyl or the alkoxy is $C_1$-$C_6$, the cycloalkyl is $C_3$-$C_{10}$, the aryl is $C_6$-$C_{20}$, and the heteroaryl and heterocycloalkyl are monovalent radicals containing a heteroatom selected from fluorine, oxygen, sulfur and nitrogen;

$X_1$ and $X_2$ are each independently nitrogen (N) or carbon (C), with the proviso that at least one carbon (C) is included;

$\overset{---}{---}$ is a single bond or a double bond; and

L is a single bond, —$CH_2$—, —NH—, —$CH_2NH$—, —O—, —S—, or —$NR_{18}$ (wherein $R_{18}$ is independently a hydrogen atom, alkyl, cycloalkyl, aryl, alkoxy, alkylalkoxy, alkyl carbonyl, cycloalkylcarbonyl, arylcarbonyl, alkoxycarbonyl, alkylalkoxycarbonyl or heteroarylcarbonyl), straight- or branched-chain alkylene, cycloalkylene, haloalkylene, arylene, heteroalkylene, heteroarylene, arylenealkylene, alkylenearylene, alkyleneheteroarylene, heteroarylenealkylene, alkylene ester or alkylene amide, wherein the alkylene is $C_1$-$C_6$, the cycloalkylene is $C_3$-$C_{10}$, the arylene is $C_6$-$C_{20}$, and the heteroalkylene or heteroarylene is a divalent radical containing a heteroatom selected from fluorine, oxygen, sulfur and nitrogen.

In the present invention, $R_1$ is a hydrogen atom, alkyl, cycloalkyl, —$NR_6R_7$, —$CONR_{10}R_{11}$, —$CH_2SO_2R_{13}$ (wherein $R_6$, $R_7$, $R_{10}$, $R_{11}$ and $R_{13}$ are independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), alkylcarbonyl, alkylarylcarbonyl, alkylaryl or heterocycloalkyl, wherein the alkyl is $C_1$-$C_6$, the cycloalkyl is $C_3$-$C_{10}$, the aryl is $C_6$-$C_{20}$, and the heterocycloalkyl is a monovalent radical containing a heteroatom selected from fluorine, oxygen, sulfur and nitrogen, $R_2$ is each independently hydroxy, cyano, halogen, —$NR_{6'}R_{7'}$, —$CH_2NR_{8'}R_{9'}$, —$CONR_{10}R_{11'}$, —$SO_2R_{12'}$, —$CH_2SO_2R_{13'}$, —N═$NR_{42}$ (wherein $R_{6'}$ to $R_{13'}$ and $R_{42}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl, heteroarylcarbonyl or hydroxy) or heteroaryl, wherein the alkyl or alkoxy is $C_1$-$C_6$, the cycloalkyl is $C_3$-$C_{10}$, the aryl is $C_6$-$C_{20}$, and the heteroaryl and heterocycloalkyl are monovalent radicals containing a heteroatom selected from fluorine, oxygen, sulfur and nitrogen, $R_3$ is a hydrogen atom, alkyl, cycloalkyl, halogen, haloalkyl, or cyclohaloalkyl, wherein the alkyl is $C_1$-$C_6$ and the cycloalkyl is $C_3$-$C_6$, and $R_4$ is a hydrogen atom, alkyl, cycloalkyl, haloalkyl, cyclohaloalkyl, halogen, carboxyl, aryl, alkoxycarbonyl, or haloalkoxycarbonyl, wherein the alkyl or the alkoxy is preferably $C_1$-$C_6$, the cycloalkyl is preferably $C_3$-$C_6$ and the aryl is preferably $C_6$-$C_{20}$.

In addition, in the present invention, more preferably, $R_5$ is aryl or a polycyclic functional group fused with 2 to 4 functional groups selected from the group consisting of aryl, heteroaryl, cycloalkyl and heterocycloalkyl, wherein the heteroaryl and heterocycloalkyl contain 1 to 4 heteroatoms selected from N, O, and S, and the aryl, heteroaryl, cycloalkyl and heterocycloalkyl are unsubstituted, or are substituted with alkyl, halogen, alkoxy, alkyl ester, —$NR_{19}R_{20}$ (wherein $R_{19}$ and $R_{20}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl) or haloalkyl.

In addition, in the present invention, more preferably, $R_5$ is aryl or a polycyclic functional group fused with 2 to 4 functional groups selected from the group consisting of aryl, heteroaryl, cycloalkyl and heterocycloalkyl, wherein the heteroaryl and heterocycloalkyl contain 1 to 4 heteroatoms selected from N, O, and S, and the aryl, heteroaryl, cycloalkyl and heterocycloalkyl are unsubstituted, or are substituted with alkyl, halogen, alkoxy, alkyl ester, —$NR_{19}R_{20}$ (wherein $R_{19}$ and $R_{20}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl) or haloalkyl.

In the present invention, $R_5$ is preferably a monovalent radical selected from the group consisting of the following Formula 2, Formula 3 and Formula 4:

[Formula 2]

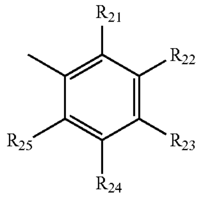

wherein $R_{21}$ to $R_{25}$ are each independently a hydrogen atom, hydroxy, amine, alkyl, —$NR_{40}R_{41}$ (wherein $R_{40}$ and $R_{41}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), heteroaryl, cyano, alkoxy, ester, halogen or haloalkyl, wherein the alkyl or the alkoxy is $C_1$-$C_6$, the cycloalkyl is $C_3$-$C_{10}$, the allyl is $C_2$-$C_{20}$, the aryl is $C_6$-$C_{20}$, and the heteroaryl is a monovalent radical containing a heteroatom selected from fluorine, oxygen, sulfur and nitrogen;

[Formula 3]

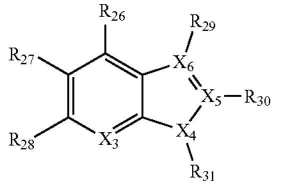

wherein $X_3$, $X_4$, $X_5$ and $X_6$ are each independently nitrogen (N), oxygen (O) or carbon (C), with the proviso that, when $X_4$, $X_5$ and $X_6$ are each oxygen, $R_{29}$, $R_{30}$ and $R_{31}$ respectively do not exist, the bond ⚌ between $X_5$ and $X_6$ and the bond ⚌ between $R_{26}$ and $R_{28}$ are each a single bond or a double bond, and $R_{26}$ to $R_{31}$ are each independently a hydrogen atom, $C_1$-$C_6$ alkyl, alkoxy, oxygen or halogen, with the proviso that any one of $R_{26}$ to $R_{31}$ does not exist and a corresponding site is connected to a linker; and

[Formula 4]

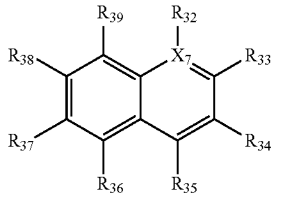

wherein $X_7$ is nitrogen (N) or carbon (C), with the proviso that, when $X_7$ is nitrogen, $R_{32}$ does not exist, $R_{32}$ to $R_{39}$ are each independently a hydrogen atom or $C_1$-$C_6$ alkyl, and the bond ⚌ between $R_{36}$, $R_{37}$, $R_{38}$ and $R_{39}$ is a single bond or a double bond, with the proviso that any one of $R_{32}$ to $R_{39}$ does not exist and a corresponding site is connected to a linker.

In Formulae 3 and 4 of the present invention, bonding to a linker (L) is possible at any position, regardless of the type of substituent to be bonded.

In the present invention, the compound of Formula 1 is preferably selected from the group consisting of pyrazole[3,4-b]pyridine of the following Formula 1-1, pyrazole[3,4-b]pyrazine of the following Formula 1-2, and pyrazole[3,5-d]pyrimidine of the following Formula 1-3:

[Formula 1-1]

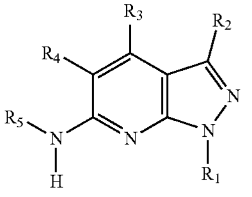

-continued

[Formula 1-2]

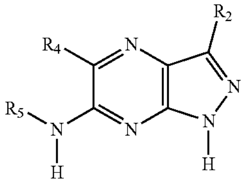

[Formula 1-3]

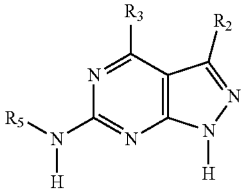

wherein $R_1$, $R_2$, $R_3$ and $R_4$ are each independently a hydrogen atom, alkyl, cycloalkyl, halogen, hydroxy, carboxyl, amino, cyano, —$NR_6R_7$, —$CH_2NR_8R_9$, —$CONR_{10}R_{11}$, —$SO_2R_{12}$, —$CH_2SO_2R_{13}$, —N═$NR_{42}$ (wherein $R_6$ to $R_{13}$ and $R_{42}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl, heteroarylcarbonyl, or hydroxy), allyl, aryl, aryl substituted with halogen or haloalkyl, alkylcarbonyl, cycloalkylcarbonyl, arylcarbonyl, alkylarylcarbonyl, alkoxycarbonyl, haloalkyl, alkoxy, cycloalkoxy, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl is $C_1$-$C_6$, the cycloalkyl is $C_3$-$C_{10}$, the allyl is $C_2$-$C_{20}$, the aryl is $C_6$-$C_{20}$, and the heteroaryl and heterocycloalkyl are monovalent radicals containing a heteroatom selected from fluorine, oxygen, sulfur and nitrogen; and $R_5$ is aryl, or a polycyclic functional group fused with 2 to 4 functional groups selected from the group consisting of aryl, heteroaryl, cycloalkyl and heterocycloalkyl, wherein the heteroaryl and heterocycloalkyl contain 1 to 4 heteroatoms selected from N, O, and S, wherein the aryl, heteroaryl, cycloalkyl and heterocycloalkyl are unsubstituted or substituted with alkyl, haloalkyl, alkylester, —$NR_{14}R_{15}$ (wherein $R_{14}$ and $R_{15}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), cycloalkyl, heterocycloalkyl, halogen, aryl, alkoxy, alkylcarbonyl, cycloalkylcarbonyl, arylcarbonyl, alkoxycarbonyl, alkylalkoxycarbonyl or heteroarylcarbonyl.

$R_5$ is preferably a monovalent radical selected from the group consisting of the following Formula 2, Formula 3 and Formula 4:

[Formula 2]

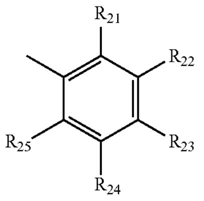

wherein $R_{21}$ to $R_{25}$ are each independently a hydrogen atom, hydroxy, amine, alkyl, —$NR_{40}R_{41}$ (wherein $R_{40}$ and $R_{41}$ are each independently a hydrogen atom, alkyl, cycloalkyl, aryl, alkoxy, alkylalkoxy, alkylcarbonyl, cycloalkylcarbonyl, arylcarbonyl, alkoxycarbonyl, alkylalkoxycarbonyl or heteroarylcarbonyl), heteroaryl, cyano, alkoxy, ester, halogen or haloalkyl, wherein the alkyl or the alkoxy is $C_1$-$C_6$, the cycloalkyl is $C_3$-$C_{10}$, the allyl is $C_2$-$C_{20}$, the aryl is $C_6$-$C_{20}$, and the heteroaryl is a monovalent radical containing a heteroatom selected from fluorine, oxygen, sulfur and nitrogen;

[Formula 3]

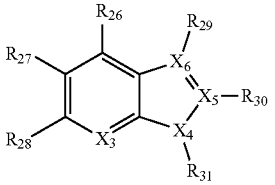

wherein $X_3$, $X_4$, $X_5$ and $X_6$ are each independently nitrogen (N) or carbon (C), the bond $\overset{\cdots}{=}$ between $X_5$ and $X_6$ and the bond $\overset{\cdots}{=}$ between $R_{26}$, $R_{27}$ and $R_{28}$ are each a single bond or a double bond, and $R_{26}$ to $R_{31}$ are each independently a hydrogen atom, $C_1$-$C_6$ alkyl, alkoxy, oxygen or halogen, with the proviso that any one of $R_{26}$ to $R_{31}$ does not exist and a corresponding site is connected to a linker; and

[Formula 4]

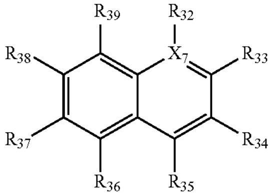

wherein $X_7$ is nitrogen (N) or carbon (C), with the proviso that, when $X_7$ is nitrogen, $R_{32}$ does not exist, and $R_{32}$ to $R_{39}$ are each independently a hydrogen atom or $C_1$-$C_6$ alkyl, with the proviso that any one of $R_{32}$ to $R_{39}$ does not exist and a corresponding site is connected to a linker.

In the present invention, a preferred novel heterocycle derivative may be selected from the following compounds, but is not limited thereto.

| Compound No. | Structure |
|---|---|
| 1 | 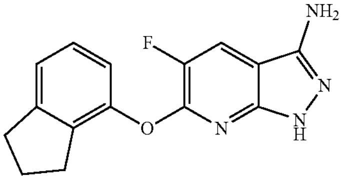 [SMILES: Nc1n[nH]c2nc(Oc3cccc4c3CCC4)c(F)cc12] |

-continued
| Compound No. | Structure |
|---|---|
| 2 | 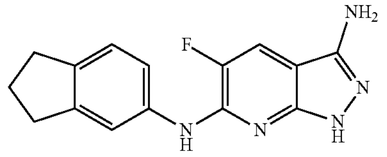 [SMILES: Nc1n[nH]c2nc(Nc3ccc4c(c3)CCC4)c(F)cc12] |
| 3 | 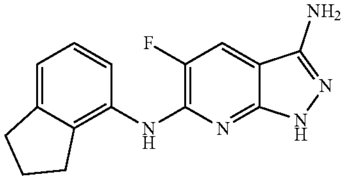 [SMILES: Nc1n[nH]c2nc(Nc3cccc4c3CCC4)c(F)cc12] |
| 4 | 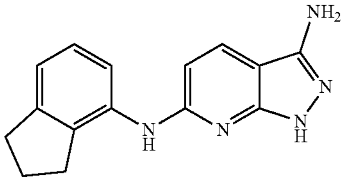 [SMILES: Nc1n[nH]c2nc(Nc3cccc4c3CCC4)ccc12] |
| 5 | 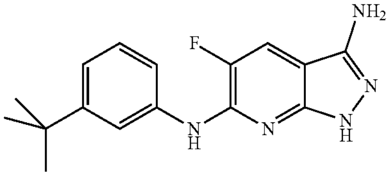 [SMILES: CC(C)(C)c1cccc(Nc2nc3[nH]nc(N)c3cc2F)c1] |
| 6 | 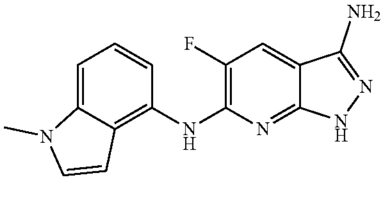 [SMILES: Cn1ccc2c(Nc3nc4[nH]nc(N)c4cc3F)cccc21] |
| 7 | 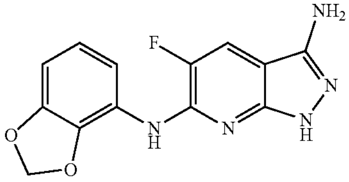 [SMILES: Nc1n[nH]c2nc(Nc3cccc4c3OCO4)c(F)cc12] |
| 8 | 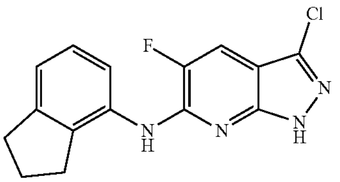 |
| 9 | 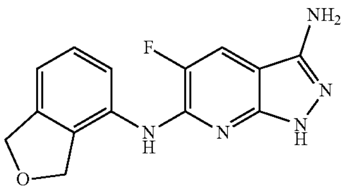 [SMILES: Nc1n[nH]c2nc(Nc3cccc4c3COC4)c(F)cc12] |
-continued
| Compound No. | Structure |
|---|---|
| 10 | 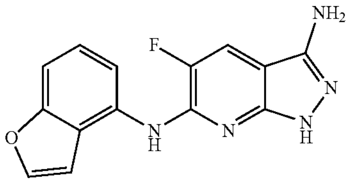 [SMILES: Nc1n[nH]c2nc(Nc3cccc4occc34)c(F)cc12] |
| 11 | 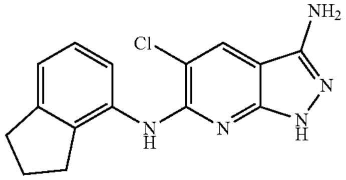 [SMILES: Nc1n[nH]c2nc(Nc3cccc4c3CCC4)c(Cl)cc12] |
| 12 | 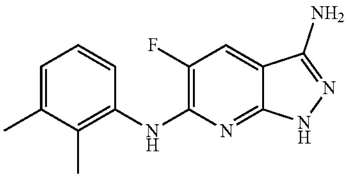 [SMILES: Cc1cccc(Nc2nc3[nH]nc(N)c3cc2F)c1C] |
| 13 | 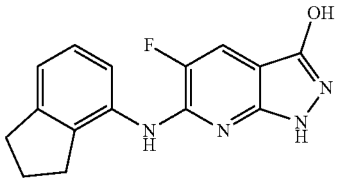 |
| 14 | 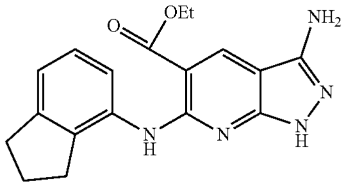 [SMILES: CCOC(=O)c1cc2c(N)n[nH]c2nc1Nc1cccc2c1CCC2] |
| 15 | 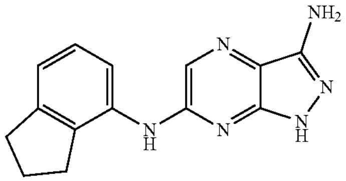 [SMILES: Nc1n[nH]c2nc(Nc3cccc4c3CCC4)cnc12] |
| 16 | 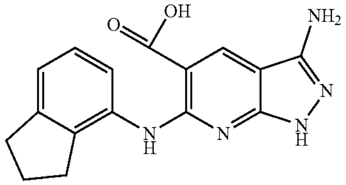 [SMILES: Nc1n[nH]c2nc(Nc3cccc4c3CCC4)c(C(=O)O)cc12] |
| 17 | 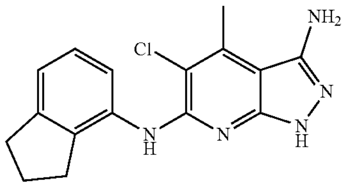 |

-continued
| Compound No. | Structure |
|---|---|
| 18 | 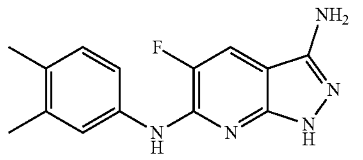 [SMILES: Cc1ccc(Nc2nc3[nH]nc(N)c3cc2F)cc1C] |
| 19 | 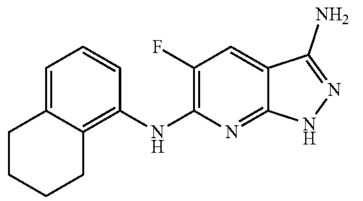 [SMILES: Nc1n[nH]c2nc(Nc3cccc4c3CCCC4)c(F)cc12] |
| 20 | 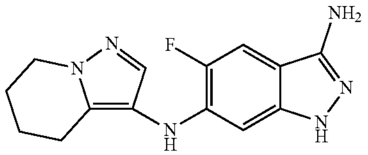 [SMILES: Nc1n[nH]c2cc(Nc3cnn4c3CCCC4)c(F)cc12] |
| 21 | 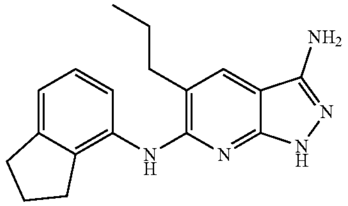 [SMILES: CCCc1cc2c(N)n[nH]c2nc1Nc1cccc2c1CCC2] |
| 22 | 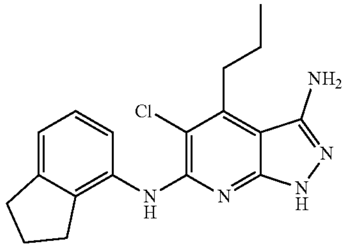 [SMILES: CCCc1c(Cl)c(Nc2cccc3c2CCC3)nc2[nH]nc(N)c12] |
| 23 | 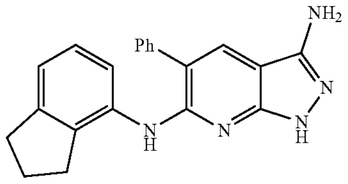 |
| 24 | 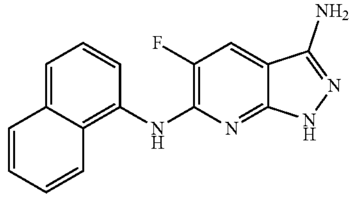 [SMILES: Nc1n[nH]c2nc(Nc3cccc4ccccc34)c(F)cc12] |
| Compound No. | Structure |
|---|---|
| 25 | 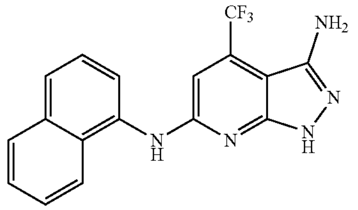 [SMILES: Nc1n[nH]c2nc(Nc3cccc4ccccc34)cc(C(F)(F)F)c12] |
| 26 | 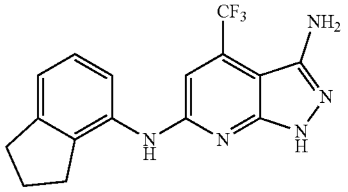 [SMILES: Nc1n[nH]c2nc(Nc3cccc4c3CCC4)cc(C(F)(F)F)c12] |
| 27 | 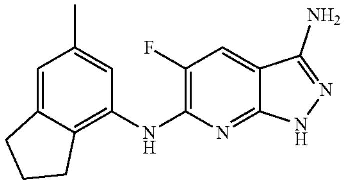 [SMILES: Cc1cc2c(c(Nc3nc4[nH]nc(N)c4cc3F)c1)CCC2] |
| 28 | 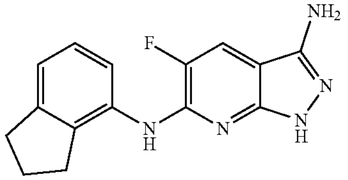 [SMILES: Nc1n[nH]c2nc(Nc3cccc4c3CCC4)c(F)cc12] |
| 29 | 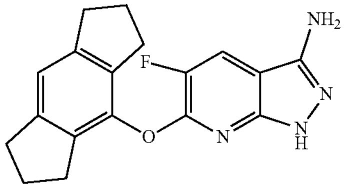 [SMILES: Nc1n[nH]c2nc(Oc3c4c(cc5c3CCC5)CCC4)c(F)cc12] |
| 30 | 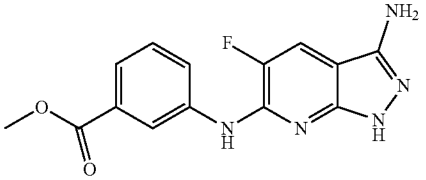 [SMILES: COC(=O)c1cccc(Nc2nc3[nH]nc(N)c3cc2F)c1] |
| 31 | 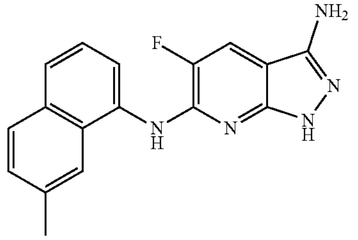 [SMILES: Cc1ccc2cccc(Nc3nc4[nH]nc(N)c4cc3F)c2c1] |

-continued
| Compound No. | Structure |
|---|---|
| 32 | 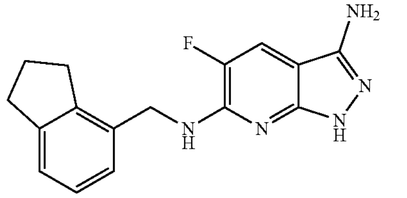 [SMILES: Nc1n[nH]c2nc(NCc3cccc4c3CCC4)c(F)cc12] |
| 33 | 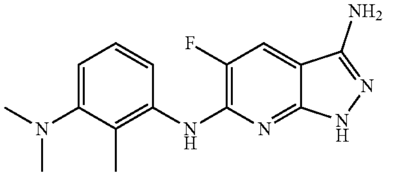 [SMILES: Cc1c(Nc2nc3[nH]nc(N)c3cc2F)cccc1N(C)C] |
| 34 | 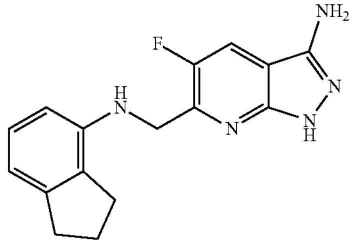 [SMILES: Nc1n[nH]c2nc(CNc3cccc4c3CCC4)c(F)cc12] |
| 35 | 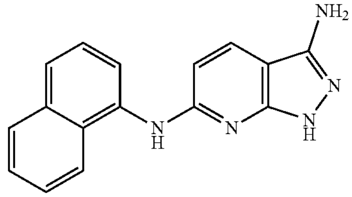 [SMILES: Nc1n[nH]c2nc(Nc3cccc4ccccc34)ccc12] |
| 36 | 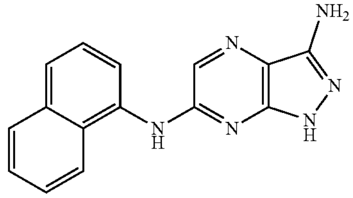 [SMILES: Nc1n[nH]c2nc(Nc3cccc4ccccc34)cnc12] |
| 37 | 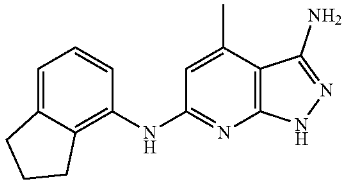 [SMILES: Cc1cc(Nc2cccc3c2CCC3)nc2[nH]nc(N)c12] |
| 38 | 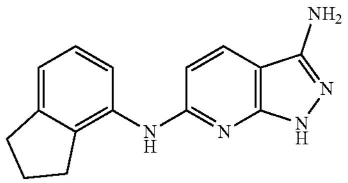 [SMILES: Nc1n[nH]c2nc(Nc3cccc4c3CCC4)ccc12] |
-continued
| Compound No. | Structure |
|---|---|
| 39 | 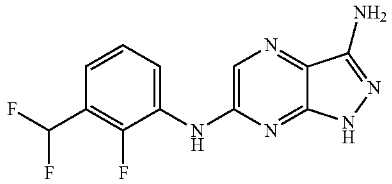 [SMILES: Nc1n[nH]c2nc(Nc3cccc(C(F)F)c3F)cnc12] |
| 40 | 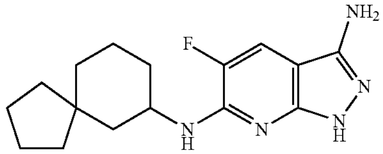 [SMILES: Nc1n[nH]c2nc(NC3CCCC4(CCCC4)C3)c(F)cc12] |
| 41 | 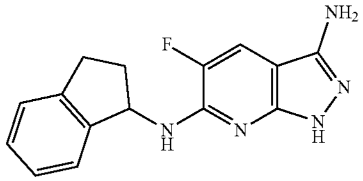 [SMILES: Nc1n[nH]c2nc(NC3CCc4ccccc43)c(F)cc12] |
| 42 | 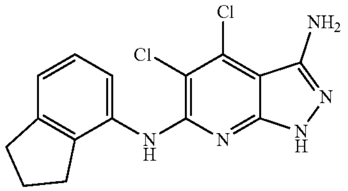 [SMILES: Nc1n[nH]c2nc(Nc3cccc4c3CCC4)c(Cl)c(Cl)c12] |
| 43 | 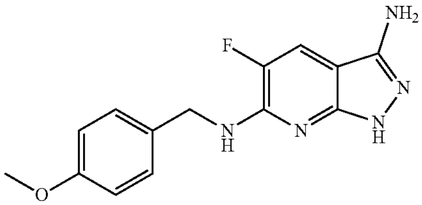 [SMILES: COc1ccc(CNc2nc3[nH]nc(N)c3cc2F)cc1] |
| 44 | 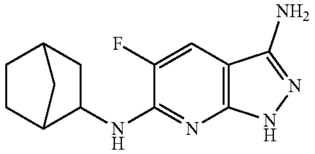 [SMILES: Nc1n[nH]c2nc(NC3CC4CCC3C4)c(F)cc12] |
| 45 | 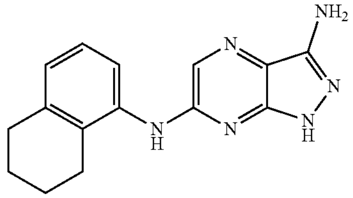 [SMILES: Nc1n[nH]c2nc(Nc3cccc4c3CCCC4)cnc12] |
| 46 | 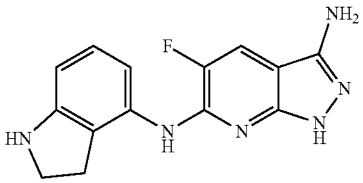 [SMILES: Nc1n[nH]c2nc(Nc3cccc4c3CCN4)c(F)cc12] |

-continued
| Compound No. | Structure |
|---|---|
| 47 | 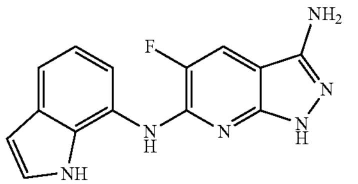 [SMILES: Nc1n[nH]c2nc(Nc3cccc4cc[nH]c34)c(F)cc12] |
| 48 | 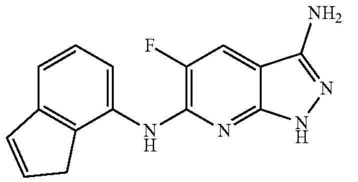 [SMILES: Nc1n[nH]c2nc(Nc3cccc4c3CC=C4)c(F)cc12] |
| 49 | 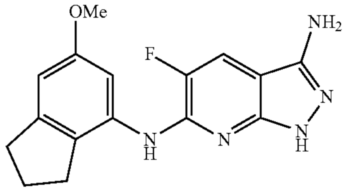 [SMILES: COc1cc2c(c(Nc3nc4[nH]nc(N)c4cc3F)c1)CCC2] |
| 50 | 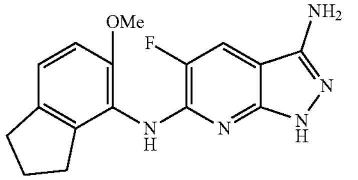 [SMILES: COc1ccc2c(c1Nc1nc3[nH]nc(N)c3cc1F)CCC2] |
| 51 | 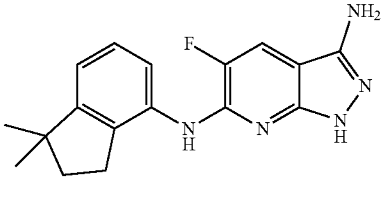 [SMILES: CC1(C)CCc2c(Nc3nc4[nH]nc(N)c4cc3F)cccc21] |
| 52 | 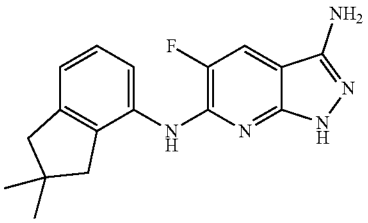 [SMILES: CC1(C)Cc2cccc(Nc3nc4[nH]nc(N)c4cc3F)c2C1] |
| 53 | 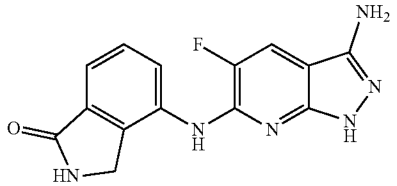 [SMILES: Nc1n[nH]c2nc(Nc3cccc4c3CNC4=O)c(F)cc12] |
-continued
| Compound No. | Structure |
|---|---|
| 54 | 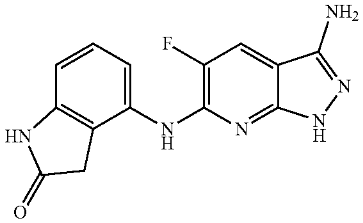 [SMILES: Nc1n[nH]c2nc(Nc3cccc4c3CC(=O)N4)c(F)cc12] |
| 55 | 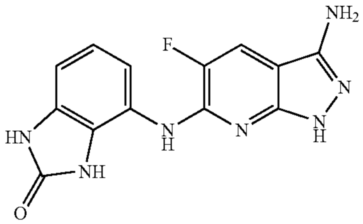 [SMILES: Nc1n[nH]c2nc(Nc3cccc4[nH]c(=O)[nH]c34)c(F)cc12] |
| 56 | 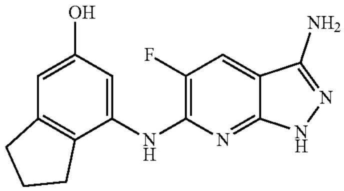 [SMILES: Nc1n[nH]c2nc(Nc3cc(O)cc4c3CCC4)c(F)cc12] |
| 57 | 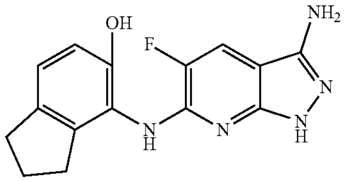 [SMILES: Nc1n[nH]c2nc(Nc3c(O)ccc4c3CCC4)c(F)cc12] |
| 58 | 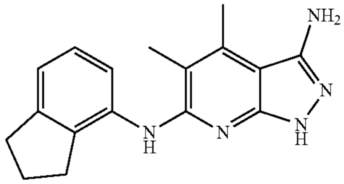 [SMILES: Cc1c(Nc2cccc3c2CCC3)nc2[nH]nc(N)c2c1C] |
| 59 | 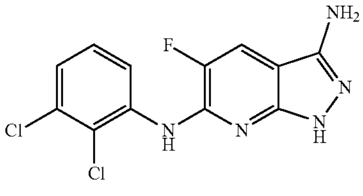 [SMILES: Nc1n[nH]c2nc(Nc3cccc(Cl)c3Cl)c(F)cc12] |
| 60 | 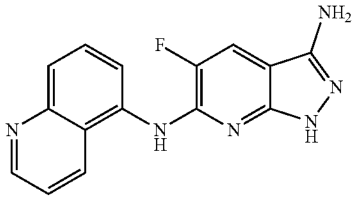 [SMILES: Nc1n[nH]c2nc(Nc3cccc4ncccc34)c(F)cc12] |

-continued
| Compound No. | Structure |
|---|---|
| 61 | 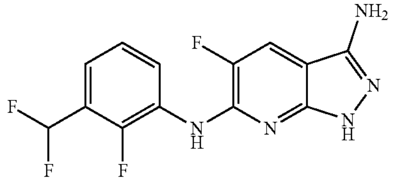 [SMILES: Nc1n[nH]c2nc(Nc3cccc(C(F)F)c3F)c(F)cc12] |
| 62 | 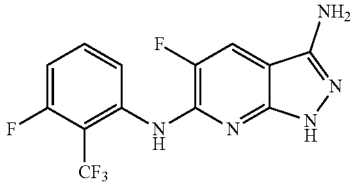 |
| 63 | 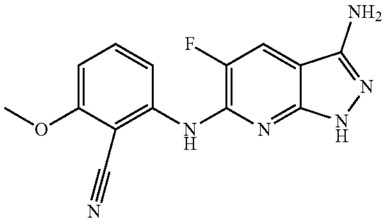 [SMILES: COc1cccc(Nc2nc3[nH]nc(N)c3cc2F)c1C#N] |
| 64 | 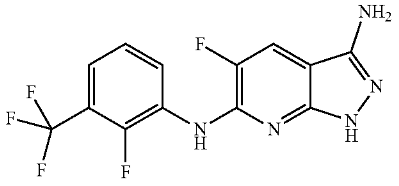 [SMILES: Nc1n[nH]c2nc(Nc3cccc(C(F)(F)F)c3F)c(F)cc12] |
| 65 | 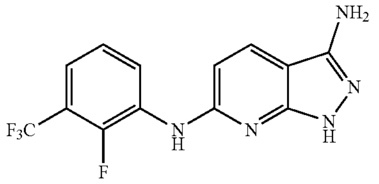 [SMILES: Nc1n[nH]c2nc(Nc3cccc(C(F)(F)F)c3F)ccc12] |
| 66 | 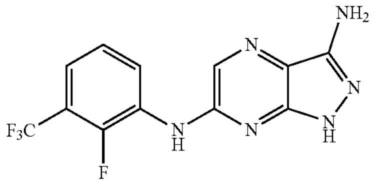 [SMILES: Nc1n[nH]c2nc(Nc3cccc(C(F)(F)F)c3F)cnc12] |
| Compound No. | Structure |
|---|---|
| 67 | 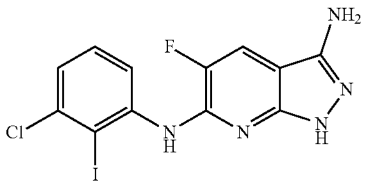 [SMILES: Nc1n[nH]c2nc(Nc3cccc(Cl)c3I)c(F)cc12] |
-continued
| Compound No. | Structure |
|---|---|
| 68 | 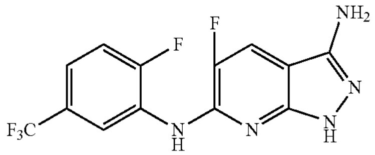 [SMILES: Nc1n[nH]c2nc(Nc3cc(C(F)(F)F)ccc3F)c(F)cc12] |
| 69 | 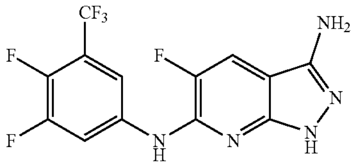 [SMILES: Nc1n[nH]c2nc(Nc3cc(F)c(F)c(C(F)(F)F)c3)c(F)cc12] |
| 70 | 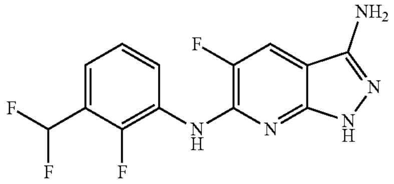 [SMILES: Nc1n[nH]c2nc(Nc3cccc(C(F)F)c3F)c(F)cc12] |
| 71 | 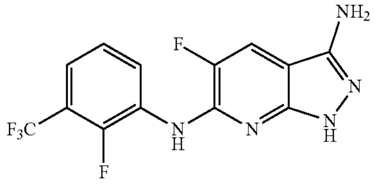 [SMILES: Nc1n[nH]c2nc(Nc3cccc(C(F)(F)F)c3F)c(F)cc12] |
| 72 | 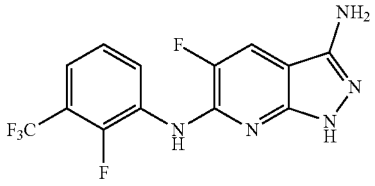 [SMILES: Nc1n[nH]c2nc(Nc3cccc(C(F)(F)F)c3F)c(F)cc12] |
| 73 | 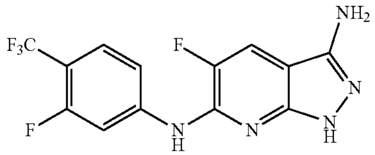 [SMILES: Nc1n[nH]c2nc(Nc3ccc(C(F)(F)F)c(F)c3)c(F)cc12] |
| 74 | 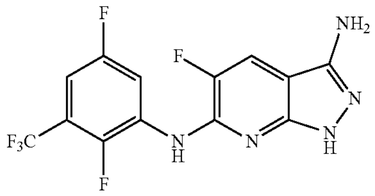 [SMILES: Nc1n[nH]c2nc(Nc3cc(F)cc(C(F)(F)F)c3F)c(F)cc12] |
| 75 | 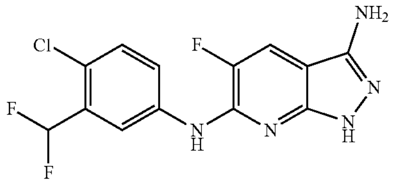 [SMILES: Nc1n[nH]c2nc(Nc3ccc(Cl)c(C(F)F)c3)c(F)cc12] |

-continued
| Compound No. | Structure |
|---|---|
| 76 | 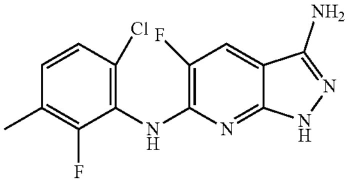 [SMILES: Cc1ccc(Cl)c(Nc2nc3[nH]nc(N)c3cc2F)c1F] |
| 77 | 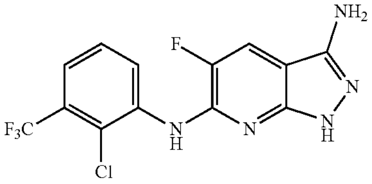 [SMILES: Nc1n[nH]c2nc(Nc3cccc(C(F)(F)F)c3Cl)c(F)cc12] |
| 78 | 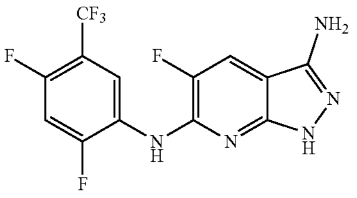 |
| 79 | 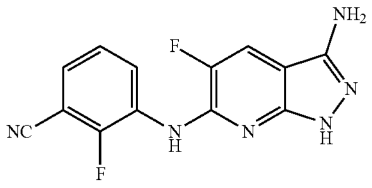 [SMILES: N#Cc1cccc(Nc2nc3[nH]nc(N)c3cc2F)c1F] |
| 80 | 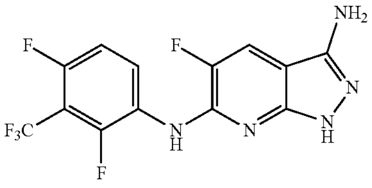 [SMILES: Nc1n[nH]c2nc(Nc3ccc(F)c(C(F)(F)F)c3F)c(F)cc12] |
| 81 | 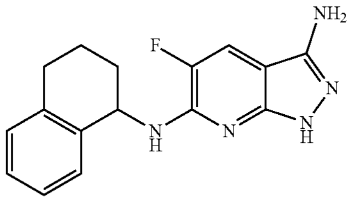 [SMILES: Nc1n[nH]c2nc(NC3CCCc4ccccc43)c(F)cc12] |
| 82 | 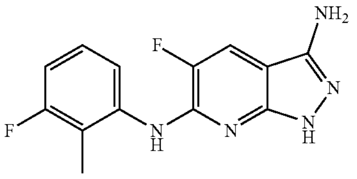 |
| 83 | 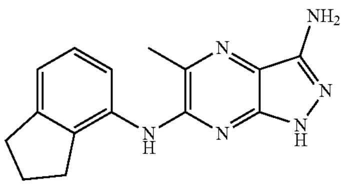 [SMILES: Cc1nc2c(N)n[nH]c2nc1Nc1cccc2c1CCC2] |
-continued
| Compound No. | Structure |
|---|---|
| 84 | 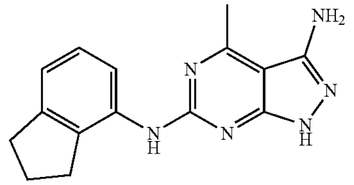 [SMILES: Cc1nc(Nc2cccc3c2CCC3)nc2[nH]nc(N)c12] |
| 85 | 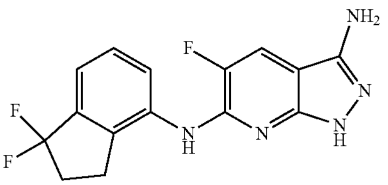 [SMILES: Nc1n[nH]c2nc(Nc3cccc4c3CCC4(F)F)c(F)cc12] |
| 86 | 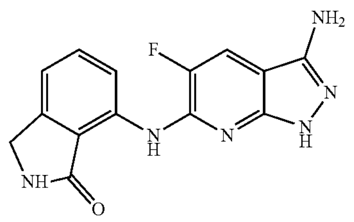 [SMILES: Nc1n[nH]c2nc(Nc3cccc4c3C(=O)NC4)c(F)cc12] |
| 87 | 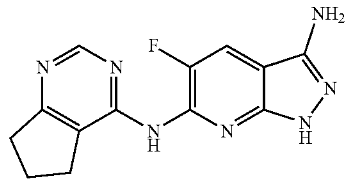 [SMILES: Nc1n[nH]c2nc(Nc3ncnc4c3CCC4)c(F)cc12] |
| 88 | 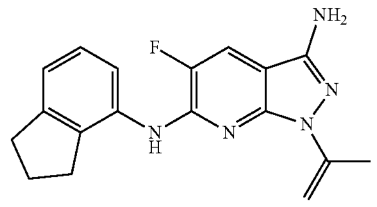 [SMILES: C=C(C)n1nc(N)c2cc(F)c(Nc3cccc4c3CCC4)nc21] |
| 89 | 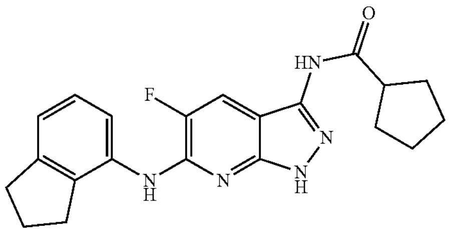 [SMILES: O=C(Nc1n[nH]c2nc(Nc3cccc4c3CCC4)c(F)cc12)C1CCCC1] |
| 90 | 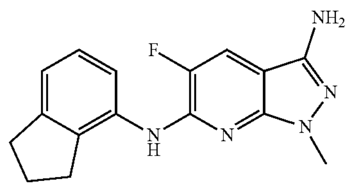 [SMILES: Cn1nc(N)c2cc(F)c(Nc3cccc4c3CCC4)nc21] |

-continued
| Compound No. | Structure |
| --- | --- |
| 91 | 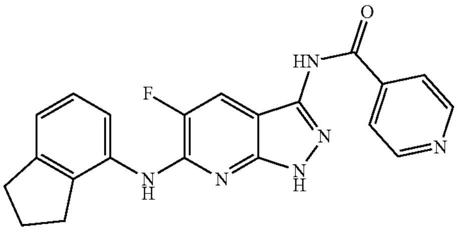 [SMILES: O=C(Nc1n[nH]c2nc(Nc3cccc4c3CCC4)c(F)cc12)c1ccncc1] |
| 92 | 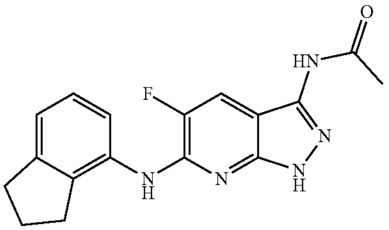 [SMILES: CC(=O)Nc1n[nH]c2nc(Nc3cccc4c3CCC4)c(F)cc12] |
| 93 | 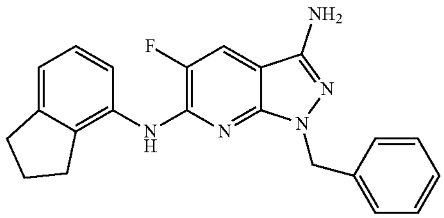 [SMILES: Nc1nn(Cc2ccccc2)c2nc(Nc3cccc4c3CCC4)c(F)cc12] |
| 94 | 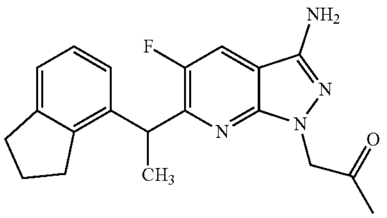 [SMILES: CC(=O)Cn1nc(N)c2cc(F)c(C(C)c3cccc4c3CCC4)nc21] |
| 95 | 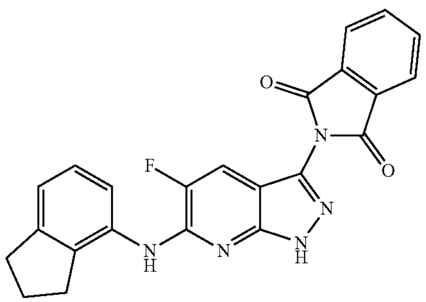 [SMILES: O=C1c2ccccc2C(=O)N1c1n[nH]c2nc(Nc3cccc4c3CCC4)c(F)cc12] |
| 96 | 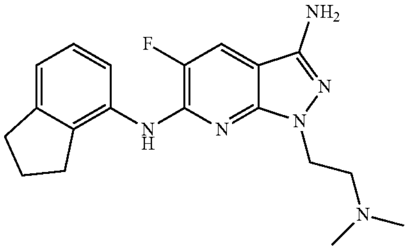 [SMILES: CN(C)CCn1nc(N)c2cc(F)c(Nc3cccc4c3CCC4)nc21] |
-continued
| Compound No. | Structure |
| --- | --- |
| 97 | 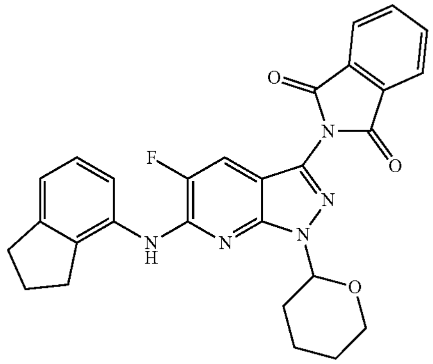 [SMILES: O=C1c2ccccc2C(=O)N1c1nn(C2CCCCO2)c2nc(Nc3cccc4c3CCC4)c(F)cc12] |
| 98 | 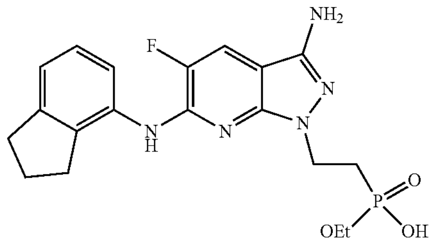 [SMILES: CCOP(=O)(O)CCn1nc(N)c2cc(F)c(Nc3cccc4c3CCC4)nc21] |
| 99 | 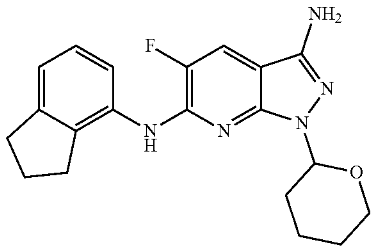 [SMILES: Nc1nn(C2CCCCO2)c2nc(Nc3cccc4c3CCC4)c(F)cc12] |
| 100 | 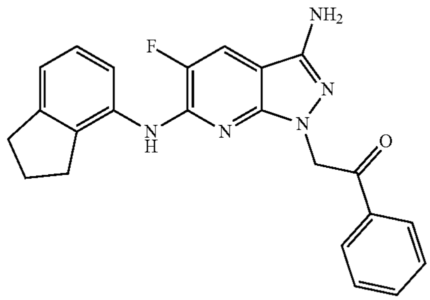 [SMILES: Nc1nn(CC(=O)c2ccccc2)c2nc(Nc3cccc4c3CCC4)c(F)cc12] |
| 101 | 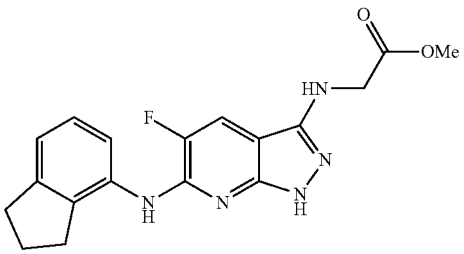 [SMILES: COC(=O)CNc1n[nH]c2nc(Nc3cccc4c3CCC4)c(F)cc12] |

-continued
| Compound No. | Structure |
|---|---|
| 102 | 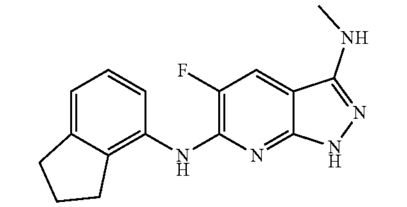 [SMILES: CNc1n[nH]c2nc(Nc3cccc4c3CCC4)c(F)cc12] |
| 103 | 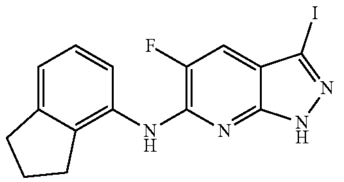 [SMILES: Fc1cc2c(I)n[nH]c2nc1Nc1cccc2c1CCC2] |
| 104 | 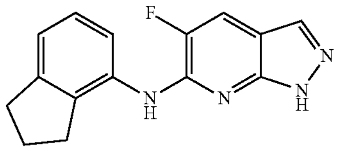 [SMILES: Fc1cc2cn[nH]c2nc1Nc1cccc2c1CCC2] |
| 105 | 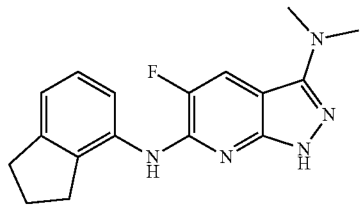 [SMILES: CN(C)c1n[nH]c2nc(Nc3cccc4c3CCC4)c(F)cc12] |
| 106 | 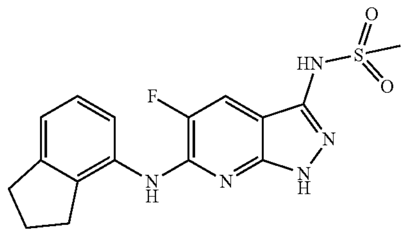 [SMILES: CS(=O)(=O)Nc1n[nH]c2nc(Nc3cccc4c3CCC4)c(F)cc12] |
| 107 | 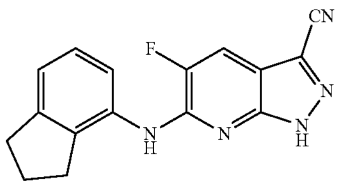 [SMILES: N#Cc1n[nH]c2nc(Nc3cccc4c3CCC4)c(F)cc12] |
| 108 | 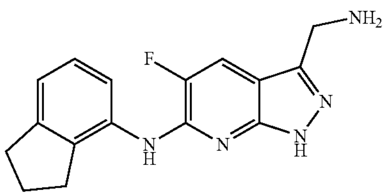 [SMILES: NCc1n[nH]c2nc(Nc3cccc4c3CCC4)c(F)cc12] |
| Compound No. | Structure |
|---|---|
| 109 | 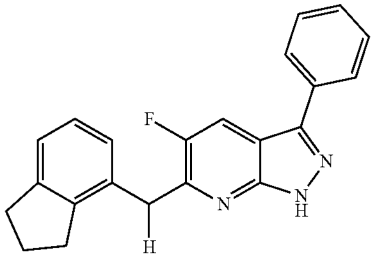 [SMILES: Fc1cc2c(-c3ccccc3)n[nH]c2nc1Cc1cccc2c1CCC2] |
| 110 | 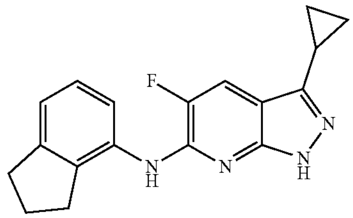 [SMILES: Fc1cc2c(C3CC3)n[nH]c2nc1Nc1cccc2c1CCC2] |
| 111 | 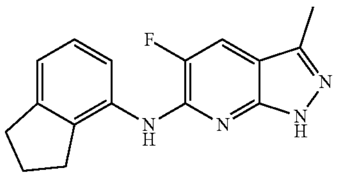 [SMILES: Cc1n[nH]c2nc(Nc3cccc4c3CCC4)c(F)cc12] |
| 112 | 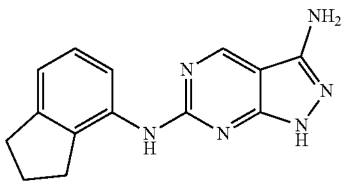 [SMILES: Nc1n[nH]c2nc(Nc3cccc4c3CCC4)ncc12] |
| 113 | 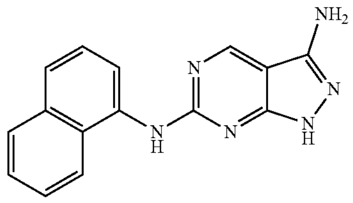 [SMILES: Nc1n[nH]c2nc(Nc3cccc4ccccc34)ncc12] |
| 114 | 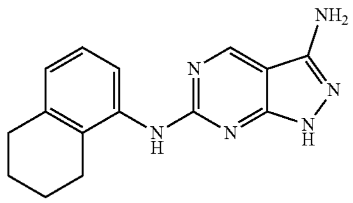 [SMILES: Nc1n[nH]c2nc(Nc3cccc4c3CCCC4)ncc12] |
| 115 | 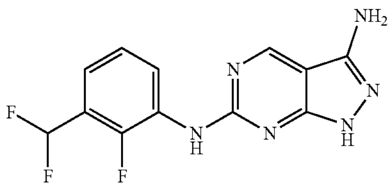 [SMILES: Nc1n[nH]c2nc(Nc3cccc(C(F)F)c3F)ncc12] |

-continued

| Compound No. | Structure |
| --- | --- |
| 116 | 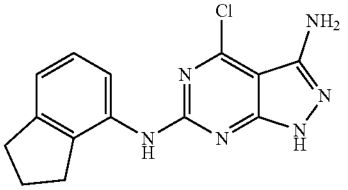 [SMILES: Nc1n[nH]c2nc(Nc3cccc4c3CCC4)nc(Cl)c12] |
| 117 | 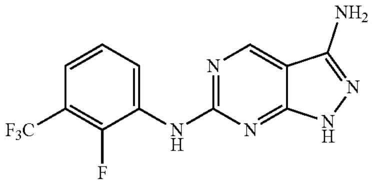 [SMILES: Nc1n[nH]c2nc(Nc3cccc(C(F)(F)F)c3F)ncc12] |
| 118 | 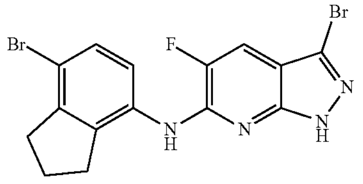 |
| 119 | 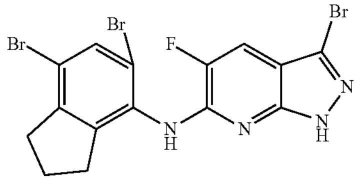 [SMILES: Fc1cc2c(Br)n[nH]c2nc1Nc1c(Br)cc(Br)c2c1CCC2] |
| 120 | 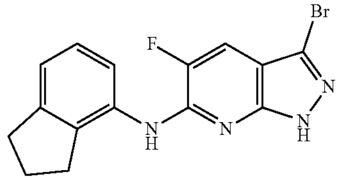 [SMILES: Fc1cc2c(Br)n[nH]c2nc1Nc1cccc2c1CCC2] |
| 121 | 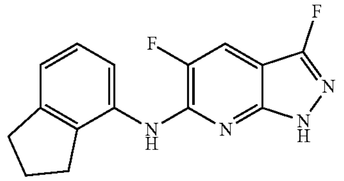 [SMILES: Fc1cc2c(F)n[nH]c2nc1Nc1cccc2c1CCC2] |
| 122 | 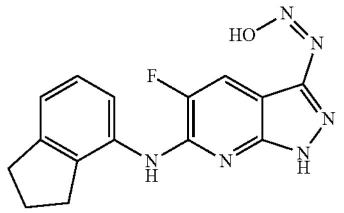 [SMILES: O/N=N\c1n[nH]c2nc(Nc3cccc4c3CCC4)c(F)cc12] |

In another aspect, the present invention is directed to a composition for preventing or treating hair loss containing the novel cycle derivative compound or a salt or isomer thereof as an active ingredient.

In the present invention, the hair loss is preferably selected from androgenic alopecia, alopecia areata, androgenetic alopecia, gynecologic alopecia, postpartum alopecia, seborrheic alopecia, non-rigid alopecia, senile alopecia, chemotherapy-induced alopecia, and radiation-induced alopecia.

The composition for preventing or treating hair loss according to the present invention may further include a suitable carrier, excipient and diluent commonly used in the preparation of pharmaceutical compositions, along with the novel heterocycle derivative or a salt or isomer thereof as an active ingredient. The novel heterocycle derivative or salt or isomer thereof according to the present invention can be formulated with a pharmaceutically acceptable carrier, diluent or excipient regardless of the administration form.

Examples of the carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

In addition, the novel heterocycle derivative or salt or isomer thereof according to the present invention may further include a pharmaceutically acceptable additive, for example, a component selected from the group consisting of: fillers and extenders such as calcium phosphate and silicic acid derivatives; binders such as starch, sugar, mannitol, trehalose, dextrin, amylopectin, sucrose, gluten, gum arabic, cellulose derivatives including methyl cellulose, carboxymethyl cellulose, sodium carboxymethyl cellulose, crystalline cellulose, hydroxypropyl cellulose or hydroxypropyl methyl cellulose, gelatin, alginate, and polyvinyl pyrrolidone; lubricants such as talc, magnesium stearate or calcium stearate, hydrogenated castor oil, talcum powder, and solid polyethylene glycol; disintegrants such as povidone, sodium croscarmellose and crospovidone; surfactants such as polysorbate, cetyl alcohol, and glycerol monostearate; and combinations thereof.

The composition for preventing or treating hair loss according to the present invention contains the novel heterocycle derivative or salt or isomer thereof as an active ingredient in an amount of 0.1 to 95% by weight, preferably 1 to 70% by weight, based on the total weight of the composition, but is not limited thereto.

The composition for preventing or treating hair loss according to the present invention may be administered to a patient in an effective amount through any of various routes, for example, oral or parenteral routes. The composition of the present invention may be formulated in various forms for the prevention or treatment of hair loss and used as a therapeutic agent, and is preferably used in an oral dosage form such as capsule, tablet, dispersion or suspension, or in an injection form, but is not limited thereto. The capsule or tablet may be enterically coated, or may contain an enterically coated pellet of a novel heterocycle derivative or salt or isomer thereof.

A general daily dosage of the novel heterocycle derivative, salt or isomer thereof may range from about 5 to about 500 mg/kg body weight, preferably about 10 to about 100 mg/kg body weight, for mammals including humans and may be administered daily in a single dose or divided into multiple doses. However, the actual dosage of the active ingredient should be determined in consideration of various related factors such as the route of administration, the patient's age, gender and weight, and the severity of the disease, and thus the dosage does not limit the scope of the present invention in any respect.

Meanwhile, the composition for preventing or treating hair loss including the novel heterocycle derivative according to the present invention may be formulated in any of various forms and used as a therapeutic agent.

In addition, in another aspect, the present invention is directed to a cosmetic containing the composition.

The cosmetic according to the present invention may further include at least one additive selected from the group consisting of cosmetically acceptable carriers, excipients, adjuvants and diluents.

In addition, the cosmetic may be one formulation selected from the group consisting of toner, emulsions, creams, gels, essences, packs, shampoos and soaps.

In another aspect, the present invention is directed to a method for preventing or treating hair loss including administering the novel cycle derivative compound or salt or isomer thereof to a subject in need of prevention or treatment.

The terms used to define the compounds according to the present invention have the following meanings.

Specific examples of the term "halogen" include fluorine (F), chlorine (Cl), bromine (Br) and iodine (I), and in particular, the halogen may be fluorine (F) or chlorine (Cl).

The term "cyano" can be represented by —CN, is an atomic group including one carbon and one nitrogen bonded to each other and having a triple bond, and may become hydrogen cyanide or metal cyanide or nitrile when another atom or functional group is bonded to the carbon atom thereof.

The term "$C_1$-$C_6$ alkyl" refers to a monovalent linear or branched saturated hydrocarbon moiety containing only carbon and hydrogen atoms having 1 to 6 carbon atoms. Examples of the alkyl group include, but are not limited to, methyl, ethyl, propyl, isopropyl, butyl, isobutyl, sec-butyl, tert-butyl and the like. Examples of the branched alkyl include isopropyl, isobutyl, tert-butyl and the like.

The term "$C_1$-$C_6$ alkoxy" refers to the formula —O—$C_{1-6}$ alkyl, and examples thereof include, but are not limited to, methoxy, ethoxy, isopropoxy, tert-butoxy, and the like.

The term "$C_3$-$C_{10}$ cyclic alkyl" refers to a cyclic saturated hydrocarbon moiety containing only carbon and hydrogen atoms and having 3 to 10 carbon atoms. Examples of the cyclic alkyl group include, but are not limited to, cyclopentyl, cyclohexyl and the like.

The term "$C_2$-$C_{20}$ allyl" refers to a linear or branched saturated hydrocarbon moiety containing a monovalent unsaturated atomic group $CH_2$═CH—$CH_2$— having 2 to 20 carbon atoms. Examples of the allyl group include, but are not limited to, 2-propenyl, 2-butenyl, 3-butenyl, 2-pentynyl, 3-pentynyl, 4-pentynyl and the like.

The term "$C_6$-$C_{20}$ aryl" includes at least one ring having a shared pi electron system, and for example includes a monocyclic or fused polycyclic (i.e., rings sharing adjacent pairs of carbon atoms) group. That is, the aryl may include phenyl, naphthyl and biaryl unless otherwise defined herein. In one embodiment of the present invention, the aryl refers to an aromatic ring having 6 to 200 carbon atoms.

The term "heteroaryl" refers to an aromatic ring having 5 or 6 ring atoms containing 1 to 4 heteroatoms selected from the group consisting of N, O and S, or a bicyclic ring having a heteroaryl ring fused to a benzene ring or another heteroaryl ring, unless otherwise defined. Examples of a monocyclic heteroaryl include, but are not limited to, thiazolyl, oxazolyl, thiophenyl, furanyl, pyrrolyl, imidazolyl, isoxazolyl, isothiazolyl, pyrazolyl, triazolyl, triazinyl, thiadiazolyl, tetrazolyl, oxadiazolyl, pyridinyl, pyridazinyl, pyrimidinyl, pyrazinyl, and groups similar thereto. Examples of the bicyclic heteroaryl include, but are not limited thereto, indolyl, azaindolyl, indolinyl, benzothiophenyl, benzofuranyl, benzimidazolyl, benzooxazolyl, benzisoxazolyl, benzothiazolyl, benzothiadiazolyl, benzotriazolyl, quinolinyl, isoquinolinyl, purinyl, furopyridinyl and groups similar thereto.

The term "heterocycloalkyl" refers to a saturated or partially unsaturated carbocyclic ring having 5 to 9 ring atoms containing 1 to 3 heteroatoms selected from N, O and S, in addition to carbon atoms. Examples of the heterocycloalkyl include azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, dihydrobenzofuranyl, benzodioxolyl, or benzodioxanyl.

In the present invention, examples of the carrier, excipient, adjuvant and diluent that may be included in the composition containing the compound include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

Hereinafter, the present invention will be described in more detail with reference to examples. However, it will be obvious to those skilled in the art that these examples are provided only for illustration of the present invention and should not be construed as limiting the scope of the present invention.

EXAMPLE

Example 1: Preparation of 6-((2,3-dihydro-1H-inden-4-yl)oxy)-5-fluoro-1H-pyrazolo[3,4-b]pyridin-3-amine The compound represented by the following formula was prepared:

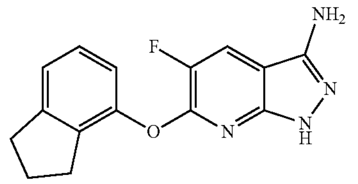 [SMILES: Nc1n[nH]c2nc(Oc3cccc4c3CCC4)c(F)cc12]

Step 1

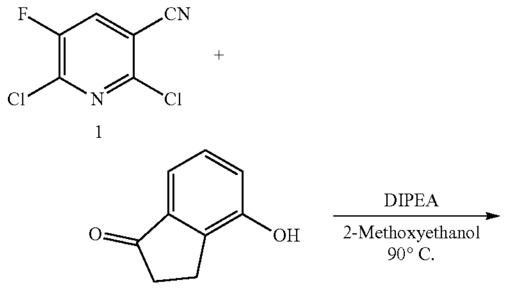

1

2

-continued

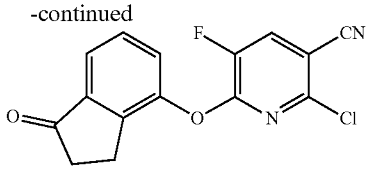

3

25 mg (0.13 mmol) of Compound 1 and 21 mg (0.143 mmol, 1.1 eq.) of Compound 2 were dissolved in 0.52 mL (0.25 M) of N-methylpyrrolidone (NMP) and then 68 μL (0.39 mmol, 3 eq.) of N,N-diisopropylethylamine was added dropwise to the resulting solution. The temperature was elevated to 90° C., and then the resulting mixture was stirred for 6 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (0.026 g, 65.7%) as a beige solid.

Step 2

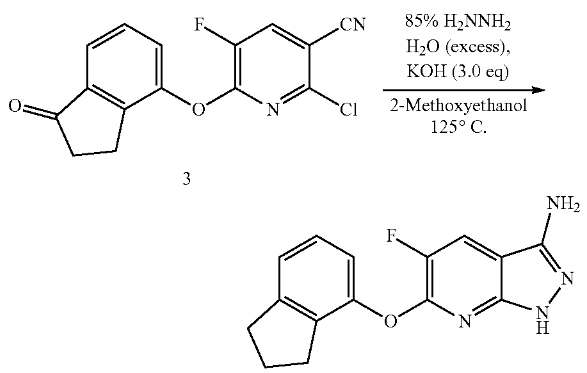

3

4

20 mg (0.07 mmol) of Compound 3 was dissolved in 2-methoxyethanol (0.2 M), and then excess hydrazine monohydrate (1.4 mmol, 20 eq.) was added dropwise to the resulting solution. The temperature was elevated to 90° C. and then the resulting mixture was stirred for 2 hours.

After completion of the reaction was detected, the organic layer was separated using $H_2O$ and ethyl acetate, dried over $MgSO_4$, filtered, and further dried under reduced pressure. The obtained residue was crystallized using dichloromethane and hexane, and then filtered to obtain the target Compound 4 (8 mg, 42.8%) as a light brown solid.

$^1$H NMR (500 MHz, Methanol-d4) δ=8.22 (d, J=8.9 Hz, 1H), 7.76 (t, J=7.7 Hz, 1H), 7.53 (d, J=7.7 Hz, 1H), 7.19 (d, J=7.8 Hz, 1H), 3.21 (d, J=6.1 Hz, 2H), 2.63 (t, J=6.0 Hz, 2H), 1.48-1.41 (m, 2H).

Example 2: Preparation of N6-(2,3-dihydro-1H-inden-5-yl)-5-fluoro-1H-pyrazolo[3,4-b]pyridine-3,6-diamine The compound represented by the following formula was prepared:

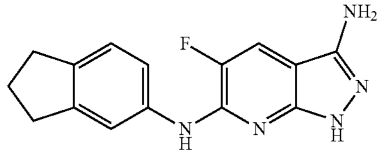 [SMILES: Nc1n[nH]c2nc(Nc3ccc4c(c3)CCC4)c(F)cc12]

Step 1

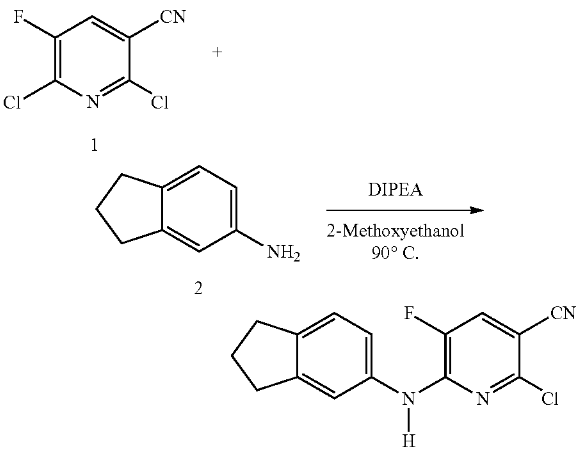

1

2

3

20 mg (0.105 mmol) of Compound 1 and 21 mg (0.116 mmol, 1.1 eq.) of Compound 2 were dissolved in 0.42 mL (0.25 M) of N-methylpyrrolidone (NMP), and then 54.4 μL (0.315 mmol, 3 eq.) of N,N-diisopropylethylamine was added dropwise to the resulting solution. The temperature was elevated to 90° C., and then the resulting mixture was stirred for 6 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (0.020 g, 60%) as a beige solid.

Step 2

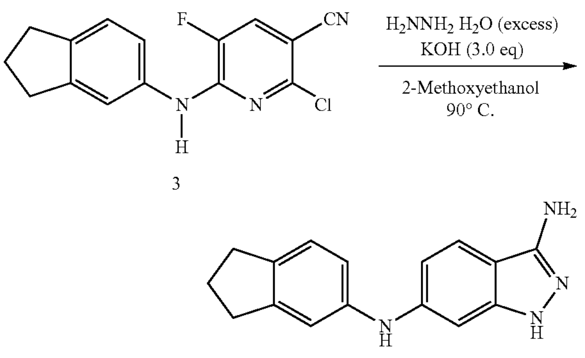

3

4

20 mg (0.07 mmol) of Compound 3 was dissolved in 2-methoxyethanol (0.2 M), and then excess hydrazine monohydrate (1.4 mmol, 20 eq.) was added dropwise to the resulting solution. The temperature was elevated to 90° C. and then the resulting mixture was stirred for 2 hours.

After completion of the reaction was detected, the organic layer was separated using $H_2O$ and ethyl acetate, dried over $MgSO_4$, filtered, and further dried under reduced pressure. The obtained residue was crystallized using dichloromethane and hexane, and then filtered to obtain the target Compound 4 (5 mg, 25.5%) as a light brown solid.

$^1$H NMR (500 MHz, Methanol-d4) δ=7.72 (d, J=9.9 Hz, 1H), 7.52 (s, 1H), 7.38 (d, J=8.4 Hz, 1H), 7.18 (d, J=8.1 Hz, 1H), 2.90 (dt, J=14.7, 7.3 Hz, 4H), 2.10 (p, J=7.6 Hz, 2H).

Example 3: Preparation of N6-(2,3-dihydro-1H-inden-4-yl)-5-fluoro-1H-pyrazolo[3,4-b]pyridine-3,6-diamine The compound represented by the following formula was prepared:

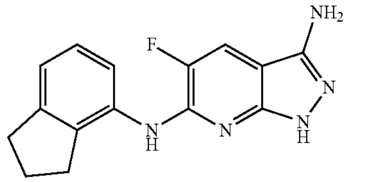 [SMILES: Nc1n[nH]c2nc(Nc3cccc4c3CCC4)c(F)cc12]

Step 1

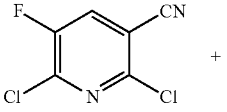

1

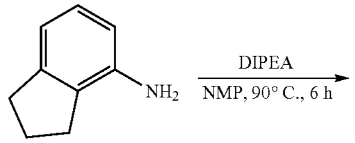

2

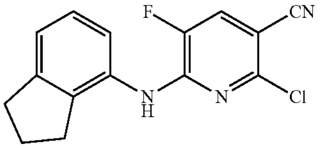

3

2 g (10.47 mmol) of Compound 1 and 1.53 g (11.52 mmol, 1.1 eq.) of Compound 2 were dissolved in 41.9 mL (0.25 M) of N-methylpyrrolidone (NMP) and then 5.49 mL (31.4 mmol, 3 eq.) of N,N-diisopropylethylamine was added dropwise to the resulting solution. The temperature was elevated to 90° C. and then the resulting mixture was stirred for 6 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (2.4 g, 80%) as a yellow solid.

Step 2

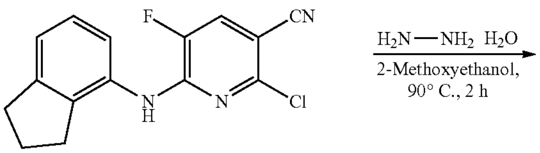

3

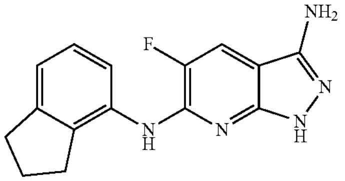

4

2.4 g (8.34 mmol) of Compound 3 was dissolved in 41.7 mL (0.2 M) of 2-methoxyethanol, and then 8.09 mL (167 mmol, 20 eq.) of hydrazine monohydrate was added dropwise to the resulting solution. The temperature was elevated to 90° C. and then the resulting mixture was stirred for 2 hours.

After completion of the reaction was detected, the organic layer was separated using $H_2O$ and ethyl acetate, dried over $MgSO_4$, filtered, and further dried under reduced pressure. The obtained residue was crystallized using dichloromethane and hexane and then filtered to obtain the target Compound 4 (2.02 g, 85%) as a light brown solid.

$^1$H NMR (400 Hz, DMSO-d6) δ=11.41 (s, 1H), 8.28 (s, 1H), 7.71 (d, J=11.2 Hz, 1H), 7.36 (d, J=8.0 Hz, 111), 7.11 (t, J=7.6 Hz, 111), 7.01 (d, J=7.2 Hz, 1H), 5.19 (s, 2H), 2.89 (t, J=7.4 Hz, 2H), 2.75 (t, J=7.2 Hz, 2H), 1.97 (quin, J=7.5 Hz, 2H).

Example 4: Preparation of N6-(2,3-dihydro-1H-inden-4-yl)-1H-pyrazolo[3,4-b]pyridine-3,6-diamine The compound re resented by the following formula was prepared:

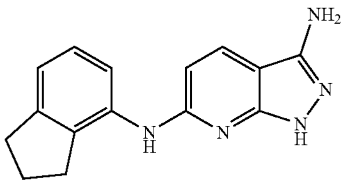 [SMILES: Nc1n[nH]c2nc(Nc3cccc4c3CCC4)ccc12]

Step 1

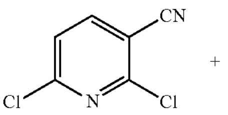

1

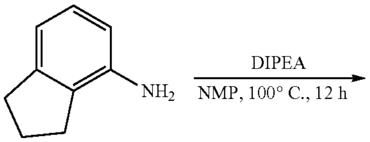

2

-continued

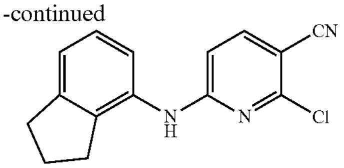

3

100 mg (0.578 mmol) of Compound 1 and 115 mg (0.867 mmol, 1.5 eq.) of Compound 2 were dissolved in 2.312 mL (0.25 M) of N-methylpyrrolidone (NMP), and then 0.303 mL (1.734 mmol, 3 eq.) of N,N-diisopropylethylamine was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (140 mg, 90%) as a yellow solid.

Step 2

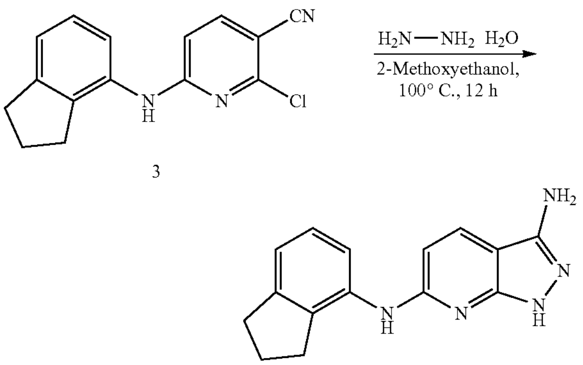

3

4

140 mg (0.519 mmol) of Compound 3 was dissolved in 2.595 mL (0.2 M) of 2-methoxyethanol, and then 0.504 mL (10.38 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (101 mg, 73%) as a white solid.

$^1$H NMR (400 Hz, DMSO-d6) δ=11.41 (s, 1H), 8.28 (s, 1H), 7.71 (d, J=11.2 Hz, 1H), 7.36 (d, J=8.0 Hz, 1H), 7.11 (t, J=7.6 Hz, 1H), 7.01 (d, J=7.2 Hz, 1H), 5.19 (s, 2H), 2.89 (t, J=7.4 Hz, 2H), 2.75 (t, J=7.2 Hz, 2H), 1.97 (quin, J=7.5 Hz, 2H).

Example 5: Preparation of N6-(3-(tert-butyl)phenyl)-5-fluoro-1H-pyrazolo[3,4-b]pyridine-3,6-diamine The compound represented by the following formula was prepared:

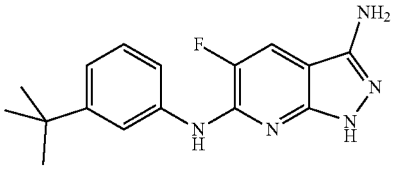 [SMILES: CC(C)(C)c1cccc(Nc2nc3[nH]nc(N)c3cc2F)c1]

Step 1

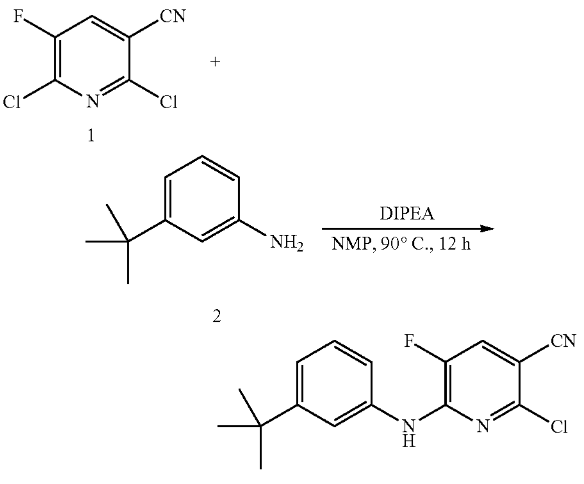

1

2

3

50 mg (0.262 mmol) of Compound 1 and 50.8 mg (0.340 mmol, 1.3 eq.) of Compound 2 were dissolved in 1.047 mL (0.25 M) of N-methylpyrrolidone (NMP), and then 0.137 mL (0.785 mmol, 3 eq.) of N,N-diisopropylethylamine was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (80.5 mg, 101%) as an orange solid.

Step 2

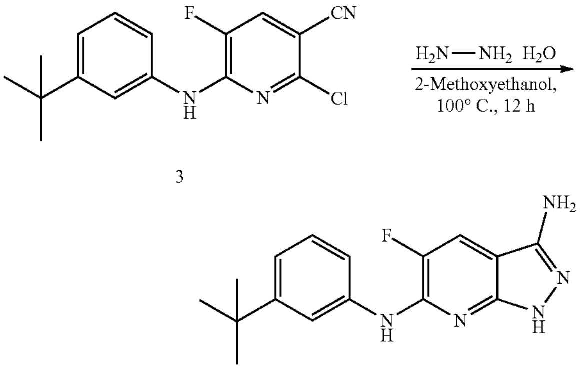

3

4

80.5 mg (0.265 mmol) of Compound 3 was dissolved in 1.325 mL (0.2 M) of 2-methoxyethanol, and then 0.257 mL (5.30 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (53.5 mg, 67%) as a light brown solid.

$^1H$ NMR (400 Hz, DMSO-d6) δ=11.53 (s, 1H), 8.81 (d, J=2.4 Hz, 1H), 7.86 (d, J=8.4 Hz, 1H), 7.78 (t, J=1.8 Hz, 1H), 7.74 (d, J=11.2 Hz, 1H), 7.21 (t, J=8.0 Hz, 1H), 7.01 (d, J=8.8 Hz, 1H), 5.23 (s, 2H), 1.30 (s, 9H).

Example 6: Preparation of 5-fluoro-N6-(1-methyl-1H-indol-4-yl)-1H-pyrazolo[3,4-b]pyridine-3,6-diamine The compound represented by the following formula was prepared:

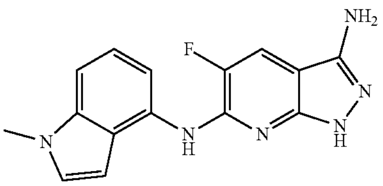 [SMILES: Cn1ccc2c(Nc3nc4[nH]nc(N)c4cc3F)cccc21]

Step 1

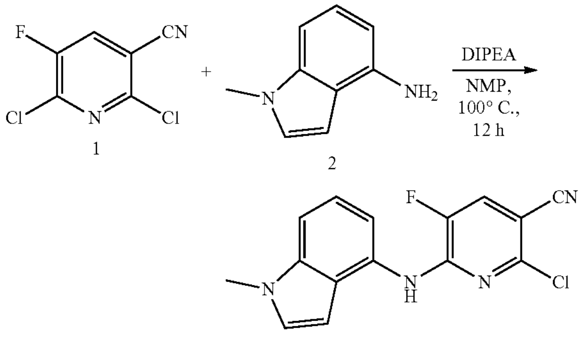

1 2

3

50 mg (0.262 mmol) of Compound 1 and 49.8 mg (0.340 mmol, 1.3 eq.) of Compound 2 were dissolved in 1.309 mL (0.2 M) of N-methylpyrrolidone (NMP) and then 0.137 mL (0.785 mmol, 3 eq.) of N,N-diisopropylethylamine was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (75.5. mg, 96%) as a brown solid.

Step 2

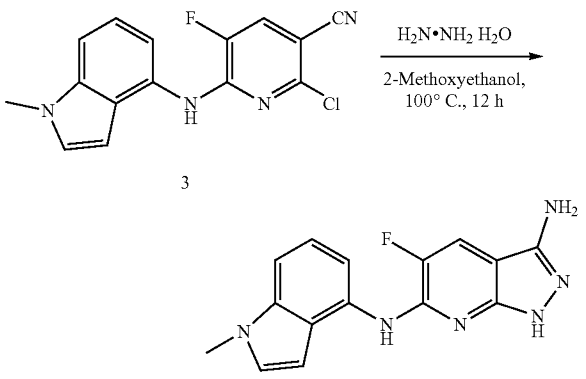

3

4

75.5 mg (0.251 mmol) of Compound 3 was dissolved in 1.255 mL (0.2 M) of 2-methoxyethanol, and then 0.244 mL (5.02 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (42.2 mg, 57%) as a light brown solid.

$^1H$ NMR (400 Hz, DMSO-d6) δ=11.45 (s, 1H), 8.44 (s, 1H), 7.75 (d, J=11.2 Hz, 1H), 7.51 (d, J=7.6 Hz, 1H), 7.23 (d, J=3.2 Hz, 1H), 7.18 (d, J=8.0 Hz, 1H), 7.12 (t, J=7.8 Hz, 1H), 6.44 (d, J=2.8 Hz, 1H), 5.22 (s, 2H), 3.78 (S, 3H).

Example 7: Preparation of N6-(benzo[d][1,3]dioxol-4-yl)-5-fluoro-1H-pyrazolo[3,4-b]pyridine-3,6-diamine The compound represented by the following formula was prepared:

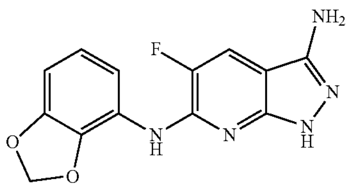 [SMILES: Nc1n[nH]c2nc(Nc3cccc4c3OCO4)c(F)cc12]

Step 1

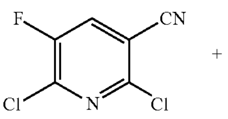

1

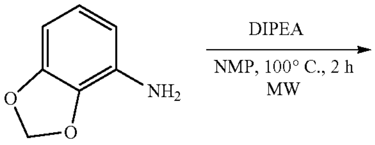

2

-continued

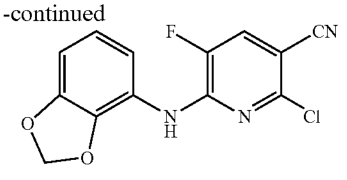

3

50 mg (0.262 mmol) of Compound 1 and 46.7 mg (0.340 mmol, 1.3 eq.) of Compound 2 were dissolved in 1.309 mL (0.2 M) of N-methylpyrrolidone (NMP) and then 0.137 mL (0.785 mmol, 3 eq.) of N,N-diisopropylethylamine was added dropwise to the resulting solution. The temperature was elevated to 100° C. and then the resulting mixture was stirred in a microwave for 2 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (52.5 mg, 69%) as a yellow solid.

Step 2

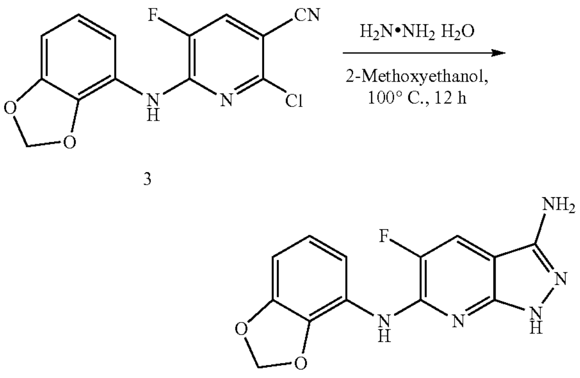

3

4

52.5 mg (0.180 mmol) of Compound 3 was dissolved in 0.9 mL (0.2 M) of 2-methoxyethanol, and then 0.175 mL (3.60 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (26 mg, 50%) as a yellow solid.

$^1H$ NMR (400 Hz, DMSO-d6) δ=11.47 (s, 1H), 8.48 (s, 1H), 7.72 (d, J=11.2 Hz, 1H), 7.05 (d, J=8.0 Hz, 1H), 6.82 (t, J=8.0 Hz, 1H), 6.74 (d, J=7.6 Hz, 1H), 5.97 (s, 2H), 5.22 (s, 2H).

Example 8: Preparation of 3-chloro-N-(2,3-dihydro-1H-inden-4-yl)-5-fluoro-1H-pyrazolo[3,4-b]pyridin-6-amine The compound represented by the following formula was prepared:

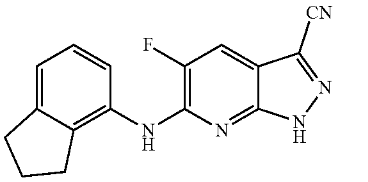

Step 1

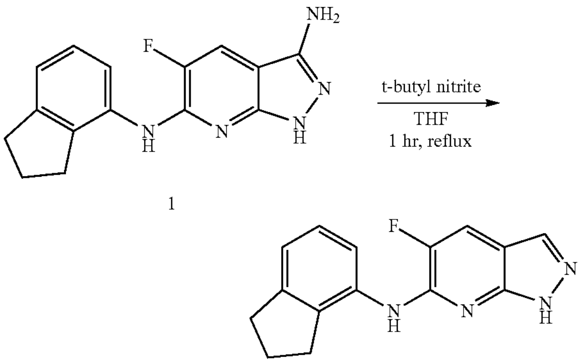

1

2

5 ml of acetonitrile was added to 100 mg (0.35 mmol) of Compound 1, 72 mg (0.7 mmol, 2 eq.) of sodium nitrite and HCl (52.5 μL, 1.75 mmol). The temperature was slowly elevated from 0° C. to 50° C. and the reaction was performed for 12 hours. After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 2 (20 mg, 21%) as a yellow solid.

Step 2

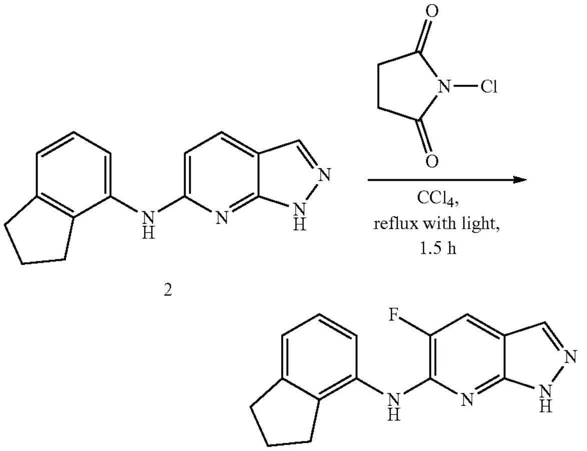

2

3 mL of $CCl_4$ was added to 10 mg (0.037 mmol) of Compound 2 and 7.5 mg (0.056 mmol, 2.5 eq.) of 1-chloropyrrolidine-2,5-dione. The resulting mixture was stirred at 100° C. for 1.5 hours to obtain the target compound (12 mg, 53.1%) as a white solid.

$^1H$ NMR (500 MHz, Methanol-d4) δ=7.82 (s, 1H), 7.70 (d, J=11.1 Hz, 1H), 7.60 (d, J=7.9 Hz, 1H), 7.14 (t, J=7.6 Hz, 1H), 7.05 (d, J=7.9 Hz, 1H), 2.96 (t, J=7.4 Hz, 2H), 2.87 (t, J=7.4 Hz, 2H), 2.09 (m, 2H).

Example 9: Preparation of N6-(1,3-dihydroisobenzofuran-4-yl)-5-fluoro-1H-pyrazolo[3,4-b]pyridine-3,6-diamine The compound represented by the following formula was prepared:

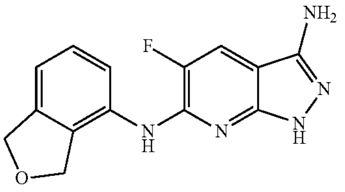 [SMILES: Nc1n[nH]c2nc(Nc3cccc4c3COC4)c(F)cc12]

Step 1

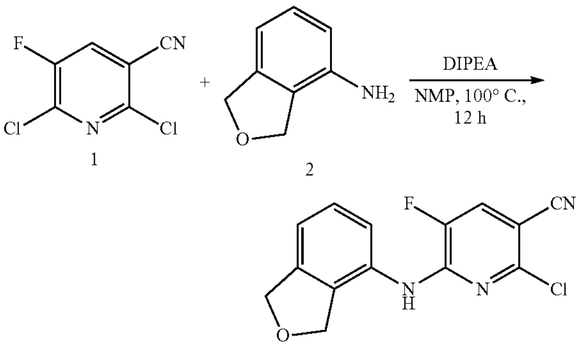

1 2

3

50 mg (0.262 mmol) of Compound 1 and 46 mg (0.340 mmol, 1.3 eq.) of Compound 2 were dissolved in 1.047 mL (0.25 M) of N-methylpyrrolidone (NMP), and then 0.137 mL (0.785 mmol, 3 eq.) of N,N-diisopropylethylamine was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (63.4 mg, 84%) as an ivory solid.

Step 2

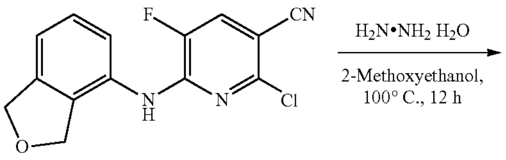

3

-continued

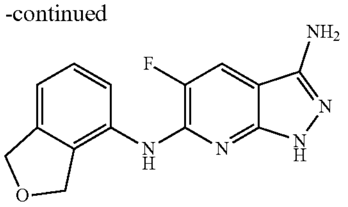

4

53.4 mg (0.184 mmol) of Compound 3 was dissolved in 0.922 mL (0.2 M) of 2-methoxyethanol, and then 0.179 mL (3.69 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (31.7 mg, 60%) as a yellow solid.

$^1$H NMR (400 Hz, DMSO-d6) δ=11.47 (br s, 1H), 8.71 (s, 1H), 7.74 (d, J=11.1 Hz, 1H), 7.36-7.24 (m, 2H), 7.08 (d, J=7.2 Hz, 1H), 5.24 (s, 2H), 5.03 (s, 2H), 4.92 (s, 2H).

Example 10: Preparation of N6-(benzofuran-4-yl)-5-fluoro-1H-pyrazolo[3,4-b]pyridine-3,6-diamine The compound represented by the following formula was prepared:

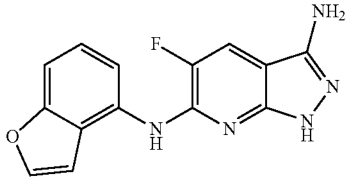 [SMILES: Nc1n[nH]c2nc(Nc3cccc4occc34)c(F)cc12]

Step 1

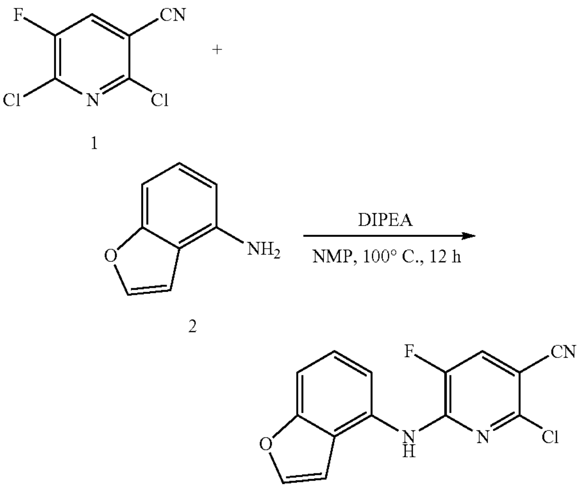

1

2

3

50 mg (0.262 mmol) of Compound 1 and 45.3 mg (0.340 mmol, 1.3 eq.) of Compound 2 were dissolved in 1.047 mL (0.25 M) of N-methylpyrrolidone (NMP) and then 0.137 mL (0.785 mmol, 3 eq.) of N,N-diisopropylethylamine was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (59.5 mg, 79%) as an ivory solid.

Step-2

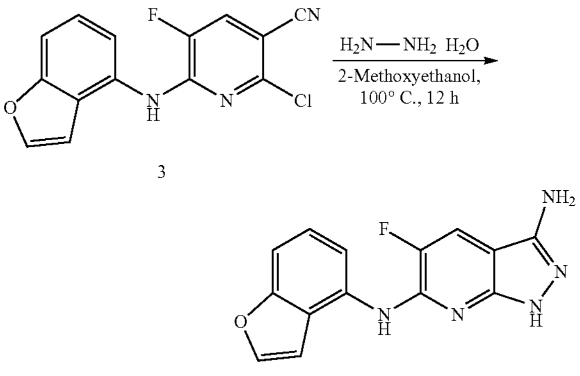

3

4

59.5 mg (0.207 mmol) of Compound 3 was dissolved in 1.034 mL (0.2 M) of 2-methoxyethanol, and then 0.201 mL (4.14 mmol, 20 eq.) of hydrazine monohydrate was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (20.8 mg, 36%) as an ivory solid.

$^1$H NMR (400 MHz, DMSO-d6) δ=11.48 (s, 1H), 8.84 (s, 1H), 7.89 (d, J=2.2 Hz, 1H), 7.80 (d, J=11.2 Hz, 1H), 7.61 (d, J=7.6 Hz, 1H), 7.35-7.25 (m, 2H), 6.95 (s, 1H), 5.24 (s, 2H).

Example 11: Preparation of 5-chloro-N6-(2,3-dihydro-1H-inden-4-yl)-1H-pyrazolo[3,4-b]pyridine-3,6-diamine The compound represented by the following formula was prepared:

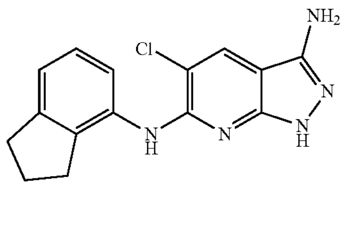 [SMILES: Nc1n[nH]c2nc(Nc3cccc4c3CCC4)c(Cl)cc12]

Step

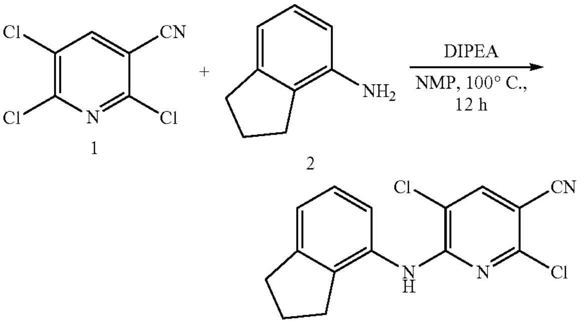

1

2

3

50 mg (0.241 mmol) of Compound 1 and 41.7 mg (0.313 mmol, 1.3 eq.) of Compound 2 were dissolved in 0.964 mL (0.25 M) of N-methylpyrrolidone (NMP), and then 0.126 mL (0.723 mmol, 3 eq.) of N,N-diisopropylethylamine was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (69.2 mg, 94%) as a yellow solid.

Step 2

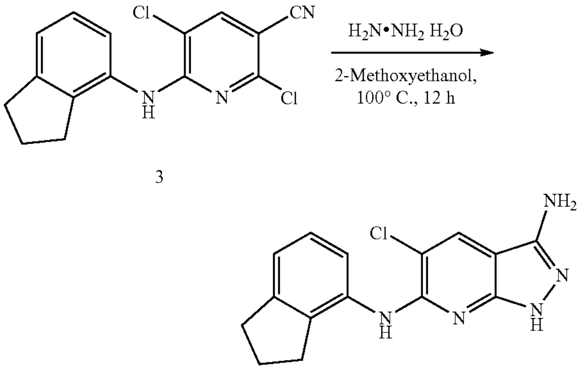

3

4

69.2 mg (0.228 mmol) of Compound 3 was dissolved in 1.138 mL (0.2 M) of 2-methoxyethanol, and then 0.221 mL (4.55 mmol, 20 eq.) of hydrazine monohydrate was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (32.5 mg, 48%) as a light yellow solid.

$^1$H NMR (400 MHz, DMSO-d6) δ=11.51 (s, 1H), 8.06 (s, 1H), 7.94 (s, 1H), 7.50 (d, J=7.9 Hz, 1H), 7.14 (t, J=7.6 Hz, 1H), 7.03 (d, J=7.2 Hz, 1H), 5.34 (s, 2H), 2.91 (t, J=7.5 Hz, 2H), 2.75 (t, J=7.4 Hz, 2H), 2.00 (quin, J=7.4 Hz, 211).

Example 12: Preparation of N6-(2,3-dimethylphenyl)-5-fluoro-1H-pyrazolo[3,4-b]pyridine-3,6-diamine The compound represented by the following formula was prepared:

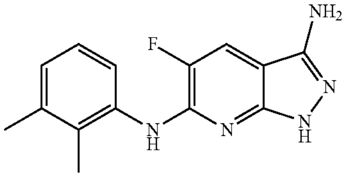 [SMILES: Cc1cccc(Nc2nc3[nH]nc(N)c3cc2F)c1C]

Step 1

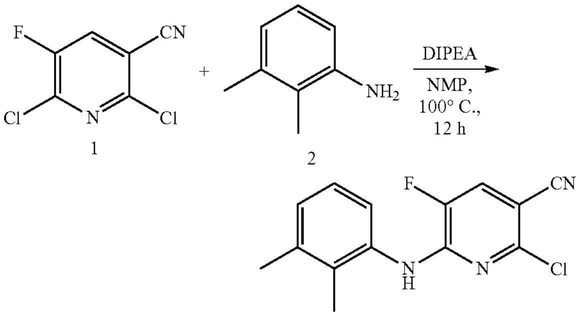

1 2 3

50 mg (0.262 mmol) of Compound 1 and 41.2 mg (0.340 mmol, 1.3 eq.) of Compound 2 were dissolved in 1.047 mL (0.25 M) of N-methylpyrrolidone (NMP), and then 0.137 mL (0.785 mmol, 3 eq.) of N,N-diisopropylethylamine was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (66.6 mg, 92%) as a yellow solid.

Step 2

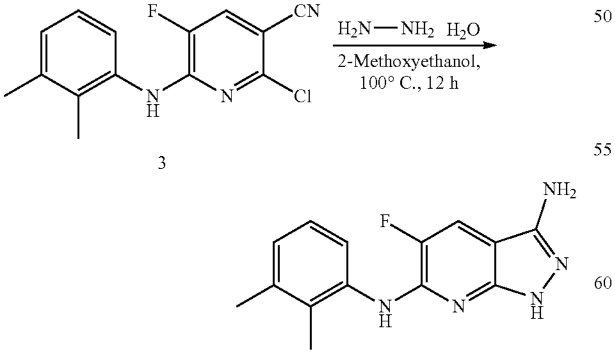

3 4

66.6 mg (0.242 mmol) of Compound 3 was dissolved in 1.208 mL (0.2 M) of 2-methoxyethanol, and then 0.234 mL (4.83 mmol, 20 eq.) of hydrazine monohydrate was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (34.7 mg, 53%) as a light yellow solid.

$^1$H NMR (400 MHz, DMSO-d6) δ=11.33 (s, 1H), 8.38 (s, 1H), 7.69 (d, J=11.4 Hz, 1H), 7.17 (d, J=7.4 Hz, 1H), 7.08 (t, J=7.7 Hz, 1H), 7.05-7.01 (m, 1H), 5.15 (s, 2H), 2.27 (s, 311), 2.06 (s, 3H).

Example 13: Preparation of 6-((2,3-dihydro-1H-inden-4-yl)amino)-5-fluoro-1H-pyrazolo[3,4-b]pyridin-3-ol The compound represented by the following formula was prepared:

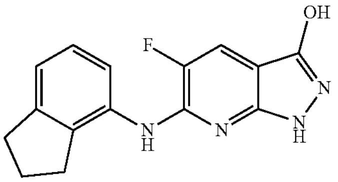

Step 1

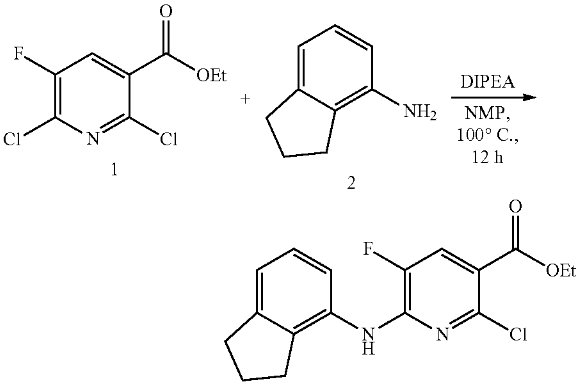

1 2 3

60 mg (0.252 mmol) of Compound 1 and 43.6 mg (0.328 mmol, 1.3 eq.) of Compound 2 were dissolved in 1.008 mL (0.25 M) of N-methylpyrrolidone (NMP) and then 0.132 mL (0.756 mmol, 3 eq.) of N,N-diisopropylethylamine was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (57 mg, 68%) as a light yellow solid.

Step 2

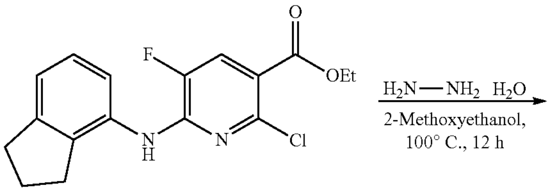

3

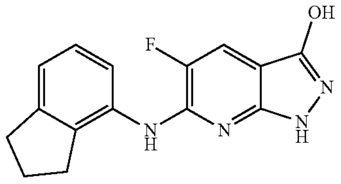

4

57 mg (0.170 mmol) of Compound 3 was dissolved in 0.851 mL (0.2 M) of 2-methoxyethanol, and then 0.165 mL (3.41 mmol, 20 eq.) of hydrazine monohydrate was added dropwise to the resulting solution. The temperature was elevated to 100° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (5.7 mg, 12%) as a light yellow solid.

$^1$H NMR (400 MHz, DMSO-d6) δ=11.24-11.02 (m, 1H), 10.55-10.33 (m, 1H), 8.56-8.50 (m, 1H), 7.58 (d, J=10.8 Hz, 1H), 7.23 (d, J=7.9 Hz, 1H), 7.06 (t, J=7.6 Hz, 1H), 6.98 (d, J=7.2 Hz, 1H), 2.83 (t, J=7.5 Hz, 2H), 2.69 (br t, J=7.4 Hz, 2H), 1.90 (t, J=7.4 Hz, 2H).

Example 14: Preparation of ethyl 3-amino-6-((2,3-dihydro-1H-inden-4-yl)amino)-1H-pyrazolo[3,4-b]pyridine-5-carboxylate The compound represented by the following formula was prepared:

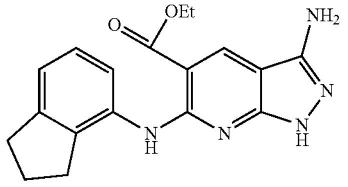 [SMILES: CCOC(=O)c1cc2c(N)n[nH]c2nc1Nc1cccc2c1CCC2]

Step 1

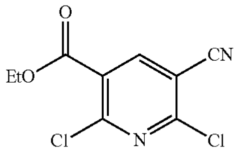

1

+

-continued

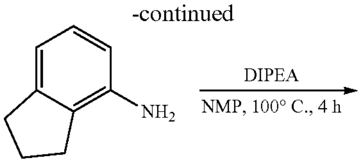

2

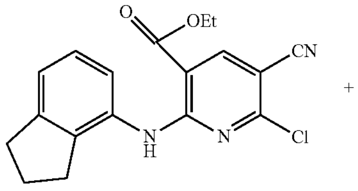

3

+

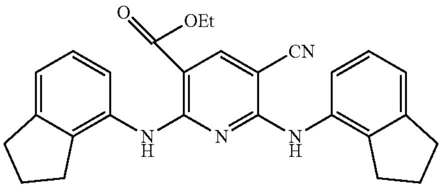

4

240 mg (0.979 mmol) of Compound 1 and 170 mg (1.273 mmol, 1.3 eq.) of Compound 2 were dissolved in 3.917 mL (0.25 M) of N-methylpyrrolidone (NMP), and then 0.513 mL (2.94 mmol, 3 eq.) of N,N-diisopropylethylamine was added dropwise to the resulting solution. The temperature was elevated to 100° C. and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (168 mg, 50%) and the target Compound 4 (97.7 mg, 23%) as yellow solids.

Step 2

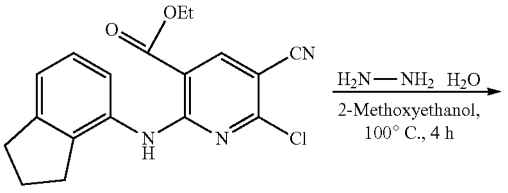

3

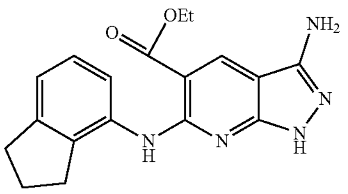

5

168 mg (0.492 mmol) of Compound 3 was dissolved in 2.458 mL (0.2 M) of 2-methoxyethanol, and then 0.477 mL (9.83 mmol, 20 eq.) of hydrazine monohydrate was added dropwise to the resulting solution. The temperature was elevated to 100° C. and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 5 (89.2 mg, 54%) as a yellow solid.

$^1$H NMR (400 MHz, DMSO-d6) δ=11.84 (s, 1H), 10.50 (s, 1H), 8.83 (s, 1H), 8.39 (d, J=7.9 Hz, 1H), 7.16-7.13 (m, 1H), 6.93 (d, J=7.5 Hz, 1H), 5.77 (d, J=3.4 Hz, 2H), 4.38 (q, J=7.0 Hz, 2H), 2.95-2.88 (m, 4H), 2.14-2.06 (m, 2H), 1.38 (t, J=7.1 Hz, 3H).

Example 15: Preparation of N6-(2,3-dihydro-1H-inden-4-yl)-1H-pyrazolo[3,4-b]pyrazine-3,6-diamine The compound represented by the following formula was prepared:

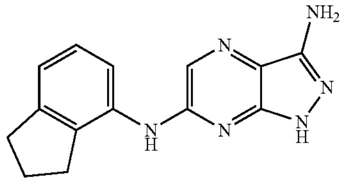 [SMILES: Nc1n[nH]c2nc(Nc3cccc4c3CCC4)cnc12]

Step 1

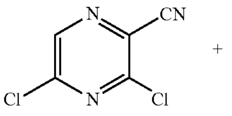

1

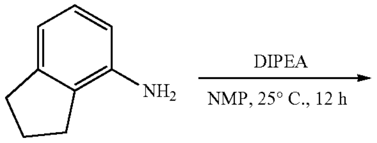

2

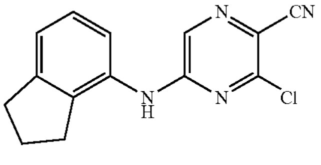

3

100 mg (0.575 mmol) of Compound 1 and 100 mg (0.747 mmol, 1.3 eq.) of Compound 2 were dissolved in 2.299 mL (0.25 M) of N-methylpyrrolidone (NMP), and then 0.301 mL (1.724 mmol, 3 eq.) of N,N-diisopropylethylamine was added dropwise to the resulting solution. The reaction solution was stirred at room temperature for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (98.7 mg, 63%) as a yellow solid.

Step 2

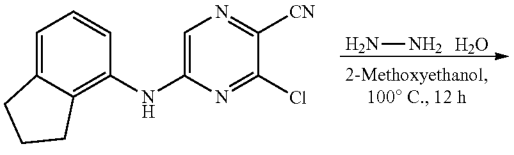

3

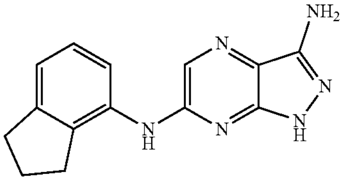

4

98.7 mg (0.365 mmol) of Compound 3 was dissolved in 1.823 mL (0.2 M) of 2-methoxyethanol, and then 0.354 mL (7.29 mmol, 20 eq.) of hydrazine monohydrate was added dropwise to the resulting solution. The temperature was elevated to 100° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (65.2 mg, 67%) as a yellow solid.

$^1$H NMR (400 MHz, DMSO-d6) δ=11.84 (s, 1H), 10.50 (s, 1H), 8.83 (s, 1H), 8.39 (d, J=7.9 Hz, 1H), 7.16-7.13 (m, 1H), 6.93 (d, J=7.5 Hz, 1H), 5.77 (d, J=3.4 Hz, 2H), 4.38 (q, J=7.0 Hz, 2H), 2.95-2.88 (m, 4H), 2.14-2.06 (m, 2H), 1.38 (t, J=7.1 Hz, 3H).

Example 16: Preparation of 3-amino-6-((2,3-dihydro-1H-inden-4-yl)amino)-1H-pyrazolo[3,4-b]pyridine-5-carboxylic acid The compound represented by the following formula was prepared:

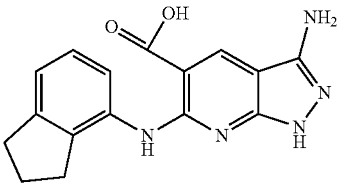 [SMILES: Nc1n[nH]c2nc(Nc3cccc4c3CCC4)c(C(=O)O)cc12]

Step 1

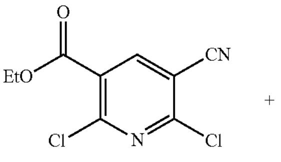

1

-continued

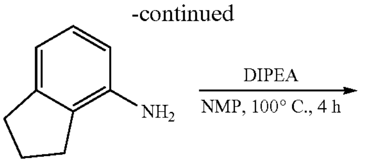

2

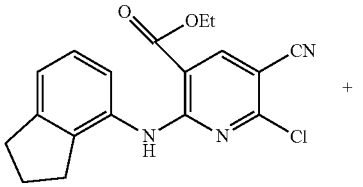

3

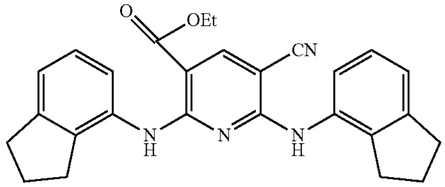

4

240 mg (0.979 mmol) of Compound 1 and 170 mg (1.273 mmol, 1.3 eq.) of Compound 2 were dissolved in 3.917 mL (0.25 M) of N-methylpyrrolidone (NMP) and then 0.513 mL (2.94 mmol, 3 eq.) of N,N-diisopropylethylamine was added dropwise to the resulting solution. The temperature was elevated to 100° C. and the reaction solution was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (168 mg, 50%) and the target Compound 4 (97.7 mg, 23%) as yellow solids.

Step 2

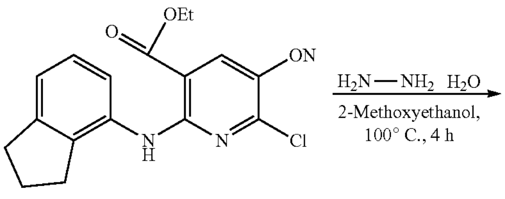

3

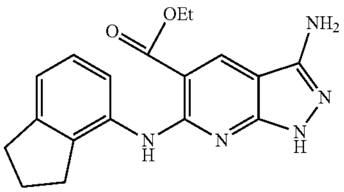

5

168 mg (0.492 mmol) of Compound 3 was dissolved in 2.458 mL (0.2 M) of 2-methoxyethanol, and then 0.477 mL (9.83 mmol, 20 eq.) of hydrazine monohydrate was added dropwise to the resulting solution. The temperature was elevated to 100° C. and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 5 (89.2 mg, 54%) as a yellow solid.

Step 3

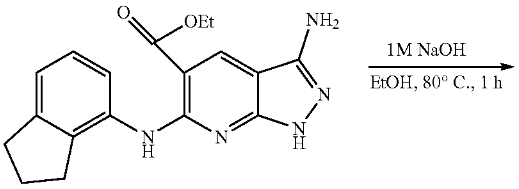

5

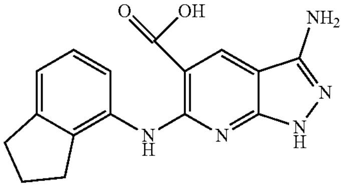

6

30 mg (0.089 mol) of Compound 5 was dissolved in 0.889 mL (0.1 M) of ethanol and then 0.445 mL (0.445 mmol, 5 eq.) of a 1 M NaOH solution was added dropwise to the resulting solution. The temperature was elevated to 80° C. and then the resulting mixture was stirred for 1 hour.

After completion of the reaction was detected, the ethanol was dried under reduced pressure. The obtained residue was purified by reverse phase chromatography to obtain the target Compound 6 (5.9 mg, 21%) as a yellow solid.

$^1$H NMR (400 MHz, DMSO-d6) δ=13.34-13.17 (m, 1H), 12.23-12.02 (m, 1H), 10.83 (s, 1H), 8.87 (s, 1H), 8.36 (d, J=8.3 Hz, 1H), 7.15 (t, J=7.8 Hz, 1H), 6.94 (d, J=7.3 Hz, 1H), 2.96-2.86 (m, 4H), 2.55 (s, 1H), 2.13-2.05 (m, 2H).

Example 17: Preparation of 5-chloro-N6-(2,3-dihydro-1H-inden-4-yl)-4-methyl-1H-pyrazolo[3,4-b]pyridine-3,6-diamine The compound represented by the following formula was prepared:

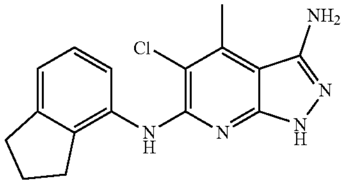 [SMILES: Cc1c(Cl)c(Nc2cccc3c2CCC3)nc2[nH]nc(N)c12]

Step 1

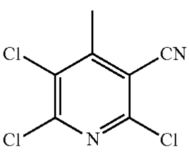

1

+

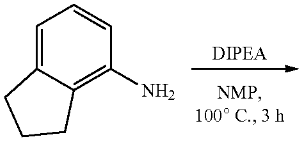

2

-continued

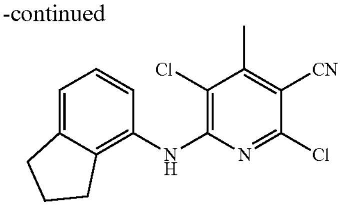

3

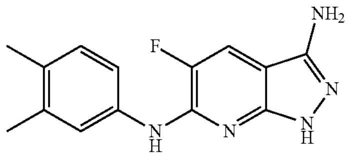 [SMILES: Cc1ccc(Nc2nc3[nH]nc(N)c3cc2F)cc1C]

Step 1

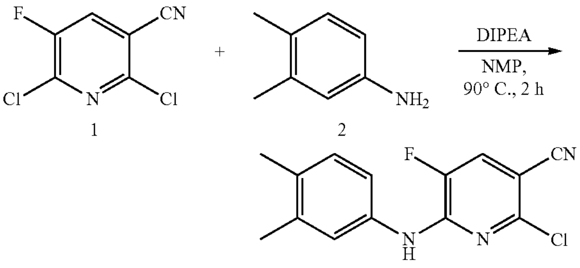

1 2 3

80 mg (0.361 mmol) of Compound 1 and 62.5 mg (0.470 mmol, 1.3 eq.) of Compound 2 were dissolved in 1.445 mL (0.25 M) of N-methylpyrrolidone (NMP), and then 0.189 mL (1.084 mmol, 3 eq.) of N,N-diisopropylethylamine was added dropwise to the resulting solution. The temperature was elevated to 100° C. and then the resulting mixture was stirred for 3 hours.

After completion of the reaction was detected, the organic layer was separated using $H_2O$ and ethyl acetate, dried over $MgSO_4$, filtered, and further dried under reduced pressure. The obtained residue was purified by reverse column chromatography to obtain the target Compound 3 (37.3 mg, 33%) as an ivory solid.

Step 2

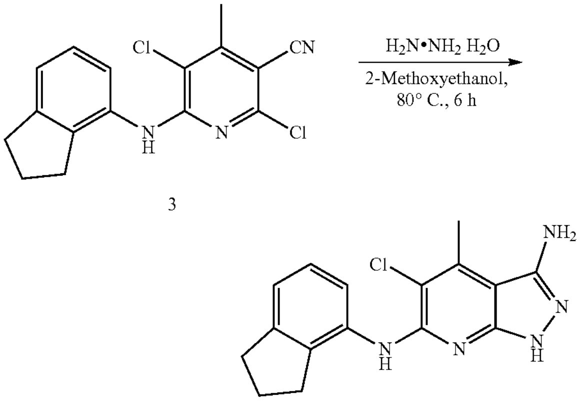

3

4

37.3 mg (0.117 mmol) of Compound 3 was dissolved in 0.586 mL (0.2 M) of 2-methoxyethanol, and then 0.114 mL (2.344 mmol, 20 eq.) of hydrazine monohydrate was added dropwise to the resulting solution. The temperature was elevated to 80° C. and then the resulting mixture was stirred for 6 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (16.5 mg, 45%) as a light brown solid.

$^1$H NMR (400 MHz, DMSO-d6) δ=11.59 (s, 1H), 7.91 (s, 1H), 7.52 (d, J=7.7 Hz, 1H), 7.13 (t, J=7.6 Hz, 1H), 7.02 (d, J=7.1 Hz, 1H), 5.01 (s, 2H), 2.91 (t, J=7.3 Hz, 2H), 2.74 (t, J=7.3 Hz, 2H), 2.60 (s, 3H), 2.04-1.97 (m, 2H).

Example 18: Preparation of N6-(3,4-dimethylphenyl)-5-fluoro-1H-pyrazolo[3,4-b]pyridine-3,6-diamine The compound represented by the following formula was prepared:

60 mg (0.314 mmol) of Compound 1 and 49.5 mg (0.408 mmol, 1.3 eq.) of Compound 2 were dissolved in 1.257 mL (0.25 M) of N-methylpyrrolidone (NMP), and then 0.165 mL (0.942 mmol, 3 eq.) of N,N-diisopropylethylamine was added dropwise to the resulting solution. The temperature was elevated to 90° C. and then the reaction solution was stirred for 2 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (87 mg, 100%) as a yellow solid.

Step 2

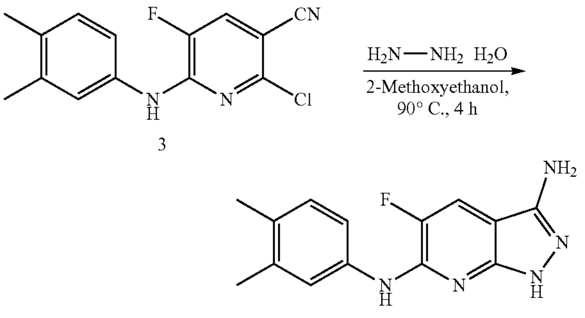

3

4

87 mg (0.316 mmol) of Compound 3 was dissolved in 1.578 mL (0.2 M) of 2-methoxyethanol and then 0.306 mL (6.31 mmol, 20 eq.) of hydrazine monohydrate was added dropwise to the resulting solution. The temperature was elevated to 90° C. and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (53.2 mg, 62%) as a white solid.

$^1$H NMR (400 MHz, DMSO-d6) δ=9.16 (br s, 1H), 7.83 (d, J=11.1 Hz, 1H), 7.57 (d, J=8.2 Hz, 1H), 7.55 (s, 1H), 7.09 (d, J=8.1 Hz, 1H), 2.21 (d, J=8.7 Hz, 6H).

Example 19: Preparation of 5-fluoro-N6-(5,6,7,8-tetrahydronaphthalen-1-yl)-1H-pyrazolo[3,4-b]pyridine-3,6-diamine The compound represented by the following formula was prepared:

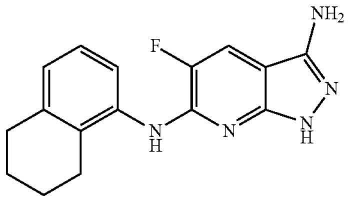 [SMILES: Nc1n[nH]c2nc(Nc3cccc4c3CCCC4)c(F)cc12]

Step 1

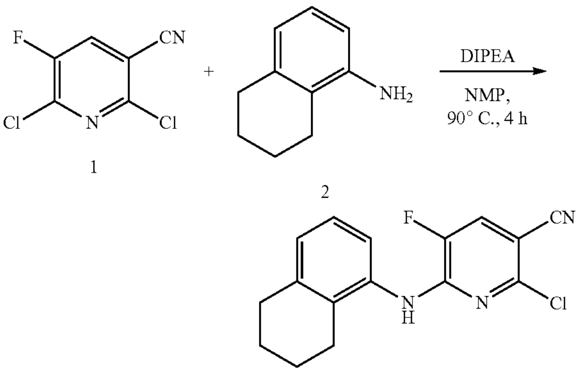

1

2

3

70 mg (0.367 mmol) of Compound 1 and 70.1 mg (0.476 mmol, 1.3 eq.) of Compound 2 were dissolved in 1.466 mL (0.25 M) of N-methylpyrrolidone (NMP), and then 0.192 mL (1.100 mmol, 3 eq.) of N,N-diisopropylethylamine was added dropwise to the resulting solution. The temperature was elevated to 90° C. and then the reaction solution was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (68 mg, 62%) as a yellow solid.

Step 2

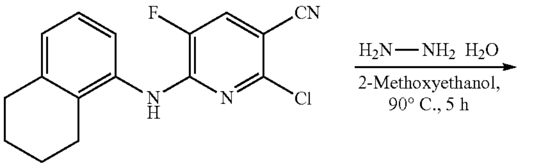

3

-continued

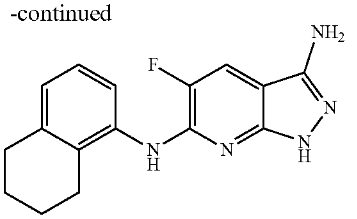

4

59.1 mg (0.196 mmol) of Compound 3 was dissolved in 0.979 mL (0.2 M) of 2-methoxyethanol, and then 0.19 mL (3.92 mmol, 20 eq.) of hydrazine monohydrate was added dropwise to the resulting solution. The temperature was elevated to 90° C. and then the resulting mixture was stirred for 5 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (40 mg, 69%) as a white solid.

$^1$H NMR (400 MHz, DMSO-d6) δ=8.87 (br s, 1H), 7.82 (d, J=10.9 Hz, 1H), 7.19-7.10 (m, 2H), 7.00 (d, J=7.1 Hz, 1H), 2.77 (br s, 2H), 2.59-2.53 (m, 2H), 1.74-1.65 (m, 4H).

Example 20: Preparation of 5-fluoro-N6-(4,5,6,7-tetrahydropyrazolo[1,5-a]pyridin-3-yl)-1H-pyrazolo[3,4-b]pyridine-3,6-diamine The compound represented by the following formula was prepared:

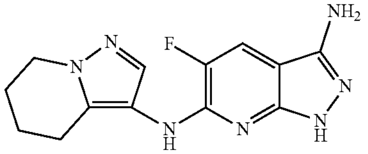 [SMILES: Nc1n[nH]c2nc(Nc3cnn4c3CCCC4)c(F)cc12]

Step 1

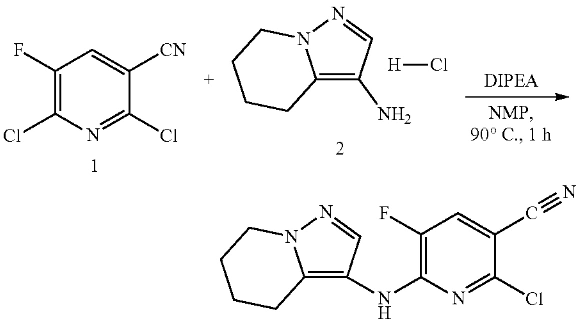

1

2

3

70 mg (0.367 mmol) of Compound 1 and 83 mg (0.476 mmol, 1.3 eq.) of Compound 2 were dissolved in 1.466 mL (0.25 M) of N-methylpyrrolidone (NMP), and then 0.192 mL (1.100 mmol, 3 eq.) of N,N-diisopropylethylamine was added dropwise to the resulting solution. The temperature was elevated to 90° C. and then the reaction solution was stirred for 1 hour.

After completion of the reaction was detected, the organic layer was separated using $H_2O$ and ethyl acetate, dried over $MgSO_4$, filtered, and further dried under reduced pressure. The obtained residue was crystallized using dichloromethane and hexane and then filtered to obtain the target Compound 3 (82 mg, 77%) as a light brown solid.

Step 2

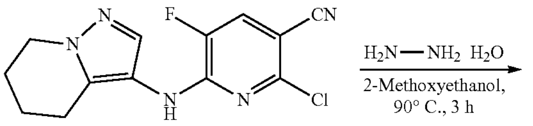

3

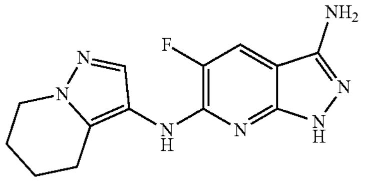

4

70.3 mg (0.241 mmol) of Compound 3 was dissolved in 1.205 mL (0.2 M) of 2-methoxyethanol, and then 0.234 mL (4.82 mmol, 20 eq.) of hydrazine monohydrate was added dropwise to the resulting solution. The temperature was elevated to 90° C. and then the resulting mixture was stirred for 3 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (58.9 mg, 85%) as a light yellow solid.

$^1H$ NMR (400 MHz, DMSO-d6) δ=8.89 (br d, J=2.7 Hz, 1H), 7.80 (d, J=10.9 Hz, 1H), 7.49 (s, 1H), 4.06 (t, J=6.1 Hz, 2H), 2.63 (t, J=6.4 Hz, 2H), 1.96 (br d, J=3.4 Hz, 2H), 1.77 (br d, J=5.9 Hz, 2H).

Example 21: Preparation of N6-(2,3-dihydro-1H-inden-4-yl)-5-propyl-1H-pyrazolo[3,4-b]pyridine-3,6-diamine The compound represented by the following formula was prepared:

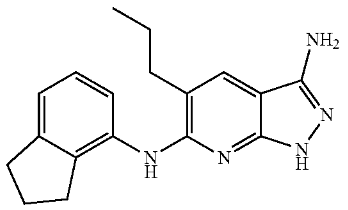 [SMILES: CCCc1cc2c(N)n[nH]c2nc1Nc1cccc2c1CCC2]

Step 1

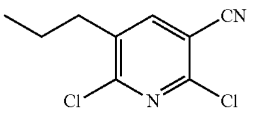

+

1

-continued

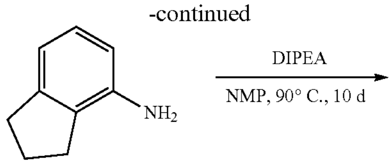

2

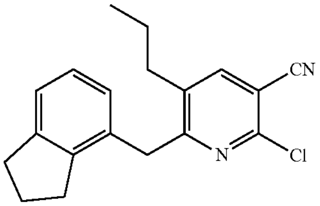

3

60 mg (0.279 mmol) of Compound 1 and 48.3 mg (0.363 mmol, 1.3 eq.) of Compound 2 were dissolved in 1.116 mL (0.25 M) of N-methylpyrrolidone (NMP), and then 0.146 mL (0.837 mmol, 3 eq.) of N,N-diisopropylethylamine was added dropwise to the resulting solution. The temperature was elevated to 90° C. and then the reaction solution was stirred for 10 days.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (46.3 mg, 53%) as a yellow solid.

Step 2

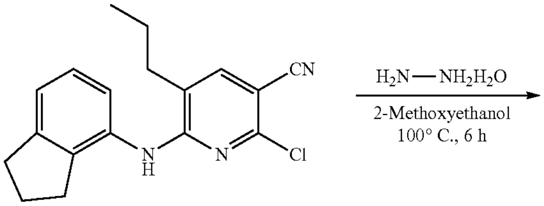

3

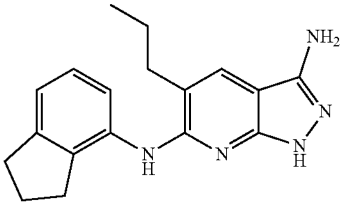

4

46 mg (0.148 mmol) of Compound 3 was dissolved in 0.738 mL (0.2 M) of 2-methoxyethanol, and then 0.143 mL (2.95 mmol, 20 eq.) of hydrazine monohydrate was added dropwise to the resulting solution. The temperature was elevated to 100° C. and then the resulting solution was stirred for 6 hours.

After completion of the reaction was detected, the organic layer was separated using $H_2O$ and ethyl acetate, dried over $MgSO_4$, filtered, and further dried under reduced pressure. The obtained residue was purified by reverse column chromatography to obtain the target Compound 4 (10.5 mg, 23%)) as a yellow solid.

$^1$H NMR (400 MHz, DMSO-d6) δ=8.45 (br s, 1H), 7.85 (s, 1H), 7.21-7.08 (m, 3H), 2.92 (t, J=7.4 Hz, 2H), 2.67 (td, J=7.4, 11.8 Hz, 4H), 1.98 (quin, J=7.4 Hz, 2H), 1.68 (sxt, J=7.4 Hz, 2H), 1.01 (t, J=7.3 Hz, 3H).

Example 22: Preparation of 5-chloro-N6-(2,3-dihydro-1H-inden-4-yl)-4-propyl-1H-pyrazolo[3,4-b]pyridine-3,6-diamine The compound represented by the following formula was prepared:

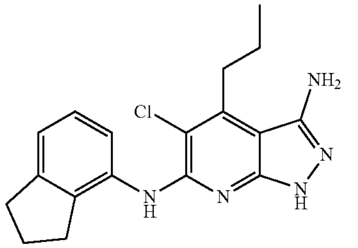 [SMILES: CCCc1c(Cl)c(Nc2cccc3c2CCC3)nc2[nH]nc(N)c12]

Step 1

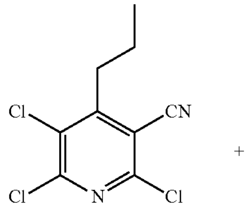

1

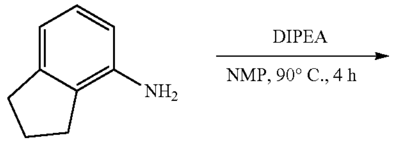

2

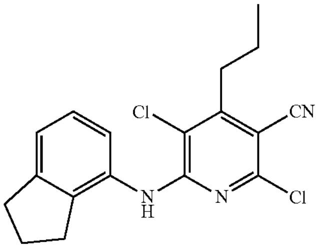

3

70 mg (0.281 mmol) of Compound 1 and 44.8 mg (0.337 mmol, 1.3 eq.) of Compound 2 were dissolved in 1.122 mL (0.25 M) of N-methylpyrrolidone (NMP) and then 0.147 mL (0.842 mL, 3 eq.) of N,N-diisopropylethylamine was added dropwise to the resulting solution. The temperature was elevated to 90° C. and then the reaction solution was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (67 mg, 69%) as a yellow solid.

Step 2

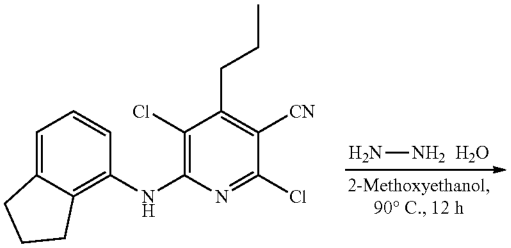

3

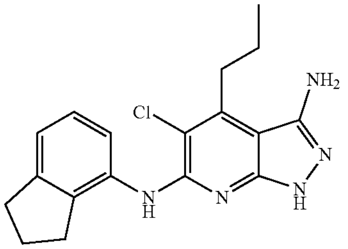

4

65 mg (0.188 mmol) of Compound 3 was dissolved in 0.939 mL (0.2 M) of 2-methoxyethanol, and then 0.182 mL (3.75 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (16.8 mg, 26%) as a white solid.

$^1$H NMR (400 MHz, DMSO-d6) δ=11.63 (s, 1H), 7.90 (s, 1H), 7.55 (d, J=7.9 Hz, 1H), 7.13 (t, J=7.6 Hz, 1H), 7.01 (d, J=7.3 Hz, 1H), 4.92 (s, 2H), 3.05-2.97 (m, 2H), 2.91 (t, J=7.5 Hz, 2H), 2.75 (t, J=7.4 Hz, 211), 2.00 (quin, J=7.4 Hz, 2H), 1.67 (sxt, J=7.6 Hz, 2H), 1.02 (t, J=7.3 Hz, 3H).

Example 23: Preparation of N6-(2,3-dihydro-1H-inden-4-yl)-5-phenyl-1H-pyrazolo[3,4-b]pyridine-3,6-diamine The compound represented by the following formula was prepared:

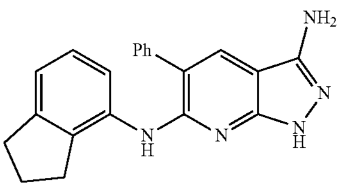 [SMILES: Nc1n[nH]c2nc(Nc3cccc4c3CCC4)c(-c3ccccc3)cc12]

Step 1

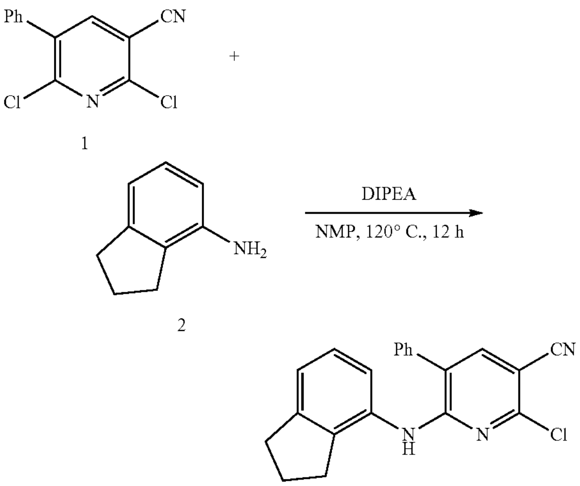

1 2 3

60 mg (0.241 mmol) of Compound 1 and 41.7 mg (0.313 mmol, 1.3 eq.) of Compound 2 were dissolved in 0.963 mL (0.25 M) of N-methylpyrrolidone (NMP) and then 0.126 mL (0.723 mmol, 3 eq.) of N,N-diisopropylethylamine was added dropwise to the resulting solution. The temperature was elevated to 120° C. and then the reaction solution was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (41 mg, 49%) as a yellow solid.

Step 2

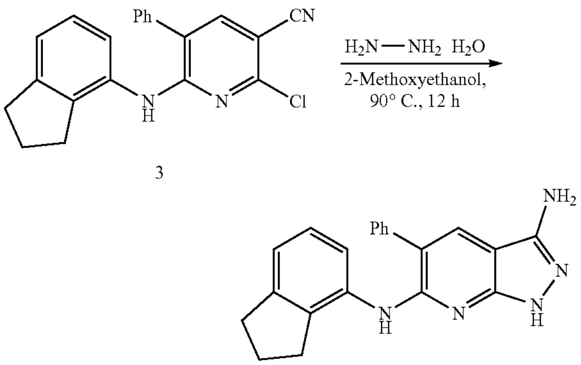

3 4

41 mg (0.119 mmol) of Compound 3 was dissolved in 0.593 mL (0.2 M) of 2-methoxyethanol, and then 0.115 mL (2.371 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by reverse column chromatography to obtain the target Compound 4 (4.1 mg, 10%) as a light brown solid.

$^1$H NMR (400 MHz, DMSO-d6) δ=7.90 (br s, 1H), 7.78-7.68 (m, 1H), 7.57 (br d, J=2.1 Hz, 2H), 7.56 (s, 2H), 7.49 (br dd, J=2.4, 5.3 Hz, 1H), 7.12 (t, J=7.7 Hz, 1H), 6.97 (br d, J=7.2 Hz, 1H), 2.88 (s, 2H), 2.58-2.53 (m, 2H), 1.97 (s, 2H).

Example 24: Preparation of 5-fluoro-N6-(naphthalen-1-yl)-1H-pyrazolo[3,4-b]pyridine-3,6-diamine The compound represented by the following formula was prepared:

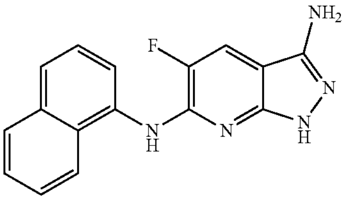 [SMILES: Nc1n[nH]c2nc(Nc3cccc4ccccc34)c(F)cc12]

2,6-dichloro-5-fluoro-3-carbonitril pyridine (1.0 g, 5.24 mmol, 1.0 eq.) and 1-naphthalamine (0.788 g, 5.5 mmol, 1.05 eq.) were dissolved in NMP. Then, DIPEA (1.369 ml, 10.59 mmol, 1.5 eq.) was added to the resulting solution, followed by stirring at 100 to 110° C. for 15 hours. Then, $NH_2NH_2$ (1.271 ml, 25.39 mmol, 5 eq.) was added to the resulting solution, followed by stirring at 25° C. for 2 hours. After completion of the reaction, the reaction solution was cooled to 25 to 30° C., and 10 mL of $H_2O$ was added dropwise thereto. 10 mL of EA was added to the reaction solution containing a solid precipitate, and layer separation was induced. The organic layer was dehydrated using $MgSO_4$ and concentrated. The concentrated residue was crystallized with 4 mL of THF and 4 mL of MC. The obtained crystals were purified using column chromatography to obtain 201 mg (98.88%) of the target compound.

$^1$H NMR (500 MHz, DMSO-d6) δ=11.34 (s, 1H), 8.92 (s, 1H), 7.95 (t, J=1.8 Hz, 1H), 7.94 (t, J=1.9 Hz, 1H), 7.81 (s, 1H), 7.79 (d, J=4.6 Hz, 1H), 7.62 (d, J=7.1 Hz, 1H), 7.57-7.45 (m, 3H), 5.20 (s, 2H).

Example 25: Preparation of N6-(1-naphthyl)-4-(trifluoromethyl)-1H-pyrazolo[3,4-b]pyridine-3,6-diamine The compound represented by the following formula was prepared:

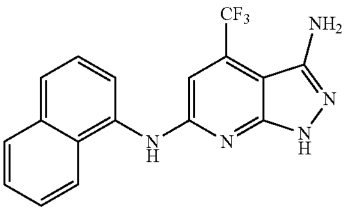 [SMILES: Nc1n[nH]c2nc(Nc3cccc4ccccc34)cc(C(F)(F)F)c12]

2,6-dichloro-4-(trifluoromethyl)pyridine-3-carbonitrile (1 g, 4.15 mmol, 1.0 eq.) and 1-naphthalamine (0.624 g, 4.36 mmol, 1.05 eq.) were dissolved in NMP. Then, DIPEA (1.369 ml, 10.59 mmol, 1.5 eq.) was added to the resulting solution, followed by stirring at 100 to 110° C. for 15 hours. Then, $NH_2NH_2$ (1.271 ml, 25.39 mmol, 5 eq.) was added to the resulting solution, followed by stirring at 25° C. for 2 hours. After completion of the reaction, the reaction solution was cooled to 25 to 30° C., and 10 mL of $H_2O$ was added dropwise thereto. 10 mL of EA was added to the reaction solution containing a solid precipitate and layer separation was induced. The organic layer was dehydrated using $MgSO_4$ and concentrated. The concentrated residue was crystallized with 4 mL of THF and 4 mL of MC. The obtained crystals were purified using column chromatography to obtain 198 mg (98.98%) of the target compound.

$^1$H NMR (500 MHz, DMSO-d6) δ=12.07 (s, 1H), 8.85 (s, 1H), 7.78 (d, J=10.0 Hz, 1H), 7.12 (t, J=10.0 Hz, 1H), 7.03 (s, 1H), 6.96 (d, J=10.0 Hz, 2H), 4.72 (s, 2H), 2.90-2.83 (m, 4H), 2.02-1.99 (m, 2H).

Example 26: Preparation of N6-indan-4-yl-4-(trifluoromethyl)-1H-pyrazolo[3,4-b]pyridine-3,6-diamine The compound represented by the following formula was prepared:

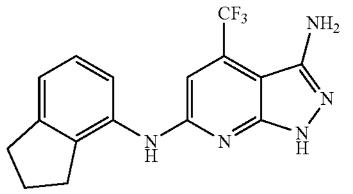 [SMILES: Nc1n[nH]c2nc(Nc3cccc4c3CCC4)cc(C(F)(F)F)c12]

2,6-dichloro-4-(trifluoromethyl)pyridine-3-carbonitrile (1 g, 4.15 mmol, 1.0 eq.) and 4-aminoindane (0.581 g, 4.36 mmol, 1.05 eq.) were dissolved in NMP. Then, DIPEA (1.369 ml, 10.59 mmol, 1.5 eq.) was added to the resulting solution, followed by stirring at 100 to 110° C. for 15 hours. Then, $NH_2NH_2$ (1.271 ml, 25.39 mmol, 5 eq.) was added to the resulting solution, followed by stirring at 25° C. for 2 hours. After completion of the reaction, the reaction solution was cooled to 25 to 30° C. and 10 mL of $H_2O$ was added dropwise thereto. 10 mL of EA was added to the reaction solution containing a solid precipitate and layer separation was induced. The organic layer was dehydrated using $MgSO_4$ and concentrated. The concentrated residue was crystallized in 4 mL of THF and 4 mL of MC. The obtained crystals were purified using column chromatography to obtain 1.34 g (99.66%) of the target compound.

$^1$H NMR (500 MHz, DMSO-d6) δ=12.04 (s, 1H), 9.48 (s, 1H), 8.14-8.12 (m, 1H), 7.97-7.93 (m, 1H), 7.93-7.92 (m, 1H), 7.72 (d, J=10.0 Hz, 1H), 7.53-7.50 (m, 3H), 7.08 (s, 1H), 4.72 (s, 2H).

Example 27: Preparation of 5-fluoro-N6-(6-methyl-2,3-dihydro-1H-inden-4-yl)-1H-pyrazolo[3,4-b]pyridine-3,6-diamine The compound represented by the following formula was prepared:

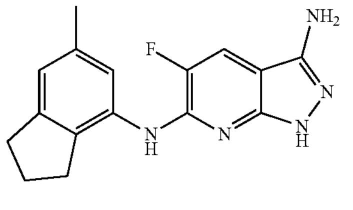 [SMILES: Cc1cc2c(c(Nc3nc4[nH]nc(N)c4cc3F)c1)CCC2]

Step 1

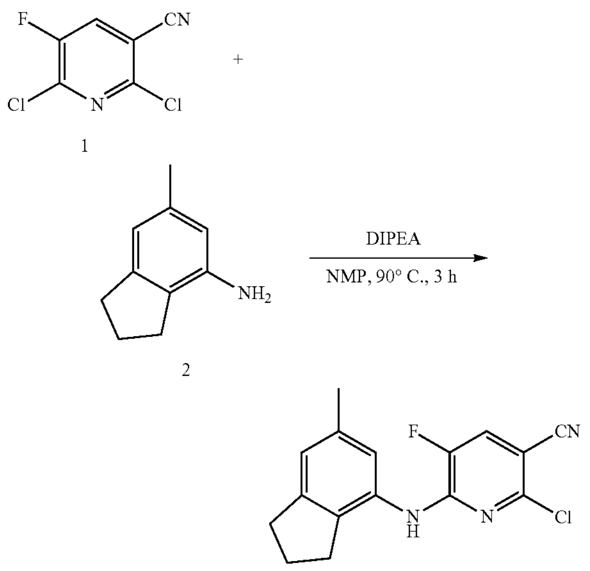

1

2

3

80 mg (0.419 mmol) of Compound 1 and 67.8 mg (0.461 mmol, 1.1 eq.) of Compound 2 were dissolved in 1.675 mL (0.25 M) of N-methylpyrrolidone (NMP), and then 0.219 mL (1.257 mmol, 3 eq.) of N,N-diisopropylethylamine was added dropwise to the resulting solution. The temperature was elevated to 90° C. and then the reaction solution was stirred for 3 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (86 mg, 68%) as a light yellow solid.

Step 2

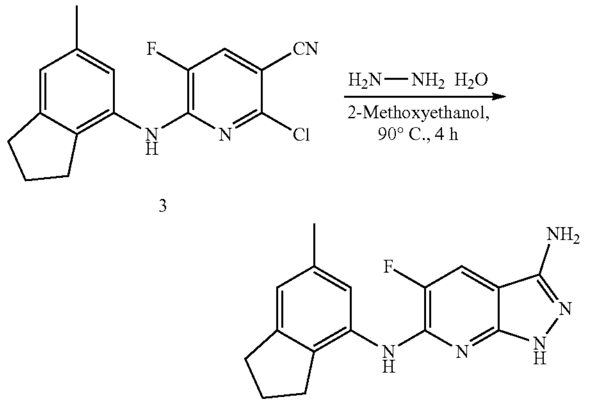

3

4

76 mg (0.252 mmol) of Compound 3 was dissolved in 1.259 mL (0.2 M) of 2-methoxyethanol, and then 0.244 mL (5.04 mmol, 20 eq.) of hydrazine monohydrate was added dropwise to the resulting solution. The temperature was elevated to 90° C. and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was crystallized using diethyl ether and filtered to obtain the target Compound 4 (39 mg, 52%) as a light yellow solid.

$^1$H NMR (400 MHz, DMSO-d6) δ=11.40 (s, 1H), 8.26 (s, 1H), 7.71 (d, J=11.2 Hz, 1H), 7.14 (s, 1H), 6.85 (s, 1H), 5.19 (s, 2H), 2.85 (t, J=7.3 Hz, 2H), 2.69 (t, J=7.2 Hz, 2H), 2.27 (s, 3H), 1.96 (quin, J=7.4 Hz, 2H).

Example 28: Preparation of N6-(2,3-dihydro-1H-inden-4-yl)-5-fluoro-N6-methyl-1H-pyrazolo[3,4-b]pyridine-3,6-diamine The compound represented by the following formula was prepared:

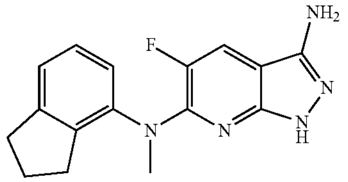 [SMILES: CN(c1cccc2c1CCC2)c1nc2[nH]nc(N)c2cc1F]

Step 1

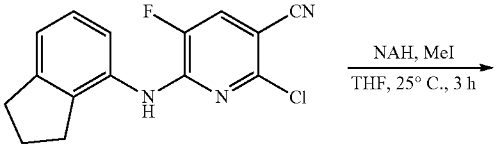

3

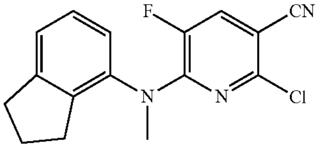

4

100 mg (0.348 mmol) of Compound 3 was dissolved in 1.159 mL (0.3 M) of tetrahydrofuran (THF) and then the resulting solution was cooled to 0° C. 18.07 mg (0.452 mmol, 1.3 eq.) of sodium hydride (NaH) was slowly added dropwise thereto, followed by stirring at the same temperature for 30 minutes. 32.6 μL (0.521 mmol, 1.5 eq.) of methyl iodide (Mel) was slowly added dropwise at the same temperature, and then the reaction solution was warmed to room temperature and stirred for 3 hours.

After completion of the reaction was detected, the organic layer was separated using $H_2O$ and dichloromethane, dried over $MgSO_4$, filtered, and dried under reduced pressure. The obtained residue, the target Compound 3 (101 mg, 96%), was used for the subsequent reaction without further purification.

Step 2

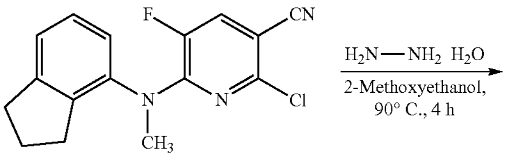

4

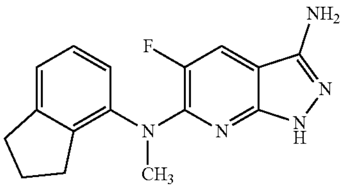

5

90 mg (0.298 mmol) of Compound 4 was dissolved in 1.491 mL (0.2 M) of 2-methoxyethanol, and then 0.289 mL (5.97 mmol, 20 eq.) of hydrazine monohydrate was added dropwise to the resulting solution. The temperature was elevated to 90° C., and then the resulting mixture was stirred for 4 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 5 (85.1 mg, 96%) as a light yellow solid.

$^1$H NMR (400 MHz, DMSO-d6) δ=7.72 (d, J=12.3 Hz, 1H), 7.15 (s, 1H), 7.16 (d, J=6.1 Hz, 1H), 6.98 (br d, J=6.4 Hz, 1H), 3.34 (s, 3H), 2.90 (t, J=7.4 Hz, 2H), 2.58 (t, J=7.3 Hz, 2H), 1.98 (quin, J=7.5 Hz, 2H).

Example 29: Preparation of 5-fluoro-N6-(1,2,3,5,6,7-hexahydro-s-indacen-4-yl)-1H-pyrazolo[3,4-b]pyridine-3,6-diamine The compound represented b the following formula was prepared:

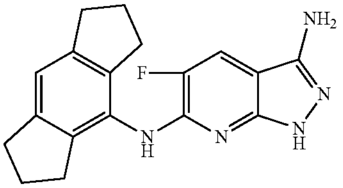 [SMILES: Nc1n[nH]c2nc(Nc3c4c(cc5c3CCC5)CCC4)c(F)cc12]

Step 1

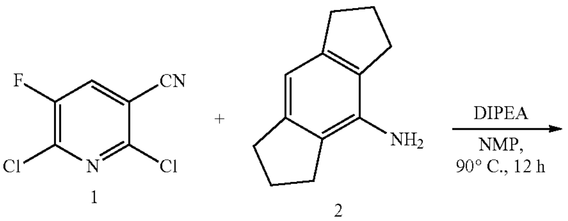

1 2

-continued

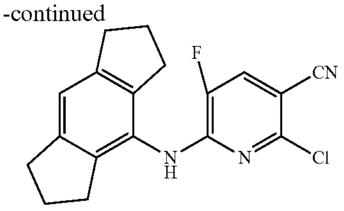

3

95 mg (0.497 mmol) of Compound 1 and 95 mg (0.547 mmol, 1.1 eq.) of Compound 2 were dissolved in 4.97 mL (0.1 M) of N-methylpyrrolidone (NMP), and then 0.261 mL (1.492 mmol, 3 eq.) of N,N-diisopropylethylamine was added dropwise to the resulting solution. The temperature was elevated to 90° C., and then the reaction solution was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (160 mg, 98%) as a dark red solid.

Step 2

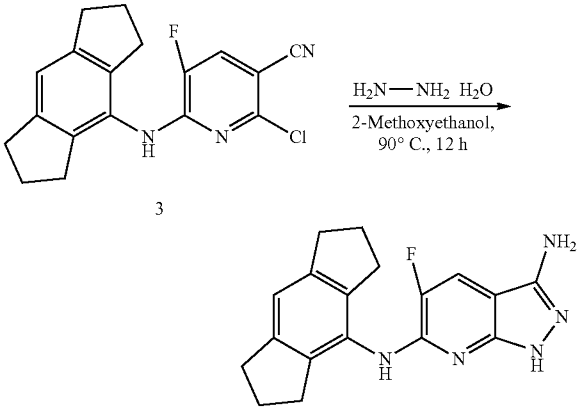

3

4

160 mg (0.488 mmol) of Compound 3 was dissolved in 4.88 mL (0.1 M) of 2-methoxyethanol, and then 0.474 mL (9.76 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (79 mg, 50%) as a light yellow solid.

$^1$H NMR (400 MHz, DMSO-d6) δ=9.08 (br s, 1H), 7.83 (d, J=11.0 Hz, 1H), 7.01 (s, 1H), 2.85 (br t, J=7.4 Hz, 4H), 2.67 (br t, J=7.2 Hz, 4H), 2.06-1.89 (m, 4H).

Example 30: Preparation of methyl 3-[(3-amino-5-fluoro-1H-pyrazolo[3,4-b]pyridin-6-yl)amino]-2-methyl-benzoate The compound represented by the following formula was prepared:

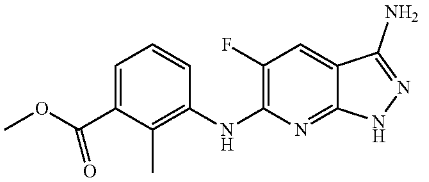 [SMILES: COC(=O)c1cccc(Nc2nc3[nH]nc(N)c3cc2F)c1C]

The titled target compound was obtained as a white solid (14.7 mg, 52%) in the same manner as in Example 3 using methyl-3-amino-2-methyl benzoate (190 mg, 1.15 mmol) and 2,6-dichloro-5-fluoro-3 carbonitrile pyridine (200 mg, 1.05 mmol).

$^1$H NMR (500 MHz, DMSO-d6) δ=11.38 (s, 1H), 8.54 (d, J=1.8 Hz, 1H), 7.73 (d, J=11.2 Hz, 1H), 7.59 (dd, J=7.8, 1.3 Hz, 1H), 7.55 (d, J=7.7 Hz, 1H), 7.31 (t, J=7.8 Hz, 1H), 5.17 (s, 2H), 3.84 (s, 3H), 2.30 (s, 3H).

Example 31: Preparation of 5-fluoro-N6-(7-methyl-1-naphthyl)-1H-pyrazolo[3,4-b]pyridine-3,6-diamine The compound represented by the following formula was prepared:

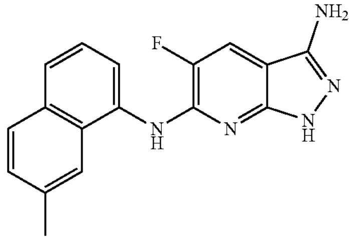 [SMILES: Cc1ccc2cccc(Nc3nc4[nH]nc(N)c4cc3F)c2c1]

The titled target compound was obtained as a white solid (32.4 mg, 65%) in the same manner as in Example 3 using 7-methylnapthalen-1-amine (99 mg, 0.6 mmol) and 2,6-dichloro-5-fluoro-3 carbonitrile pyridine (100 mg, 0.5 mmol).

$^1$H NMR (500 MHz, DMSO-d6) δ=11.32 (s, 1H), 8.81 (d, J=2.1 Hz, 1H), 7.85 (d, J=8.3 Hz, 1H), 7.79-7.71 (m, 3H), 7.57 (d, J=7.2 Hz, 1H), 7.44 (t, J=7.7 Hz, 1H), 7.36 (dd, J=8.4, 1.6 Hz, 1H), 5.17 (s, 2H), 2.42 (s, 3H).

Example 32: Preparation of N6-((2,3-dihydro-1H-inden-4-yl)methyl)-5-fluoro-1H-pyrazolo[3,4-b]pyridine-3,6-diamine The compound represented by the following formula was prepared:

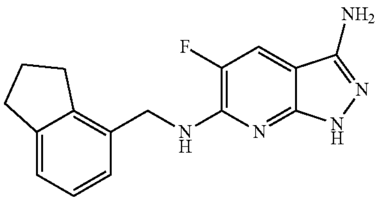 [SMILES: Nc1n[nH]c2nc(NCc3cccc4c3CCC4)c(F)cc12]

Step 1

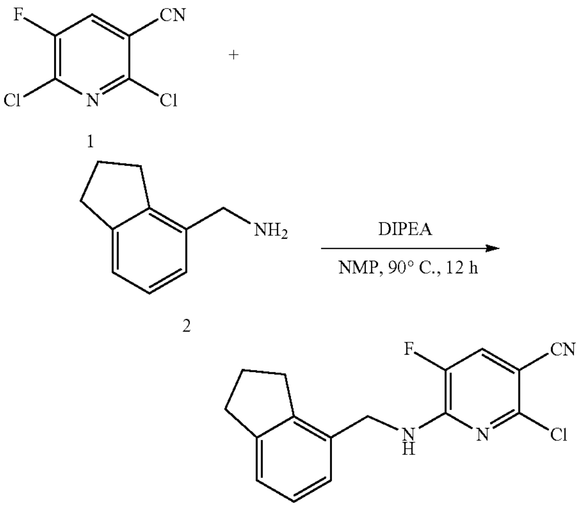

1 2 3

95 mg (0.497 mmol) of Compound 1 and 81 mg (0.547 mmol, 1.1 eq.) of Compound 2 were dissolved in 4.97 mL (0.1 M) of N-methylpyrrolidone (NMP), and then 0.261 mL (1.492 mmol, 3 eq.) of N,N-diisopropylethylamine was added dropwise to the resulting solution. The temperature was elevated to 90° C., and then the reaction solution was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (150 mg, 100%) as a yellow solid.

Step 2

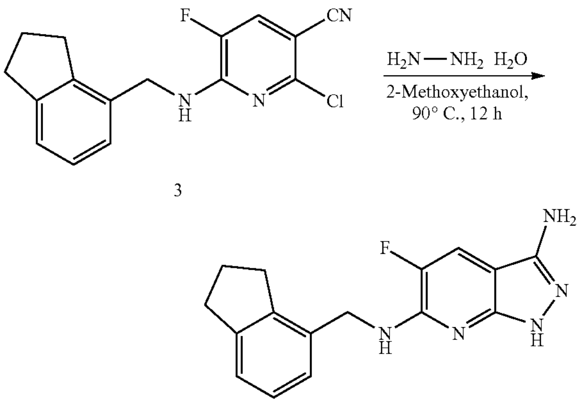

3 4

150 mg (0.497 mmol) of Compound 3 was dissolved in 4.97 mL (0.1 M) of 2-methoxyethanol, and then 0.482 mL (9.94 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was crystallized using dichloromethane and hexane, and then filtered to obtain the target Compound 4 (148 mg, 100%) as a white solid.

$^1$H NMR (400 MHz, DMSO-d6) δ=8.18 (br s, 1H), 7.75 (d, J=11.0 Hz, 1H), 7.12-7.00 (m, 3H), 4.55 (br d, J=5.6 Hz, 2H), 2.89 (td, J=7.5, 15.4 Hz, 4H), 2.04 (quin, J=7.3 Hz, 2H).

Example 33: Preparation of N6-(3-(dimethylamino)-2-methylphenyl)-5-fluoro-1H-pyrazolo[3,4-b]pyridine-3,6-diamine The compound represented by the following formula was prepared:

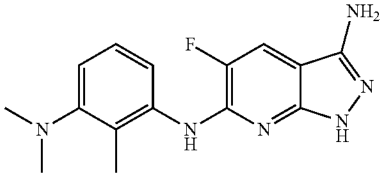 [SMILES: Cc1c(Nc2nc3[nH]nc(N)c3cc2F)cccc1N(C)C]

Step 1

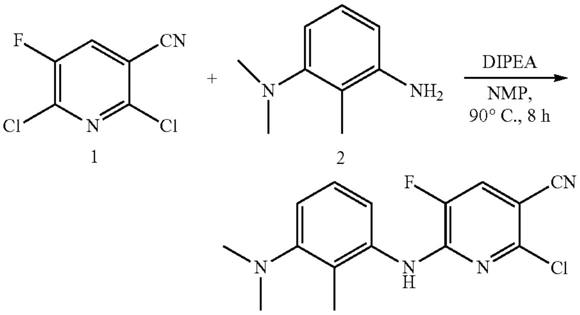

1 2 3

80 mg (0.419 mmol) of Compound 1 and 69.2 mg (0.461 mmol, 1.1 eq.) of Compound 2 were dissolved in 1.675 mL (0.25 M) of N-methylpyrrolidone (NMP), and then 0.219 mL (1.257 mmol, 3 eq.) of N,N-diisopropylethylamine was added dropwise to the resulting solution. The temperature was elevated to 90° C., and then the reaction solution was stirred for 8 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (76 mg, 60%) as a yellow solid.

Step 2

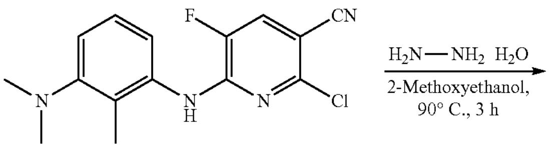

3

-continued

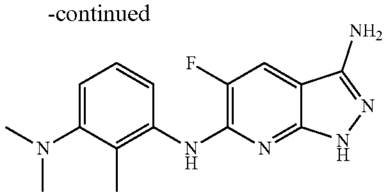

4

64.3 mg (0.211 mmol) of Compound 3 was dissolved in 1.055 mL (0.2 M) of 2-methoxyethanol, and then 0.205 mL (4.22 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 4 (36.5 mg, 58%) as a white solid.

$^1$H NMR (400 MHz, DMSO-d6) δ=11.35 (br s, 1H), 8.29 (br s, 1H), 7.70 (br d, J=11.4 Hz, 1H), 7.16-7.08 (m, 2H), 6.91 (br d, J=7.7 Hz, 1H), 5.18 (br s, 2H), 2.64 (s, 6H), 2.12 (s, 3H).

Example 34: Preparation of 5-fluoro-6-[(indan-4-ylamino)methyl]-1H-pyrazolo[3,4-b]pyridin-3-amine The compound represented b the following formula was prepared:

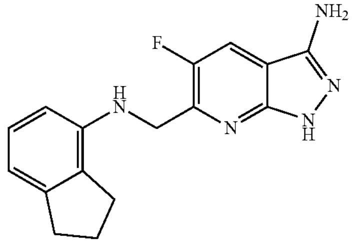 [SMILES: Nc1n[nH]c2nc(CNc3cccc4c3CCC4)c(F)cc12]

The titled target compound was obtained as a white solid (11.5 mg, 45%) in the same manner as in Example 3 using 4-aminoindane (21 ul, 0.17 mmol) and 6-(bromomethyl)-2-chloro-5-fluoro-pyridine-3-carbonitrile (40 mg, 0.16 mmol).

$^1$H NMR (500 MHz, DMSO-d6) δ=12.04 (s, 1H), 7.92 (d, J=10.0 Hz, 1H), 6.88 (t, J=7.7 Hz, 1H), 6.48 (d, J=7.4 Hz, 1H), 6.40 (d, J=8.0 Hz, 1H), 5.51 (m, 3H), 4.48 (dd, J=5.7, 1.7 Hz, 2H), 2.79 (t, J=7.5 Hz, 2H), 2.70 (t, J=7.4 Hz, 2H), 2.06-1.92 (m, 2H).

Example 35: Preparation of N6-(naphthalen-1-yl)-1H-pyrazolo[3,4-b]pyridine-3,6-diamine The compound represented by the following formula was prepared:

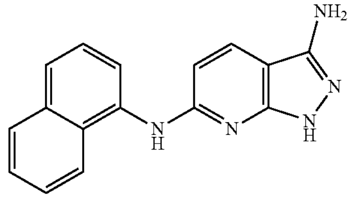 [SMILES: Nc1n[nH]c2nc(Nc3cccc4ccccc34)ccc12]

The target compound was obtained as a white solid (52 mg, 90%) in the same manner as in Example 3 using 173 mg (1.0 mmol) of 2,6-dichloro-3-cyanopyridine and 143 mg (1.1 mmol) of 1-naphthalamine.

$^1$H NMR (500 MHz, DMSO-d6) δ=11.31 (s, 1H), 8.99 (s, 1H), 8.16-8.10 (m, 1H), 7.92 (ddd, J=15.6, 7.2, 2.5 Hz, 2H), 7.80 (d, J=8.6 Hz, 1H), 7.65 (d, J=8.1 Hz, 1H), 7.52-7.43 (m, 4H), 6.58 (d, J=8.6 Hz, 1H), 5.21 (s, 2H).

Example 36: Preparation of N6-(1-naphthyl)-1H-pyrazolo[3,4-b]pyrazine-3,6-diamine The compound represented by the following formula was prepared:

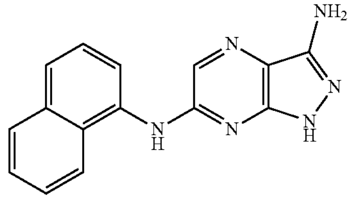 [SMILES: Nc1n[nH]c2nc(Nc3cccc4ccccc34)cnc12]

The titled target compound was obtained as a white solid (13 mg, 5%) in the same manner as in Example 3 using 1-Naphthylamine (181 mg, 1.26 mmol) and 3-5-dichloro-pyrazine-2-carbonitrile (200 mg, 1.14 mmol).

$^1$H NMR (500 MHz, DMSO-d6) δ=11.60 (s, 1H), 9.50 (s, 1H), 8.16-8.11 (m, 2H), 7.94 (m, 2H), 7.72 (d, J=8.2 Hz, 1H), 7.56-7.48 (m, 4H), 5.30 (s, 2H)

Example 37: Preparation of N6-(2,3-dihydro-1H-inden-4-yl)-4-methyl-1H-pyrazolo[3,4-b]pyridine-3,6-diamine The compound represented by the following formula was prepared:

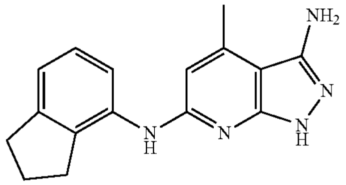 [SMILES: Cc1cc(Nc2cccc3c2CCC3)nc2[nH]nc(N)c12]

The target compound was obtained as a white solid (65 mg, 75%) in the same manner as in Example 3 using 187 mg (1.0 mmol) of 2,6-dichloro-3-cyano-4-methylpyridine and 146 mg (1.1 mmol) of 4-aminoindane.

$^1$H NMR (500 MHz, DMSO-d6) δ=11.36 (s, 1H), 8.19 (s, 1H), 7.72 (d, J=7.9 Hz, 1H), 7.05 (t, J=7.7 Hz, 1H), 6.87 (d,

J=7.3 Hz, 1H), 6.28 (d, J=1.1 Hz, 1H), 4.85 (s, 2H), 2.85 (t, J=7.5 Hz, 2H), 2.80 (t, J=7.4 Hz, 2H), 2.44 (s, 3H), 1.98 (q, J=7.5 Hz, 2H).

Example 38: Preparation of N6-(5,6,7,8-tetrahydronaphthalen-1-yl)-1H-pyrazolo[3,4-b]pyridine-3,6-diamine The compound represented by the following formula was prepared:

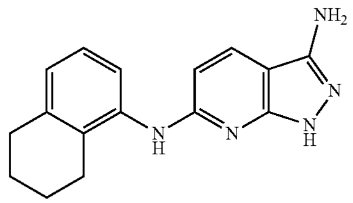 [SMILES: Nc1n[nH]c2nc(Nc3cccc4c3CCCC4)ccc12]

The target compound was obtained as a white solid (49 mg, 84%) in the same manner as in Example 3 using 173 mg (1.0 mmol) of 2,6-dichloro-3-cyanopyridine and 162 mg (1.1 mmol) of 5,6,7,8-tetrahydro-naphthalen-1-amine.

$^1$H NMR (500 MHz, DMSO-d6) δ=11.24 (s, 1H), 8.11 (s, 1H), 7.74-7.69 (m, 1H), 7.37 (d, J=7.9 Hz, 1H), 7.04 (t, J=7.7 Hz, 1H), 6.82 (d, J=7.6 Hz, 1H), 6.39-6.35 (m, 1H), 2.72 (s, 2H), 2.59 (s, 2H), 2.49 (p, J=1.9 Hz, 7H), 1.68 (q, J=3.4 Hz, 4H).

Example 39: Preparation of N6-[3-(difluoromethyl)-2-fluoro-phenyl]-1H-pyrazolo[3,4-b]pyrazine-3,6-diamine The compound represented by the following formula was prepared:

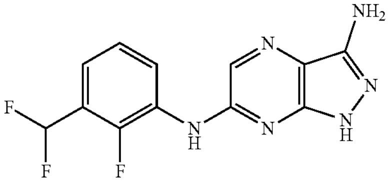 [SMILES: Nc1n[nH]c2nc(Nc3cccc(C(F)F)c3F)cnc12]

The titled target compound was obtained as a white solid (11.5 mg, 15%) in the same manner as in Example 3 using 2-(difluoromethyl)-2-fluoro-aniline (203 mg, 1.26 mmol) and 3-5-dichloropyrazine-2-carbonitrile (200 mg, 1.14 mmol).

$^1$H NMR (500 MHz, DMSO-d6) δ=11.80 (s, 1H), 9.52 (s, 1H), 8.44 (s, 1H), 8.16 (s, 1H), 7.42-7.21 (m, 3H), 5.38 (s, 2H).

Example 40: Preparation of 5-fluoro-N6-(spiro[4.5]decan-7-yl)-1H-pyrazolo[3,4-b]pyridine-3,6-diamine The compound represented b the following formula was prepared:

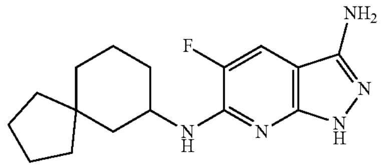 [SMILES: Nc1n[nH]c2nc(NC3CCCC4(CCCC4)C3)c(F)cc12]

The target compound was obtained as a white solid (130 mg, 78%) in the same manner as in Example 3 using 191 mg (1.0 mmol) of 2,6-dichloro-5-fluoro-3-cyanopyridine and 190 mg (1.1 mmol) of spiro[4,5]decan-7-amine HCl.

$^1$H NMR (500 MHz, DMSO-d6) δ=11.26 (s, 1H), 7.49 (dd, J=11.4, 0.7 Hz, 1H), 6.42 (dd, J=8.3, 2.0 Hz, 1H), 5.05 (s, 2H), 3.92 (dt, J=7.9, 3.8 Hz, 1H), 1.92 (d, J=12.2 Hz, 1H), 1.69-1.27 (m, 15H).

Example 41: Preparation of N6-(2,3-dihydro-1H-inden-1-yl)-5-fluoro-1H-pyrazolo[3,4-b]pyridine-3,6-diamine The compound represented by the following formula was prepared:

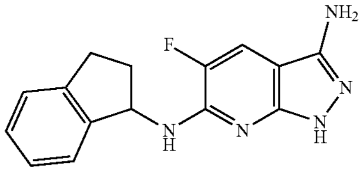 [SMILES: Nc1n[nH]c2nc(NC3CCc4ccccc43)c(F)cc12]

The target compound was obtained as a white solid (83 mg, 84%) in the same manner as in Example 3 using 191 mg (1.0 mmol) of 2,6-dichloro-5-fluoro-3-cyanopyridine and 147 mg (1.1 mmol) of 1-aminoindane.

$^1$H NMR (500 MHz, DMSO-d6) δ=11.34 (s, 1H), 7.58 (d, J=11.3 Hz, 1H), 7.28-7.19 (m, 3H), 7.22-7.15 (m, 2H), 7.16-7.07 (m, 3H), 5.66 (q, J=8.1 Hz, 1H), 5.14 (s, 2H), 3.02-2.93 (m, 1H), 2.87-2.78 (m, 1H), 2.49-2.42 (m, 3H), 2.07-1.96 (m, 1H).

Example 42: Preparation of 4,5-dichloro-N6-indan-4-yl-1H-pyrazolo[3,4-b]pyridine-3,6-diamine The compound represented by the following formula was prepared:

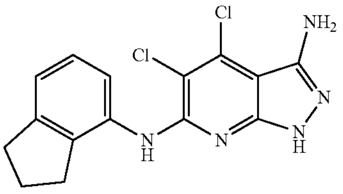 [SMILES: Nc1n[nH]c2nc(Nc3cccc4c3CCC4)c(Cl)c(Cl)c12]

Step 1

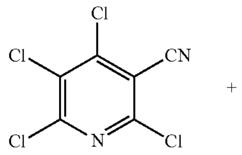

1

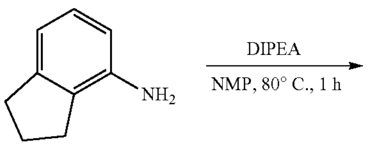

2

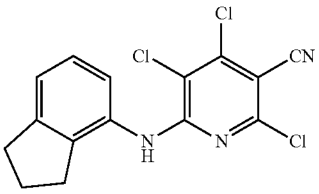

3

250 mg (1.034 mmol) of Compound 1 and 165 mg (1.240 mmol, 1.2 eq.) of Compound 2 were dissolved in 5.168 mL (0.2 M) of N-methylpyrrolidone (NMP), and then 0.542 mL (3.10 mmol, 3 eq.) of N,N-diisopropylethylamine was added dropwise to the resulting solution. The temperature was elevated to 80° C. and then the reaction solution was stirred for 1 hour.

After completion of the reaction was detected, the organic layer was separated using $H_2O$ and ethyl acetate, dried over $MgSO_4$, filtered, and further dried under reduced pressure. The obtained residue was crystallized using dichloromethane and hexane, and then filtered to obtain the target Compound 3 (227 mg, 65%) as a light yellow solid.

Step 2

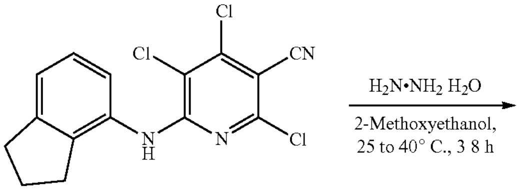

3

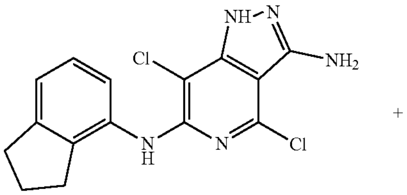

4

-continued

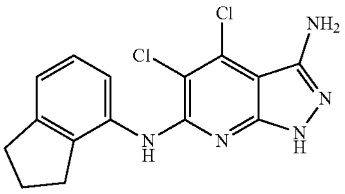

5

190 mg (0.561 mmol) of Compound 3 was dissolved in 2.806 mL (0.2 M) of 2-methoxyethanol, and then 0.544 mL (11.22 mmol, 20 eq.) of hydrazine monohydrate was added dropwise to the resulting solution. The temperature was elevated to 40° C., and then the resulting mixture was stirred for 150 minutes.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (70.3 mg, 38%) and the target Compound 5 (26.4 mg, 14%) as white solids.

$^1H$ NMR (400 MHz, DMSO-d6) δ=8.35 (br d, J=2.0 Hz, 1H), 7.33 (d, J=7.8 Hz, 1H), 7.15 (t, J=7.5 Hz, 1H), 7.10-7.05 (m, 1H), 2.91 (t, J=7.5 Hz, 2H), 2.72 (t, J=7.2 Hz, 2H), 1.99 (t, J=7.3 Hz, 2H).

Example 43: Preparation of 5-fluoro-N6-[(4-methoxyphenyl)methyl]-1H-pyrazolo[3,4-b]pyridine-3,6-diamine The compound represented by the following formula was prepared:

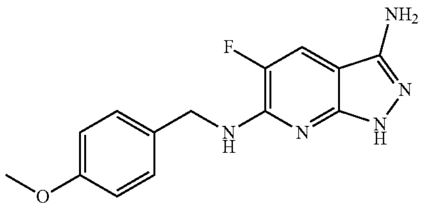 [SMILES: COc1ccc(CNc2nc3[nH]nc(N)c3cc2F)cc1]

Step 1

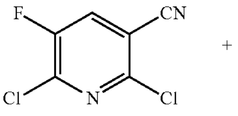

1

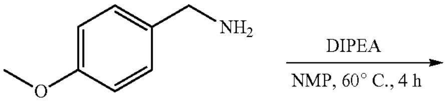

2

-continued

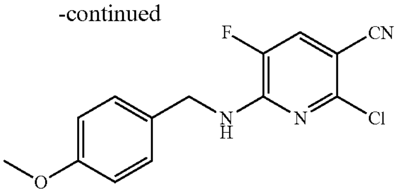

3

500 mg (2.62 mmol) of Compound 1 and 0.410 mL (3.14 mmol, 1.2 eq.) of Compound 2 were dissolved in 12.6 mL (0.2 M) of N-methylpyrrolidone (NMP), and then 1.372 mL (7.85 mmol, 3 eq.) of N,N-diisopropylethylamine was added dropwise to the resulting solution. The temperature was elevated to 60° C., and then the reaction solution was stirred for 4 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (688 mg, 90%) as a yellow solid.

Step 2

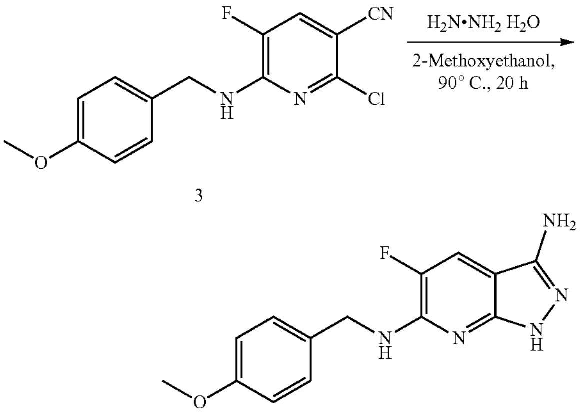

3

4

675 mg (2.314 mmol) of Compound 3 was dissolved in 11.6 mL (0.2 M) of 2-methoxyethanol, and then 2.245 mL (46.3 mmol, 20 eq.) of hydrazine monohydrate was added dropwise to the resulting solution. The temperature was elevated to 90° C. and then the resulting mixture was stirred for 20 hours.

After completion of the reaction was detected, the organic layer was separated using $H_2O$ and ethyl acetate, dried over $MgSO_4$, filtered, and further dried under reduced pressure. The obtained residue was crystallized using dichloromethane and hexane, and then filtered to obtain the target Compound 4 (490 mg, 74%) as a light yellow solid.

$^1$H NMR (400 MHz, DMSO-d6) δ=11.27 (s, 1H), 7.57 (d, J=11.4 Hz, 1H), 7.34-7.30 (m, 1H), 7.28-7.23 (m, 2H), 6.87 (s, 1H), 6.85 (s, 1H), 5.07 (s, 2H), 4.51 (d, J=6.1 Hz, 2H), 3.71 (s, 3H).

Example 44: Preparation of 5-fluoro-N6-norbornan-2-yl-1H-pyrazolo[3,4-b]pyridine-3,6-diamine The compound represented by the following formula was prepared:

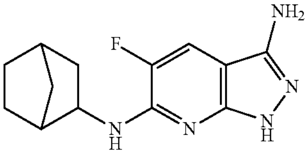 [SMILES: Nc1n[nH]c2nc(NC3CC4CCC3C4)c(F)cc12]

The target compound was obtained as a yellow solid (39 mg, 90%) in the same manner as in Example 3 using 191 mg (1.0 mmol) of 2,6-dichloro-5-fluoro-3-cyanopyridine and 148 mg (1 mmol) of 2-aminonorbornane.

$^1$H NMR (500 MHz, DMSO-d6) δ=11.29 (s, 1H), 7.52 (d, J=11.5 Hz, 1H), 6.63 (d, J=6.3 Hz, 1H), 5.07 (s, 2H), 4.16-4.07 (m, 1H), 2.58-2.53 (m, 1H), 2.20-2.13 (m, 1H), 1.96-1.85 (m, 1H), 1.60-1.50 (m, 1H), 1.49-1.33 (m, 3H), 1.31-1.27 (m, 1H), 1.27-1.19 (m, 2H).

Example 45: Preparation of N6-tetralin-5-yl-1H-pyrazolo[3,4-b]pyrazine-3,6-diamine The compound represented by the following formula was prepared:

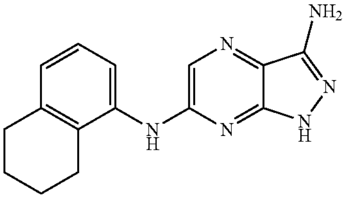 [SMILES: Nc1n[nH]c2nc(Nc3cccc4c3CCCC4)cnc12]

The target compound was obtained as a beige solid (149 mg, 92.7%) in the same manner as in Example 3 using 188 mg (1.08 mmol) of 3,5-dichloro-pyrazine-2-carbonitrile and 160 mg (1.08 mmol) of 5,6,7,8-hydro naphthylamine.

$^1$H NMR (500 MHz, DMSO-d6) δ=11.81 (s, 1H), 8.66 (s, 1H), 7.93 (s, 1H), 7.40 (d, J=8.0 Hz, 1H), 7.07 (t, J=7.8 Hz, 1H), 6.88 (d, J=7.7 Hz, 1H), 5.24 (s, 2H), 2.74 (t, J=6.3 Hz, 2H), 2.60 (t, J=6.2 Hz, 211), 1.71-1.67 (m, 4H).

Example 46: Preparation of 5-fluoro-N6-indolin-4-yl-1H-pyrazolo[3,4-b]pyridine-3,6-diamine The compound represented by the following formula was prepared:

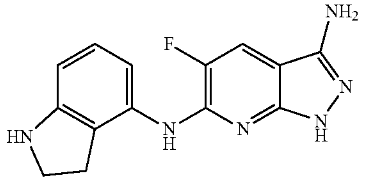 [SMILES: Nc1n[nH]c2nc(Nc3cccc4c3CCN4)c(F)cc12]

The titled target compound was obtained as a white solid (34.8 mg, 53%) in the same manner as in Step 1 and Step 2 of the reaction scheme in Example 3 using indolin-4-amine (76.7 mg, 0.57 mmol) and 2,6-dichloro-5-fluoro-3 carbonitrile pyridine (100 mg, 0.5 mmol).

$^1$H NMR (500 MHz, DMSO-d6) δ=11.65 (s, 1H), 8.31 (s, 1H), 7.86 (d, J=12.3 Hz, 1H), 6.79 (t, J=8.0 Hz, 1H), 6.55 (dd, J=8.0, 3.8 Hz, 1H), 6.17 (d, J=7.9 Hz, 1H), 5.34 (s, 2H), 4.90 (s, 2H), 4.11 (t, J=7.8 Hz, 2H), 2.87 (t, J=8.3 Hz, 2H).

Example 47: Preparation of 5-fluoro-N6-(1H-indol-7-yl)-1H-pyrazolo[3,4-b]pyridine-3,6-diamine The compound represented by the following formula was prepared:

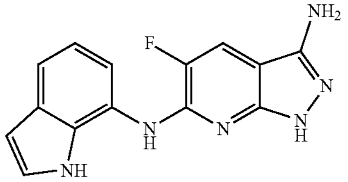 [SMILES: Nc1n[nH]c2nc(Nc3cccc4cc[nH]c34)c(F)cc12]

The target compound was obtained as a brown solid (50 mg, 58%) in the same manner as in Example 3 using 57 mg (0.3 mmol) of 2,6-dichloro-5-fluoro-3-cyanopyridine and 40 mg (0.3 mmol) of 7-aminoindole.

$^1$H NMR (500 MHz, DMSO-d6) δ=11.39 (s, 1H), 10.91 (s, 1H), 8.54 (d, J=2.3 Hz, 1H), 7.71 (d, J=11.4 Hz, 1H), 7.38 (d, J=7.5 Hz, 1H), 7.31 (d, J=7.8 Hz, 1H), 7.28-7.23 (m, 1H), 6.94 (t, J=7.7 Hz, 1H), 6.44-6.39 (m, 1H), 5.16 (s, 2H).

Example 48: Preparation of 5-fluoro-N6-(1H-inden-7-yl)-1H-pyrazolo[3,4-b]pyridine-3,6-diamine The compound represented by the following formula was prepared:

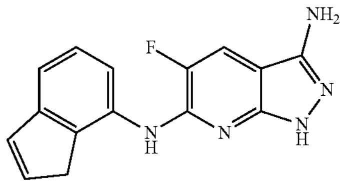 [SMILES: Nc1n[nH]c2nc(Nc3cccc4c3CC=C4)c(F)cc12]

The target compound was obtained as a brown solid (5 mg, 33%) in the same manner as in Example 3 using 60 mg (0.3 mmol) of 2,6-dichloro-5-fluoro-3-cyanopyridine and 43.3 mg (0.33 mmol) of 7-1H-inden-7-amine.

$^1$H NMR (500 MHz, Chloroform-d) 6=7.82 (dd, J=7.8 Hz, 1H), 7.49 (d, J=9.9 Hz, 1H), 7.38 (d, 1H), 7.31 (d, J=7.8 Hz, 1H), 6.96-6.88 (m, 3H), 6.62-6.58 (m, 1H), 3.38-3.34 (m, 2H).

Example 49: Preparation of 5-fluoro-N6-(6-methoxy-2,3-dihydro-1H-inden-4-yl)-1H-pyrazolo[3,4-b]pyridine-3,6-diamine The compound represented by the following formula was prepared:

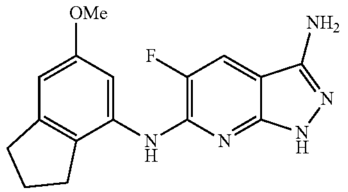 [SMILES: COc1cc2c(c(Nc3nc4[nH]nc(N)c4cc3F)c1)CCC2]

Step 1

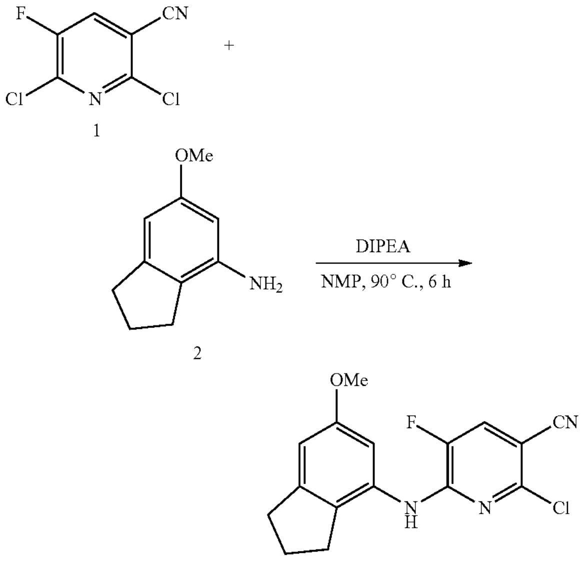

1

2

3

95 mg (0.50 mmol) of Compound 1 and 89 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (140 mg, 89%) as an orange solid.

Step 2

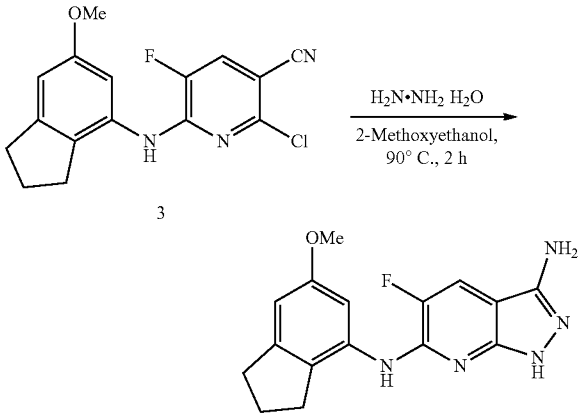

3

4

130 mg (0.41 mmol) of Compound 3 was dissolved in 2.05 mL (0.2 M) of 2-methoxyethanol, and then 0.40 mL (8.18 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (82 mg, 64%) as a white solid.

$^1H$ NMR (400 MHz, DMSO-d6) δ=8.08 (br d, J=8.4 Hz, 2H), 7.66 (br d, J=11.0 Hz, 1H), 7.05 (br s, 1H), 6.54 (br s, 1H), 5.16 (br s, 2H), 3.65 (s, 3H), 2.78 (br t, J=6.8 Hz, 2H), 2.66-2.57 (m, 2H), 1.90 (br t, J=6.5 Hz, 2H)

Example 50: Preparation of 5-fluoro-N6-(5-methoxy-2,3-dihydro-1H-inden-4-yl)-1H-pyrazolo[3,4-b]pyridine-3,6-diamine The compound represented by the following formula was prepared:

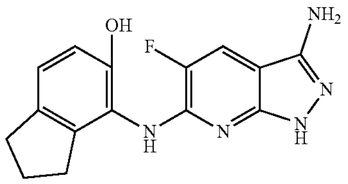 [SMILES: Nc1n[nH]c2nc(Nc3c(O)ccc4c3CCC4)c(F)cc12]

Step 1

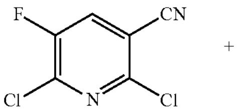

1

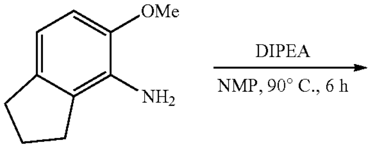

2

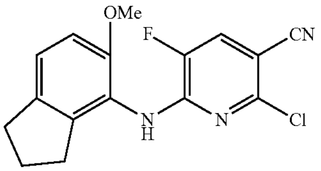

3

95 mg (0.50 mmol) of Compound 1 and 89 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered, and further dried under reduced pressure. The obtained residue was purified by column chromatography to obtain the target Compound 3 (130 mg, 82%) as an orange solid.

Step 2

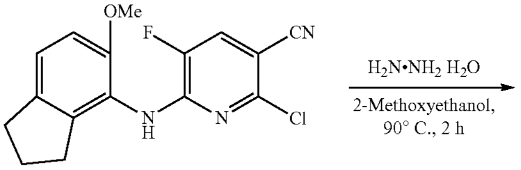

3

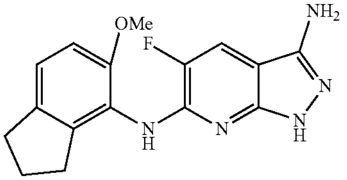

4

120 mg (0.38 mmol) of Compound 3 was dissolved in 1.89 mL (0.2 M) of 2-methoxyethanol, and then 0.37 mL (7.55 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered, and further dried under reduced pressure. The obtained residue was purified by reverse phase chromatography to obtain the target Compound 4 (110 mg, 93%) as a light yellow solid.

$^1H$ NMR (400 MHz, DMSO-d6) δ=11.25 (br s, 1H), 7.91 (br s, 1H), 7.62-7.54 (m, 1H), 6.99 (br d, J=7.9 Hz, 1H), 6.76 (br d, J=7.6 Hz, 1H), 5.08 (br s, 2H), 3.62 (br s, 3H), 2.77 (br s, 2H), 2.61 (br s, 2H), 1.96-1.80 (m, 2H)

Example 51: Preparation of N6-(1,1-dimethyl-2,3-dihydro-1H-inden-4-yl)-5-fluoro-1H-pyrazolo[3,4-b]pyridine-3,6-diamine The compound represented by the following formula was prepared:

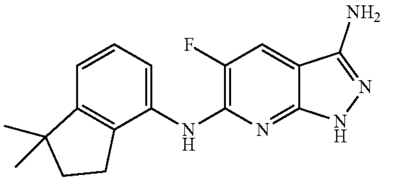 [SMILES: CC1(C)CCc2c(Nc3nc4[nH]nc(N)c4cc3F)cccc21]

Step 1

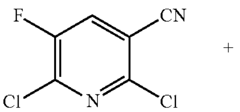

1

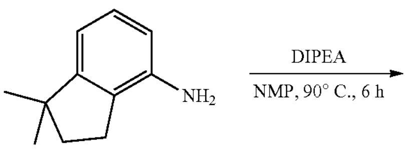

2

-continued

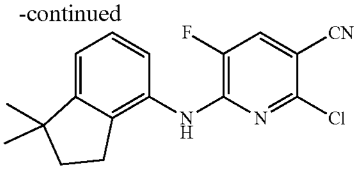

3

95 mg (0.50 mmol) of Compound 1 and 88 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (150 mg, 96%) as an orange solid.

Step 2

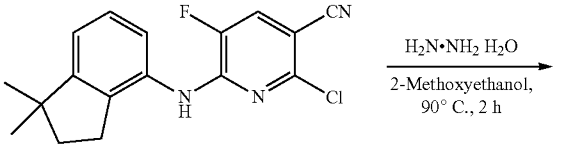

3

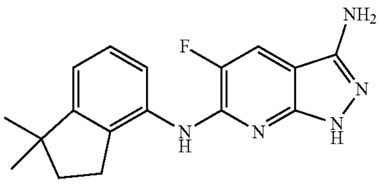

4

140 mg (0.44 mmol) of Compound 3 was dissolved in 2.22 mL (0.2 M) of 2-methoxyethanol, and then 0.43 mL (8.87 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (120 mg, 87%) as a white solid.

$^1H$ NMR (400 MHz, DMSO-d6) δ=8.14 (d, J=2.0 Hz, 1H), 8.08 (s, 1H), 7.65 (d, J=11.4 Hz, 1H), 7.36 (d, J=7.3 Hz, 1H), 7.09 (t, J=7.6 Hz, 1H), 6.88 (d, J=7.0 Hz, 1H), 5.14 (br s, 2H), 2.74-2.61 (m, 2H), 1.77 (t, J=7.2 Hz, 2H), 1.17 (s, 6H)

Example 52: Preparation of N6-(2,2-dimethyl-2,3-dihydro-1H-inden-4-yl)-5-fluoro-1H-pyrazolo[3,4-b]pyridine-3,6-diamine The compound represented by the following formula was prepared:

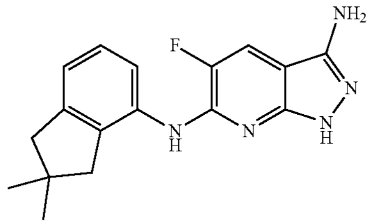 [SMILES: CC1(C)Cc2cccc(Nc3nc4[nH]nc(N)c4cc3F)c2C1]

Step 1

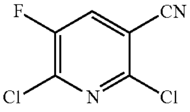

1

+

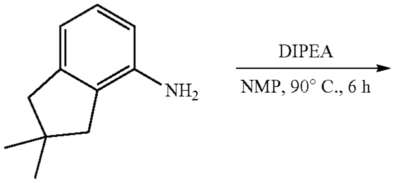

2

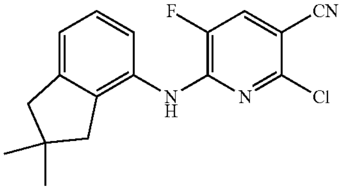

3

95 mg (0.50 mmol) of Compound 1 and 88 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (150 mg, 96%) as an orange solid.

Step 2

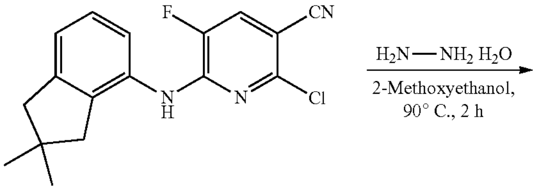

3

-continued

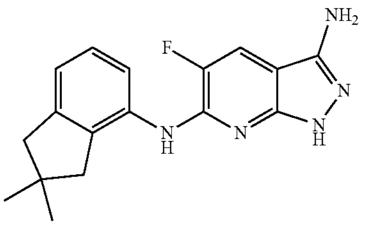

4

140 mg (0.44 mmol) of Compound 3 was dissolved in 2.22 mL (0.2 M) of 2-methoxyethanol, and then 0.43 mL (8.87 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (130 mg, 94%) as a white solid.

$^1H$ NMR (400 MHz, DMSO-d6) δ=8.28-8.24 (m, 1H), 8.07 (s, 1H), 7.64 (d, J=11.2 Hz, 1H), 7.25 (d, J=7.8 Hz, 1H), 7.03 (t, J=7.6 Hz, 1H), 6.89 (d, J=7.5 Hz, 1H), 5.15 (br s, 2H), 2.66-2.61 (m, 2H), 2.51-2.45 (m, 3H), 1.01 (s, 6H)

Example 53: Preparation of 4-((3-amino-5-fluoro-1H-pyrazolo[3,4-b]pyridin-6-yl)amino)isoindolin-1-one The compound represented b the following formula was prepared:

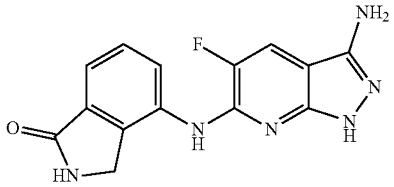 [SMILES: Nc1n[nH]c2nc(Nc3cccc4c3CNC4=O)c(F)cc12]

Step 1

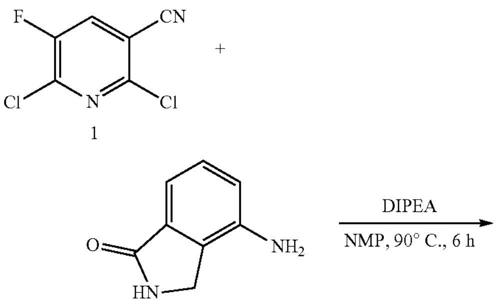

1

2

-continued

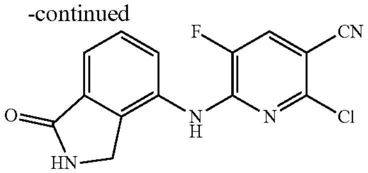

3

95 mg (0.50 mmol) of Compound 1 and 81 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C., and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (47 mg, 32%) as a light yellow solid.

Step 2

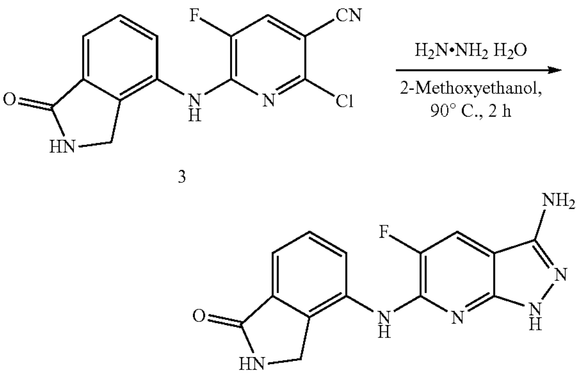

3

4

46 mg (0.15 mmol) of Compound 3 was dissolved in 0.76 mL (0.2 M) of 2-methoxyethanol, and then 0.15 mL (3.04 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (17 mg, 38%) as a light ivory solid.

$^1H$ NMR (400 MHz, DMSO-d6) δ=11.45 (br s, 1H), 8.78 (s, 1H), 8.49 (s, 1H), 7.72 (d, J=11.2 Hz, 1H), 7.68 (dd, J=1.3, 7.2 Hz, 1H), 7.43-7.36 (m, 2H), 5.22 (br s, 2H), 4.27 (s, 2H)

Example 54: Preparation of 4-((3-amino-5-fluoro-1H-pyrazolo[3,4-b]pyridin-6-yl)amino)indolin-2-one The compound represented by the following formula was prepared:

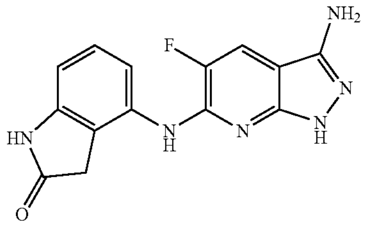 [SMILES: Nc1n[nH]c2nc(Nc3cccc4c3CC(=O)N4)c(F)cc12]

Step 1

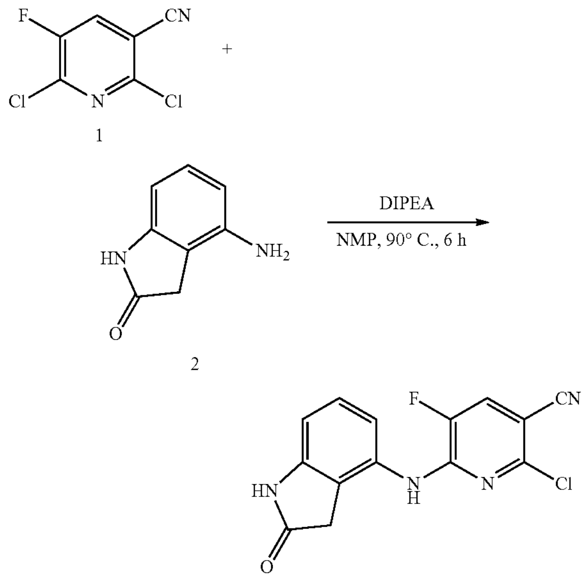

1
2
3

95 mg (0.50 mmol) of Compound 1 and 81 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (120 mg, 80%) as a brown solid.

Step 2

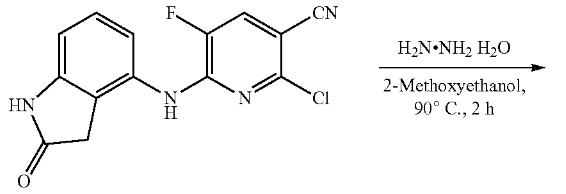

3

-continued

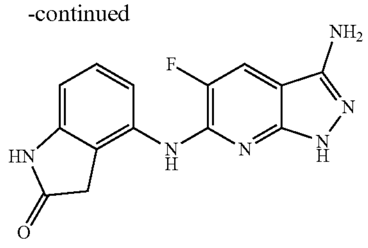

4

110 mg (0.36 mmol) of Compound 3 was dissolved in 1.82 mL (0.2 M) of 2-methoxyethanol, and then 0.35 mL (7.27 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (28 mg, 26%) as a light yellow solid.

$^1H$ NMR (400 MHz, DMSO-d6) δ=11.42 (br s, 1H), 10.34 (s, 1H), 8.55 (s, 1H), 7.69 (d, J=11.2 Hz, 1H), 7.14-7.05 (m, 2H), 6.53 (dd, J=2.9, 5.7 Hz, 1H), 5.21 (s, 2H), 3.36-3.35 (m, 2H)

Example 55: Preparation of 4-((3-amino-5-fluoro-1H-pyrazolo[3,4-b]pyridin-6-yl)amino)-1,3-dihydro-2H-benzo[d]imidazol-2-one The compound represented b the following formula was prepared:

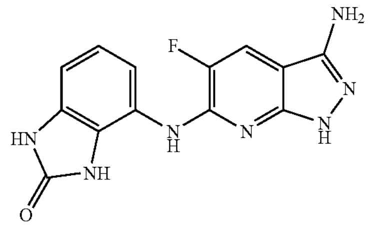 [SMILES: Nc1n[nH]c2nc(Nc3cccc4[nH]c(=O)[nH]c34)c(F)cc12]

Step 1

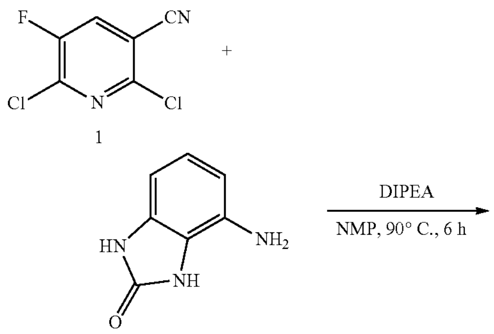

1
2

-continued

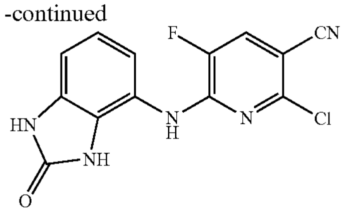

3

95 mg (0.50 mmol) of Compound 1 and 82 mg (0.55 mmol, 1.1 eq.) of Compound 2 were dissolved in 2.49 mL (0.2 M) of N-methylpyrrolidone (NMP), and then 0.26 mL (1.49 mmol, 3 eq.) of N,N-diisopropylethylamine was added dropwise to the resulting solution. The temperature was elevated to 90° C. and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (96 mg, 64%) as a yellow solid.

Step 2

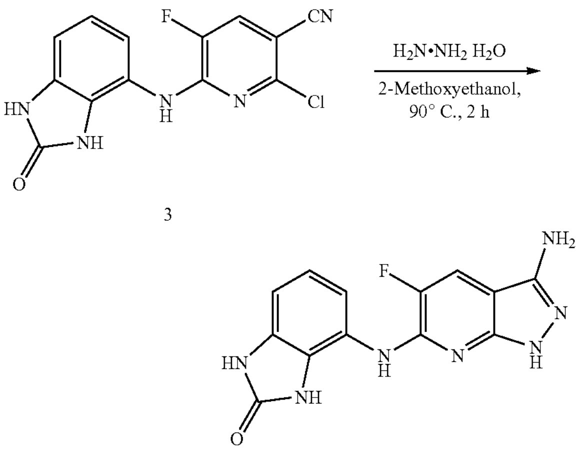

3

4

95 mg (0.31 mmol) of Compound 3 was dissolved in 1.56 mL (0.2 M) of 2-methoxyethanol, and then 0.30 mL (46.3 mmol, 20 eq.) of hydrazine monohydrate was added dropwise to the resulting solution. The temperature was elevated to 90° C. and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (48 mg, 52%) as a white solid.

$^1$H NMR (400 MHz, DMSO-d6) δ=11.36 (br s, 1H), 10.53 (br s, 1H), 10.36 (br s, 1H), 8.40 (br s, 1H), 7.64 (br d, J=11.1 Hz, 1H), 7.12 (br d, J=7.6 Hz, 1H), 6.83 (br t, J=7.6 Hz, 1H), 6.66 (br d, J=7.5 Hz, 1H), 5.13 (br s, 2H)

Example 56: Preparation of 7-[(3-amino-5-fluoro-1H-pyrazolo[3,4-b]pyridin-6-yl)amino]indan-5-ol The compound represented by the following formula was prepared:

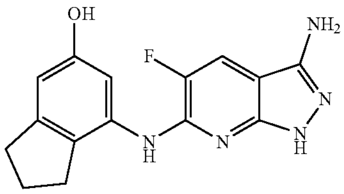 [SMILES: Nc1n[nH]c2nc(Nc3cc(O)cc4c3CCC4)c(F)cc12]

Step 1

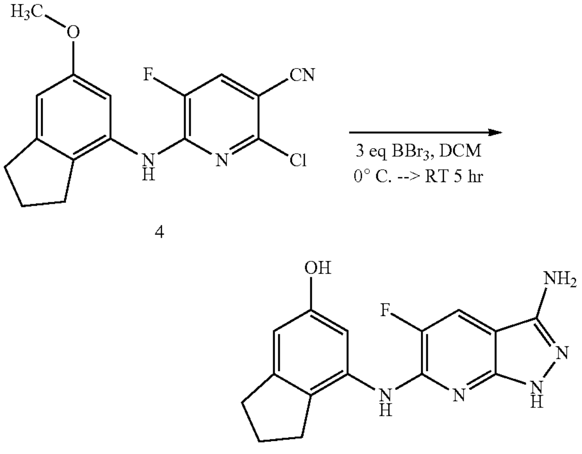

4

5

30 mg (0.09 mmol) of Compound 4 (Example 49) was dissolved in dichloromethane (DCM) and then 270 ul (0.27 mmol) of 1M $BBr_3$ dichloro solution was added at 0° C. dropwise to the resulting solution. The temperature was warmed to room temperature and then the resulting mixture was stirred for 5 hours. After completion of the reaction was detected, the solvent was dried under reduced pressure. The obtained residue was purified by reverse phase chromatography to obtain the target compound 5 (11.5 mg, 40%) as a white solid.

$^1$H NMR (500 MHz, DMSO-d6) δ=11.39 (s, 1H), 9.03 (s, 1H), 8.07 (s, 1H), 7.68 (d, J=11.3 Hz, 1H), 6.83 (d, J=2.2 Hz, 1H), 6.42 (d, J=2.1 Hz, 1H), 5.16 (s, 2H), 2.77 (t, J=7.4 Hz, 2H), 2.61 (t, J=7.3 Hz, 2H), 1.95-1.87 (m, 2H).

Example 57: Preparation of 4-[(3-amino-5-fluoro-1H-pyrazolo[3,4-b]pyridin-6-yl)amino]indan-5-ol The compound represented by the following formula was prepared:

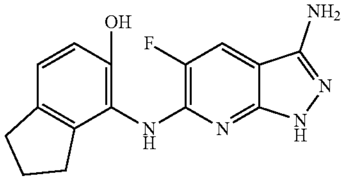 [SMILES: Nc1n[nH]c2nc(Nc3c(O)ccc4c3CCC4)c(F)cc12]

Step 1

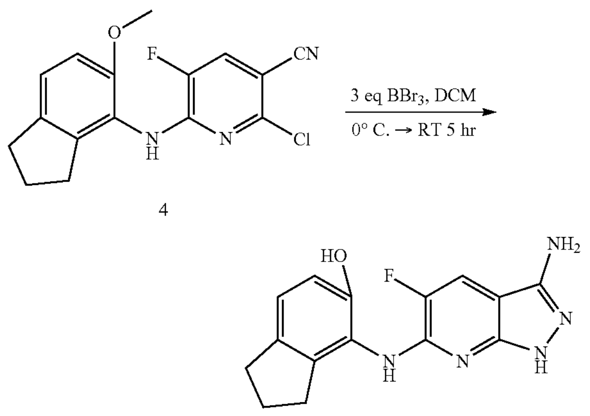

4

5

30 mg (0.09 mmol) of Compound 4 (Example 50) was dissolved in dichloromethane (DCM) and then 270 ul (0.27 mmol) of a 1M $BBr_3$ dichloro solution was added at 0° C. dropwise to the resulting solution. The temperature was elevated to room temperature and then the resulting mixture was stirred for 5 hours. After completion of the reaction was detected, the solvent was dried under reduced pressure. The obtained residue was purified by reverse phase chromatography to obtain the target compound 5 (5.2 mg, 19%) as a white solid.

$^1$H NMR (500 MHz, DMSO-d6) δ=11.31 (s, 1H), 8.91 (s, 1H), 7.85 (s, 1H), 7.63 (d, J=11.2 Hz, 1H), 6.88 (d, J=7.3 Hz, 1H), 6.65 (d, J=8.0 Hz, 1H), 5.11 (s, 2H), 2.82-2.74 (m, 2H), 2.70-2.63 (m, 2H), 1.97-1.85 (m, 2H).

Example 58: Preparation of N6-(2,3-dihydro-1H-inden-4-yl)-4,5-dimethyl-1H-pyrazolo[3,4-b]pyridine-3,6-diamine The compound represented by the following formula was prepared:

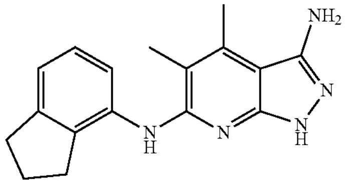 [SMILES: Cc1c(Nc2cccc3c2CCC3)nc2[nH]nc(N)c2c1C]

Step 1

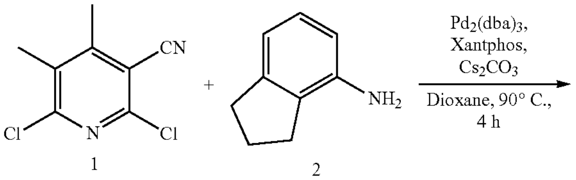

1

2

-continued

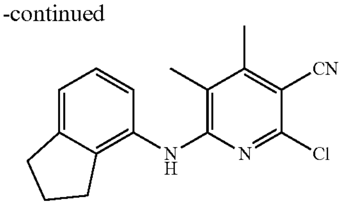

3

1.99 mL (0.2 M) of 1,4-dioxane was added to 80 mg (0.398 mmol) of Compound 1, 68.9 mg (0.517 mmol, 1.3 eq.) of Compound 2, 46 mg (0.080 mmol, 0.2 eq.) of Xantphos, and 389 mg (1.194 mmol, 3 eq.) of cesium carbonate. 36.4 mg (0.040 mmol, 0.1 eq.) of $Pd_2(dba)_3$ was adioed to the resulting mixture. The temperature was elevated to 90° C. and then the resulting mixture was stirred for 4 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (51.3 mg, 43%) as a yellow solid.

Step 2

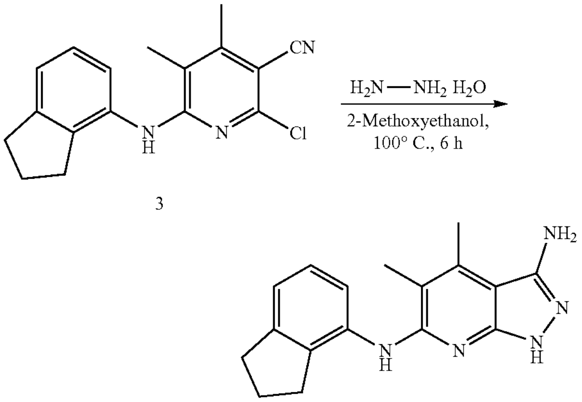

3

4

51.3 mg (0.172 mmol) of Compound 3 was dissolved in 0.861 mL (0.2 M) of 2-methoxyethanol, and then 0.167 mL (3.45 mmol, 20 eq.) of hydrazine monohydrate was added dropwise to the resulting solution. The temperature was elevated to 100° C. and then the resulting mixture was stirred for 6 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (11.5 mg, 23%) as a light yellow solid.

$^1$H NMR (400 MHz, METHANOL-d4) δ=7.24-7.19 (m, 3H), 2.99 (t, J=7.4 Hz, 2H), 2.78 (t, H=7.4 Hz, 2H), 2.62 (s, 3H), 2.28 (s, 3H), 2.08 (quin, J=7.4 Hz, 2H).

Example 59: Preparation of N6-(2,3-dichlorophenyl)-5-fluoro-1H-pyrazolo[3,4-b]pyridine-3,6-diamine The compound represented by the following formula was prepared:

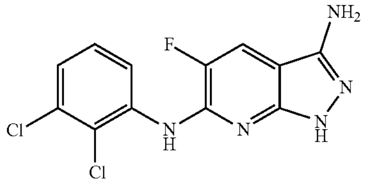

Step 1

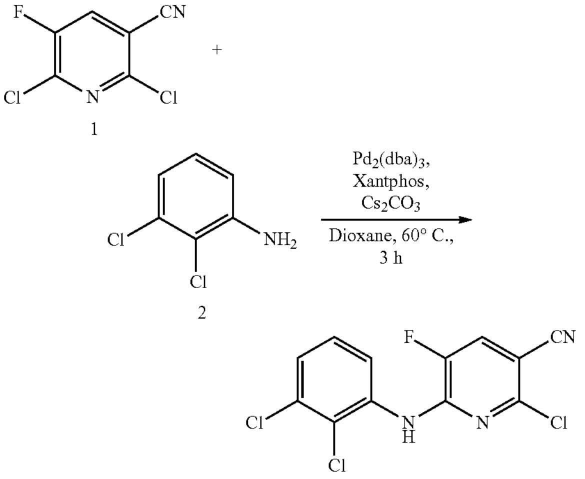

1

2

3

2.094 mL (0.2 M) of 1,4-dioxane was added to 80 mg (0.419 mmol) of Compound 1, 71.3 mg (0.440 mmol, 1.05 eq.) of Compound 2, 48.5 mg (0.084 mmol, 0.2 eq.) of Xantphos, and 409 mg (1.257 mmol, 3 eq.) of cesium carbonate. 38.4 mg (0.042 mmol, 0.1 eq.) of Pd$_2$(dba)$_3$ was added to the resulting mixture. The temperature was elevated to 60° C. and then the resulting mixture was stirred for 3 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (139 mg, 105%) as a yellow solid.

Step 2

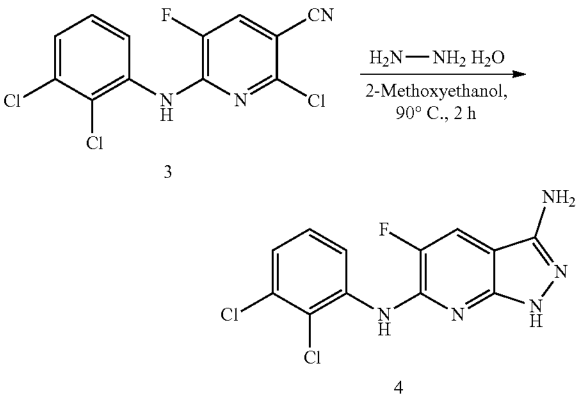

3

4

133 mg (0.420 mmol) of Compound 3 was dissolved in 2.101 mL (0.2 M) of 2-methoxyethanol, and then 0.408 mL (8.40 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and then filtered to obtain the target compound 4 (60.5 mg, 46%) as a white solid.

$^1$H NMR (400 MHz, DMSO-d6) δ=11.58 (s, 1H), 8.56 (s, 1H), 7.87-7.81 (m, 2H), 7.46-7.37 (m, 2H), 5.28 (s, 2H).

Example 60: Preparation of 5-fluoro-N6-(quinolin-5-yl)-1H-pyrazolo[3,4-b]pyridine-3,6-diamine The compound represented b the following formula was prepared:

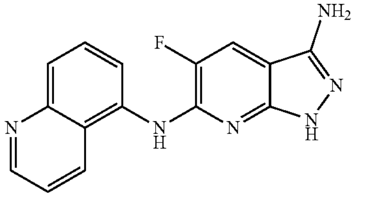

Step 1

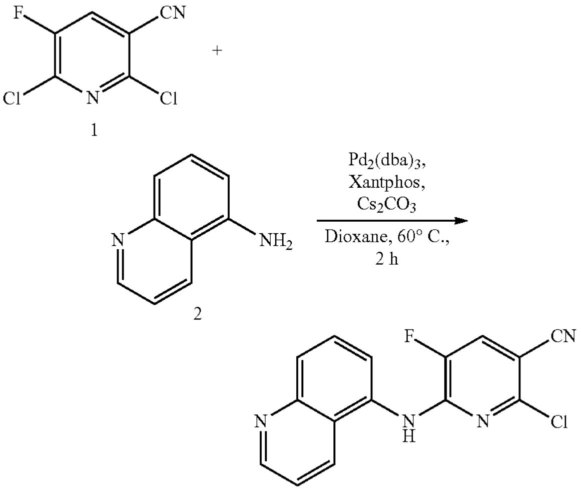

1

2

3

2.094 mL (0.2 M) of 1,4-dioxane was added to 80 mg (0.419 mmol) of Compound 1, 63.4 mg (0.440 mmol, 1.05 eq.) of Compound 2, 48.5 mg (0.084 mmol, 0.2 eq.) of Xantphos and 409 mg (1.257 mmol, 3 eq.) of cesium carbonate. 38.4 mg (0.042 mmol, 0.1 eq.) of Pd$_2$(dba)$_3$ was added to the resulting mixture. The temperature was elevated to 60° C. and then the resulting mixture was stirred for 2 hours.

After completion of the reaction was detected, the organic layer was separated using $H_2O$ and ethyl acetate, dried over $MgSO_4$, filtered and further dried under reduced pressure.

The obtained residue, the target Compound 3 (151 mg, 121%) was used in the subsequent reaction without additional purification.

Step 2

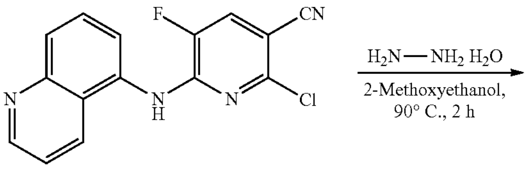

3

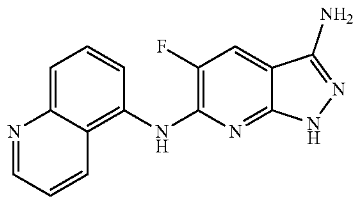 [SMILES: Nc1n[nH]c2nc(Nc3cccc4ncccc34)c(F)cc12]

4

151 mg (crude) of Compound 3 was dissolved in 2.092 mL (0.2 M) of 2-methoxyethanol, and then 0.406 mL (8.37 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (17.8 mg, 14%) as a yellow solid.

$^1$H NMR (400 MHz, DMSO-d6) δ=11.35 (br s, 1H), 9.08 (s, 1H), 8.90 (dd, J=1.5, 4.1 Hz, 1H), 8.31 (d, J=7.8 Hz, 1H), 7.90 (d, J=8.3 Hz, 1H), 7.83-7.75 (m, 2H), 7.68 (d, J=7.3 Hz, 1H), 7.49 (dd, J=4.2, 8.4 Hz, 1H), 5.22 (s, 2H).

Example 61: Preparation of N6-(3-(difluoromethyl)-2-fluorophenyl)-5-fluoro-1H-pyrazolo[3,4-b]pyridine-3,6-diamine The compound represented by the following formula was prepared:

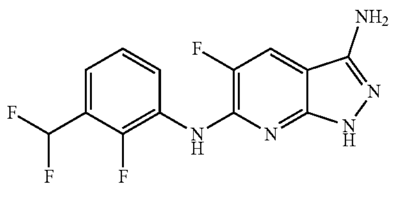 [SMILES: Nc1n[nH]c2nc(Nc3cccc(C(F)F)c3F)c(F)cc12]

Step 1

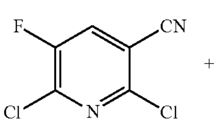

1

-continued

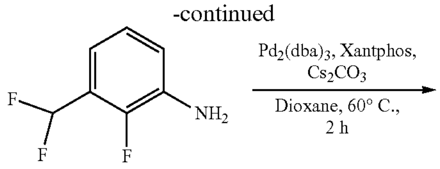

2

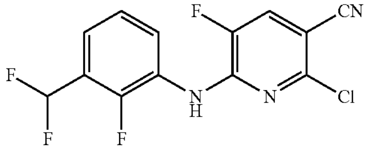

3

2.094 mL (0.2 M) of 1,4-dioxane was added to 80 mg (0.419 mmol) of Compound 1, 70.9 mg (0.440 mmol, 1.05 eq.) of Compound 2, 48.5 mg (0.084 mmol, 0.2 eq.) of Xantphos, and 409 mg (1.257 mmol, 3 eq.) of cesium carbonate. 38.4 mg (0.042 mmol, 0.1 eq.) of $Pd_2(dba)_3$ was added to the resulting mixture. The temperature was elevated to 60° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (103 mg, 78%) as a light brown solid.

Step 2

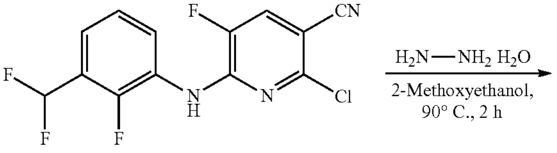

3

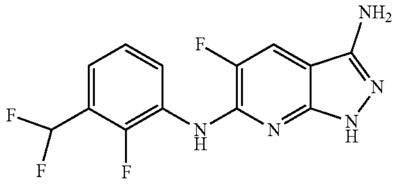

4

92 mg (0.291 mmol) of Compound 3 was dissolved in 1.457 mL (0.2 M) of 2-methoxyethanol, and then 0.283 mL (5.83 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (52.5 mg, 58%) as a white solid.

$^1$H NMR (400 MHz, DMSO-d6) δ=9.14-9.05 (m, 1H), 7.88 (br d, J=10.9 Hz, 1H), 7.84 (s, 1H), 7.50-7.43 (m, 1H), 7.38 (d, J=9.3 Hz, 1H), 7.35-7.11 (m, 1H).

Example 62: Preparation of 5-fluoro-N6-(3-fluoro-2-(trifluoromethyl)phenyl)-1H-pyrazolo[3,4-b]pyridine-3,6-diamine The compound re resented b the following formula was prepared:

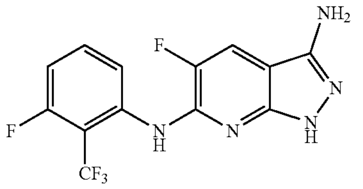 [SMILES: Nc1n[nH]c2nc(Nc3cccc(F)c3C(F)(F)F)c(F)cc12]

Step 1

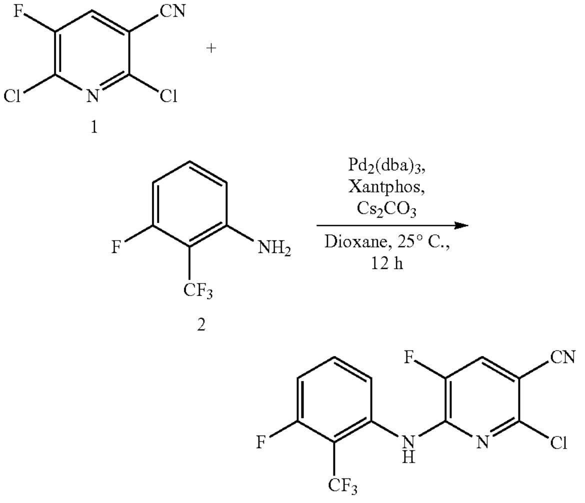

1 2 3

1.396 mL (0.3 M) of 1,4-dioxane was added to 80 mg (0.419 mmol) of Compound 1, 75 mg (0.419 mmol, 1 eq.) of Compound 2, and 409 mg (1.257 mmol, 3 eq.) of cesium carbonate. 38.4 mg (0.042 mmol, 0.1 eq.) of $Pd_2(dba)_3$ was added to the resulting mixture. The reaction solution was stirred at room temperature for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (84.5 mg, 61%) as a brown solid.

Step 2

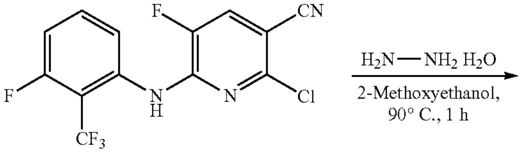

3

-continued

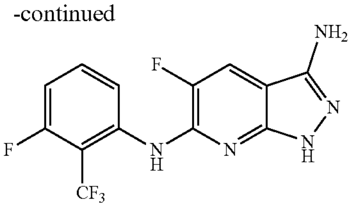

4

73 mg (0.219 mmol) of Compound 3 was dissolved in 0.875 mL (0.25 M) of 2-methoxyethanol, and then 0.212 mL (4.38 mmol, 20 eq.) of hydrazine monohydrate was added dropwise to the resulting solution. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (54.8 mg, 76%) as a white solid.

$^1$H NMR (400 MHz, DMSO-d6) δ=9.29 (br s, 1H), 7.88 (d, J=10.6 Hz, 1H), 7.79-7.72 (m, 1H), 7.46-7.35 (m, 2H).

Example 63: Preparation of 2-[(3-amino-5-fluoro-1H-pyrazolo[3,4-b]pyridin-6-yl)amino]-6-methoxybenzonitrile The compound represented by the following formula was prepared:

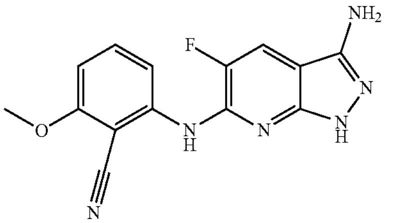 [SMILES: COc1cccc(Nc2nc3[nH]nc(N)c3cc2F)c1C#N]

The titled target compound was obtained as a yellow solid (6.5 mg, 66%) in the same manner as in Step 1 and Step 2 of reaction scheme in Example 58 using 2-amino-6-methoxy benzonitrile (186 mg, 1.26 mmol) and 2,6-dichloro-5-fluoro-3 carbonitrile pyridine (200 mg, 1.04 mmol).

$^1$H NMR (500 MHz, DMSO-d6) δ=11.56 (s, 1H), 8.92 (s, 1H), 7.80 (d, J=11.0 Hz, 1H), 7.59 (t, J=8.3 Hz, 1H), 7.28 (d, J=8.1 Hz, 1H), 6.94 (dd, J=8.6, 0.8 Hz, 1H), 5.26 (s, 2H), 3.90 (s, 3H).

Example 64: Preparation of 5-fluoro-N6-(2-fluoro-3-(trifluoromethyl)phenyl)-1H-pyrazolo[3,4-b]pyridine-3,6-diamine The compound represented by the following formula was prepared:

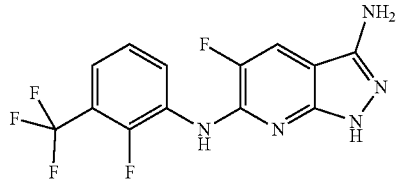 [SMILES: Nc1n[nH]c2nc(Nc3cccc(C(F)(F)F)c3F)c(F)cc12]

The titled target compound was obtained as a white solid (42.9 mg, 33%) in the same manner as in Step 1 and Step 2 of reaction scheme in Example 58 using (160 ul, 1.24 mmol) of 2-fluoro-3-trifluoromethyl aniline and 2,6-dichloro-5-fluoro-3 carbonitrile pyridine (200 mg, 1.04 mmol).

$^1H$ NMR (500 MHz, DMSO-d6) δ=11.53 (s, 1H), 8.81 (s, 1H), 8.01 (t, J=8.1 Hz, 1H), 7.81 (d, J=11.1 Hz, 1H), 7.51 (t, J=6.8 Hz, 1H), 7.39 (t, J=8.0 Hz, 1H), 5.28 (s, 2H).

Example 65: Preparation of N6-[2-fluoro-3-(trifluoromethyl)phenyl]-1H-pyrazolo[3,4-b]pyridine-3,6-diamine The compound represented by the following formula was prepared:

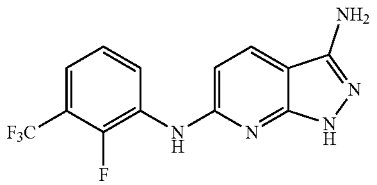 [SMILES: Nc1n[nH]c2nc(Nc3cccc(C(F)(F)F)c3F)ccc12]

The titled target compound was obtained as a white solid (67.6 mg, 37%) in the same manner as in Step 1 and Step 2 of reaction scheme in Example 58 using 2-fluoro-3-trifluoromethyl aniline (89 ul, 0.69 mmol) and 2,6-dichloro-3 cyano-pyridine (100 mg, 0.57 mmol).

$^1H$ NMR (500 MHz, DMSO-d6) δ=11.52 (s, 1H), 9.13 (d, J=1.8 Hz, 1H), 8.74-8.63 (m, 1H), 7.88 (d, J=8.6 Hz, 1H), 7.40-7.25 (m, 2H), 6.68 (d, J=8.6 Hz, 1H), 5.31 (s, 2H).

Example 66: Preparation of N6-[2-fluoro-3-(trifluoromethyl)phenyl]-1H-pyrazolo[3,4-b]pyrazine-3,6-diamine The compound represented by the following formula was prepared:

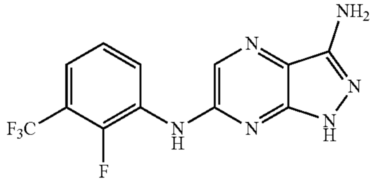 [SMILES: Nc1n[nH]c2nc(Nc3cccc(C(F)(F)F)c3F)cnc12]

The target compound was obtained as a white solid (16 mg, 43%) in the same manner as in Example 58 using 87 mg (0.5 mmol) of 3,5-dichloropyrazine-2-carbonitrile and 90 mg (0.5 mmol) of 2-fluoro-3-(trifluoromethyl)aniline.

$^1H$ NMR (500 MHz, DMSO-d6) δ=11.83 (s, 1H), 9.63 (s, 1H), 8.58 (d, J=8.9 Hz, 1H), 8.16 (s, 1H), 7.43-7.37 (m, 2H), 5.40 (s, 2H).

Example 67: Preparation of N6-(3-chloro-2-methylphenyl)-5-fluoro-1H-pyrazolo[3,4-b]pyridine-3,6-diamine The compound represented by the following formula was prepared:

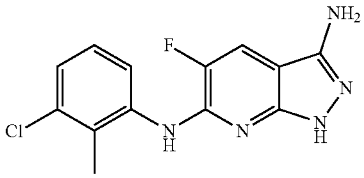 [SMILES: Cc1c(Cl)cccc1Nc1nc2[nH]nc(N)c2cc1F]

Step 1

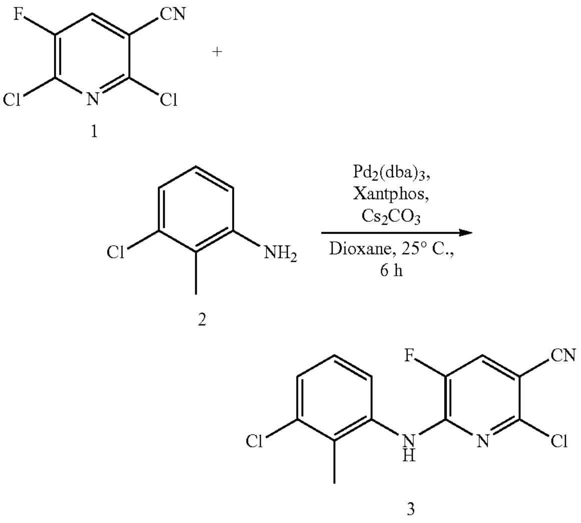

1.396 mL (0.3 M) of 1,4-dioxane was added to 80 mg (0.419 mmol) of Compound 1, 65.2 mg (0.461 mmol, 1.1 eq.) of Compound 2, and 409 mg (1.257 mmol, 3 eq.) of cesium carbonate. 38.4 mg (0.042 mmol, 0.1 eq.) of $Pd_2(dba)_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and filtered to obtain the target Compound 3 (121 mg, 98%) as a yellow solid.

Step 2

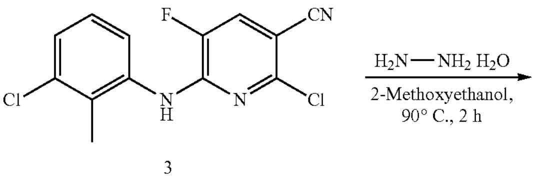

-continued

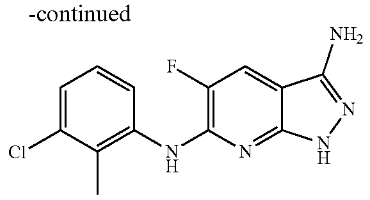

4

105 mg (0.355 mmol) of Compound 3 was dissolved in 1.773 mL (0.2 M) of 2-methoxyethanol, and then 0.344 mL (7.09 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (75.2 mg, 73%) as a white solid.

$^1$H NMR (400 MHz, DMSO-d6) δ=12.56-12.04 (m, 1H), 9.18 (br s, 1H), 7.86 (d, J=10.9 Hz, 1H), 7.37-7.24 (m, 3H), 2.20 (s, 3H).

Example 68: Preparation of 5-fluoro-N6-(2-fluoro-5-(trifluoromethyl)phenyl)-1H-pyrazolo[3,4-b]pyridine-3,6-diamine The compound represented by the following formula was prepared:

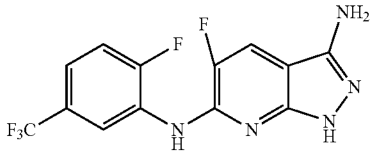 [SMILES: Nc1n[nH]c2nc(Nc3cc(C(F)(F)F)ccc3F)c(F)cc12]

Step 1

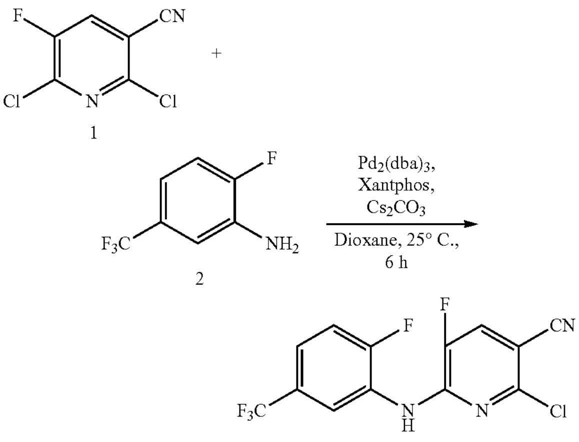

1

2

3

1.396 mL (0.3 M) of 1,4-dioxane was added to 80 mg (0.419 mmol) of Compound 1, 83 mg (0.461 mmol, 1.1 eq.) of Compound 2, and 409 mg (1.257 mmol, 3 eq.) of cesium carbonate. 38.4 mg (0.042 mmol, 0.1 eq.) of $Pd_2(dba)_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (128 mg, 92%) as a white solid.

Step 2

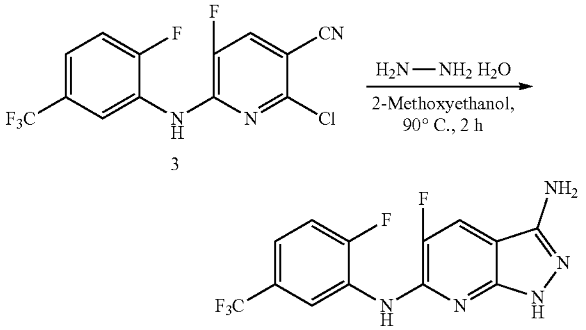

3

4

110 mg (0.330 mmol) of Compound 3 was dissolved in 1.648 mL (0.2 M) of 2-methoxyethanol, and then 0.320 mL (6.59 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (67 mg, 62%) as a white solid.

$^1$H NMR (400 MHz, DMSO-d6) δ=9.16 (br s, 1H), 8.07 (br d, J=5.5 Hz, 1H), 7.91 (d, J=11.0 Hz, 1H), 7.61 (br s, 1H), 7.58-7.51 (m, 1H).

Example 69: Preparation of N6-(3,4-difluoro-5-(trifluoromethyl)phenyl)-5-fluoro-1H-pyrazolo[3,4-b]pyridine-3,6-diamine The compound represented by the following formula was prepared:

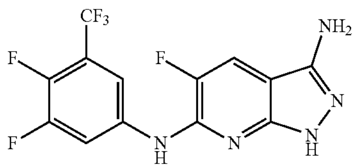 [SMILES: Nc1n[nH]c2nc(Nc3cc(F)c(F)c(C(F)(F)F)c3)c(F)cc12]

Step 1

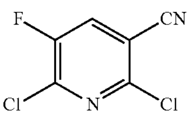

\+

1

-continued

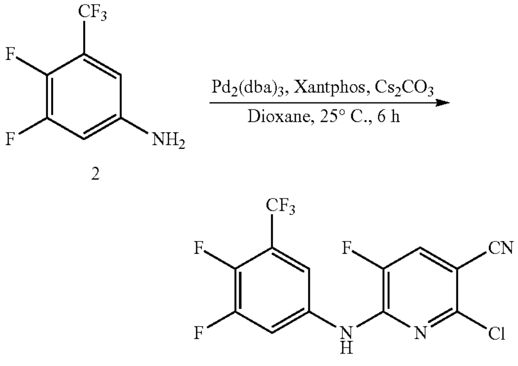

2

3

1.396 mL (0.3 M) of 1,4-dioxane was added to 80 mg (0.419 mmol) of Compound 1, 91 mg (0.461 mmol, 1.1 eq.) of Compound 2, and 409 mg (1.257 mmol, 3 eq.) of cesium carbonate. 38.4 mg (0.042 mmol, 0.1 eq.) of $Pd_2(dba)_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and filtered to obtain the target Compound 3 (135 mg, 92%) as a brown solid.

Step 2

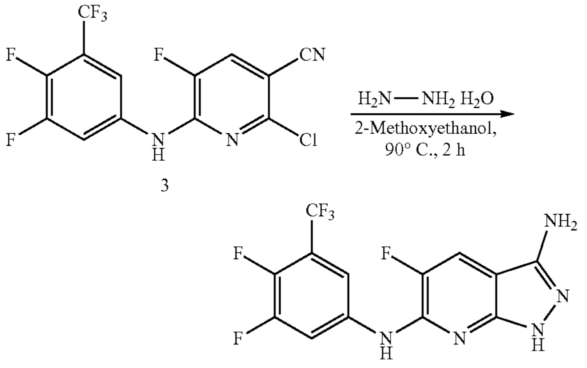

3

4

120 mg (0.341 mmol) of Compound 3 was dissolved in 1.706 mL (0.2 M) of 2-methoxyethanol, and then 0.331 mL (6.83 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (108 mg, 91%) as a white solid.

$^1H$ NMR (400 MHz, DMSO-d6) δ=9.71 (br s, 1H), 8.53 (ddd, J=2.4, 7.1, 13.3 Hz, 1H), 8.11 (d, J=5.4 Hz, 1H), 7.94 (d, J=11.0 Hz, 1H).

Example 70: Preparation of N6-[3-(difluoromethyl)-2-fluoro-phenyl]-1H-pyrazolo[3,4-b]pyridine-3,6-diamine The compound represented by the following formula was prepared:

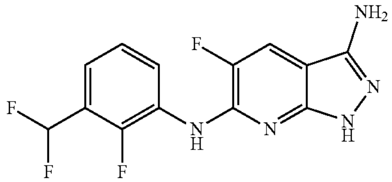 [SMILES: Nc1n[nH]c2nc(Nc3cccc(C(F)F)c3F)c(F)cc12]

The target compound was obtained as a yellow solid (34 mg, 58%) in the same manner as in Example 58 using 173 mg (1.0 mmol) of 2,6-dichloro-3-cyanopyridine and 161 mg (1.0 mmol) of 3-(difluoromethyl)-2-fluoroaniline.

$^1H$ NMR (500 MHz, DMSO-d6) δ=11.49 (s, 1H), 8.99 (d, J=1.8 Hz, 1H), 8.54 (t, J=8.1 Hz, 1H), 7.85 (d, J=8.6 Hz, 1H), 7.36-7.12 (m, 3H), 6.66 (d, J=8.7 Hz, 1H), 5.28 (s, 2H).

Example 71: Preparation of 5-fluoro-N6-[3-(trifluoromethyl)phenyl]-1H-pyrazolo[3,4-b]pyridine-3,6-diamine The compound represented by the following formula was prepared:

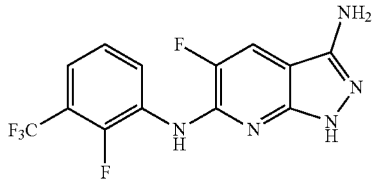 [SMILES: Nc1n[nH]c2nc(Nc3cccc(C(F)(F)F)c3F)c(F)cc12]

The target compound was obtained as a white solid (55 mg, 88%) in the same manner as in Example 58 using 191 mg (1.0 mmol) of 2,6-dichloro-5-fluoro-3-cyanopyridine and 161 mg (1.0 mmol) of 3-(trifluoromethyll)aniline.

$^1H$ NMR (500 MHz, DMSO-d6) δ=11.69 (s, 1H), 9.29 (d, J=2.6 Hz, 1H), 8.33 (s, 1H), 8.24 (d, J=8.4 Hz, 1H), 7.84 (d, J=11.2 Hz, 1H), 7.54 (t, J=8.0 Hz, 1H), 7.31 (d, J=7.3 Hz, 1H), 5.33 (s, 2H).

Example 72: Preparation of 5-fluoro-N6-[3-fluoro-4-(trifluoromethyl)phenyl]-1H-pyrazolo[3,4-b]pyridine-3,6-diamine The compound represented by the following formula was prepared:

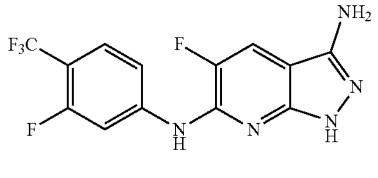 [SMILES: Nc1n[nH]c2nc(Nc3ccc(C(F)(F)F)c(F)c3)c(F)cc12]

The target compound was obtained as a white solid (54 mg, 82%) in the same manner as in Example 58 using 191 mg (1.0 mmol) of 2,6-dichloro-5-fluoro-3-cyanopyridine and 179 mg (1.0 mmol) of 3-fluoro-4-(trifluoromethyll) aniline.

$^1$H NMR (500 MHz, DMSO-d6) δ=11.81 (s, 1H), 9.62 (s, 1H), 8.28 (d, J=14.6 Hz, 1H), 7.90 (d, J=11.2 Hz, 1H), 7.79 (d, J=8.8 Hz, 1H), 7.67 (t, J=8.7 Hz, 1H), 5.39 (s, 2H).

Example 73: Preparation of N6-[2,5-difluoro-3-(trifluoromethyl)phenyl]-5-fluoro-1H-pyrazolo[3,4-b]pyridine-3,6-diamine The compound represented by the following formula was prepared:

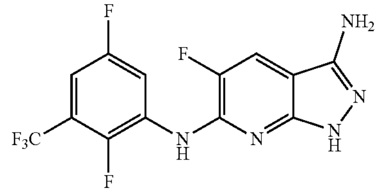 [SMILES: Nc1n[nH]c2nc(Nc3cc(F)cc(C(F)(F)F)c3F)c(F)cc12]

The titled target compound was obtained as a white solid (107 mg, 64%) in the same manner as in Step 1 and Step 2 of reaction scheme in Example 58 using 2,5-difluoro-3-trifluoromethyl aniline (170.3 mg, 0.86 mmol) and 2,6-dichloro-5-fluoro-3 carbonitrile pyridine (150 mg, 0.78 mmol).

$^1$H NMR (500 MHz, DMSO-d6) δ=11.66 (s, 1H), 8.86 (s, 1H), 8.17 (ddd, J=9.8, 5.9, 3.1 Hz, 1H), 7.87 (d, J=10.9 Hz, 1H), 7.40 (dt, J=8.0, 4.0 Hz, 1H), 5.32 (s, 2H).

Example 74: Preparation of N6-(3-chloro-2-fluoro-phenyl)-5-fluoro-1H-pyrazolo[3,4-b]pyridine-3,6-diamine The compound represented by the following formula was prepared:

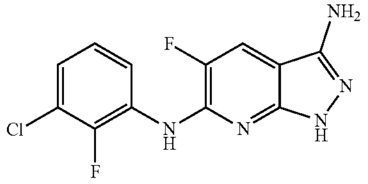

The target compound was obtained as a white solid (49 mg, 83%) in the same manner as in Example 58 using 191 mg (1.0 mmol) of 2,6-dichloro-5-fluoro-3-cyanopyridine and 146 mg (1.0 mmol) of 3-chloro-2-fluoroaniline.

$^1$H NMR (500 MHz, DMSO-d6) δ=11.51 (s, 1H), 8.73 (s, 1H), 7.77 (d, J=11.1 Hz, 1H), 7.60 (t, J=7.6 Hz, 1H), 7.32 (t, J=7.4 Hz, 1H), 7.19 (t, J=8.1 Hz, 1H), 5.23 (s, 2H).

Example 75: Preparation of N6-(4-chloro-3-(difluoromethyl)phenyl)-5-fluoro-1H-pyrazolo[3,4-b]pyridine-3,6-diamine The compound represented by the following formula was prepared:

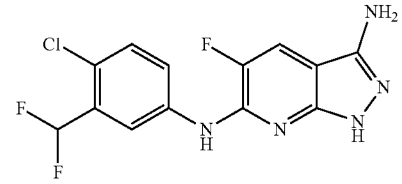 [SMILES: Nc1n[nH]c2nc(Nc3ccc(Cl)c(C(F)F)c3)c(F)cc12]

Step 1

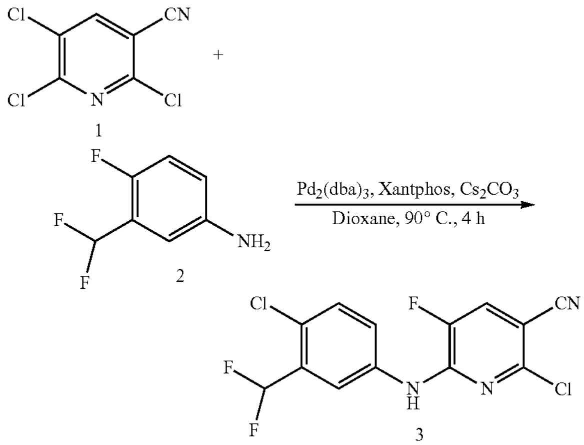

1

2

3

1.40 mL (0.3 M) of 1,4-dioxane was added to 80 mg (0.419 mmol) of Compound 1, 82 mg (0.46 mmol, 1.1 eq.) of Compound 2, 46 mg (0.080 mmol, 0.2 eq.) of Xantphos, and 409 mg (1.257 mmol, 3 eq.) of cesium carbonate. 38.4 mg (0.042 mmol, 0.1 eq.) of Pd$_2$(dba)$_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and filtered to obtain the target Compound 3 (115 mg, 83%) as a white solid.

Step 2

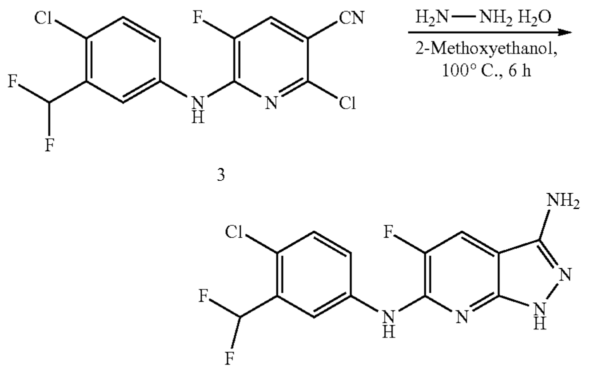

3

4

120 mg (0.36 mmol) of Compound 3 was dissolved in 3.61 mL (0.1 M) of 2-methoxyethanol, and then 0.35 mL (7.23 mmol, 20 eq.) of hydrazine monohydrate was added dropwise to the resulting solution. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (110 mg, 93%) as a white solid.

$^1H$ NMR (500 MHz, DMSO-d6) δ=9.63 (br s, 1H), 8.26 (d, J=2.2 Hz, 1H), 8.14 (br d, J=8.8 Hz, 1H), 7.93 (d, J=10.9 Hz, 1H), 7.56 (d, J=8.8 Hz, 1H), 7.21 (t, J=54.4 Hz, 1H), 2.56-2.54 (m, 1H)

Example 76: Preparation of N6-(6-chloro-2-fluoro-3-methylphenyl)-5-fluoro-1H-pyrazolo[3,4-b]pyridine-3,6-diamine The compound represented by the following formula was prepared:

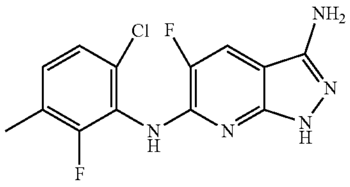 [SMILES: Cc1ccc(Cl)c(Nc2nc3[nH]nc(N)c3cc2F)c1F]

Step 1

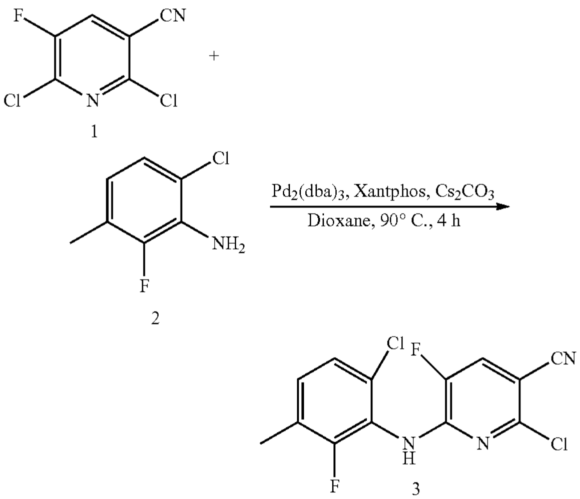

1
2
3

1.40 mL (0.3 M) of 1,4-dioxane was added to 80 mg (0.42 mmol) of Compound 1, 74 mg (0.46 mmol, 1.1 eq.) of Compound 2, 46 mg (0.080 mmol, 0.2 eq.) of Xantphos, and 409 mg (1.26 mmol, 3 eq.) of cesium carbonate. 38 mg (0.042 mmol, 0.1 eq.) of $Pd_2(dba)_3$ was added to the resulting mixture. The reaction solution was stirred at room temperature for 20 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and filtered to obtain the target Compound 3 (45 mg, 35%) as a light yellow solid.

Step 2

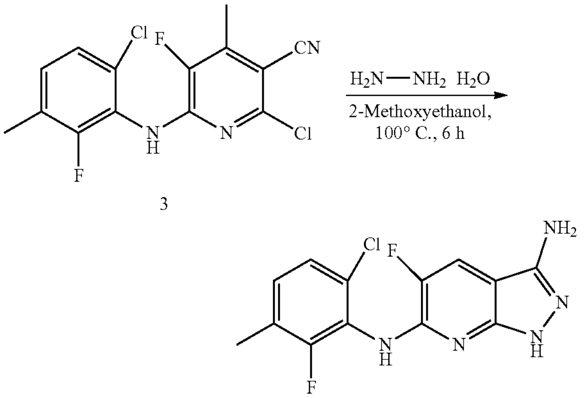

3
4

44 mg (0.14 mmol) of Compound 3 was dissolved in 1.40 mL (0.1 M) of 2-methoxyethanol, and then 0.14 mL (2.80 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (42 mg, 97%) as a white solid.

$^1H$ NMR (400 MHz, DMSO-d6) δ=9.19 (s, 1H), 7.90 (d, J=10.8 Hz, 1H), 7.35-7.26 (m, 2H), 2.28-2.24 (m, 3H)

Example 77: Preparation of N6-(2-chloro-3-(trifluoromethyl)phenyl)-5-fluoro-1H-pyrazolo[3,4-b]pyridine-3,6-diamine The compound represented by the following formula was prepared:

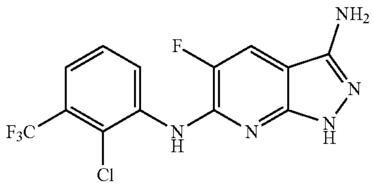 [SMILES: Nc1n[nH]c2nc(Nc3cccc(C(F)(F)F)c3Cl)c(F)cc12]

Step 1

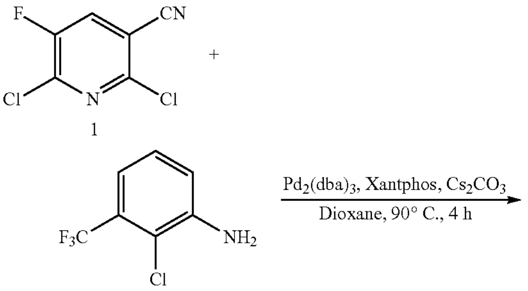

1
2

-continued

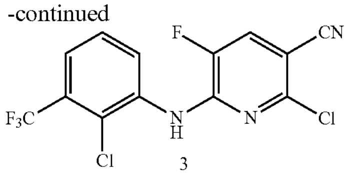

3

1.40 mL (0.3 M) of 1,4-dioxane was added to 80 mg (0.42 mmol) of Compound 1, 90 mg (0.46 mmol, 1.1 eq.) of Compound 2, 46 mg (0.080 mmol, 0.2 eq.) of Xantphos, and 409 mg (1.26 mmol, 3 eq.) of cesium carbonate. 38 mg (0.042 mmol, 0.1 eq.) of $Pd_2(dba)_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was crystallized using dichloromethane and hexane, and filtered to obtain the target Compound 3 (101 mg, 69%) as a light brown solid.

Step 2

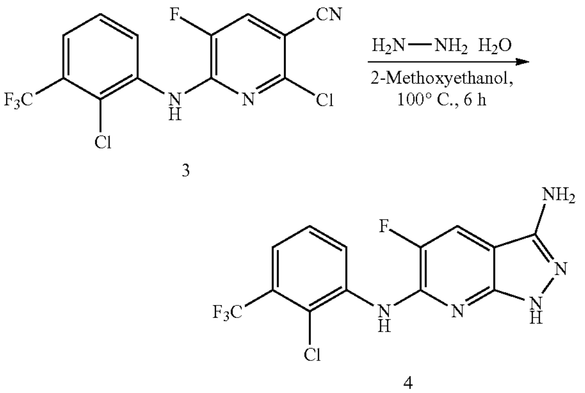

90 mg (0.26 mmol) of Compound 3 was dissolved in 1.29 mL (0.2 M) of 2-methoxyethanol, and then 0.25 mL (5.14 mmol, 20 eq.) of hydrazine monohydrate was added dropwise to the resulting solution. The temperature was elevated to 90° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (82 mg, 92%) as a white solid.

$^1H$ NMR (400 MHz, DMSO-d6) δ=9.14-8.97 (m, 1H), 8.06 (br d, J=7.7 Hz, 1H), 7.91 (d, J=10.9 Hz, 1H), 7.73 (d, J=7.5 Hz, 1H), 7.61 (t, J=7.9 Hz, 1H)

Example 78: Preparation of N6-(2,4-difluoro-5-(trifluoromethyl)phenyl)-5-fluoro-1H-pyrazolo[3,4-b]pyridine-3,6-diamine The compound represented by the following formula was prepared:

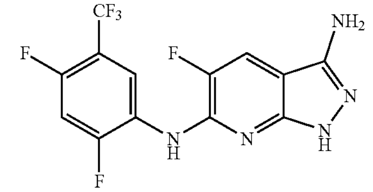 [SMILES: Nc1n[nH]c2nc(Nc3cc(C(F)(F)F)c(F)cc3F)c(F)cc12]

Step 1

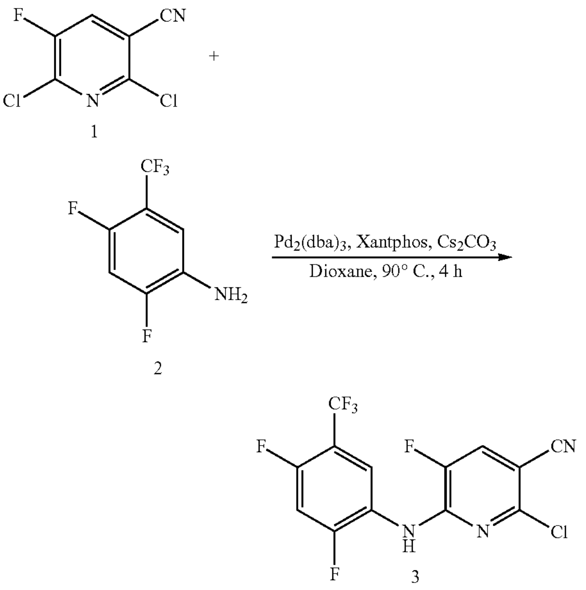

1.40 mL (0.3 M) of 1,4-dioxane was added to 80 mg (0.42 mmol) of Compound 1, 91 mg (0.46 mmol, 1.1 eq.) of Compound 2, 46 mg (0.080 mmol, 0.2 eq.) of Xantphos, and 409 mg (1.26 mmol, 3 eq.) of cesium carbonate. 38 mg (0.042 mmol, 0.1 eq.) of $Pd_2(dba)_3$ was added to the resulting mixture. The reaction solution was stirred at room temperature for 6 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (124 mg, 84%) as a light brown solid.

Step 2

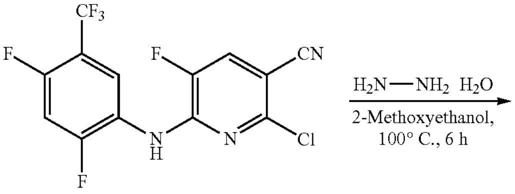

3

-continued

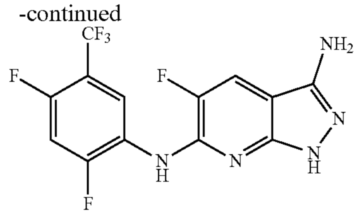

4

100 mg (0.28 mmol) of Compound 3 was dissolved in 1.42 mL (0.2 M) of 2-methoxyethanol, and then 0.069 mL (1.42 mmol, 5 eq.) of hydrazine monohydrate was added dropwise to the resulting solution. The temperature was elevated to 90° C., and then the resulting mixture was stirred for 3 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (43 mg, 43%) as a light yellow solid.

$^1$H NMR (400 MHz, DMSO-d6) δ=9.19-9.09 (m, 1H), 8.05 (t, J=7.9 Hz, 1H), 7.89 (d, J=10.8 Hz, 1H), 7.77 (t, J=10.6 Hz, 1H)

Example 79: Preparation of 3-[(3-amino-5-fluoro-1H-pyrazolo[3,4-b]pyridin-6-yl)amino]-2-fluoro-benzonitrile The compound represented by the following formula was prepared:

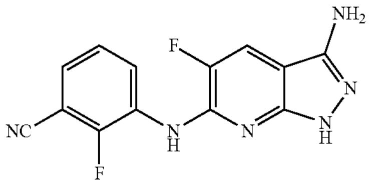 [SMILES: N#Cc1cccc(Nc2nc3[nH]nc(N)c3cc2F)c1F]

The titled target compound was obtained as a white solid (12 mg, 53%) in the same manner as in Step 1 and Step 2 of reaction scheme in Example 58 using 2-amino-2-fluorobenzo nitrile (85 mg, 0.62 mmol) and 2,6-dichloro-5-fluoro-3 carbonitrile pyridine (100 mg, 0.52 mmol).

$^1$H NMR (500 MHz, DMSO-d6) δ=11.55 (s, 1H), 8.94 (s, 1H), 7.98 (t, J=8.0 Hz, 1H), 7.82 (d, J=11.0 Hz, 1H), 7.67 (t, J=6.8 Hz, 1H), 7.40 (t, J=8.0 Hz, 1H), 5.28 (s, 2H).

Example 80: Preparation of N6-(2,4-difluoro-3-(trifluoromethyl)phenyl)-5-fluoro-1H-pyrazolo[3,4-b]pyridine-3,6-diamine The compound represented by the following formula was prepared:

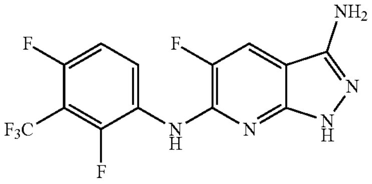 [SMILES: Nc1n[nH]c2nc(Nc3ccc(F)c(C(F)(F)F)c3F)c(F)cc12]

Step 1

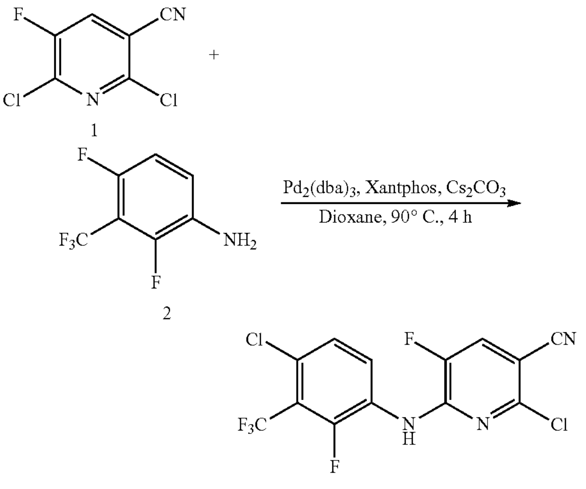

1 2 3

4.97 mL (0.1 M) of 1,4-dioxane was added to 95 mg (0.50 mmol) of Compound 1, 108 mg (0.55 mmol, 1.1 eq.) of Compound 2, 58 mg (0.099 mmol, 0.2 eq.) of Xantphos, and 486 mg (1.49 mmol, 3 eq.) of cesium carbonate. 46 mg (0.050 mmol, 0.1 eq.) of $Pd_2(dba)_3$ was added to the resulting mixture. The reaction solution was stirred at room temperature for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (120 mg, 69%) as a light brown solid.

Step 2

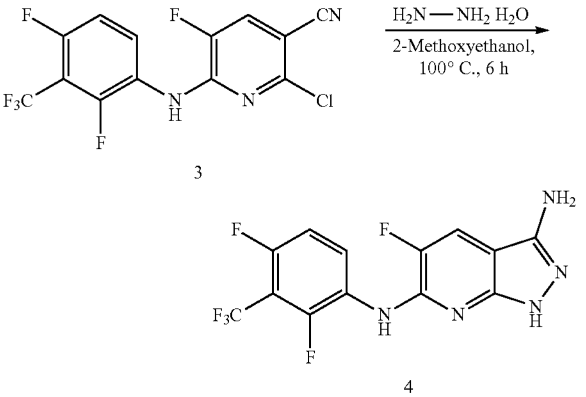

3 4

110 mg (0.31 mmol) of Compound 3 was dissolved in 3.13 mL (0.1 M) of 2-methoxyethanol, and then 0.30 mL (6.26 mmol, 20 eq.) of hydrazine monohydrate was added dropwise to the resulting solution. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (73 mg, 68%) as a light ivory solid.

$^1$H NMR (400 MHz, DMSO-d6) δ=9.21 (s, 1H), 7.96 (dt, J=6.0, 8.8 Hz, 1H), 7.91 (d, J=10.9 Hz, 1H), 7.44 (t, J=9.9 Hz, 1H)

Example 81: Preparation of 5-fluoro-N6-(1,2,3,4-tetrahydronaphthalen-1-yl)-1H-pyrazolo[3,4-b]pyridine-3,6-diamine The compound represented by the following formula was prepared:

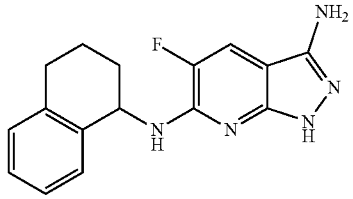 [SMILES: Nc1n[nH]c2nc(NC3CCCc4ccccc43)c(F)cc12]

The target compound was obtained as a brown solid (2 mg, 3%) in the same manner as in Example 3 using 130 mg (0.79 mmol) of 2,6-dichloro-5-fluoro-3-cyanopyridine and 128 mg (0.3 mmol) of 1,2,3,4-tetrahydronaphthalen-1-amine.

$^1$H NMR (500 MHz, DMSO-d6) δ=11.28 (s, 1H), 7.54 (d, J=11.2 Hz, 1H), 7.15 (s, 1H), 7.10 (d, 1H), 7.06 (d, J=7.9 Hz, 1H), 6.97-6.93 (m, 1H), 5.34-5.29 (m, 1H), 5.06 (s, 2H), 2.82-2.68 (m, 4H), 1.95-1.91 (m, 2H).

Example 82: Preparation of 5-fluoro-N6-(3-fluoro-2-methylphenyl)-1H-pyrazolo[3,4-b]pyridine-3,6-diamine The compound represented by the following formula was prepared:

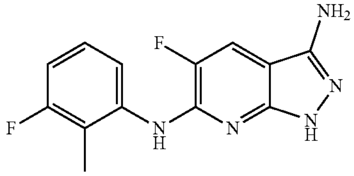 [SMILES: Cc1c(F)cccc1Nc1nc2[nH]nc(N)c2cc1F]

The target compound was obtained as a brown solid (5 mg, 46%) in the same manner as in Example 3 using 12 mg (0.062 mmol) of 2,6-dichloro-5-fluoro-3-cyanopyridine and 8.8 mg (0.068 mmol) of 3-fluoro-2-methylaniline.

$^1$H NMR (500 MHz, DMSO-d) 6=11.40 (s, 1H), 8.52 (s, 1H), 7.74 (d, 1H), 7.25 (d, 2H), 7.00 (d, 1H), 5.19 (s, 21), 2.06 (s, 3H).

Example 83: Preparation of N6-(2,3-dihydro-1H-inden-4-yl)-5-methyl-1H-pyrazolo[3,4-b]pyrazine-3,6-diamine The compound represented by the following formula was prepared:

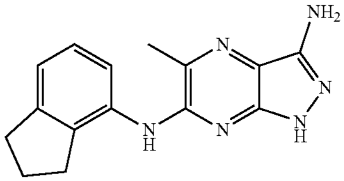 [SMILES: Cc1nc2c(N)n[nH]c2nc1Nc1cccc2c1CCC2]

The target compound was obtained as a white solid 1 (5 mg, 50.5%) in the same manner as in Example 3 using 100 mg (0.53 mmol) of 3,5-dichloro-6-methylpyrazine-2-carbonitrile and 77.6 mg (0.583 mmol) of 2,3-dihydro-1H-inden-4-amine.

$^1$H NMR (500 MHz, DMSO-d6) δ=11.39 (s, 1H), 8.04 (s, 1H), 7.26 (d, J=7.8 Hz, 1H), 7.10 (t, 1H), 7.02 (d, J=7.4 Hz, 1H), 5.11 (s, 2H), 2.87 (t, 2H), 2.66 (t, 2H), 2.51 (s, 3H), 1.95 (m, 2H).

Example 84: Preparation of N6-(2,3-dihydro-1H-inden-4-yl)-4-methyl-1H-pyrazolo[3,4-d]pyrimidine-3,6-diamine The compound represented by the following formula was prepared:

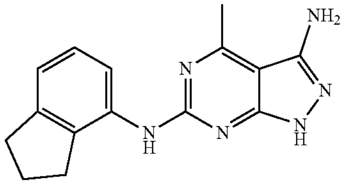 [SMILES: Cc1nc(Nc2cccc3c2CCC3)nc2[nH]nc(N)c12]

The target compound was obtained as a yellow solid (5 mg, quantitative) in the same manner as in Example 3 using 6 mg (0.03 mmol) of 2,4-dichloro-6-methylpyrimidine-5-carbonitrile and 4.4 mg (0.033 mmol) of 2,3-dihydro-1H-inden-4-amine.

$^1$H NMR (500 MHz, DMSO-d6) δ=11.68 (s, 1H), 8.61 (s, 1H), 7.58 (d, J=8 Hz, 1H), 7.09 (t, 1H), 6.94 (d, J=8 Hz, 1H), 5.32 (s, 2H), 2.88 (t, 2H), 2.84 (t, 2H), 2.57 (s, 3H), 1.98 (m, 2H).

Example 85: Preparation of N6-(1,1-difluoro-2,3-dihydro-1H-inden-4-yl)-5-fluoro-1H-pyrazolo[3,4-b]pyridine-3,6-diamine The compound represented by the following formula was prepared:

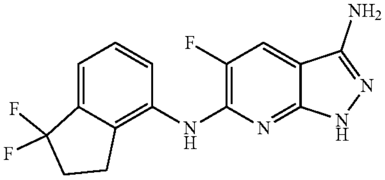 [SMILES: Nc1n[nH]c2nc(Nc3cccc4c3CCC4(F)F)c(F)cc12]

The target compound was obtained as a white solid (140 mg, 88%) in the same manner as in Example 58 using 191 mg (1.0 mmol) of 2,6-dichloro-5-fluoro-3-cyanopyridine and 169 mg (1.0 mmol) of 1,1-difluoro-2,3-dihydro-1H-inden-4-amine.

$^{1}$H NMR (500 MHz, DMSO-d6) δ=11.46 (s, 1H), 8.57 (d, J=2.0 Hz, 1H), 7.76 (d, J=11.2 Hz, 1H), 7.70 (d, J=7.9 Hz, 1H), 7.38 (t, J=7.7 Hz, 1H), 7.29 (d, J=7.7 Hz, 1H), 5.21 (s, 2H), 2.96-2.89 (m, 2H), 2.55 (dq, J=14.3, 7.2 Hz, 3H).

Example 86: Preparation of 7-((3-amino-5-fluoro-1H-pyrazolo[3,4-b]pyridin-6-yl)amino)isoindolin-1-one The compound represented by the following formula was prepared:

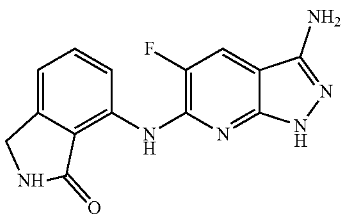 [SMILES: Nc1n[nH]c2nc(Nc3cccc4c3C(=O)NC4)c(F)cc12]

Step 1

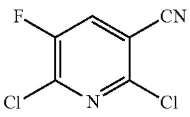

1

+

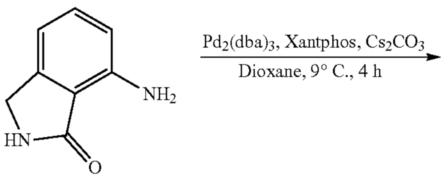

2

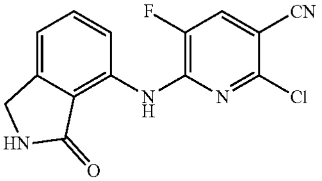

3

2.49 mL (0.2 M) of 1,4-dioxane was added to 95 mg (0.50 mmol) of Compound 1, 81 mg (0.55 mmol, 1.1 eq.) of Compound 2, 58 mg (0.099 mmol, 0.2 eq.) of Xantphos, and 486 mg (1.49 mmol, 3 eq.) of cesium carbonate. 46 mg (0.050 mmol, 0.1 eq.) of $Pd_2(dba)_3$ was added to the resulting mixture. The temperature was elevated to 90° C. and the reaction solution was stirred for 1 hour.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (27 mg, 18%) as a light yellow solid.

Step 2

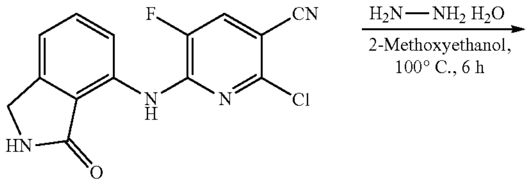

3

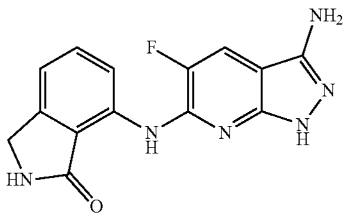

4

26 mg (0.341 mmol) of Compound 3 was dissolved in 0.43 mL (0.2 M) of 2-methoxyethanol, and then 0.083 mL (1.72 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (9 mg, 36%) as a light ivory solid.

$^{1}$H NMR (400 MHz, DMSO-d6) δ=12.01 (br s, 1H), 8.01 (br d, J=8.9 Hz, 1H), 7.24 (br s, 1H), 6.65 (br d, J=7.0 Hz, 1H), 6.58 (br d, J=8.3 Hz, 1H), 6.15 (br s, 2H), 5.53 (br s, 2H), 4.88 (br s, 2H)

Example 87: Preparation of 1-(3-amino-6-((2,3-dihydro-1H-inden-4-yl)amino)-5-fluoro-1H-pyrazolo[3,4-b]pyridin-1-yl)ethan-1-one The compound represented by the following formula was prepared:

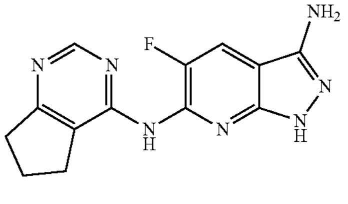 [SMILES: Nc1n[nH]c2nc(Nc3ncnc4c3CCC4)c(F)cc12]

Step 1

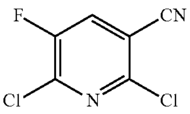

+

1

-continued

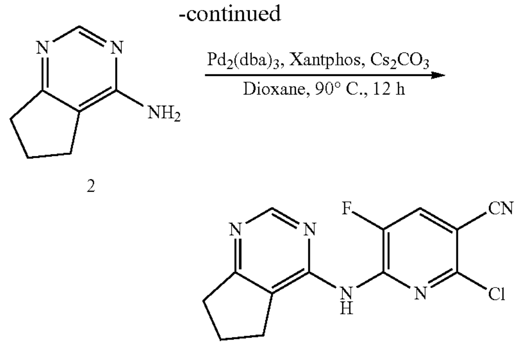

2

3

2.49 mL (0.2 M) of 1,4-dioxane was added to 95 mg (0.50 mmol) of Compound 1, 74 mg (0.55 mmol, 1.1 eq.) of Compound 2, 58 mg (0.099 mmol, 0.2 eq.) of Xantphos, and 486 mg (1.49 mmol, 3 eq.) of cesium carbonate. 46 mg (0.050 mmol, 0.1 eq.) of $Pd_2(dba)_3$ was added to the resulting mixture. The temperature was elevated to 90° C. and the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (120 mg, 83%) as a light yellow solid.

Step 2

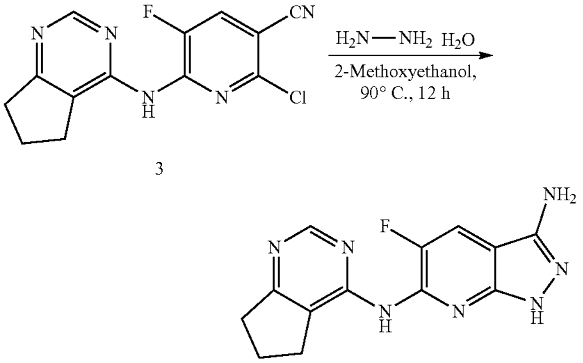

3

4

110 mg (0.38 mmol) of Compound 3 was dissolved in 1.90 mL (0.2 M) of 2-methoxyethanol, and then 0.37 mL (7.59 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (24 mg, 23%) as a light ivory solid.

$^1H$ NMR (400 MHz, DMSO-d6) δ=11.79 (br s, 1H), 9.49 (s, 1H), 8.35 (s, 1H), 7.84 (d, J=10.1 Hz, 1H), 5.39 (s, 2H), 2.78 (t, J=7.8 Hz, 2H), 2.70-2.61 (m, 2H), 1.93 (quin, J=7.6 Hz, 2H)

Example 88: Preparation of 1-(3-amino-6-((2,3-dihydro-1H-inden-4-yl)amino)-5-fluoro-1H-pyrazolo[3,4-b]pyridin-1-yl)ethan-1-one The compound represented by the following formula was prepared:

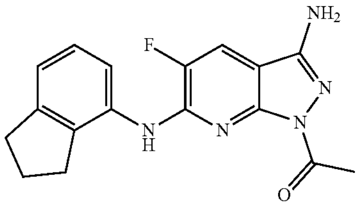 [SMILES: CC(=O)n1nc(N)c2cc(F)c(Nc3cccc4c3CCC4)nc21]

Step 1

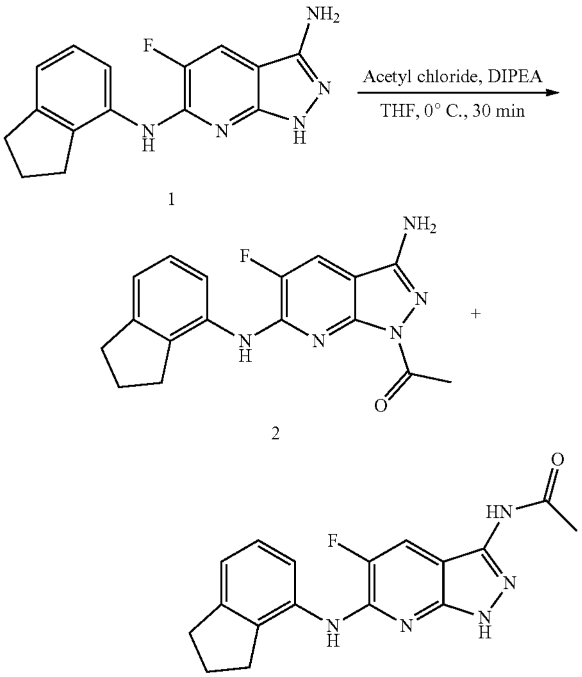

1

2

3

50 mg (0.176 mmol) of Compound 1 was dissolved in 0.882 mL (0.2 M) of tetrahydrofuran (THF), and then 33.9 uL (0.194 mmol, 1.1 eq.) of N,N-diisopropylethylamine was added dropwise to the resulting solution. The temperature was dropped to 0° C., and then a dilution of 12.55 μL (0.176 mmol, 1 eq.) of acetyl chloride in 0.2 mL of tetrahydrofuran (THF) was slowly added dropwise thereto and the resulting mixture was stirred at the same temperature for 30 minutes.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target Compound 2 (16.1 mg, 28%) as a yellow solid and the target Compound 3 (2.0 mg, 3%) as a white solid.

$^1H$ NMR (400 Hz, DMSO-d6) δ=8.68 (d, J=1.2 Hz, 1H), 7.64 (d, J=11.6 Hz, 1H), 7.51 (s, 2H), 7.38 (d, J=8.0 Hz, 1H), 7.15 (t, J=7.6 Hz, 1H), 7.08 (d, J=7.2 Hz, 1H), 2.92 (t, J=7.2 Hz, 2H), 2.78 (t, J=7.2 Hz, 2H), 2.55 (s, 3H), 1.98 (quin, J=7.4 Hz 2H).

Example 89: Preparation of N-(6-((2,3-dihydro-1H-inden-4-yl)amino)-5-fluoro-1H-pyrazolo[3,4-b]pyridin-3-yl)cyclopentanecarboxamide The compound represented by the following formula was prepared:

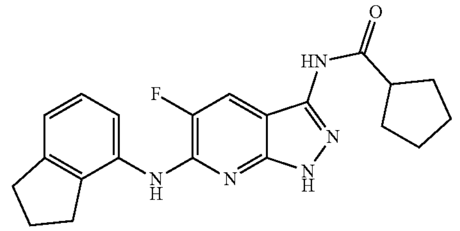 [SMILES: O=C(Nc1n[nH]c2nc(Nc3cccc4c3CCC4)c(F)cc12)C1CCCC1]

Step 1

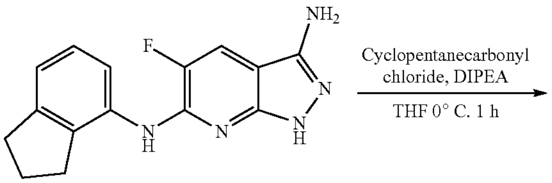

1

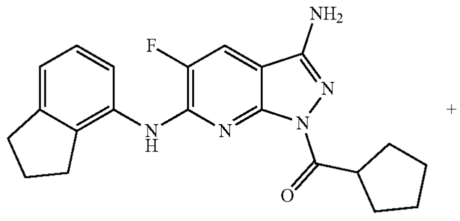

2

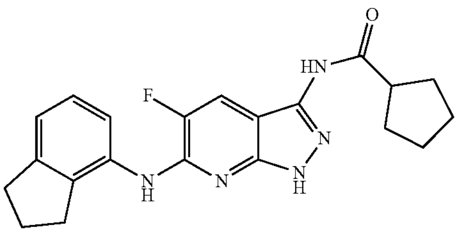

3

60 mg (0.212 mmol) of Compound 1 was dissolved in 1.059 mL (0.2 M) of tetrahydrofuran (THF), and then 40.7 uL (0.233 mmol, 1.1 eq.) of N,N-diisopropylethylamine was added dropwise to the resulting solution. The temperature was dropped to 0° C., and then a dilution of 28.3 μL (0.233 mmol, 1.1 eq.) of cyclopentanecarbonyl chloride in 0.2 mL of tetrahydrofuran (THF) was slowly added dropwise thereto and the resulting mixture was stirred at the same temperature for 1 hour.

After completion of the reaction was detected, the organic layer was separated using $H_2O$ and ethyl acetate, dried over $MgSO_4$, filtered and further dried under reduced pressure.

The obtained residue was purified by reverse phase chromatography to obtain the target Compound 3 (10.6 mg, 13%) as an ivory solid.

$^1$H NMR (400 Hz, DMSO-d6) δ=12.55 (s, 1H), 10.45 (s, 1H), 8.58 (s, 1H), 7.33 (d, J=8.0 Hz, 1H), 7.14 (t, J=7.6 Hz, 1H), 7.05 (d, J=7.2 Hz, 1H), 2.90 (t, J=7.4 Hz, 2H), 2.87 (d, J=7.3 Hz, 1H), 1.97 (quin, J=7.3 Hz, 2H), 1.90-1.84 (m, 2H), 1.76-1.66 (m, 4H), 1.57-1.54 (m, 2H).

Example 90: Preparation of N6-(2,3-dihydro-1H-inden-4-yl)-5-fluoro-1-methyl-1H-pyrazolo[3,4-b]pyridine-3,6-diamine The compound represented by the following formula was prepared:

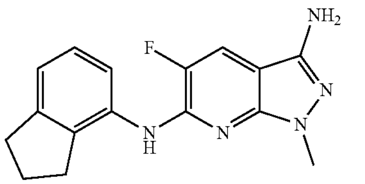

Step 1

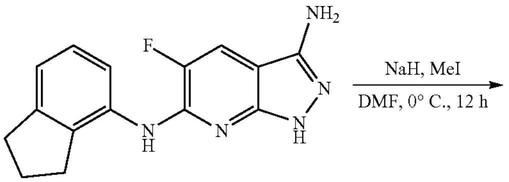

1

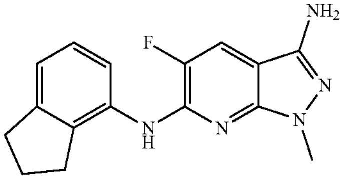 [SMILES: Cn1nc(N)c2cc(F)c(Nc3cccc4c3CCC4)nc21]

2

70 mg (0.247 mmol) of Compound 1 was dissolved in 1.235 mL (0.2 M) of N,N-dimethylmethanamide and then the temperature was dropped to 0° C. 10.87 mg (0.272 mmol, 1.1 eq.) of sodium hydride (NaH) was slowly added dropwise thereto and the resulting mixture was stirred at the same temperature for 30 minutes. A dilution of 16.99 μL (0.272 mmol, 1.1 eq.) of methyl iodide (MeI) in 1.235 mL of N,N-dimethylmethanamide was slowly added dropwise thereto at 0° C. and the resulting mixture was stirred at the same temperature for 12 hours.

After completion of the reaction was detected, the organic layer was separated using $H_2O$ and ethyl acetate, dried over $MgSO_4$, filtered and further dried under reduced pressure. The obtained residue was purified by column chromatography and reverse phase chromatography to obtain the target Compound 2 (13.5 mg, 18%) as a white solid.

$^1$H NMR (400 MHz, DMSO-d6) δ=8.38 (br s, 1H), 7.75 (d, J=11.2 Hz, 1H), 7.52 (d, J=7.7 Hz, 1H), 7.14 (t, J=7.7 Hz, 1H), 7.03 (d, J=7.2 Hz, 1H), 2.91 (t, J=7.2 Hz, 2H), 2.82 (t, J=7.5 Hz, 2H), 2.04-1.96 (m, 3H).

Example 91: Preparation of N-(6-((2,3-dihydro-1H-inden-4-yl)amino)-5-fluoro-1H-pyrazolo[3,4-b]pyridin-3-yl)isonicotinamide The compound represented by the following formula was prepared:

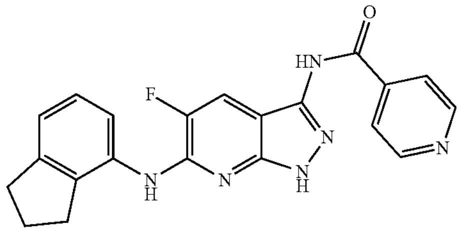 [SMILES: O=C(Nc1n[nH]c2nc(Nc3cccc4c3CCC4)c(F)cc12)c1ccncc1]

Step 1

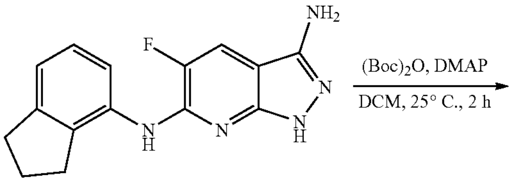

1

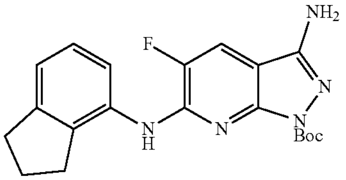

2

500 mg (1.765 mmol) of Compound 1 was dissolved in 17.6 mL (0.1 M) of dichloromethane and then 21.56 mg (0.176 mmol, 0.1 eq.) of 4-dimethylaminopyridine was added to the resulting solution. 0.41 mL (1.765 mmol, 1 eq.) of di-tert-butyl dicarbonate was added dropwise thereto and the resulting mixture was stirred at the same temperature for 2 hours.

After completion of the reaction was detected, the organic layer was separated using $H_2O$ and dichloromethane, dried over $MgSO_4$, filtered and further dried under reduced pressure. The obtained residue was crystallized using dichloromethane and hexane, and filtered to obtain the target Compound 2 (290 mg, 43%) as a yellow solid.

Step 2

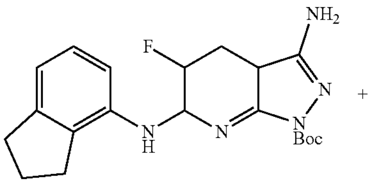

2

-continued

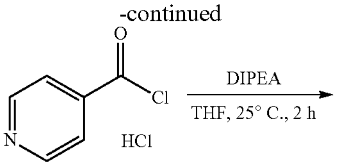

3

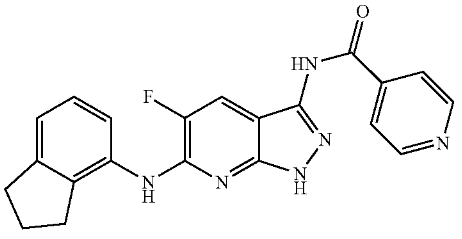

4

50 mg (0.130 mmol) of Compound 2 and 34.8 mg (0.196 mmol, 1.5 eq.) of Compound 3 were dissolved in 0.652 mL (0.2 M) of tetrahydrofuran (THF) and then 68.3 μL (0.391 mmol, 3 eq.) of N,N-diisopropylethylamine was added dropwise thereto. The reaction solution was stirred at room temperature for 2 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 4 (16.2 mg, 32%) as a white solid.

$^1$H NMR (400 MHz, DMSO-d6) δ=12.83 (s, 1H), 11.23 (s, 1H), 8.80 (d, J=4.9 Hz, 2H), 8.69-8.64 (m, 1H), 7.99-7.91 (m, 3H), 7.36 (d, J=7.6 Hz, 1H), 7.16 (t, J=7.6 Hz, 1H), 7.08 (d, J=7.3 Hz, 1H), 2.93 (t, J=7.4 Hz, 2H), 2.80 (t, J=7.4 Hz, 2H), 2.00 (t, J=7.5 Hz, 2H).

Example 92: Preparation of N-(6-((2,3-dihydro-1H-inden-4-yl)amino)-5-fluoro-1H-pyrazolo[3,4-b]pyridin-3-yl)acetamide The compound represented by the following formula was prepared:

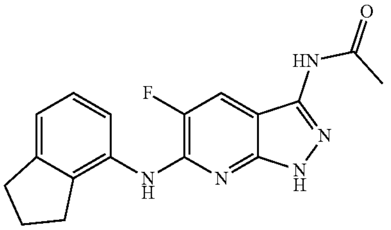 [SMILES: CC(=O)Nc1n[nH]c2nc(Nc3cccc4c3CCC4)c(F)cc12]

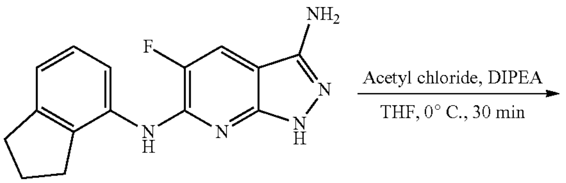

1

-continued

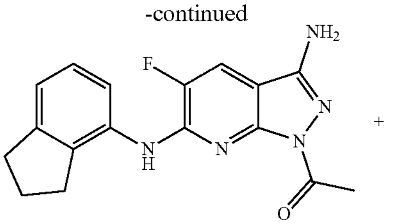

2

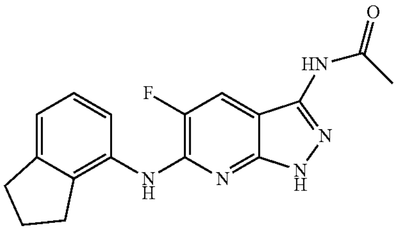

3

50 mg (0.176 mmol) of Compound 1 was dissolved in 0.882 mL (0.2 M) of tetrahydrofuran (THF), and 33.9 uL (0.194 mmol, 1.1 eq.) of N,N-diisopropylethylamine was added dropwise thereto. The temperature was dropped to 0° C. and then a dilution of 12.55 μL (0.176 mmol, 1 eq.) of acetyl chloride in 0.2 mL of tetrahydrofuran (THF) was slowly added dropwise thereto and the resulting mixture was stirred at the same temperature for 30 minutes.

After completion of the reaction was detected, the organic layer was separated using $H_2O$ and ethyl acetate, dried over $MgSo_4$, filtered and further dried under reduced pressure. The obtained residue was purified by reverse phase chromatography to obtain the target Compound 2 (16.1 mg, 28%) as a yellow solid.

$^1$H NMR (400 MHz, DMSO-d6) δ=12.56 (br s, 1H), 10.49 (s, 1H), 8.59 (s, 1H), 7.93 (d, J=11.9 Hz, 1H), 7.33 (d, J=7.6 Hz, 1H), 7.15 (t, J=7.6 Hz, 1H), 7.06 (d, J=7.5 Hz, 1H), 2.91 (t, J=7.4 Hz, 2H), 2.77 (t, J=7.6 Hz, 2H), 2.08 (s, 3H), 2.02-1.96 (m, 2H).

Example 93: Preparation of 1-benzyl-N6-(2,3-dihydro-1H-inden-4-yl)-5-fluoro-1H-pyrazolo[3,4-b]pyridine-3,6-diamine The compound represented by the following formula was prepared:

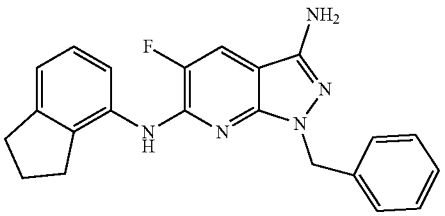 [SMILES: Nc1nn(Cc2ccccc2)c2nc(Nc3cccc4c3CCC4)c(F)cc12]

Step 1

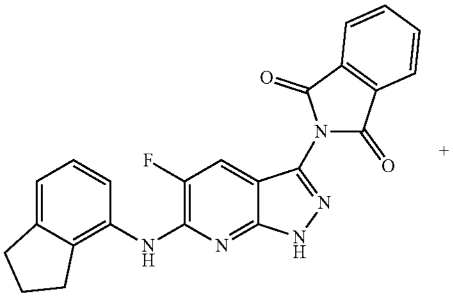

2

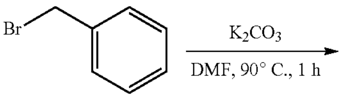

5

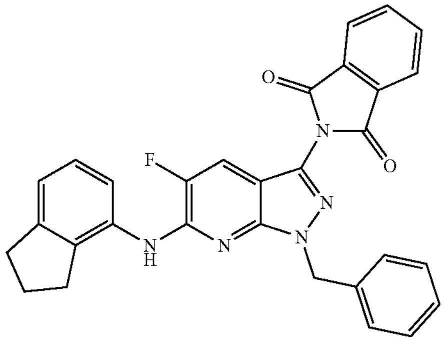

6

33 mg (crude) of Compound 2 was dissolved in 0.235 mL (0.3 M) of N,N-dimethylmethanamide, and then 12.59 μL (0.106 mmol, 1.5 eq.) of compound 5, and 29.3 mg (0.212 mmol, 3 eq.) of potassium carbonate were added thereto. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue, the target compound 6 (41 mg, 114%) was used in the subsequent reaction without additional purification.

Step 2

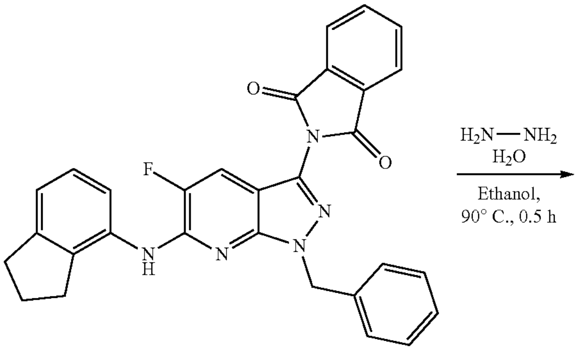

6

-continued

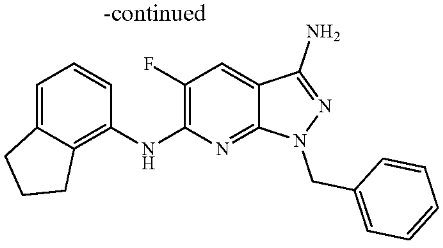

7

41 mg (crude) of compound 6 was dissolved in 0.235 mL (0.3 M) of ethanol and 68.5 μL (1.412 mmol, 20 eq.) of hydrazine monohydrate was added dropwise to the resulting solution. The temperature was elevated to 90° C., and then the resulting mixture was stirred for 30 minutes.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 7 (13.2 mg, 50%) as a light yellow solid.

$^1H$ NMR (400 MHz, DMSO-d6) δ=8.43 (brs, 1H), 7.76 (d, J=11.2 Hz, 1H), 7.44 (d, J=8.0 Hz, 1H), 7.30-7.20 (m, 3H), 7.12 (t, J=7.6 Hz, 3H), 7.00 (d, J=7.6 Hz, 1H), 5.10 (s, 2H), 2.86 (t, J=7.4 Hz, 2H), 2.70 (t, J=7.4 Hz, 2H), 1.88 (quin, J=7.4 Hz, 2H).

Example 94: Preparation of 1-(3-amino-6-((2,3-dihydro-1H-inden-4-yl)amino)-5-fluoro-1H-pyrazolo[3,4-b]pyridin-1-yl)propan-2-one The compound represented by the following formula was prepared:

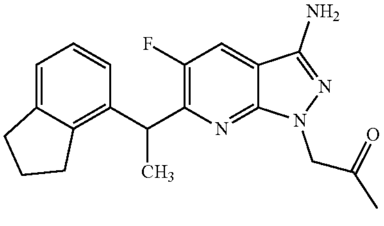 [SMILES: CC(=O)Cn1nc(N)c2cc(F)c(C(C)c3cccc4c3CCC4)nc21]

Step 1

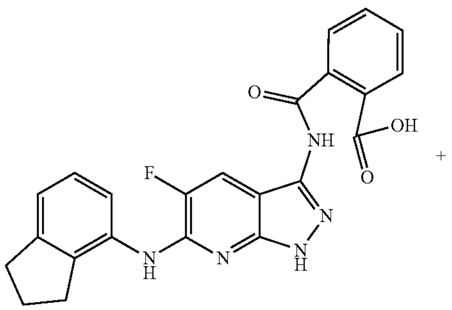

2

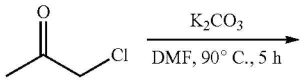

5

-continued

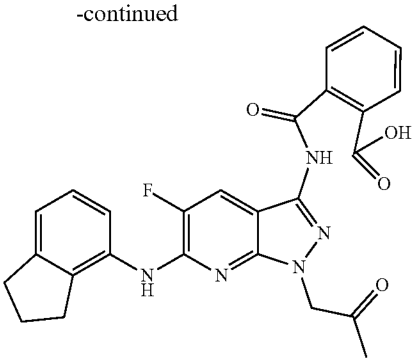

6

70 mg (0.162 mmol) of Compound 2 was dissolved in 0.541 mL (0.3 M) of N,N-dimethylmethanamide, and 38.8 μL (0.487 mmol, 3 eq.) of compound 5 and 112 mg (0.811 mmol, 5 eq.) of potassium carbonate were added to the resulting solution. The temperature was elevated to 90° C., and then the resulting mixture was stirred for 5 hours.

After completion of the reaction was detected, the organic layer was separated using $H_2O$ and ethyl acetate, dried over $MgSO_4$, filtered and further dried under reduced pressure. The obtained residue, the target compound 6 (91 mg, 115%) was used in the subsequent reaction without additional purification.

Step 2

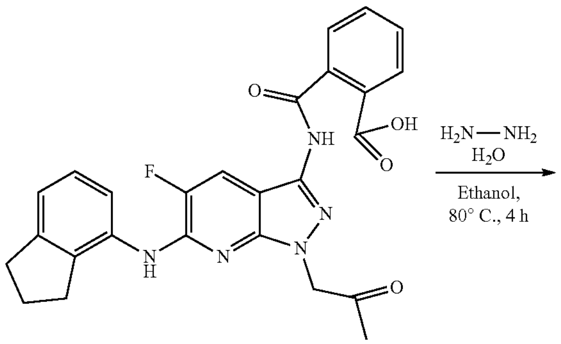

6

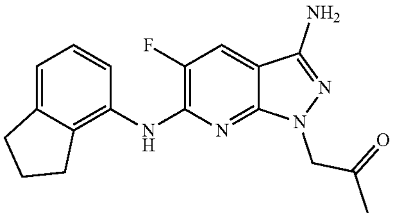

7

79 mg (crude) of compound 6 was dissolved in 0.810 mL (0.3 M) of ethanol and then 0.157 mL (3.24 mmol, 20 eq.) of hydrazine monohydrate was added dropwise to the resulting solution. The temperature was elevated to 80° C., and then the resulting mixture was stirred for 4 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 7 (19.3 mg, 35%) as a light yellow solid.

$^1$H NMR (400 MHz, DMSO-d6) δ=8.48 (brs, 1H), 7.78 (d, J=11.2 Hz, 1H), 7.40 (d, J=8.0 Hz, 1H), 7.10 (t, J=7.8 Hz, 1H), 7.00 (d, J=7.2 Hz, 1H), 4.74 (s, 2H), 2.88 (t, J=7.4 Hz, 2H), 2.73 (t, J=7.2 Hz, 2H), 2.00 (s, 3H), 1.95 (quin, J=7.4 Hz, 2H).

Example 95: Preparation of 2-(6-((2,3-dihydro-1H-inden-4-yl)amino)-5-fluoro-1H-pyrazolo[3,4-b]pyridin-3-yl)isoindoline-1,3-dione The compound represented by the following formula was prepared:

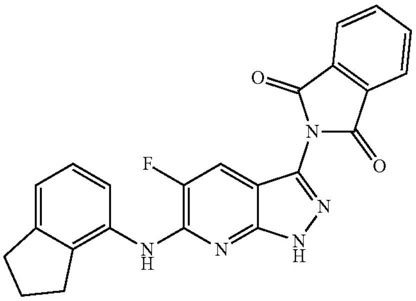 [SMILES: O=C1c2ccccc2C(=O)N1c1n[nH]c2nc(Nc3cccc4c3CCC4)c(F)cc12]

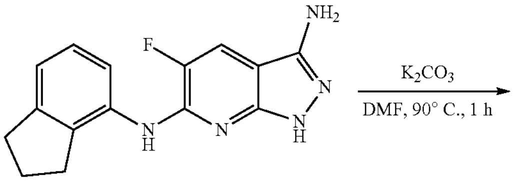

2

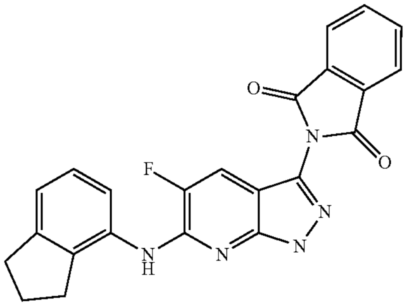

2

1 g (3.53 mmol) of Compound 1 was dissolved in 17.65 mL (0.2 M) of 1,4-dioxane and then 1.586 g (10.59 mmol, 3 eq.) of phthalic anhydride was added dropwise to the resulting solution. The reaction solution was stirred at an elevated temperature 8 hours. After completion of the reaction was detected, the reaction solution was precipitated into a slury in ethanol and filtered to obtain the target Compound 2 (1.39 g, 95%) as a yellow solid.

$^1$H NMR (400 MHz, DMSO-d6) δ=13.38 (s, 1H), 8.83-8.79 (m, 1H), 8.05-8.01 (m, 2H), 7.99-7.94 (m, 2H), 7.87 (d, J=11.2 Hz, 1H), 7.32 (d, J=7.5 Hz, 1H), 7.18 (t, J=7.6 Hz, 1H), 7.13-7.07 (m, 1H), 2.94 (t, J=7.4 Hz, 2H), 2.80 (t, J=7.4 Hz, 2H), 2.00 (quin, J=7.5 Hz, 2H).

Example 96: Preparation of N6-(2,3-dihydro-1H-inden-4-yl)-1-(2-(dimethylamino)ethyl)-5-fluoro-1H-pyrazolo[3,4-b]pyridine-3,6-diamine The compound represented by the following formula was prepared:

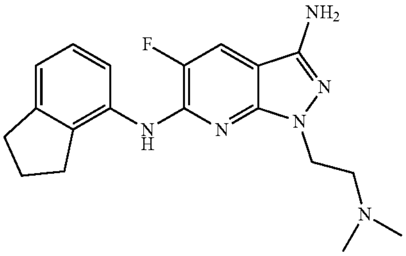 [SMILES: CN(C)CCn1nc(N)c2cc(F)c(Nc3cccc4c3CCC4)nc21]

Step 1

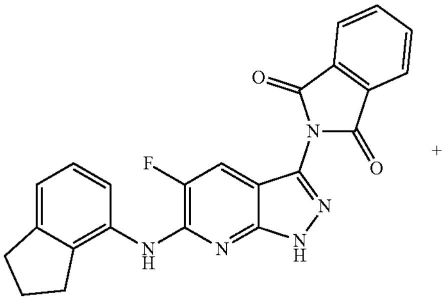

2

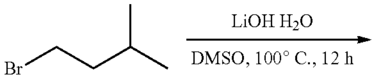

5

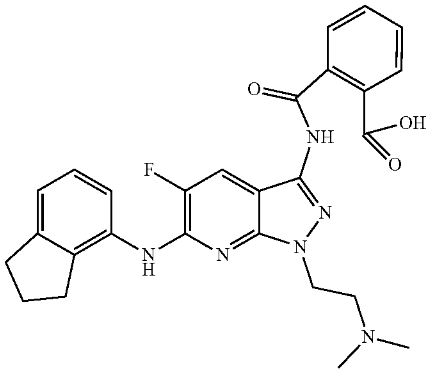

6

200 mg (0.484 mmol) of Compound 2 was dissolved in 3.225 mL (0.15 M) of dimethylsulfoxide and 338 mg (1.451 mmol, 3 eq.) of compound 5 and 406 mg (9.68 mmol, 20 eq.) of LiOH monohydrate were added thereto. The temperature was elevated to 100° C., and then the resulting mixture was stirred for 12 hours.

After completion of the reaction was detected, the reaction solution was purified in 10 mL of $H_2O$ by reverse phase chromatography to obtain the target compound 6 (124 mg, 51%).

Step 2

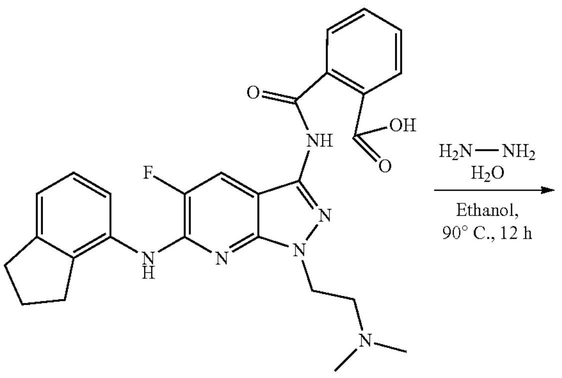

6

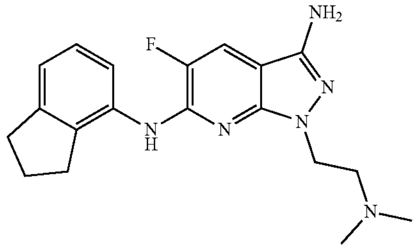

7

120 mg (0.239 mmol) of compound 6 was dissolved in 2.388 mL (0.1 M) of ethanol and then 0.232 mL (4.78 mmol, 20 eq.) of hydrazine monohydrate was added dropwise to the resulting solution. The temperature was elevated to 90° C., and then the resulting mixture was stirred for 12 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 7 (12.2 mg, 14%) as a white solid.

$^1$H NMR (400 MHz, DMSO-d6) δ=8.28 (s, 1H), 7.72 (d, J=11.2 Hz, 1H), 7.53 (d, J=8.1 Hz, 1H), 7.11 (t, J=7.7 Hz, 1H), 7.01 (d, J=7.2 Hz, 1H), 5.32 (s, 2H), 3.98 (t, J=6.8 Hz, 2H), 2.90 (t, J=7.4 Hz, 2H), 2.83 (t, J=7.4 Hz, 2H), 2.58-2.54 (m, 2H), 2.11 (s, 6H), 2.05-1.94 (m, 2H).

Example 97: Preparation of 2-(6-((2,3-dihydro-1H-inden-4-yl)amino)-5-fluoro-1-(tetrahydro-2H-pyran-2-yl)-1H-pyrazolo[3,4-b]pyridin-3-yl)isoindoline-1,3-dione The compound represented by the following formula was prepared:

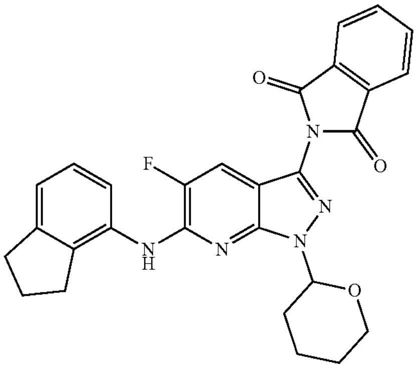

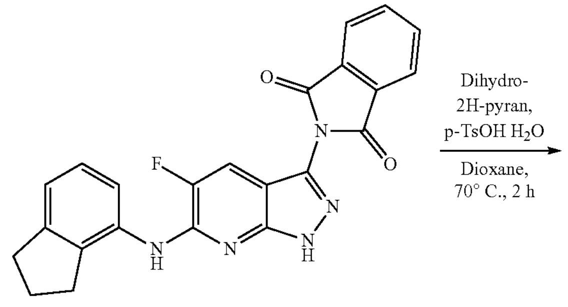

6

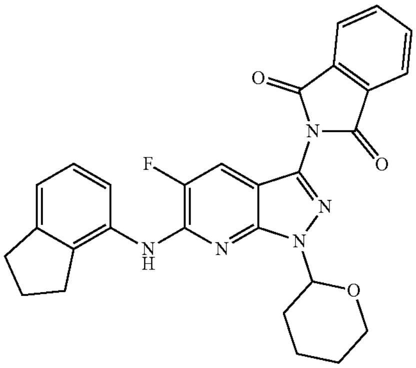 [SMILES: O=C1c2ccccc2C(=O)N1c1nn(C2CCCCO2)c2nc(Nc3cccc4c3CCC4)c(F)cc12]

7

200 mg (0.484 mmol) of Example 95 was dissolved in 2.419 mL (0.2 M) of 1,4-dioxane, and then 88 μL (0.968 mmol, 2 eq.) of dihydro-2H-pyran and 9.20 mg (0.048 mmo, 0.1 eq.) of p-toluenesulfonic acid monohydrate were added dropwise to the resulting solution. The temperature was elevated to 70° C., and then the resulting mixture was stirred for 2 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (239 mg, 99%) as a white solid.

$^1$H NMR (400 MHz, DMSO-d6) δ=9.01 (s, 1H), 8.06-8.02 (m, 2H), 7.99-7.95 (m, 2H), 7.92 (d, J=11.0 Hz, 1H), 7.38 (d, J=7.7 Hz, 1H), 7.22-7.16 (m, 1H), 7.14-7.08 (m, 1H), 5.66 (dd, J=2.2, 10.4 Hz, 1H), 3.97 (br d, J=11.1 Hz, 1H), 3.61-3.51 (m, 1H), 2.99-2.90 (m, 3H), 2.77-2.67 (m, 1H), 2.34 (br s, 1H), 2.05-1.95 (m, 3H), 1.88 (br d, J=10.4 Hz, 1H), 1.73-1.64 (m, 1H), 1.54 (br d, J=7.8 Hz, 2H).

Example 98: Preparation of ethyl hydrogen (2-(3-amino-6-((2,3-dihydro-1H-inden-4-yl)amino)-5-fluoro-1H-pyrazolo[3,4-b]pyridin-1-yl)ethyl)phosphonate The compound represented by the following formula was prepared:

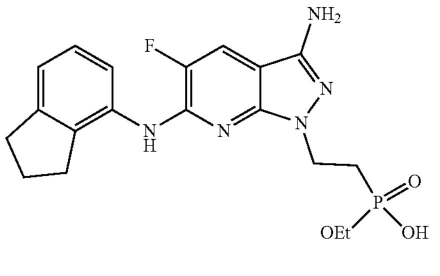 [SMILES: CCOP(=O)(O)CCn1nc(N)c2cc(F)c(Nc3cccc4c3CCC4)nc21]

Step 1

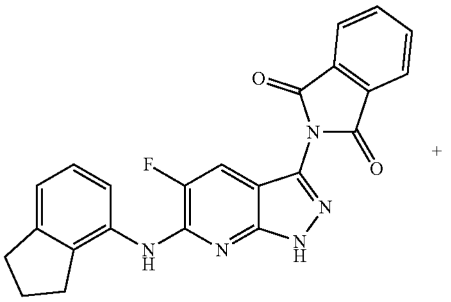

2

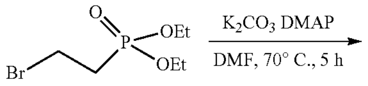

5

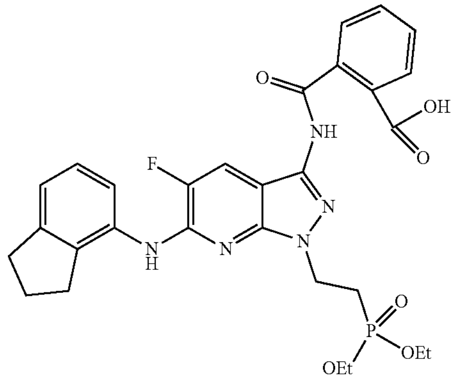

6

90 mg (0.218 mmol) of Compound 2 was dissolved in 1.451 mL (0.15 M) of N,N-dimethylmethanamide and then 107 mg (0.435 mmol, 2 eq.) of compound 5, 150 mg (1.089 mmol, 5 eq.) of potassium carbonate, and 2.66 mg (0.022 mmol, 0.1 eq.) of 4-dimethylaminopyridine were added to the resulting solution. The temperature was elevated to 70° C., and then the resulting mixture was stirred for 5 hours.

After completion of the reaction was detected, the reaction solution was purified in 2 mL of dimethylsulfoxide by reverse phase chromatography to obtain the target compound 6 (93 mg, 72%).

Step 2

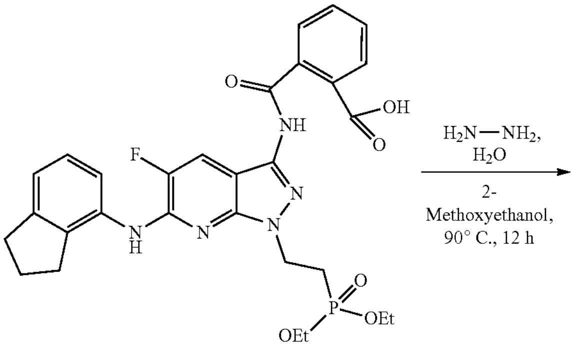

6

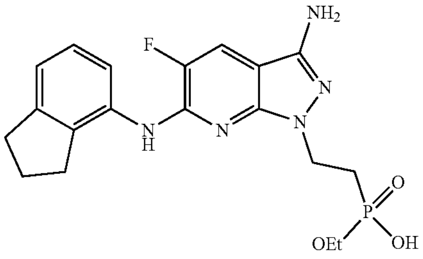

7

93 mg (0.156 mmol) of compound 6 was dissolved in 1.562 mL (0.1 M) of 2-methoxyethanol and then 0.151 mL (3.12 mmol, 20 eq.) of hydrazine monohydrate was added dropwise to the resulting solution. The temperature was elevated to 90° C., and then the resulting mixture was stirred for 12 hours.

After completion of the reaction was detected, the reaction solution was purified in 2 mL of dimethylsulfoxide by reverse phase chromatography to obtain the target compound 7 (36.5 mg, 56%).

$^1$H NMR (400 MHz, DMSO-d6) δ=8.45 (br s, 1H), 7.75 (d, J=11.2 Hz, 1H), 7.48 (d, J=7.9 Hz, 1H), 7.12 (t, J=7.6 Hz, 1H), 7.03 (d, J=7.3 Hz, 1H), 4.11-4.04 (m, 2H), 3.86 (quin, J=7.4 Hz, 2H), 2.91 (t, J=7.3 Hz, 2H), 2.80 (t, J=7.3 Hz, 2H), 2.11-1.98 (m, 4H), 1.14 (t, J=7.0 Hz, 3H).

Example 99: Preparation of N6-(2,3-dihydro-1H-inden-4-yl)-5-fluoro-1-(tetrahydro-2H-pyran-2-yl)-1H-pyrazolo[3,4-b]pyridine-3,6-diamine The compound represented by the following formula was prepared:

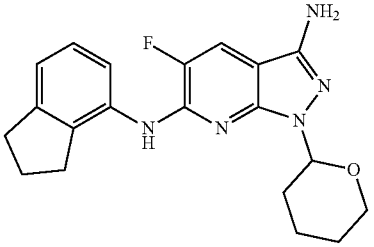 [SMILES: Nc1nn(C2CCCCO2)c2nc(Nc3cccc4c3CCC4)c(F)cc12]

Step 1

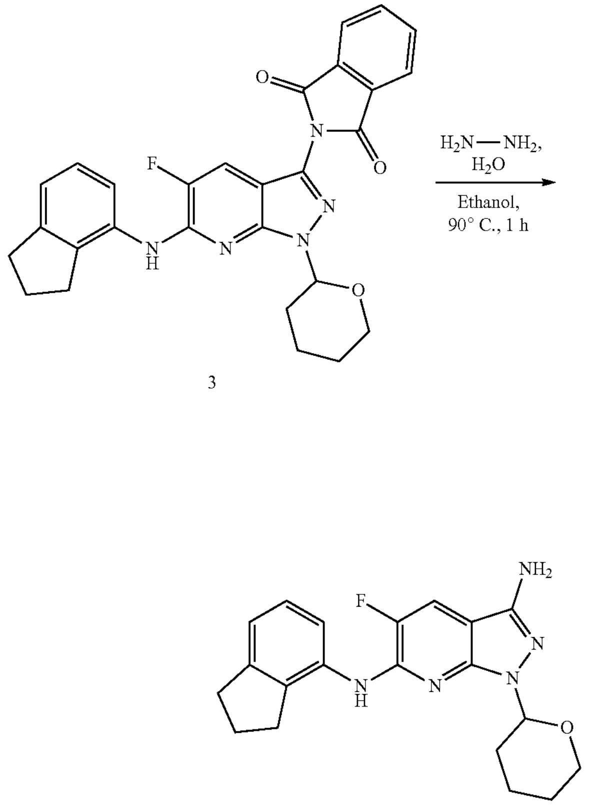

3

4

215 mg (0.432 mmo) of Compound 3 (Example 97) was dissolved in 4.321 mL (0.1 M) of ethanol and then 0.419 mL (8.64 mmol, 20 eq.) of hydrazine monohydrate was added to the resulting solution. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 4 (130 mg, 82%) as a white solid.

$^1H$ NMR (400 MHz, DMSO-d6) δ=8.54 (s, 1H), 7.75 (d, J=11.1 Hz, 1H), 7.39 (d, J=7.9 Hz, 1H), 7.13 (t, J=7.6 Hz, 1H), 7.03 (d, J=7.2 Hz, 1H), 5.46 (s, 2H), 5.34 (br d, J=8.9 Hz, 1H), 3.88 (br d, J=11.0 Hz, 1H), 3.48-3.36 (m, 1H), 2.95-2.85 (m, 3H), 2.72-2.64 (m, 1H), 2.34-2.28 (m, 1H), 2.03-1.90 (m, 3H), 1.73 (br d, J=13.4 Hz, 1H), 1.61 (br d, J=12.2 Hz, 1H), 1.47 (br s, 2H).

Example 100: Preparation of 2-(3-amino-6-((2,3-dihydro-1H-inden-4-yl)amino)-5-fluoro-1H-pyrazolo [3,4-b]pyridin-1-yl)-1-phenylethan-1-one The compound represented by the following formula was prepared:

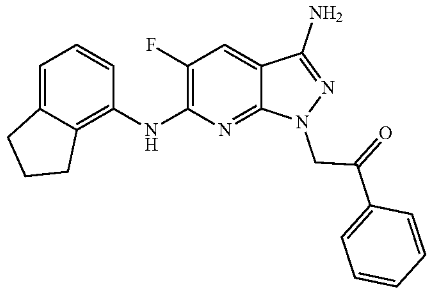 [SMILES: Nc1nn(CC(=O)c2ccccc2)c2nc(Nc3cccc4c3CCC4)c(F)cc12]

Step 1

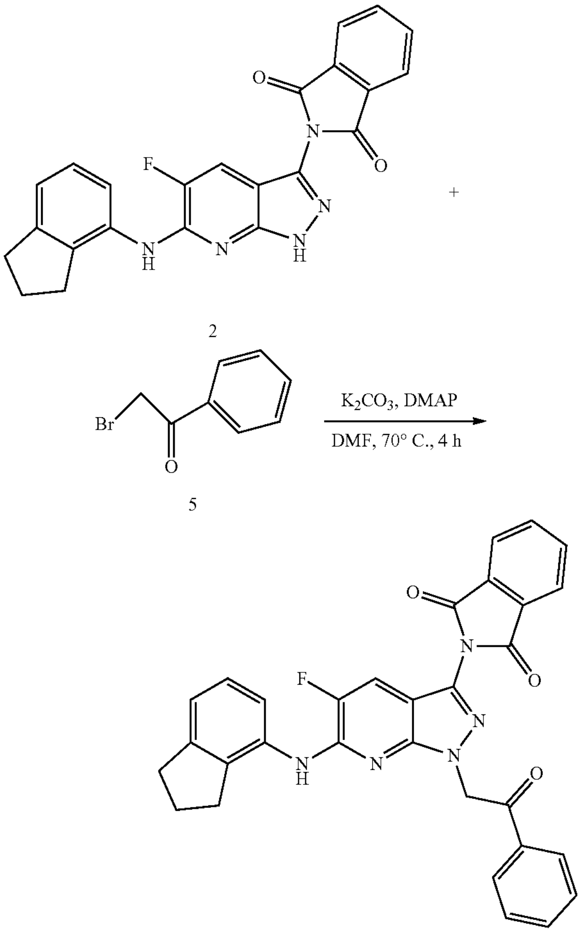

2

5

6

120 mg (0.290 mmol) of Compound 2 was dissolved in 1.935 mL (0.15 M) of N,N-dimethylmethanamide and then 116 mg (0.581 mmol, 2 eq.) of compound 5, 201 mg (1.451 mmol, 5 eq.) of potassium carbonate, and 3.55 mg (0.029 mmol, 0.1 eq.) of 4-dimethylaminopyridine were added to the resulting mixture. The temperature was elevated to 70° C., and then the resulting mixture was stirred for 4 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 6 (81 mg, 53%) as a brown solid.

Step 2

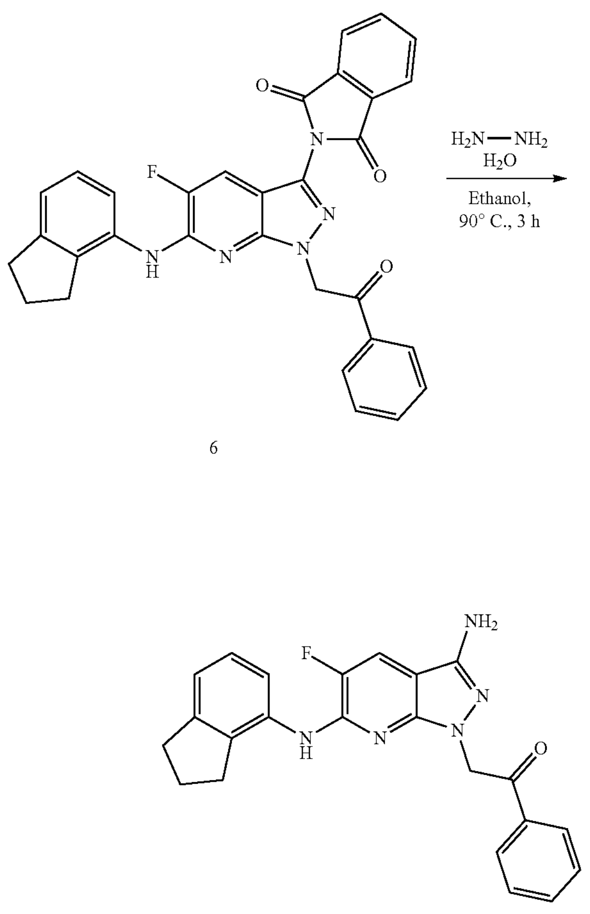

6

7

81 mg (0.152 mmol) of compound 6 was dissolved in 1.524 mL (0.1 M) of ethanol and then 0.148 mL (3.05 mmol, 20 eq.) of hydrazine monohydrate was added dropwise to the resulting solution. The temperature was elevated to 90° C., and then the resulting mixture was stirred for 3 hours. 0.1 mL of trifluoroacetic acid was added dropwise thereto and then the reaction solution was stirred for 12 hours.

After completion of the reaction was detected, the reaction solution was concentrated under reduced pressure. The organic layer was separated using an aqueous sodium hydrogen carbonate solution (aq. $NaHCO_3$) and ethyl acetate, dried over $MgSO_4$, filtered and further dried under reduced pressure. The obtained residue was purified by reverse phase chromatography to obtain the target compound 7 (11.5 mg, 19%).

$^1$H NMR (400 MHz, DMSO-d6) δ=8.55 (br s, 1H), 8.00 (d, J=7.6 Hz, 2H), 7.81 (d, J=11.4 Hz, 1H), 7.70 (t, J=7.5 Hz, 1H), 7.55 (t, J=7.7 Hz, 2H), 7.30 (br d, J=7.2 Hz, 1H), 6.97-6.90 (m, 2H), 5.47 (s, 2H), 2.71-2.63 (m, 4H), 1.83-1.74 (m, 2H).

Example 101: Preparation of methyl (6-((2,3-dihydro-1H-inden-4-yl)amino)-5-fluoro-1H-pyrazolo [3,4-b]pyridin-3-yl)glycinate The compound represented by the following formula was prepared:

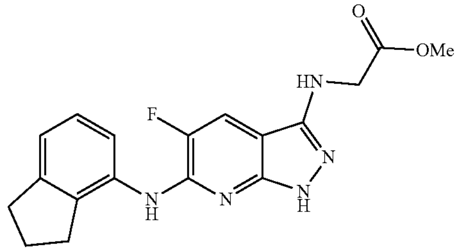 [SMILES: COC(=O)CNc1n[nH]c2nc(Nc3cccc4c3CCC4)c(F)cc12]

Step 1

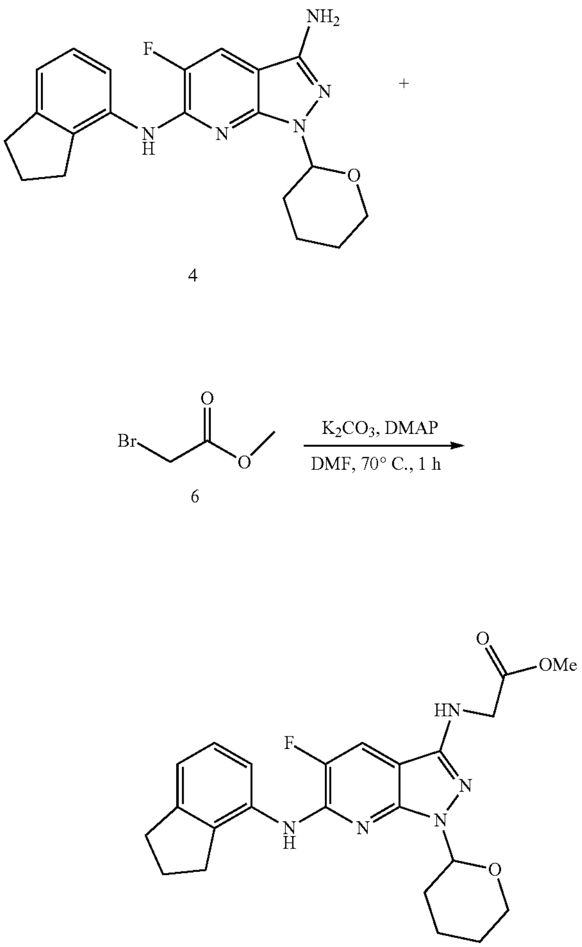

4

6

9

80 mg (0.218 mmol) of compound 4 was dissolved in 1.089 mL (0.2 M) of N,N-dimethylmethanamide and then 103 μL (1.089 mmol, 5 eq.) of compound 8, 90 mg (0.653 mmol, 3 eq.) of potassium carbonate, and 5.32 mg (0.044 mmol, 0.2 eq.) of 4-dimethylaminopyridine were added to the resulting solution. The temperature was elevated to 70° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 9 (70.5 mg, 74%) as a light yellow solid.

Step 2

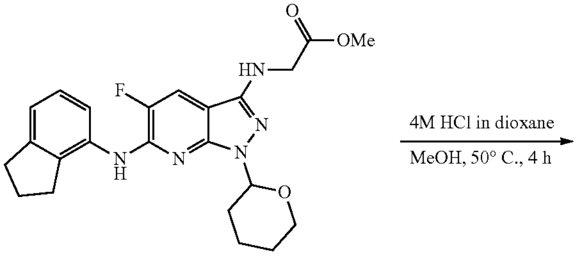

9

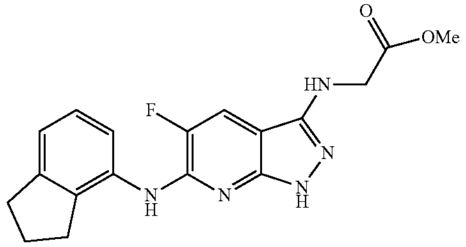

10

70.5 mg (0.160 mmol) of compound 9 was dissolved in 1.604 mL (0.1 M) of methanol and then a hydrogen chloride solution, 4 M in dioxane 48.7 L (1.604 mmol, 10 eq.) was added dropwise to the resulting solution. The temperature was elevated to 50° C., and then the resulting mixture was stirred for 4 hours.

After completion of the reaction was detected, the organic layer was separated using an aqueous sodium hydrogen carbonate solution (aq. $NaHCO_3$) and ethyl acetate, dried over $MgSO_4$, filtered and further dried under reduced pressure. The obtained residue was purified by reverse phase chromatography to obtain the target Compound 10 (39.1 mg, 69%).

$^1$H NMR (400 MHz, DMSO-d6) δ=8.55-8.44 (m, 1H), 7.81 (d, J=10.8 Hz, 1H), 7.37-7.32 (m, 1H), 7.18-7.10 (m, 1H), 7.06-6.99 (m, 1H), 4.01 (s, 2H), 3.64 (s, 3H), 2.91 (t, J=7.5 Hz, 2H), 2.76 (t, J=7.5 Hz, 2H), 1.98 (br t, J=7.3 Hz, 2H).

Example 102: Preparation of 5-fluoro-N6-indan-4-yl-N3-methyl-1H-pyrazolo[3,4-b]pyridine-3,6-diamine The compound represented by the following formula was prepared:

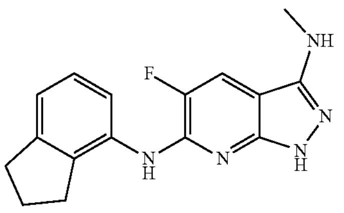 [SMILES: CNc1n[nH]c2nc(Nc3cccc4c3CCC4)c(F)cc12]

Step 1

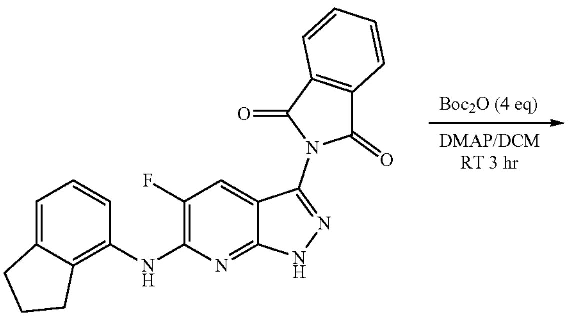

2

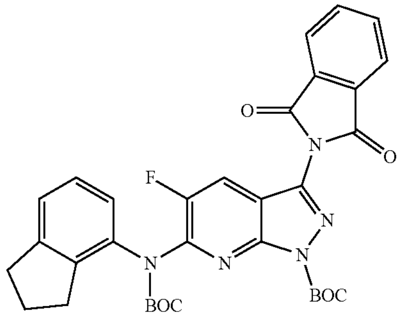

3

1.3 g (3.1 mmol) of Compound 2 was dissolved in 5 mL of dichloromethane, and then 2.4 g (12.4 mmol, 4 eq.) of di-tert butyl dicarbonate and 37 mg (0.3 mmol, 0.1 eq.) of DMAP were added thereto and the resulting solution was stirred at room temperature for 3 hours. After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (1.6 g, 83%) as a white solid.

Step 2

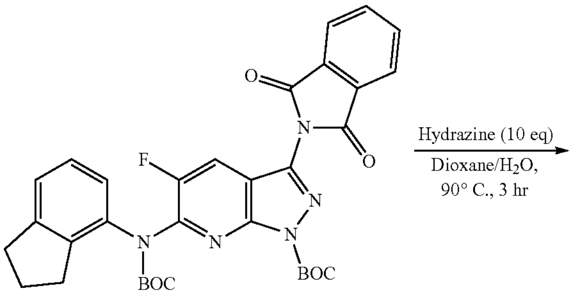

3

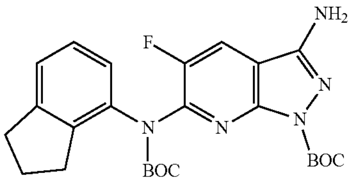

4

900 mg (1.46 mmol) of Compound 3 was dissolved in dioxane/$H_2O$ (1:1, 5 mL) and then 571 mg (11.4 mmol, 9 eq.) of hydrazine monohydrate was added dropwise to the resulting solution. The temperature was elevated to 90° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 4 (700 mg, 99%).

Step 3

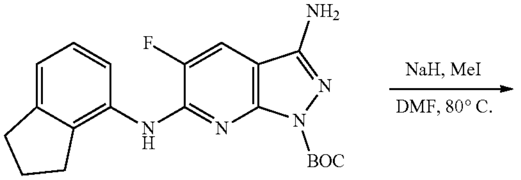

4

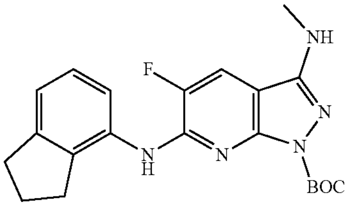

5

50 mg (0.1 mmol) of compound 4 was dissolved in 1 mL of N,N-dimethylmethanamide and then 8 mg (0.2 mmol, 2 eq.) of sodium hydride, and 6.18 ul (0.1 mmol, 1 eq.) of iodomethane were added to the resulting solution. The temperature was elevated to 80° C., and then the resulting mixture was stirred for 1 hour.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 5 (20 mg, 55%) as a white solid.

Step 4

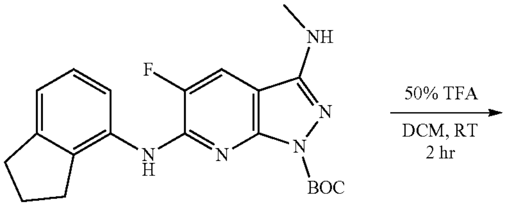

5

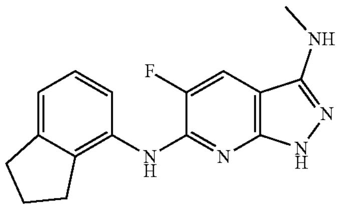

6

3 ml of 50% trifluoroacetic acid/dichloromethane were slowly added dropwise to 22 mg (0.055 mmol) of compound 5. The resulting solution was stirred at room temperature for 2 hours. After completion of the reaction was detected, the reaction solution was concentrated under reduced pressure. The organic residue was purified by reverse phase chromatography to obtain the target compound 6 (8.6 mg, 50%) as a white solid.

)$^1$H NMR (500 MHz, DMSO-d6) δ=8.25 (s, 1H), 7.70 (d, J=11.3 Hz, 1H), 7.51 (d, J=8.0 Hz, 1H), 7.11 (t, J=7.7 Hz, 1H), 6.99 (d, J=7.4 Hz, 1H), 5.28 (s, 1H), 3.51 (s, 3H), 2.89 (t, J=7.4 Hz, 2H), 2.79 (t, J=7.3 Hz, 2H), 2.00-1.94 (m, 2H).

Example 103: Preparation of N-(2,3-dihydro-1H-inden-4-yl)-5-fluoro-3-iodo-1H-pyrazolo[3,4-b]pyridin-6-amine The compound represented by the following formula was prepared:

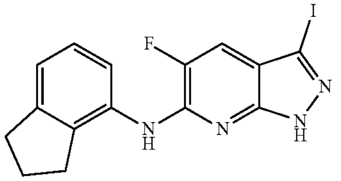 [SMILES: Fc1cc2c(I)n[nH]c2nc1Nc1cccc2c1CCC2]

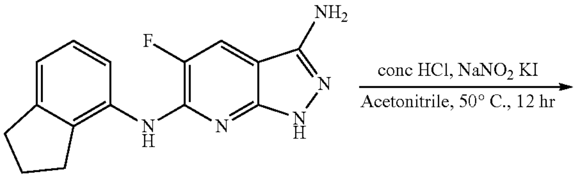

1

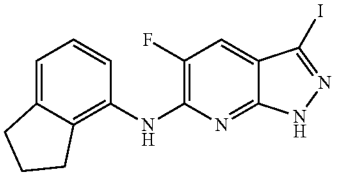

2

1 g (3.53 mmol) of Compound 1 was dissolved in 14.12 mL (0.25 M) of acetonitrile, the temperature was dropped to 0° C., and 609 mg (8.82 mmol, 2.5 eq.) of sodium nitrite and 0.536 mL (17.65 mmol, 5 eq.) of conc. HCl were added dropwise to the resulting solution. The mixture was stirred for 10 minutes and then 1.465 g (8.82 mmol, 2.5 eq.) of potassium iodide was added to the reaction solution. The temperature was elevated to 50° C., and then the resulting mixture was stirred for 12 hours.

After completion of the reaction was detected, the organic layer was separated using an aqueous sodium thiosulfate solution (aq. $Na_2S_2O_3$), an aqueous sodium hydrogen carbonate solution (aq. $NaHCO_3$) and ethyl acetate, dried over $MgSO_4$, filtered and further dried under reduced pressure. The obtained residue was purified by column chromatography to obtain the target Compound 2 (720 mg, 52%) as a yellow solid.

$^1$H NMR (400 MHz, DMSO-d6) δ=13.41 (s, 1H), 8.81 (s, 1H), 7.55 (d, J=10.6 Hz, 1H), 7.30 (d, J=7.5 Hz, 1H), 7.15

(t, J=7.5 Hz, 1H), 7.11-7.06 (m, 1H), 2.91 (t, J=7.3 Hz, 2H), 2.80-2.69 (m, 2H), 2.02-1.93 (m, 2H).

Example 104: Preparation of N-(2,3-dihydro-1H-inden-4-yl)-5-fluoro-1H-pyrazolo[3,4-b]pyridin-6-amine The compound represented by the following formula was prepared:

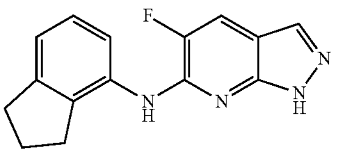

Step 1

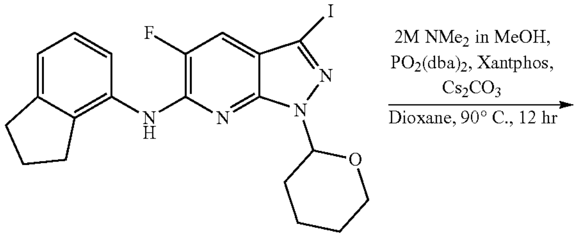

3

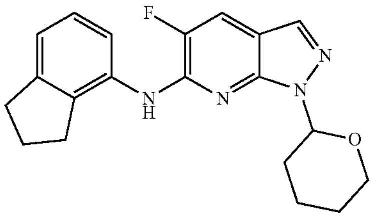

4

0.523 mL (0.2 M) of 1,4-dioxane was added to 50 mg (0.105 mmol) of Compound 3, 2.0 M dimethylamine in MeOH 0.105 mL (0.209 mmol, 2 eq.), 12.10 mg (0.021 mmol, 0.2 eq.) of Xantphos, and 102 mg (0.314 mmol, 3 eq.) of cesium carbonate. 9.57 mg (10.45 μmol, 0.1 eq.) of $Pd_2(dba)_3$ was added to the resulting mixture. The temperature was elevated to 90° C. and the reaction solution was stirred for 12 hours. The deiodinated compound 4 was produced as a by-product.

After completion of the reaction was detected, the organic layer was separated using $H_2O$ and ethyl acetate, dried over $MgSO_4$, filtered and further dried under reduced pressure. The obtained residue was purified by column chromatography to obtain the target compound 4 (23.5 mg, 64%) as a yellow solid.

Step 2

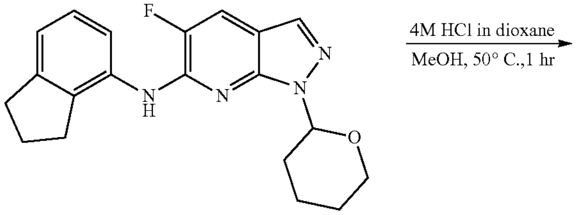

4

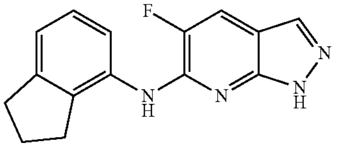 [SMILES: Fc1cc2cn[nH]c2nc1Nc1cccc2c1CCC2]

5

23.50 mg (0.067 mmol) of compound 4 was dissolved in 0.667 mL (0.1 M) of methanol and then a hydrogen chloride solution, 4 M in dioxane 20.26 μL (0.667 mmol, 10 eq.) was added dropwise to the resulting solution. The temperature was elevated to 50° C. and the reaction solution was stirred for 1 hour.

After completion of the reaction was detected, the organic layer was separated using an aqueous sodium hydrogen carbonate solution (aq. $NaHCO_3$) and dichloromethane, dried over $MgSO_4$, filtered and further dried under reduced pressure. The obtained residue was purified by reverse phase chromatography to obtain the target compound 5 (15.2 mg, 85%).

$^1H$ NMR (400 MHz, DMSO-d6) δ=8.54 (s, 1H), 7.85 (d, J=11.2 Hz, 1H), 7.82 (s, 1H), 7.36 (d, J=7.7 Hz, 1H), 7.15 (t, J=7.6 Hz, 1H), 7.06 (d, J=7.3 Hz, 1H), 2.92 (t, J=7.3 Hz, 2H), 2.77 (t, J=7.3 Hz, 2H), 1.98 (quin, J=7.3 Hz, 2H).

Example 105: Preparation of N6-(2,3-dihydro-1H-inden-4-yl)-5-fluoro-N3,N3-dimethyl-1H-pyrazolo[3,4-b]pyridine-3,6-diamine The compound represented by the following formula was prepared:

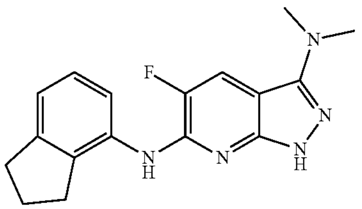 [SMILES: CN(C)c1n[nH]c2nc(Nc3cccc4c3CCC4)c(F)cc12]

Step 1

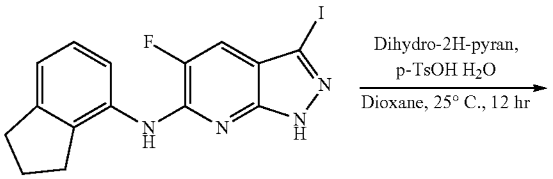

2

-continued

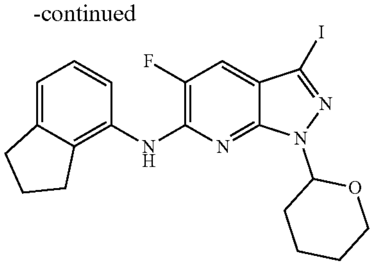

3

63.5 mg (0.161 mmol) of Compound 2 (Example 103) was dissolved in 0.805 mL (0.2 M) of 1,4-dioxane and then 29.4 μL (0.322 mmol, 2 eq.) of dihydro-2H-pyran, and 3.06 mg (0.016 mmol, 0.1 eq.) of p-toluenesulfonic acid monohydrate were added dropwise to the resulting solution. The reaction solution was stirred at room temperature for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (63.1 mg, 82%) as a white solid.

Step 2

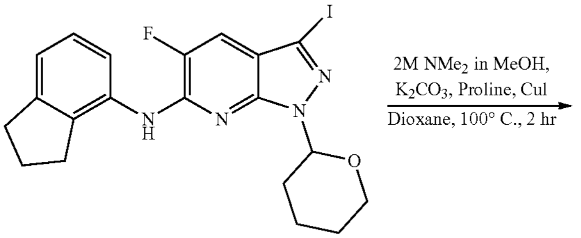

3

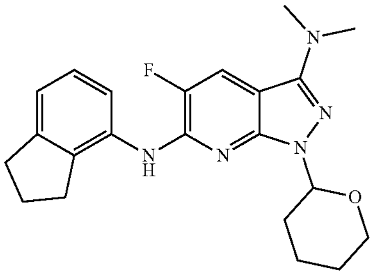

4

120 mg (0.251 mmol) of Compound 3, 2.0 M dimethylamine in MeOH 0.502 mL (1.004 mmol, 4 eq.), 208 mg (1.505 mg, 6 eq.) of potassium carbonate, and 14.44 mg (0.125 mmol, 0.5 eq.) of DL-proline were dissolved in 1.004 mL (0.25 M) of dimethylsulfoxide. 9.56 mg (0.050 mmol, 0.2 eq.) of copper (I) iodide was added to the reaction solution. The temperature was elevated to 100° C. and the reaction solution was stirred for 2 hours.

After completion of the reaction was detected, the organic layer was separated using an aqueous ammonium chloride solution (aq. $NH_4Cl$) and ethyl acetate, dried over $MgSO_4$, filtered and further dried under reduced pressure. The obtained residue was purified by column chromatography to obtain the target compound 4 (67 mg, 68%) as a light yellow solid.

Step 3

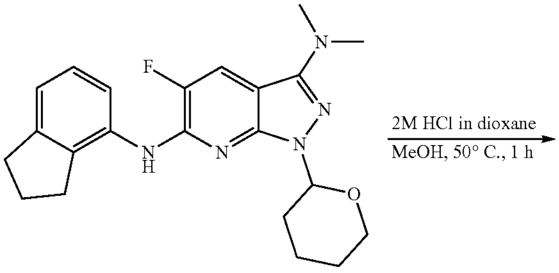

4

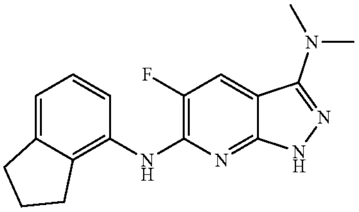

5

66 mg (0.167 mmol) of compound 4 was dissolved in 1.669 mL (0.1 M) of methanol and then a hydrogen chloride solution, 4 M in dioxane 50.7 μL (1.669 mmol, 10 eq.) was added dropwise to the resulting solution. The temperature was elevated to 50° C. and the reaction solution was stirred for 1 hour.

After completion of the reaction was detected, the organic layer was separated using an aqueous sodium hydrogen carbonate solution (aq. $NaHCO_3$) and dichloromethane, dried over $MgSO_4$, filtered and further dried under reduced pressure. The obtained residue was purified by reverse phase chromatography to obtain the target compound 5 (17.3 mg, 33%).

$^1$H NMR (400 MHz, DMSO-d6) δ=11.85 (s, 1H), 8.40 (s, 1H), 7.95 (d, J=12.0 Hz, 1H), 7.36 (d, J=7.7 Hz, 1H), 7.13 (t, J=7.6 Hz, 1H), 7.04 (d, J=7.3 Hz, 1H), 2.94-2.88 (m, 8H), 2.77 (t, J=7.5 Hz, 2H), 1.98 (quin, J=7.4 Hz, 2H).

Example 106: Preparation of N-(6-((2,3-dihydro-1H-inden-4-yl)amino)-5-fluoro-1H-pyrazolo[3,4-b]pyridin-3-yl)methanesulfonamide The compound represented by the following formula was prepared:

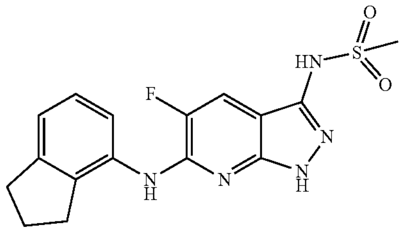 [SMILES: CS(=O)(=O)Nc1n[nH]c2nc(Nc3cccc4c3CCC4)c(F)cc12]

Step 1

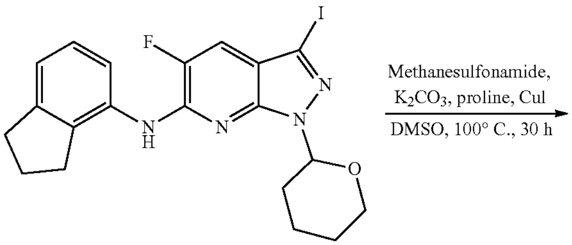

3

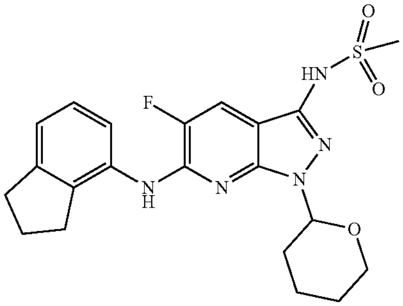

4

120 mg (0.251 mmol) of Compound 3, 95 mg (1.004 mmol, 4 eq.) of methanesulfonamide, 208 mg (1.505 mmol, 6 eq.) of potassium carbonate, and 4.44 mg (0.125 mmol, 0.5 eq.) of DL-proline were dissolved in 1.004 mL (0.25 M) of dimethylsulfoxide. 9.56 mg (0.050 mmol, 0.2 eq.) of copper (I) iodide was added to the reaction solution. The temperature was elevated to 100° C. and the reaction solution was stirred for 30 hours.

After completion of the reaction was detected, the organic layer was separated using an aqueous ammonium chloride solution (aq. $NH_4Cl$) and ethyl acetate, dried over $MgSO_4$, filtered and further dried under reduced pressure. The obtained residue was purified by column chromatography to obtain the target compound 4 (85.1 mg, 76%) as a yellow solid.

Step 2

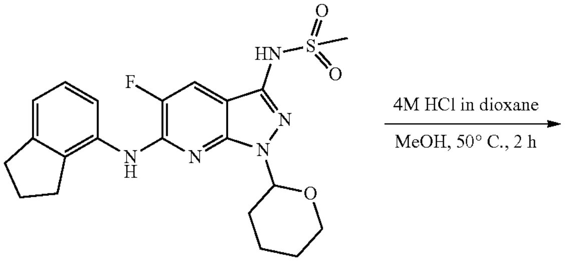

4

-continued

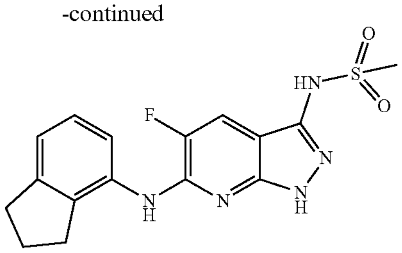

5

75 mg (0.168 mmol) of compound 4 was dissolved in 1.683 mL (0.1 M) of methanol and then a hydrogen chloride solution, 4 M in dioxane 51.2 μL (1.683 mmol, 10 eq.) was added dropwise to the resulting solution. The temperature was elevated to 50° C. and the reaction solution was stirred for 2 hours.

After completion of the reaction was detected, the organic layer was separated using an aqueous sodium hydrogen carbonate solution (aq. $NaHCO_3$) and dichloromethane, dried over $MgSO_4$, filtered and further dried under reduced pressure. The obtained residue was purified by reverse phase chromatography to obtain the target compound 5 (39.7 mg, 65%).

1H NMR (400 MHz, DMSO-d6) δ=12.73 (s, 1H), 10.10 (s, 1H), 8.70 (s, 1H), 7.72 (d, J=11.0 Hz, 1H), 7.31 (d, J=7.8 Hz, 1H), 7.15 (t, J=7.6 Hz, 1H), 7.07 (d, J=7.3 Hz, 1H), 3.14 (s, 3H), 2.92 (t, J=7.4 Hz, 2H), 2.77 (t, J=7.4 Hz, 2H), 1.98 (quin, J=7.4 Hz, 2H).

Example 107: Preparation of 6-((2,3-dihydro-1H-inden-4-yl)amino)-5-fluoro-1H-pyrazolo[3,4-b]pyridine-3-carbonitrile The compound represented by the following formula was prepared:

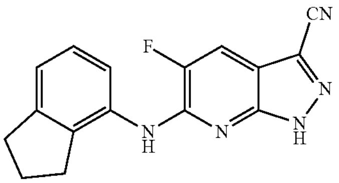

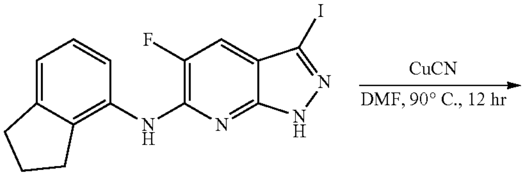

2

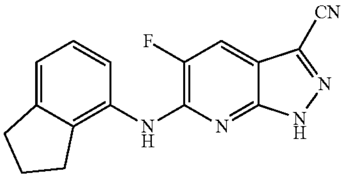

3

150 mg (0.381 mmol) of Compound 2 was dissolved in 1.903 mL (0.2 M) of N,N-dimethylmethanamide and then 102 mg (1.142 mmol, 3 eq.) of copper (I) cyanide was added dropwise to the resulting solution. The temperature was elevated to 90° C., and then the reaction solution was stirred for 12 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (75 mg, 67%) as a white solid.

$^1$H NMR (400 MHz, DMSO-d6) δ=14.23 (s, 1H), 9.06 (s, 1H), 8.09 (d, J=10.6 Hz, 1H), 7.27 (d, J=7.7 Hz, 1H), 7.17 (t, J=7.3 Hz, 1H), 7.13-7.10 (m, 1H), 2.92 (t, J=7.3 Hz, 2H), 2.76 (t, J=7.3 Hz, 2H), 1.98 (quin, J=7.5 Hz, 2H).

Example 108: Preparation of 3-(aminomethyl)-N-(2,3-dihydro-1H-inden-4-yl)-5-fluoro-1H-pyrazolo[3,4-b]pyridin-6-amine The compound represented by the following formula was prepared:

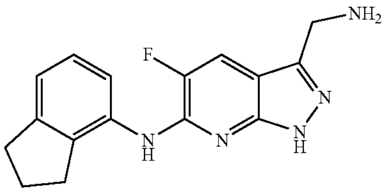 [SMILES: NCc1n[nH]c2nc(Nc3cccc4c3CCC4)c(F)cc12]

Step 1

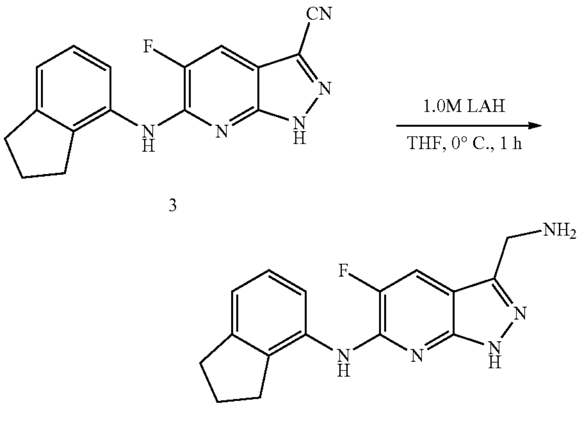

3

4

50 mg (0.170 mmol) of Compound 3 (Example 107) was dissolved in 0.852 mL (0.2 M) of tetrahydrofuran (THF), the temperature was dropped to 0° C. and 1.0 M lithium aluminium hydride in THF 0.205 mL (0.205 mmol, 1.2 eq.) was slowly added dropwise to the resulting solution. The reaction solution was stirred at the same temperature for 1 hour.

An aqueous potassium sodium tartrate solution was added to stop the reaction and the reaction solution was stirred at room temperature for 1 hour. The organic layer was separated using dichloromethane, dried over $MgSo_4$, filtered and further dried under reduced pressure. The obtained residue was purified by reverse phase chromatography to obtain the target compound 4 (7.5 mg, 15%) as a white solid.

$^1$H NMR (400 MHz, DMSO-d6) δ=12.89-12.80 (m, 1H), 8.53 (br s, 1H), 8.29 (br s, 1H), 8.00 (d, J=11.2 Hz, 1H), 7.36 (d, J=7.7 Hz, 1H), 7.14 (t, J=7.6 Hz, 1H), 7.08-7.04 (m, 1H), 4.01 (s, 2H), 2.91 (t, J=7.2 Hz, 2H), 2.76 (t, J=7.5 Hz, 2H), 2.02-1.94 (m, 2H).

Example 109: Preparation of 5-fluoro-N-indan-4-yl-3-phenyl-1H-pyrazolo[3,4-b]pyridin-6-amine The compound represented by the following formula was prepared:

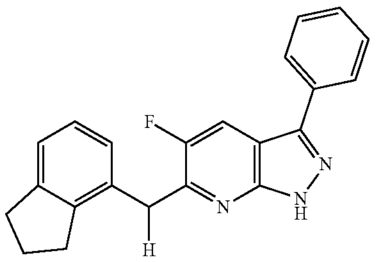 [SMILES: Fc1cc2c(-c3ccccc3)n[nH]c2nc1Cc1cccc2c1CCC2]

Step 1

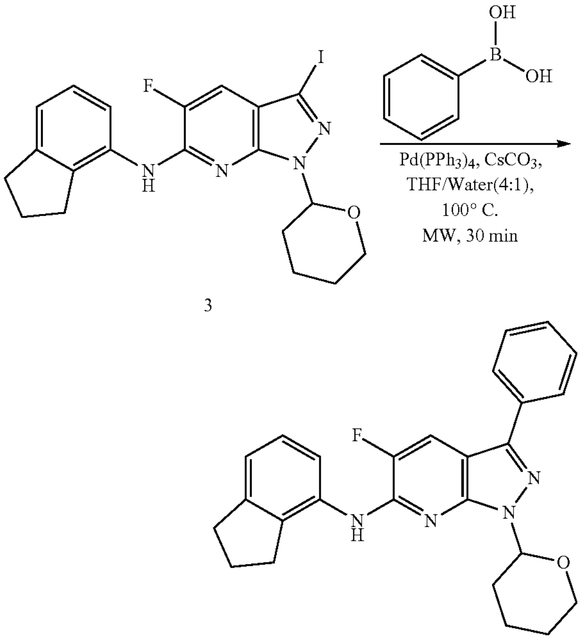

3

4

2 mL of a tetrahydrofuran (THF)/water ($H_2O$) solution (4:1) was added to 60 mg (0.12 mmol) of Compound 3, 22 mg (0.18 mmol, 1.5 eq.) of phenylboronic acid, and 117 mg (0.36 mmol, 3 eq.) of cesium carbonate. 13 mg (0.012 mmol, 0.1 eq.) of $Pd(PPh_3)_4$ was added to the resulting solution. The reaction solution was stirred in a microwave reactor at an elevated temperature of 100° C. for 30 minutes. After completion of the reaction was detected, the organic layer was separated using $H_2O$ and ethyl acetate, dried over $MgSo_4$, filtered and further dried under reduced pressure.

The obtained residue was purified by column chromatography to obtain the target compound 4 (11 mg, 20%).

Step 2

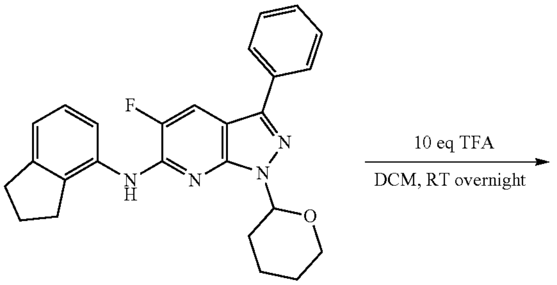

4

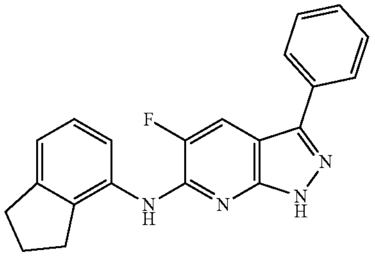

5

1 ml of 50% trifluoroacetic acid/dichloromethane was slowly added dropwise to 11 mg (0.025 mmol) of Compound 4. After completion of the reaction was detected, the reaction solution was concentrated under reduced pressure. The obtained residue was purified by reverse phase chromatography to obtain the target compound 5 (4.5 mg, 52%) as a white solid.

$^1$H NMR (500 MHz, DMSO-d6) δ=13.17 (s, 1H), 8.61 (s, 1H), 8.19 (d, J=11.6 Hz, 1H), 7.96-7.90 (m, 2H), 7.47 (t, J=7.7 Hz, 2H), 7.39-7.32 (m, 2H), 7.14 (t, J=7.6 Hz, 1H), 7.05 (d, J=7.4 Hz, 1H), 2.91 (t, J=7.4 Hz, 2H), 2.78 (t, J=7.4 Hz, 2H), 1.97 (p, J=7.5 Hz, 2H).

Example 110: Preparation of 3-cyclopropyl-5-fluoro-N-indan-4-yl-1H-pyrazolo[3,4-b]pyridin-6-amine The compound represented by the following formula was prepared:

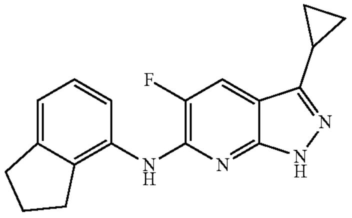 [SMILES: Fc1cc2c(C3CC3)n[nH]c2nc1Nc1cccc2c1CCC2]

Step 1

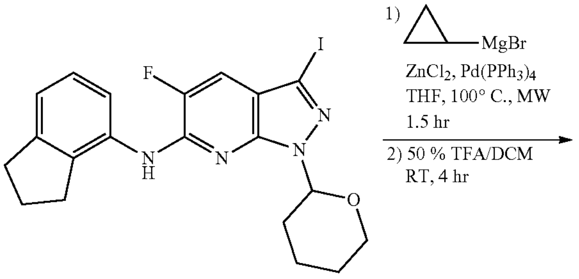

1

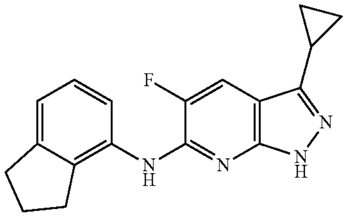

2

2 mL of tetrahydrofuran (THF) was added to 30 mg (0.062 mmol) of Compound 1, a cyclopropyl magnesium bromide 1M THF solution, 93 ul (0.093 mmol, 1.5 eq.), and 8.4 mg (0.062 mmol, 1 eq.) of zinc chloride. 7.1 mg (0.0062 mmol, 0.1 eq.) of $Pd(PPh_3)_4$ was added to the resulting solution. The reaction solution was stirred in a microwave reactor at an elevated temperature of 100° C. for 90 minutes. After completion of the reaction was detected, the organic layer was separated using $H_2O$ and ethyl acetate, dried over $MgSO_4$, filtered and further dried under reduced pressure. The obtained residue was stirred in 2 ml of a 50% TFA/dichloromethane solution at room temperature for 4 hours. After completion of the reaction, the solvent was dried under reduced pressure and the organic layer was separated using an aqueous $NaHCO_3$ solution and ethyl acetate, dried over $MgSO_4$, filtered and further dried under reduced pressure. The obtained residue was purified by reverse phase chromatography to obtain the target Compound 2 (12.8 mg, 67%) as a white solid.

$^1$H NMR (500 MHz, Chloroform-d) δ=8.07 (d, J=8.1 Hz, 1H), 7.56 (d, J=10.8 Hz, 1H), 7.22 (t, J=7.7 Hz, 1H), 7.02 (d, J=7.4 Hz, 1H), 6.68 (s, 1H), 3.00 (t, J=7.5 Hz, 2H), 2.89 (t, J=7.4 Hz, 2H), 2.15 (p, J=7.4 Hz, 2H), 2.08 (m, 1H), 1.01 (m, 4H).

Example 111: Preparation of 5-fluoro-N-indan-4-yl-3-methyl-1H-pyrazolo[3,4-b]pyridin-6-amine The compound represented b the following formula was prepared:

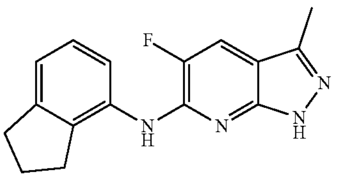 [SMILES: Cc1n[nH]c2nc(Nc3cccc4c3CCC4)c(F)cc12]

Step 1

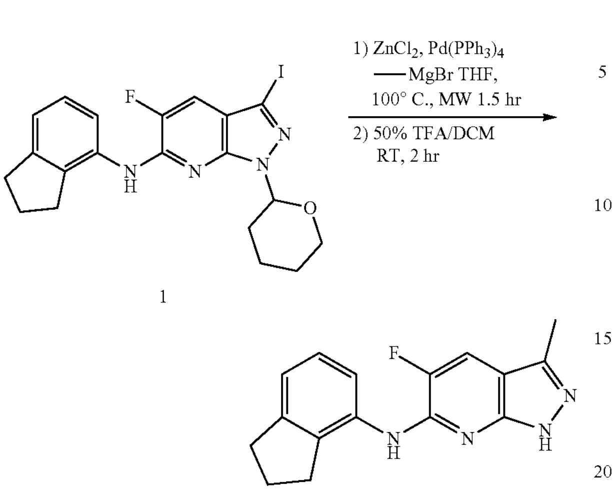

1

2

2 mL of tetrahydrofuran (THF) was added to 30 mg (0.062 mmol) of Compound 1, a methyl magnesium bromide 1M THF solution, 93 ul (0.093 mmol, 1.5 eq.), and 8.4 mg (0.062 mmol, 1 eq.) of zinc chloride. 7.1 mg (0.0062 mmol, 0.1 eq.) of $Pd(PPh_3)_4$ was added to the resulting solution. The reaction solution was stirred in a microwave reactor at an elevated temperature of 100° C. for 90 minutes. After completion of the reaction was detected, the organic layer was separated using $H_2O$ and ethyl acetate, dried over $MgSO_4$, filtered and further dried under reduced pressure. The obtained residue was stirred in 2 ml of a 50% TFA/dichloromethane solution at room temperature for 2 hours. After completion of the reaction, the solvent was dried under reduced pressure and the organic layer was separated using an aqueous $NaHCO_3$ solution and ethyl acetate, dried over $MgSO_4$, filtered and further dried under reduced pressure. The obtained residue was purified by reverse phase chromatography to obtain the target Compound 2 (2.4 mg, 15%) as a white solid.

$^1$H NMR (500 MHz, Chloroform-d) δ=8.09 (d, J=8.1 Hz, 1H), 7.50 (d, J=10.7 Hz, 1H), 7.23 (t, J=7.7 Hz, 1H), 7.02 (d, J=7.4 Hz, 1H), 6.69 (s, 1H), 3.00 (t, J=7.5 Hz, 2H), 2.89 (t, J=7.4 Hz, 2H), 2.47 (s, 3H), 2.15 (p, J=7.5 Hz, 2H).

Example 112: Preparation of N6-(2,3-dihydro-1H-inden-4-yl)-1H-pyrazolo[3,4-d]pyrimidine-3,6-diamine The compound represented by the following formula was prepared:

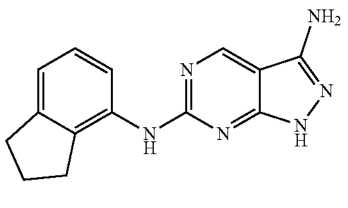 [SMILES: Nc1n[nH]c2nc(Nc3cccc4c3CCC4)ncc12]

Step 1

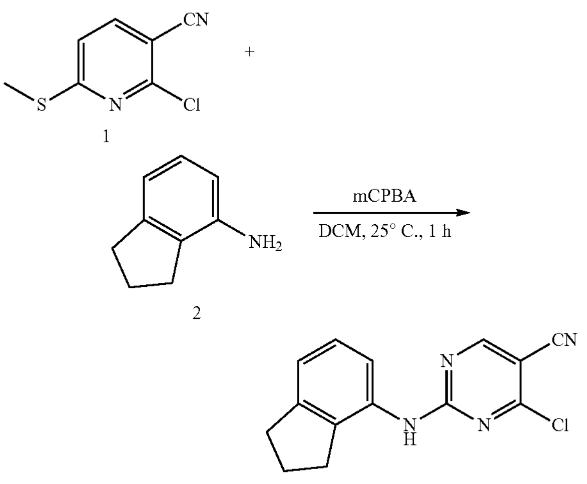

1

2

3

120 mg (0.646 mmol) of Compound 1 was dissolved in 3.232 mL (0.2 M) of dichloromethane and then 319 mg (1.422 mmol, 2.2 eq.) of mCPBA (77%, m-chloroperoxybenzoic acid) was added dropwise to the resulting solution. The reaction solution was stirred at room temperature for 30 minutes and then 86 mg (0.646 mmol, 1 eq.) of Compound 2 was slowly added dropwise to the resulting solution. The reaction solution was stirred at room temperature for 20 minutes.

After completion of the reaction was detected, the organic layer was separated using a 1N aqueous HCl solution, an aqueous sodium hydrogen carbonate solution (aq. $NaHCO_3$), an aqueous sodium thiosulfate solution (aq. $Na_2S_2O_3$) and dichloromethane, dried over $MgSO_4$, filtered and further dried under reduced pressure. The obtained residue was purified by column chromatography to obtain the target Compound 3 (153 mg, 87%) as a white solid.

Step 2

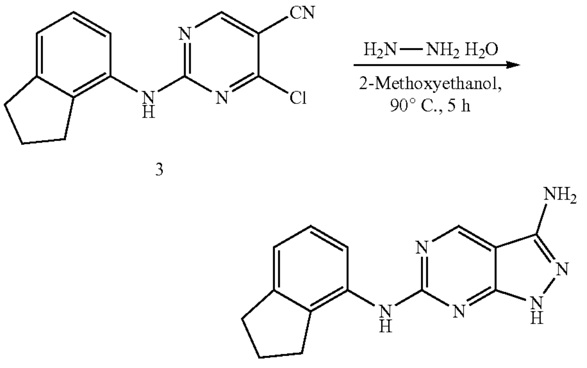

3

4

70 mg (0.259 mmol) of Compound 3 was dissolved in 1.034 mL (0.25 M) of 2-methoxyethanol and then 0.251 mL (5.17 mmol, 20 eq.) of hydrazine monohydrate was added dropwise to the resulting solution. The temperature was elevated to 90° C., and the resulting mixture was stirred for 5 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (38.1 mg, 55%) as a yellow solid.

$^1$H NMR (400 MHz, DMSO-d6) δ=9.19 (br s, 1H), 8.84 (s, 1H), 7.49 (d, J=7.9 Hz, 1H), 7.14 (t, J=7.6 Hz, 1H), 7.04 (d, J=7.3 Hz, 1H), 2.93-2.87 (m, 2H), 2.85-2.80 (m, 2H), 2.00 (t, J=7.4 Hz, 2H).

Example 113: Preparation of N6-(naphthalen-1-yl)-1H-pyrazolo[3,4-d]pyrimidine-3,6-diamine The compound represented by the following formula was prepared:

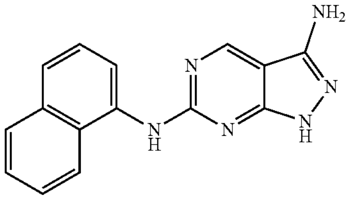 [SMILES: Nc1n[nH]c2nc(Nc3cccc4ccccc34)ncc12]

Step 1

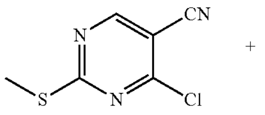

1

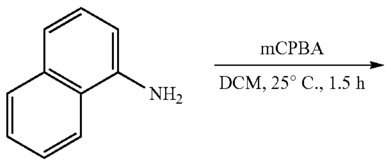

2

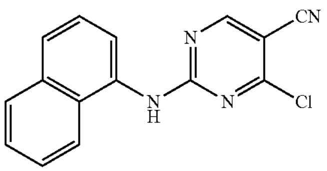

3

70 mg (0.377 mmol) of Compound 1 was dissolved in 1.885 mL (0.2 M) of dichloromethane and then 143 mg (0.830 mmol, 2.2 eq.) of mCPBA (77%, m-chloroperoxybenzoic acid) was added dropwise to the resulting solution. The reaction solution was stirred at room temperature for 30 minutes and then 54 mg (0.377 mmol, 1 eq.) of Compound 2 was slowly added dropwise to the resulting solution. The reaction solution was stirred at room temperature for 1 hour.

After completion of the reaction was detected, the organic layer was separated using a 1N aqueous HCl solution, an aqueous sodium hydrogen carbonate solution (aq. $NaHCO_3$), an aqueous sodium thiosulfate solution (aq. $Na_2S_2O_3$) and dichloromethane, dried over $MgSO_4$, filtered and further dried under reduced pressure. The obtained residue was purified by column chromatography to obtain the target Compound 3 (86 mg, 81%) as a light yellow solid.

Step 2

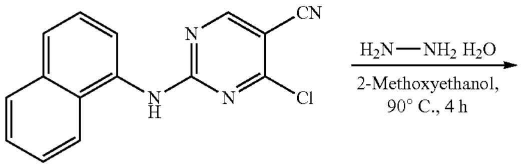

3

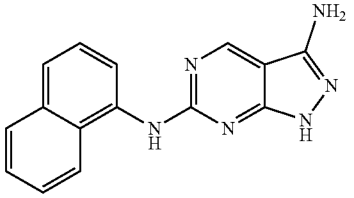

4

75 mg (0.267 mmol) of Compound 3 was dissolved in 1.069 mL (0.25 M) of 2-methoxyethanol and then 0.259 mL (5.34 mmol, 20 eq.) of hydrazine monohydrate was added dropwise to the resulting solution. The temperature was elevated to 90° C., and then the reaction solution was stirred for 4 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (23.5 mg, 32%) as a yellow solid.

$^1$H NMR (400 MHz, DMSO-d6) δ=9.77 (br s, 1H), 8.84 (s, 1H), 8.03 (d, J=7.8 Hz, 1H), 7.97 (d, J=8.0 Hz, 1H), 7.82 (d, J=8.2 Hz, 1H), 7.72 (d, J=7.3 Hz, 1H), 7.58-7.49 (m, 2H), 2.55-2.52 (m, 1H).

Example 114: Preparation of N6-(5,6,7,8-tetrahydronaphthalen-1-yl)-1H-pyrazolo[3,4-d]pyrimidine-3,6-diamine The compound represented by the following formula was prepared:

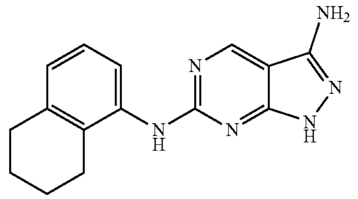 [SMILES: Nc1n[nH]c2nc(Nc3cccc4c3CCCC4)ncc12]

Step 1

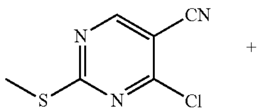

1

-continued

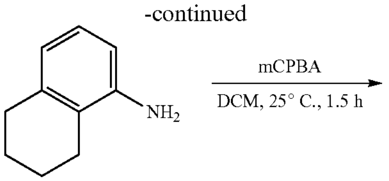

2

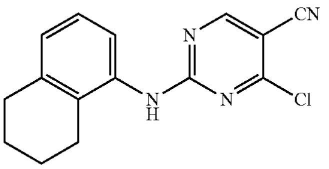

3

70 mg (0.377 mmol) of Compound 1 was dissolved in 1.885 mL (0.2 M) of dichloromethane and then 143 mg (0.830 mmol, 2.2 eq.) of mCPBA (77%, m-Chloroperoxybenzoic acid) was added dropwise to the resulting solution. The reaction solution was stirred at room temperature for 30 minutes and then 55.5 mg (0.377 mmol, 1 eq.) of Compound 2 was slowly added dropwise to the resulting solution. The reaction solution was stirred at room temperature for 1 hour.

After completion of the reaction was detected, the organic layer was separated using a 1N aqueous HCl solution, an aqueous sodium hydrogen carbonate solution (aq. $NaHCO_3$), an aqueous sodium thiosulfate solution (aq. $Na_2S_2O_3$) and dichloromethane, dried over $MgSO_4$, filtered and further dried under reduced pressure. The obtained residue was purified by column chromatography to obtain the target Compound 3 (93.2 mg, 87%) as a white solid.

Step 2

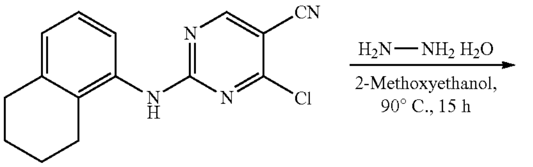

3

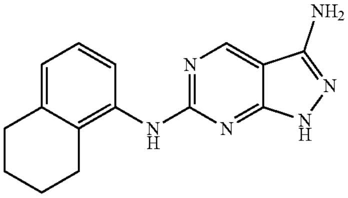

4

80 mg (0.279 mmol) of Compound 3 was dissolved in 1.117 mL (0.25 M) of 2-methoxyethanol and then 0.271 mL (5.58 mmol, 20 eq.) of hydrazine monohydrate was added dropwise to the resulting solution. The temperature was elevated to 90° C., and then the reaction solution was stirred for 15 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (23.7 mg, 30%) as a yellow solid.

$^1$H NMR (400 MHz, DMSO-d6) δ=9.14 (br s, 1H), 8.80 (s, 1H), 7.26 (d, J=7.7 Hz, 1H), 7.12 (t, J=7.7 Hz, 1H), 6.98 (d, J=7.5 Hz, 1H), 2.79-2.69 (m, 2H), 2.61 (br s, 2H), 1.71 (br t, J=3.1 Hz, 4H).

Example 115: Preparation of N6-(3-(difluoromethyl)-2-fluorophenyl)-1H-pyrazolo[3,4-d]pyrimidine-3,6-diamine The compound represented by the following formula was prepared:

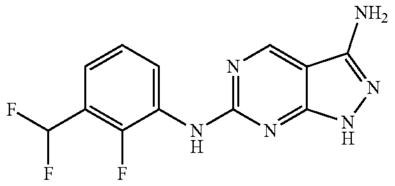 [SMILES: Nc1n[nH]c2nc(Nc3cccc(C(F)F)c3F)ncc12]

Step 1

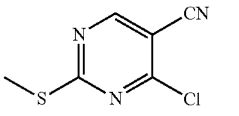

1

+

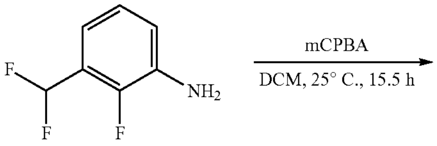

2

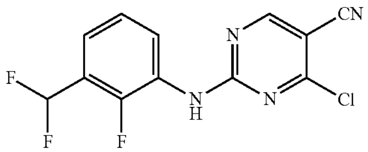

3

70 mg (0.377 mmol) of Compound 1 was dissolved in 1.885 mL (0.2 M) of dichloromethane and then 143 mg (0.830 mmol, 2.2 eq.) of mCPBA (77%, m-chloroperoxybenzoic acid) was added dropwise to the resulting solution. The reaction solution was stirred at room temperature for 30 minutes and then 60.8 mg (0.377 mmol, 1 eq.) of Compound 2 was slowly added dropwise to the resulting solution. The reaction solution was stirred at room temperature for 15 hours.

After completion of the reaction was detected, the organic layer was separated using a 1N aqueous HCl solution, an aqueous sodium hydrogen carbonate solution (aq. $NaHCO_3$), an aqueous sodium thiosulfate solution (aq. $Na_2S_2O_3$) and dichloromethane, dried over $MgSO_4$, filtered and further dried under reduced pressure. The obtained residue was purified by column chromatography to obtain the target Compound 3 (86 mg, 76%) as a white solid.

Step 2

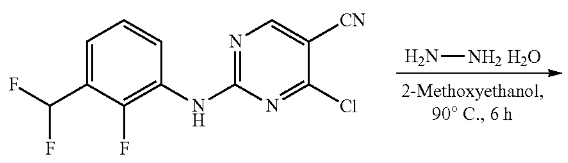

3

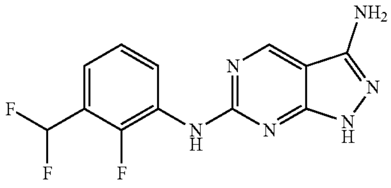

4

72 mg (0.241 mmol) of Compound 3 was dissolved in 0.964 mL (0.25 M) of 2-methoxyethanol and then 0.234 mL (4.82 mmol, 20 eq.) of hydrazine monohydrate was added dropwise to the resulting solution. The temperature was elevated to 90° C., and then the reaction solution was stirred for 6 hours.

After completion of the reaction was detected, the organic layer was separated using $H_2O$ and ethyl acetate, dried over $MgSO_4$, filtered and further dried under reduced pressure. The obtained residue was purified by reverse phase chromatography to obtain the target compound 4 (33.1 mg, 47%) as a yellow solid.

$^1$H NMR (400 MHz, DMSO-d6) δ=9.32 (br s, 1H), 8.84 (s, 1H), 8.06 (br t, J=7.0 Hz, 1H), 7.40-7.33 (m, 2H), 7.33-7.10 (m, 1H).

Example 116: Preparation of 4-chloro-N6-indan-4-yl-3a,4-didehydro-1H-pyrazolo[3,4-d]pyrimidine-3,6-diamine The compound represented by the following formula was prepared:

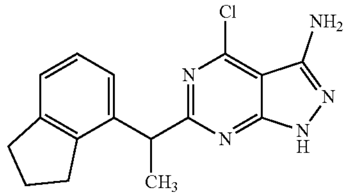 [SMILES: CC(c1nc(Cl)c2c(N)n[nH]c2n1)c1cccc2c1CCC2]

The target compound was obtained as a white solid (14 mg, 29%) in the same manner as in Example 12 using 200 mg (0.9 mmol) of 4,6-dichloro-2-(methylthio)pyrimidine-5 carbonitrile and 4-aminoindane (0.9 mmol).

$^1$H NMR (500 MHz, DMSO-d6) δ=11.94 (s, 1H), 8.38 (s, 1H), 7.24 (t, J=7.5 Hz, 1H), 7.19 (d, J=7.4 Hz, 111), 7.09 (d, J=7.6 Hz, 1H), 5.65 (s, 1H), 5.53 (s, 2H), 2.94 (t, J=7.4 Hz, 2H), 2.71 (t, J=7.4 Hz, 2H), 2.05-1.92 (m, 2H).

Example 117: Preparation of N6-[2-fluoro-3-(trifluoromethyl)phenyl]-1H-pyrazolo[3,4-d]pyrimidine-3,6-diamine The compound represented by the following formula was prepared:

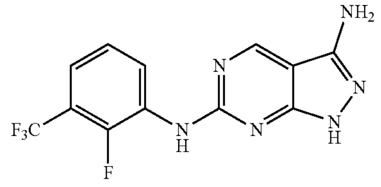 [SMILES: Nc1n[nH]c2nc(Nc3cccc(C(F)(F)F)c3F)ncc12]

The target compound was obtained as a white solid (8 mg, 23%) in the same manner as in Example 112 using 70 mg (0.37 mmol) of 4-chloro-2-(methylthio) pyrimidine-5-carbonitrile and 2-fluoro-3-(trifluoromethyl)aniline.

$^1$H NMR (500 MHz, DMSO-d6) δ=11.82 (s, 1H), 9.31 (s, 1H), 8.80 (s, 1H), 8.24 (d, J=8.0 Hz, 1H), 7.45 (t, J=6.9 Hz, 1H), 7.37 (t, J=8.1 Hz, 1H), 5.78 (s, 2H).

Example 118: Preparation of 3-bromo-N-(7-bromoindan-4-yl)-5-fluoro-1H-pyrazolo[3,4-b]pyridin-6-amine The compound represented by the following formula was prepared:

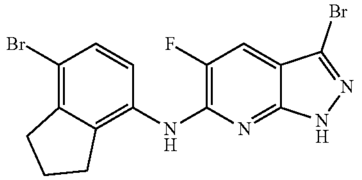 [SMILES: Fc1cc2c(Br)n[nH]c2nc1Nc1ccc(Br)c2c1CCC2]

Step 1

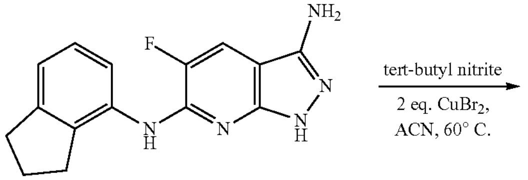

1

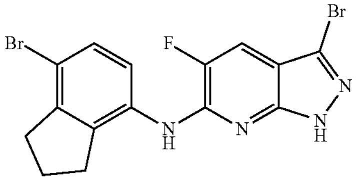

\+

2

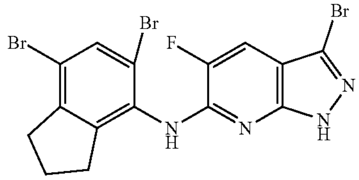

3

5 ml of acetonitrile was added to 200 mg (0.7 mmol) of Compound 1, and 189 mg (0.84 mmol, 1.2 eq.) of $CuBr_2$. 158 mg (1.54 mmol, 2.2 eq.) of tert-butyl nitrite was slowly added at 0° C. to the resulting solution, the temperature was elevated to 60° C. and the reaction solution was stirred for 12 hours. After completion of the reaction was detected, the organic layer was separated using $H_2O$ and ethyl acetate, dried over $MgSO_4$, filtered and further dried under reduced pressure. The obtained residue was purified by column chromatography to obtain the target Compound 2 (10.7 mg, 3.5%) as a white solid.

$^1H$ NMR (500 MHz, DMSO-d6) δ=13.36 (s, 1H), 8.92 (s, 1H), 7.73 (d, J=10.5 Hz, 1H), 7.35 (d, J=8.4 Hz, 1H), 7.26 (d, J=8.4 Hz, 1H), 2.91-2.85 (m, 4H), 2.02-1.96 (m, 2H).

Example 119: Preparation of 3-bromo-N-(5,7-dibromoindan-4-yl)-5-fluoro-1H-pyrazolo[3,4-b]pyridin-6-amine

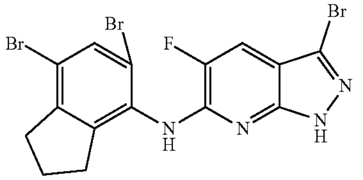 [SMILES: Fc1cc2c(Br)n[nH]c2nc1Nc1c(Br)cc(Br)c2c1CCC2]

Step 1

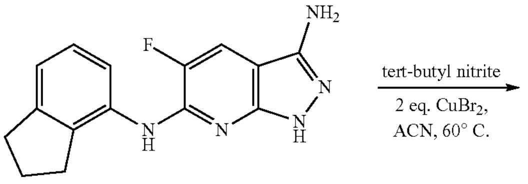

1

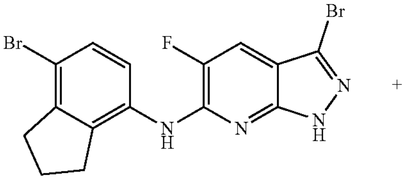

\+

2

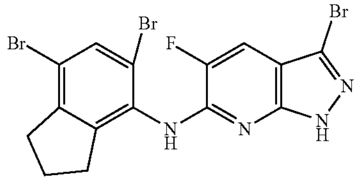

3

5 ml of acetonitrile was added to 200 mg (0.7 mmol) of Compound 1, and 189 mg (0.84 mmol, 1.2 eq.) of $CuBr_2$. 158 mg (1.54 mmol, 2.2 eq.) of tert-butyl nitrite was slowly added at 0° C. to the resulting solution, the temperature was elevated to 60° C. and the reaction solution was stirred for 12 hours. After completion of the reaction was detected, the organic layer was separated using $H_2O$ and ethyl acetate, dried over $MgSO_4$, filtered and further dried under reduced pressure. The obtained residue was purified by column chromatography to obtain the target Compound 3 (4.6 mg, 1.8%) as a white solid.

$^1H$ NMR (500 MHz, DMSO-d6) δ=13.36 (s, 1H), 9.36 (s, 1H), 8.05 (s, 1H), 7.80 (d, J=10.4 Hz, 1H), 3.03-2.94 (m, 4H), 2.07 (p, J=7.6 Hz, 2H).

Example 120: Preparation of 3-bromo-5-fluoro-N-indan-4-yl-1H-pyrazolo[3,4-b]pyridin-6-amine The compound represented by the following formula was prepared:

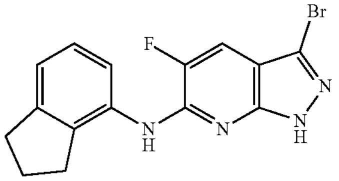 [SMILES: Fc1cc2c(Br)n[nH]c2nc1Nc1cccc2c1CCC2]

Step 1

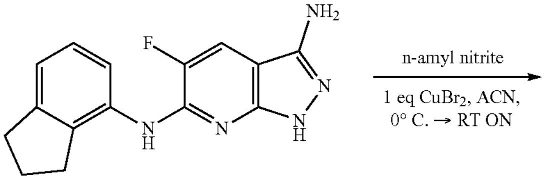

1

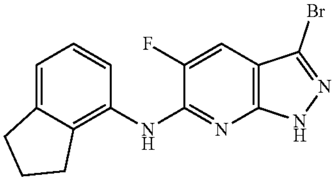

2

5 ml of acetonitrile was added to 100 mg (0.35 mmol) of Compound 1, and 117 mg (0.52 mmol, 1.5 eq.) of $CuBr_2$. 124 mg (1.05 mmol, 3 eq.) of n-amyl nitrite was slowly added at 0° C. to the resulting solution, the temperature was allowed to warm to room temperature and the reaction solution was stirred for 12 hours. After completion of the reaction was detected, the organic layer was separated using $H_2O$ and ethyl acetate, dried over $MgSO_4$, filtered and further dried under reduced pressure. The obtained residue was purified by column chromatography to obtain the target Compound 2 (3 mg, 2.4%) as a white solid.

$^1H$ NMR (500 MHz, DMSO-d6) δ=13.33 (s, 1H), 8.86 (s, 1H), 7.70 (d, J=10.6 Hz, 1H), 7.26 (d, J=7.8 Hz, 1H), 7.13 (t, J=7.6 Hz, 1H), 7.06 (d, J=7.4 Hz, 1H), 2.89 (t, J=7.4 Hz, 2H), 2.73 (t, J=7.4 Hz, 2H), 1.95 (p, J=7.4 Hz, 2H)

Example 121: Preparation of N-(2,3-dihydro-1H-inden-4-yl)-3,5-difluoro-1H-pyrazolo[3,4-b]pyridin-6-amine The compound represented by the following formula was prepared:

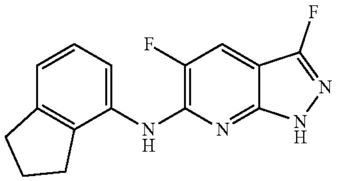 [SMILES: Fc1cc2c(F)n[nH]c2nc1Nc1cccc2c1CCC2]

Step 1

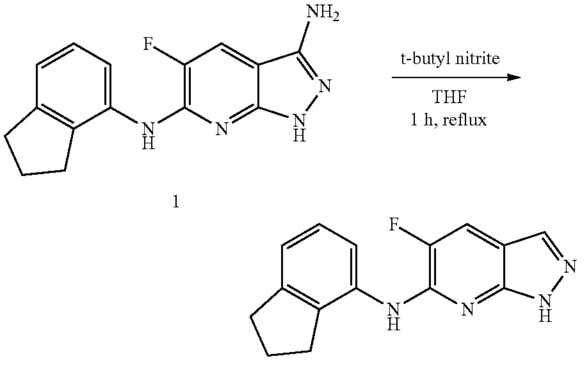

1

2

5 ml of acetonitrile was added to 50 mg (0.18 mmol) of Compound 1, 31 mg (0.45 mmol, 2.5 eq.) of sodium nitrite, and HCl (27 uL, 0.9 mmol). 158 mg (1.54 mmol, 2.2 eq.) of tert-butyl nitrite was slowly added at 0° C. to the resulting solution, the temperature was elevated to 50° C. and the reaction solution was stirred for 12 hours. After completion of the reaction was detected, the organic layer was separated using $H_2O$ and ethyl acetate, dried over $MgSO_4$, filtered and further dried under reduced pressure. The obtained residue was purified by column chromatography to obtain the target Compound 2 (18 mg, 33%) as a yellow solid.

Step 2

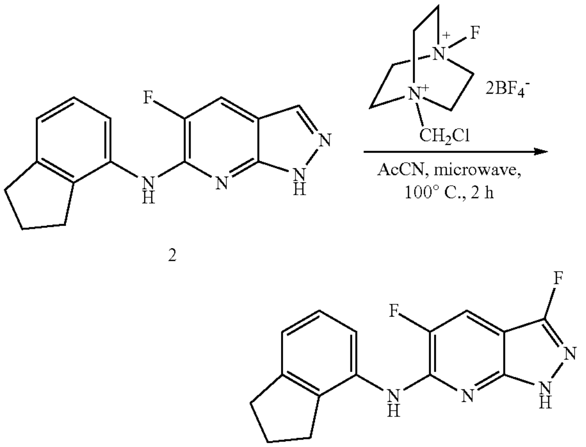

2

5 ml of acetonitrile was added to 5 mg (0.018 mmol) of Compound 2 and 2.6 mg (0.045 mmol, 2.5 eq.) of KF. The reaction solution was stirred at 100° C. in a microwave for 2 hours.

After completion of the reaction was detected, the organic layer was separated using $H_2O$ and ethyl acetate, dried over $MgSO_4$, filtered and further dried under reduced pressure. The obtained residue was purified by column chromatography to obtain the target compound (1.8 mg, 36%) as a yellow solid.

$^1$H NMR (500 MHz, Chloroform-d) δ=8.68 (d, J=9.2 Hz, 1H), 8.19 (d, J=9.2 Hz, 1H), 7.95 (s, 1H), 7.70 (d, J=10.5 Hz, 1H), 7.03 (t, J=7.6 Hz, 1H), 3.54 (t, J=7.6 Hz, 2H), 3.00 (t, J=7.7 Hz, 2H), 2.30 (m, 2H)

Example 122: Preparation of (Z)-N-(2,3-dihydro-1H-inden-4-yl)-5-fluoro-3-(hydroxydiazenyl)-1H-pyrazolo[3,4-b]pyridin-6-amine The compound represented b the following formula was prepared:

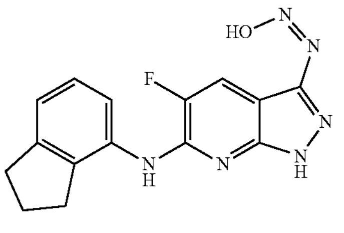 [SMILES: O/N=N\c1n[nH]c2nc(Nc3cccc4c3CCC4)c(F)cc12]

Step 1

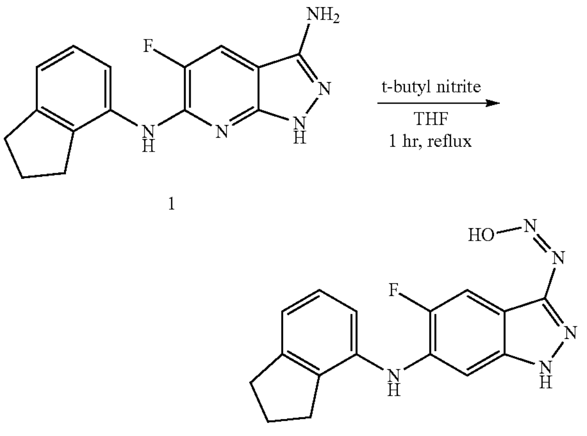

1

2

The target compound was obtained as a yellow solid (18 mg, 33%) in the same manner as in Step 1 in Example 121 using 50 mg (0.18 mmol) of 2,6-dichloro-5-fluoro-3-cyano-pyridine and 31 mg (0.45 mmol) of sodium nitrite.

$^1$H NMR (500 MHz, DMSO-d6) δ=12.99 (s, 1H), 9.03 (s, 1H), 7.90 (d, J=10 Hz, 1H), 7.81 (t, 1H), 7.81 (s, 1H), 7.29 (d, J=5 Hz, 1H), 2.99 (t, 2H), 2.83 (t, 2H), 2.04 (m, 2H).

Experimental Example

Table 1 shows the results of tests on the effect of promoting the proliferation of human dermal papilla cells according to the present invention.

The effect of promoting cell proliferation by the drug was analyzed using human dermal papilla cells (ScienCell, 2499). Human dermal papilla cells cultured using Mesenchymal Stem Cell Medium (ScienCell, 7501) medium were seeded at a density of $3\times10^3$ cells/well and in a volume of 100 μl in a 96-well plate, incubated overnight at 37° C. and 5% $CO_2$, treated with the drug at different concentrations ranging from 0 to 30 μM in a volume of 100 μL, and incubated at 37° C. and 5% $CO_2$ for 48 hours. CellTiter-Glo Luminescent cell viability assay was performed according to the manufacturer's protocol (Promega, G7573) to detect cell proliferation. Luminescence was measured using an Envision 2102 multilabeled reader (PerkinElmer) equipment, and the cell proliferation rate was analyzed by the activity of the drug-treated group compared to the DMSO-treated group (control group), which is a solvent of the drug. The results are shown in Table 1 below.

TABLE 1

| Compound example # | Maximum DP cell proliferation (%) |
|---|---|
| DMSO | 0 |
| 3 | 23 |
| 4 | 4 |
| 5 | 7.4 |
| 6 | 7 |
| 8 | 7.9 |
| 9 | 2.6 |
| 10 | 13 |
| 12 | 5.4 |
| 14 | 5.3 |
| 15 | 24 |
| 16 | 6.1 |
| 17 | 6 |
| 18 | 7.8 |
| 19 | 9 |
| 21 | 3 |
| 23 | 5 |
| 24 | 8 |
| 27 | 6.8 |
| 29 | 4.6 |
| 31 | 3.2 |
| 33 | 6.3 |
| 34 | 6.8 |
| 35 | 1.2 |
| 38 | 2.2 |
| 39 | 7.9 |
| 42 | 16 |
| 45 | 7 |
| 48 | 11 |
| 51 | 8.7 |
| 52 | 11 |
| 53 | 2.4 |
| 54 | 4.4 |
| 56 | 7.3 |
| 57 | 3.1 |
| 58 | 13 |
| 59 | 15 |
| 60 | 6.1 |
| 61 | 11 |
| 62 | 6.2 |
| 64 | 16 |
| 65 | 10 |
| 66 | 25 |
| 67 | 13 |
| 68 | 4.5 |
| 71 | 0.7 |
| 72 | 6.8 |
| 73 | 14 |
| 75 | 3 |
| 76 | 4 |
| 77 | 15 |
| 79 | 3.6 |
| 80 | 6 |
| 82 | 14 |
| 84 | 7.4 |
| 85 | 15 |
| 87 | 3.8 |
| 88 | 8 |
| 89 | 0.4 |
| 90 | 13 |
| 91 | 6.4 |
| 92 | 8 |
| 93 | 2.8 |
| 94 | 18 |
| 96 | 1.2 |
| 97 | 10 |
| 100 | 0.8 |
| 101 | 9.7 |
| 102 | 13 |
| 104 | 15 |
| 105 | 12 |
| 106 | 4.8 |

TABLE 1-continued

| Compound example # | Maximum DP cell proliferation (%) |
|---|---|
| 109 | 3.6 |
| 112 | 2 |
| 115 | 3.7 |
| 116 | 5.9 |
| 117 | 6.7 |
| 119 | 1.3 |
| 122 | 5.3 |

As can be seen from Table 1, the novel heterocycle derivatives of Examples 1 to 122 exhibit better effect of promoting the differentiation of human follicle dermal papilla cells (HFDPCs) compared to the control group. Accordingly, the compound of Formula 1 of the present invention, or a salt and isomer thereof exhibits an effect of promoting differentiation of human follicle dermal papilla cells (HFDPCs), and can be used as a composition containing the same for preventing hair loss and can be used as a drug or cosmetic for preventing or treating hair loss containing the same.

INDUSTRIAL APPLICABILITY

The compounds or salts or isomers thereof according to the present invention have the effect of promoting the differentiation and proliferation of human follicle dermal papilla cells (HFDPC) that play a pivotal role in hair growth, and thus can be used as functional cosmetics for inhibiting hair loss, and preventive or therapeutic agents for hair loss.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A compound represented by Formula 1, or a salt thereof:

[Formula 1]

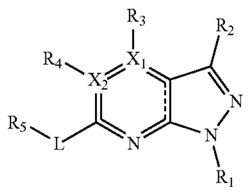

wherein:

$X_1$ is nitrogen (N) or carbon (C), and $X_2$ is carbon (C);

$\overset{---}{=\!=}$ is a single bond or a double bond;

L is —NH—;

$R_1$ is a hydrogen atom or $C_1$-$C_6$ alkyl;

$R_2$ is $NH_2$;

$R_3$ is absent, a hydrogen atom or $C_1$-$C_6$ alkyl;

$R_4$ is halogen, or $C_1$-$C_6$ alkyl; and $R_5$ is a monovalent radical selected from the group consisting of Formula 3 and Formula 4:

[Formula 3]

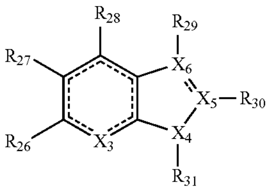

wherein $X_3$, $X_4$, $X_5$ and $X_6$ are carbon (C), $X_3$ is connected to a linker (L), $R_{26}$ to $R_{31}$ are each independently a hydrogen atom, or $C_1$-$C_6$ alkyl, $\overline{\overline{---}}$ between $X_5$ and $X_6$ is a single bond or a double bond;

[Formula 4]

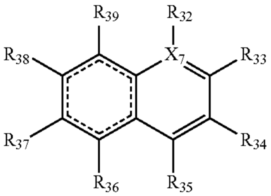

wherein $X_7$ is carbon (C), $R_{33}$ to $R_{39}$ are a hydrogen atom or $C_1$-$C_6$ alkyl, $R_{32}$ is connected to a linker (L), $\overline{\overline{---}}$ between $R_{38}$ and $R_{39}$ and $\overline{\overline{---}}$ between $R_{37}$ and $R_{36}$ are single bond or a double bond.

2. The compound, or a salt thereof, of claim 1, wherein the compound is selected from the following compounds:

| Compound No. | Structure |
|---|---|
| 3 | 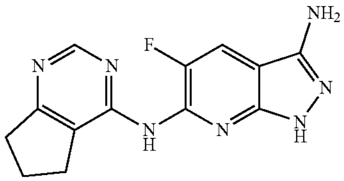 [SMILES: Nc1n[nH]c2nc(Nc3ncnc4c3CCC4)c(F)cc12] |
| 11 | 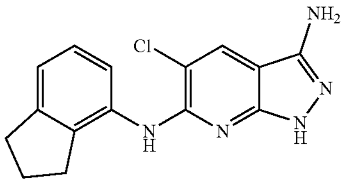 [SMILES: Nc1n[nH]c2nc(Nc3cccc4c3CCC4)c(Cl)cc12] |
| 17 | 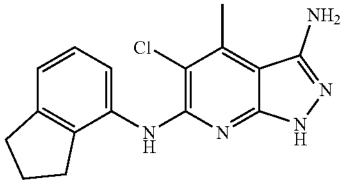 [SMILES: Cc1c(Cl)c(Nc2cccc3c2CCC3)nc2[nH]nc(N)c12] |

-continued

| Compound No. | Structure |
|---|---|
| 19 | 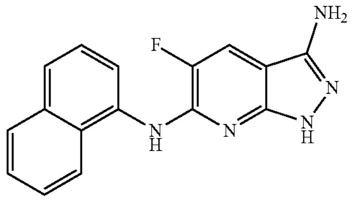 [SMILES: Nc1n[nH]c2nc(Nc3cccc4ccccc34)c(F)cc12] |
| 21 | 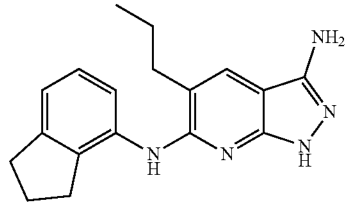 [SMILES: CCCc1cc2c(N)n[nH]c2nc1Nc1cccc2c1CCC2] |
| 22 | 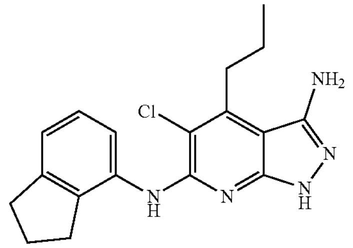 [SMILES: CCCc1c(Cl)c(Nc2cccc3c2CCC3)nc2[nH]nc(N)c12] |
| 24 | 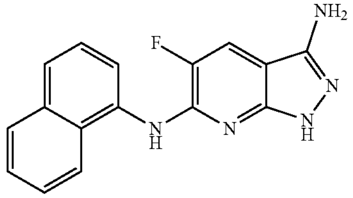 [SMILES: Nc1n[nH]c2nc(Nc3cccc4ccccc34)c(F)cc12] |
| 27 | 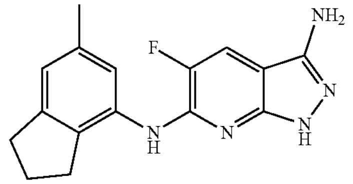 [SMILES: Cc1cc2c(c(Nc3nc4[nH]nc(N)c4cc3F)c1)CCC2] |
| 31 | 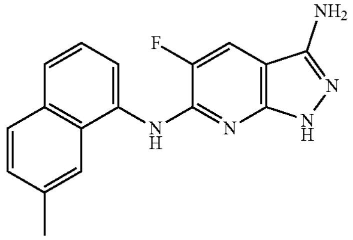 [SMILES: Cc1ccc2cccc(Nc3nc4[nH]nc(N)c4cc3F)c2c1] |
| 48 | 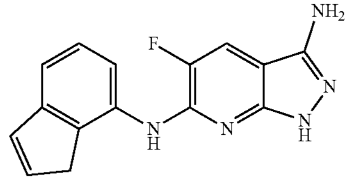 [SMILES: Nc1n[nH]c2nc(Nc3cccc4c3CC=C4)c(F)cc12] |

-continued

| Compound No. | Structure |
| --- | --- |
| 51 | 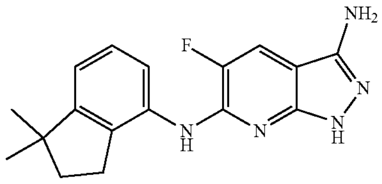 [SMILES: CC1(C)CCc2c(Nc3nc4[nH]nc(N)c4cc3F)cccc21] |
| 52 | 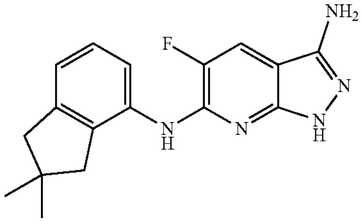 [SMILES: CC1(C)Cc2cccc(Nc3nc4[nH]nc(N)c4cc3F)c2C1] |
| 58 | 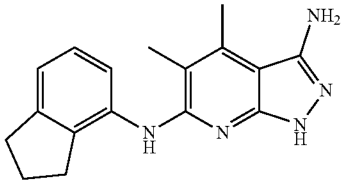 [SMILES: Cc1c(Nc2cccc3c2CCC3)nc2[nH]nc(N)c2c1C] |
| 83 | 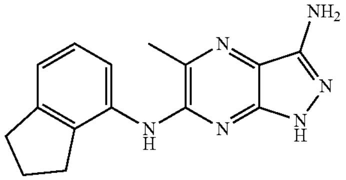 [SMILES: Cc1nc2c(N)n[nH]c2nc1Nc1cccc2c1CCC2] |

-continued

| Compound No. | Structure |
| --- | --- |
| 90 | 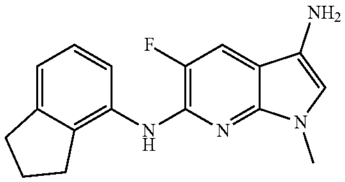 . |

3. A method of preventing or treating hair loss comprising administering a composition comprising the compound, or a salt thereof, of claim 1 as an active ingredient to a subject in need thereof.

4. The method of preventing or treating hair loss of claim 3, wherein the hair loss is selected from androgenic alopecia, alopecia areata, androgenetic alopecia, gynecologic alopecia, postpartum alopecia, seborrheic alopecia, non-rigid alopecia, senile alopecia, chemotherapy-induced alopecia and radiation-induced alopecia.

5. A cosmetic composition comprising the compound, or a salt thereof, of claim 1 as an active ingredient.

6. The cosmetic composition of claim 5, further comprising at least one additive selected from the group consisting of cosmetically acceptable carriers, excipients, adjuvants and diluents.

* * * * *